(12) United States Patent
Bergsma et al.

(10) Patent No.: US 10,724,092 B2
(45) Date of Patent: Jul. 28, 2020

(54) METHODS FOR CHARACTERIZING ALTERNATIVELY OR ABERRANTLY SPLICED MRNA ISOFORMS

(71) Applicant: Erasmus University Medical Center Rotterdam, Rotterdam (NL)

(72) Inventors: Atze Jacobus Bergsma, Rotterdam (NL); Erik van der Wal, Rotterdam (NL); Wilhelmus Wenceslaus Matthias Pijnappel, Rotterdam (NL); Antje Tjitske van der Ploeg, Rotterdam (NL); Arnoldus Reuser, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 272 days.

(21) Appl. No.: 15/315,879

(22) PCT Filed: Jun. 10, 2015

(86) PCT No.: PCT/NL2015/050420
§ 371 (c)(1),
(2) Date: Dec. 2, 2016

(87) PCT Pub. No.: WO2015/190921
PCT Pub. Date: Dec. 17, 2015

(65) Prior Publication Data
US 2017/0306399 A1    Oct. 26, 2017

(30) Foreign Application Priority Data

Jun. 10, 2014  (WO) ................ PCT/NL2014/050375
Sep. 4, 2014   (EP) .................................... 14183623

(51) Int. Cl.
| | | |
|---|---|---|
| *C12Q 1/68* | (2018.01) | |
| *C12Q 1/6876* | (2018.01) | |
| *C12Q 1/6883* | (2018.01) | |
| *C12Q 1/6844* | (2018.01) | |
| *C12Q 1/6851* | (2018.01) | |
| *C12N 15/11* | (2006.01) | |
| *C12N 15/113* | (2010.01) | |

(52) U.S. Cl.
CPC .......... *C12Q 1/6876* (2013.01); *C12N 15/111* (2013.01); *C12N 15/113* (2013.01); *C12Q 1/6846* (2013.01); *C12Q 1/6851* (2013.01); *C12Q 1/6883* (2013.01); *C12N 2310/11* (2013.01); *C12N 2320/33* (2013.01); *C12N 2330/30* (2013.01); *C12N 2330/50* (2013.01); *C12N 2330/51* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

2011/0092375 A1* 4/2011 Zamore .............. C12N 15/1031
                                                    506/7

FOREIGN PATENT DOCUMENTS

| WO | 01/77380 A2 | 10/2001 |
| WO | 2007/135105 A1 | 11/2007 |
| WO | 2013/043878 A2 | 3/2013 |

OTHER PUBLICATIONS

New England Biolabs 96/97 catalog, p. 111. (Year: 1997).*
Collin, et al., "Mid-frequency DFNA8/12 hearing loss caused by a synonymous TECTA mutation that affects an exonic splice enhancer," European Journal of Human Genetics, Jun. 25, 2008, pp. 1430-1436, vol. 16, No. 12, United States.
International Search Report issued in International Application No. PCT/NL2015/050420 dated Jan. 15, 2016.
Ohnuma, et al., "Cancer-associated splicing variants of the CDCA1 and MSMB genes expressed in cancer cell lines and surgically resected gastric cancer tissues," Surgery, Mosby, Inc., Jan. 1, 2009, pp. 57-68, vol. 145, No. 1.
Veistinen, et al, "Quantification of human Aiolos splice variants by real-time PCR," Journal of Immonological Methods, Dec. 20, 2002, pp. 113-123, vol. 271, No. 1-2, Amsterdam, Netherlands.
Yen, et al., "Novel Mutations of the OPA1 Gene in Chinese Dominant Optic Atrophy," American Academy of Ophthalmology, Feb. 1, 2010, pp. 392-396, vol. 117, No. 2, Philadelphia, Pennsylvania, United States.
Yu, et al., "Using a minigene approach to characterize a novel splice site mutation in human F7 gene causing inherited factor VII deficiency in a Chinese pedigree," Haemophilia, Nov. 1, 2009, pp. 1262-1266, vol. 15, No. 6.

* cited by examiner

*Primary Examiner* — James Martinell
(74) *Attorney, Agent, or Firm* — Dentons US LLP

(57) ABSTRACT

The disclosure provides method and kits for characterizing spliced m RNA isoforms. The disclosure also provides methods of screening for mutations and oligonucleotides that modulate splicing.

21 Claims, 57 Drawing Sheets
Specification includes a Sequence Listing.

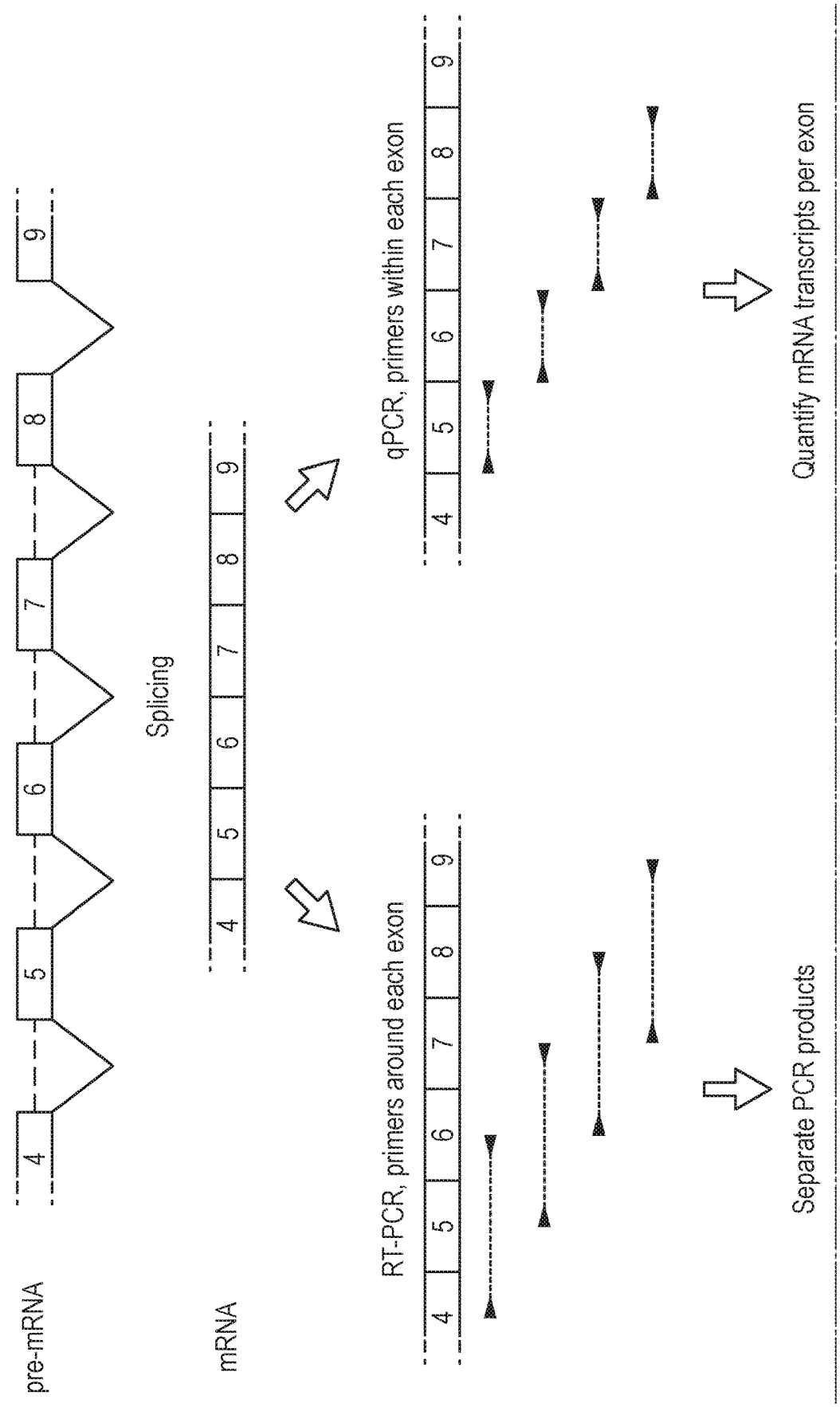

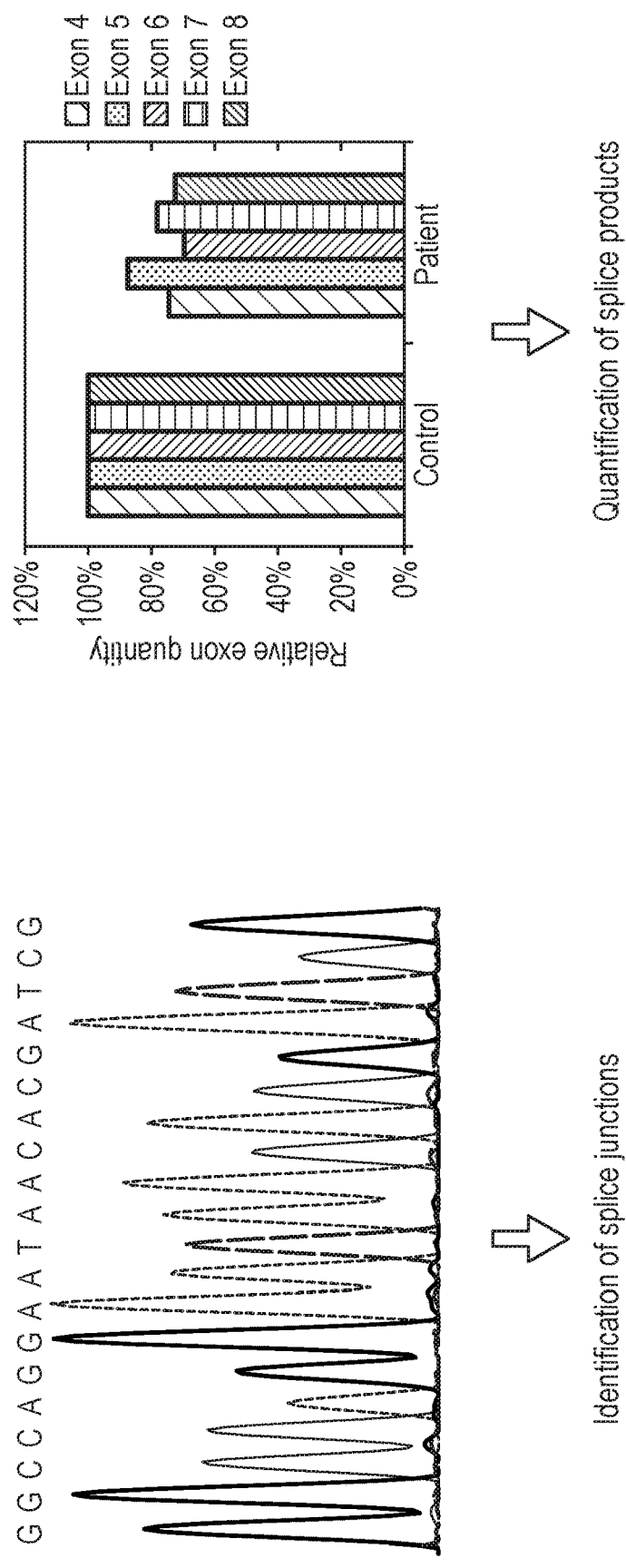
Fig. 1(Cont. A)

Fig. 6

| | Mutation allele 1 | Mutation allele 2 | GAA activity in primary fibroblasts on 4-MU substrate (nmol 4-MU/hr/mg protein) | GAA activity in primary fibroblasts on Glycogen substrate (nmol glucose/hr/mg protein) | Age at diagnosis | Onset infantile/juvenile/adult |
|---|---|---|---|---|---|---|
| Control | - | - | 122.4 | 1998.2 | - | none |
| Patient 1 | c.-32-13T>G | c.1636+5G>T | 14.1 | 190.6 | 59 years | adult |
| Patient 2 | c.525delT | c.525delT | 1.3 | 0.0 | 0.5 months | infantile |
| Patient 3 | c.1548G>A | c.2481+102_246+31del | 0.1 | 0.0 | 3.5 months | infantile |
| Patient 4 | c.-32-3C>G | c.1551+1G>A | 6.9 | 42.8 | 8.5 years | juvenile |
| Patient 5 | c.1075G>A | c.1075G>A | 0.6 | 0.0 | 8.5 motnhs | infantile |
| Patient 6 | c.1552-3C>G | c.1552-3C>G | 12.6 | 138.8 | 16 years | adult |
| Patient 7 | c.1437G>A | c.1437G>A | 3.0 | 0.0 | 37 years | adult |
| Patient 8 | c.1256A>T | c.1551+1G>T | 5.4 | 10.5 | 1.3 years | juvenile |

Fig. 7

| patient | Mutation (cDNA HGV nomenclature) | Location | codon change | ref on patient/codon change | effect on RNA processing | RNA HGV nomenclature | reading frame | Protein HGV nomenclature | Reference on Splicing |
|---|---|---|---|---|---|---|---|---|---|
| 1 | c.-32-13T>G (IVS1) | intron 1 | | Hüie et al., Hum Mol Gen. 1994 | leaky wt splicing | | in frame | | Boerkoel et al., Am. J. Hum. Gen. 1995 |
| | | | | Hüie et al., Hum Mol Gen. 1994 | Perfect skipping exon 2 | r.-32_546del | out of frame | p.? | Boerkoel et al., Am. J. Hum. Gen. 1995 |
| | | | | Hüie et al., Hum Mol Gen. 1994 | Partial skipping exon 2 | r.-32_486del | out of frame | p.? | Boerkoel et al., Am. J. Hum. Gen. 1995 |
| 1 | c.1636+5G>T | intron 11 | | Kroos et al., JIMD 2006 | intron 11 inclusion | r.1636_1637ins1636+1_1636+957+r.1636+5g>t | out of frame | p.G546_V547ins145X146 | Kroos et al., JIMD 2006 |
| 2 | c.526delT | exon 2 | p.E176fs*45 | Hemans et al., Hum Mol Gen. 1994 | premature stop codon | r.526delt | out of frame | p.E176fs*45 | Hemans et al., Hum Mol Gen. 1994 |
| 3 | c.1548G>A | exon 10 | p.W516* | Hemans et al., Hum Mut 2004 | premature stop codon | r.1548g>a | new stop codon | p.W516* | Hemans et al., Hum Mut 2004 |
| 3 | c.2481-102_2646+31del (del ex18) | intron 17-intron 18 | p.G828_N882del | Hüie et al., Hum Mol Gen. 1994 | deletion of full exon 18 | r.2481_2646del | in frame | p.G828_N882del | Hüie et al., Hum Mol Gen. 1994 |
| 4 | c.-32-3C>G | intron 1 | | this study | leaky wt splicing | | in frame | | this study |
| | | | | this study | Partial skipping exon 2 | r.-32_486del | out of frame | p.? | this study |
| | | | | this study | Perfect skipping exon 2 | r.-32_546del | out of frame | p.? | this study |
| 4 | 1551+1G>A | intron 10 | | Orinkowski et al., Neuromus. Dis. 2011 | perfect skipping exon 10 | r.1439_1551del | in frame | p.V480_D517del | this study |
| 5 | c.1075G>A | exon 6 | p.G359R | Schoser et al., Neuromus. Dis. 2007 | deletion of 4 nt of exon 6 | r.1072_1075del | out of frame | p.D375fs*33 | this study |
| 6 | c.1552-3C>G | intron 10 | | Kroos et al., JIMD 2006 | leaky wt splicing | r.1551_1552ins1551+1_1552-1+r.1552-3c>g | in frame | | Kroos et al., JIMD 2006 |
| | | | | | full intron 10 inclusion | | out of frame | p.D517fs*5 | this study |
| | | | | Kroos et al., JIMD 2006 | partial inclusion intron 10 | r.1551_1552ins1552-30_1551+100+r.1552-3c>g | in frame | p.D517_V518ins10 | Kroos et al., JIMD 2006 |
| 7 | c.1437G>A | exon 9 | silent | Kroos et al., Hum Mut 2008 | leaky wt splicing | r.1437g>a | in frame | p.D443_K479del | Kroos et al., Hum Mut 2008, this study |
| | | | | | perfect skipping exon 9 | r.1327_1437del | in frame | | this study |
| 8 | c.1256A>T | exon 8 | p.D419V | Kroos et al., Hum Mut 2012 | leaky wt splicing | r.1256a>t | in frame | p.D419V | this study |
| | | | | this study | partial skip of exon 8 | r.1255_1326del | in frame | p.K418_D443del | this study |
| 8 | c.1551+1G>T | intron 10 | | Kroos et al., Hum Mut 2012 | leaky wt splicing | | in frame | | this study |
| | | | | this study | perfect skipping of exon 10 | r.1438_1551del | in frame | p.V480_D517del | this study |

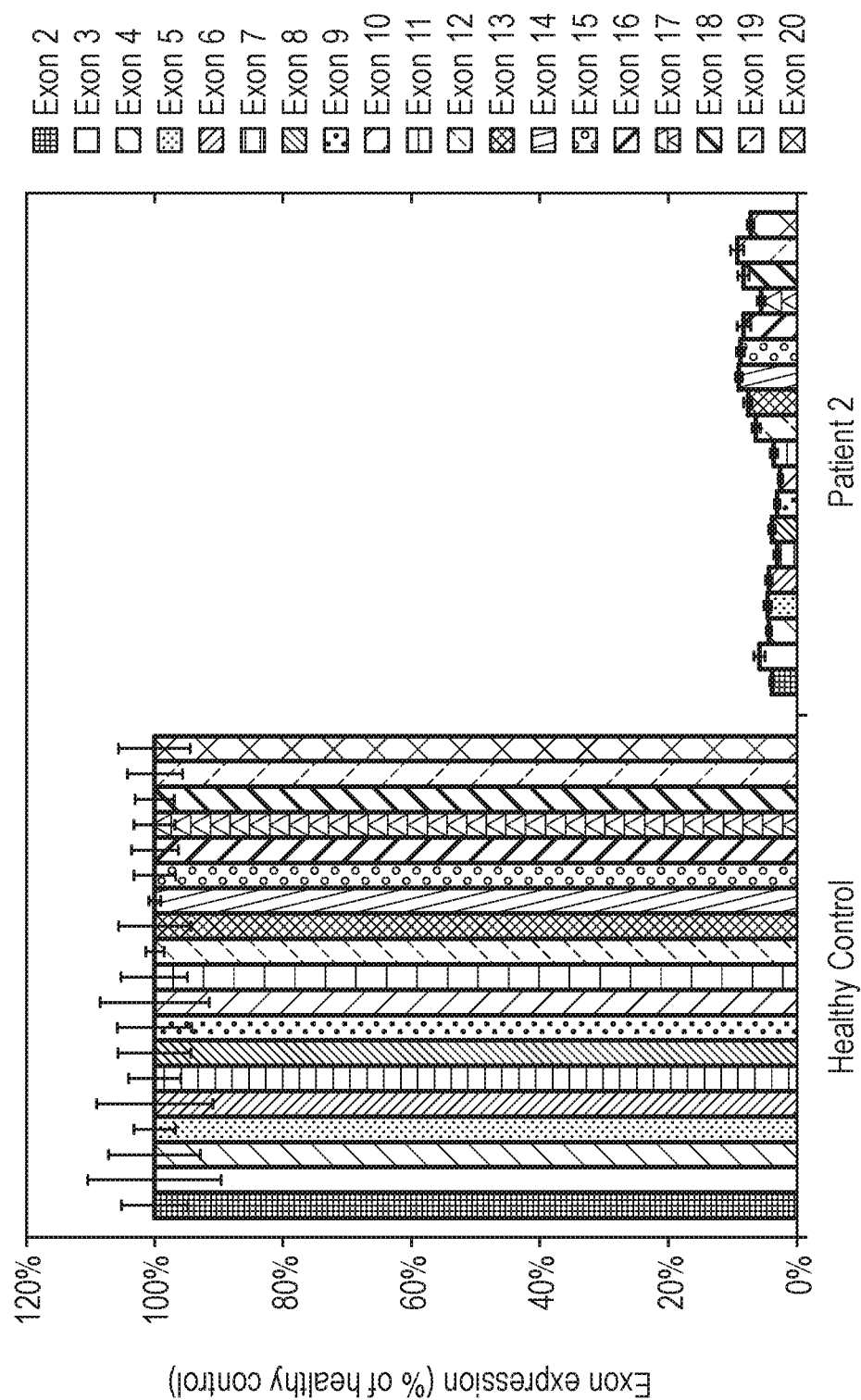

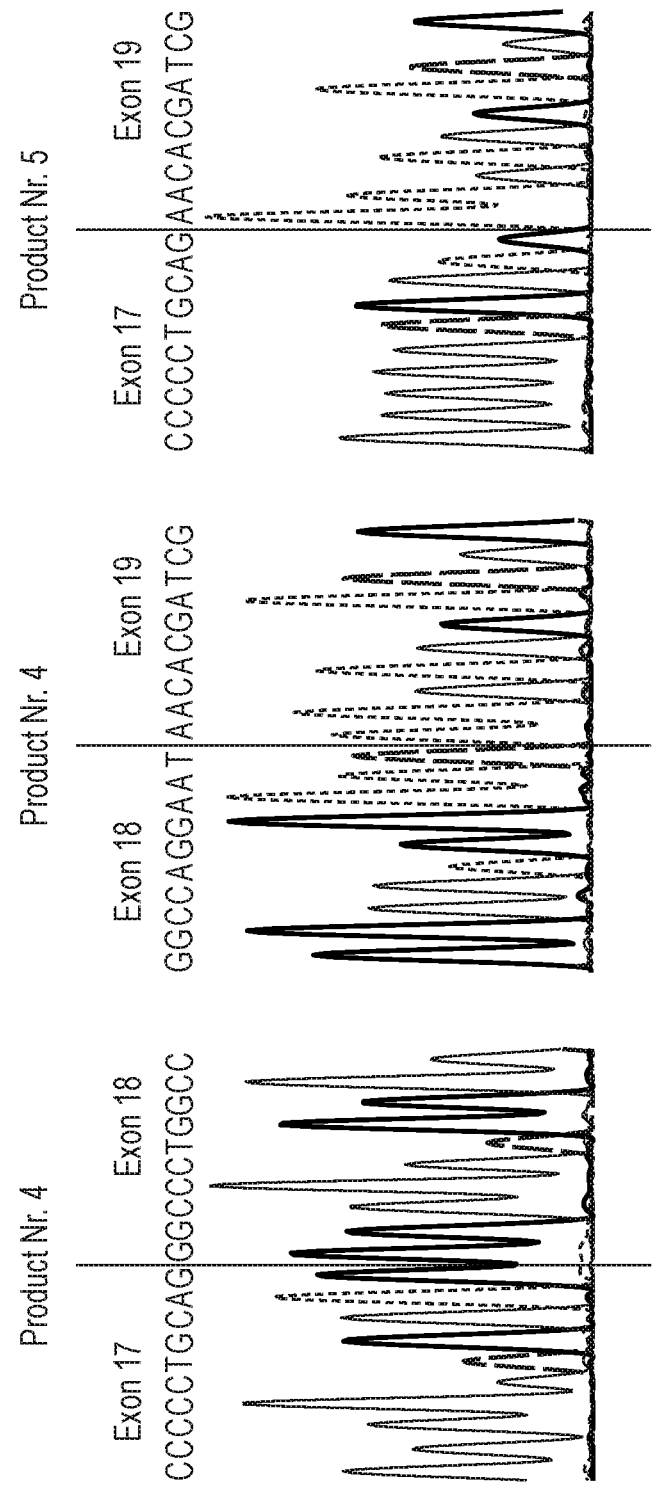

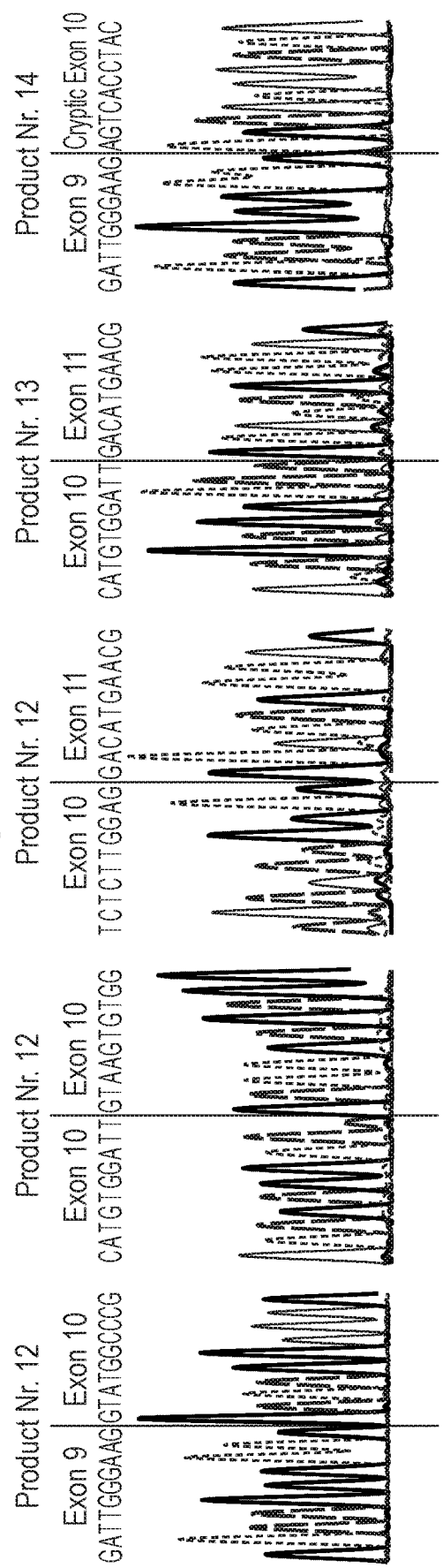
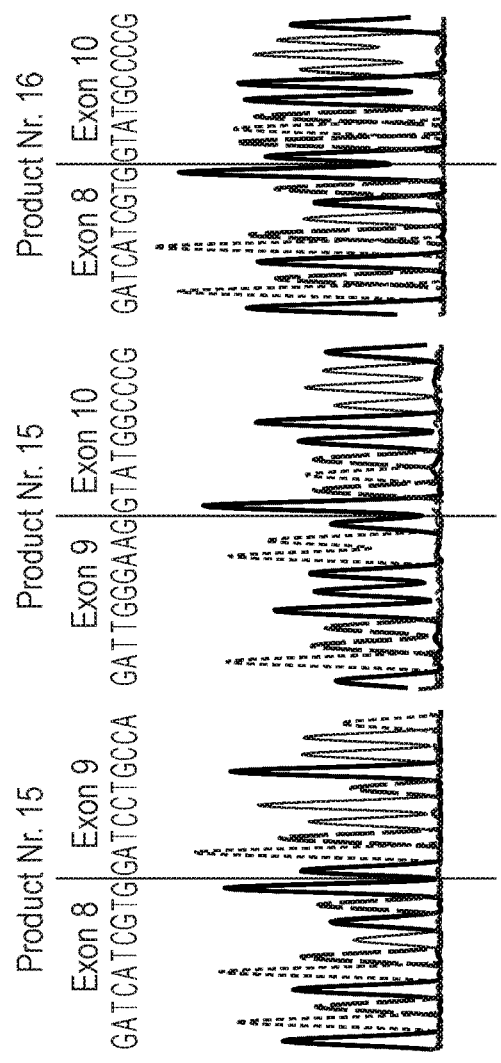
Fig. 11C
Fig. 11D

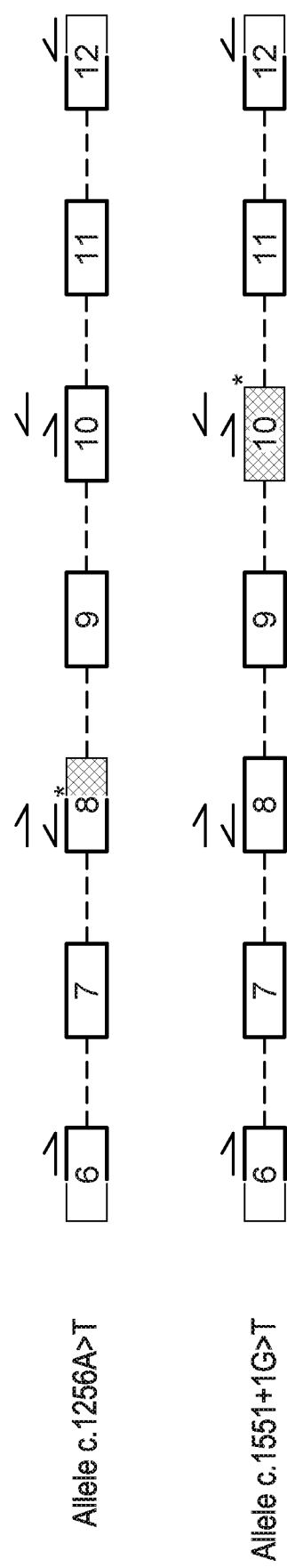

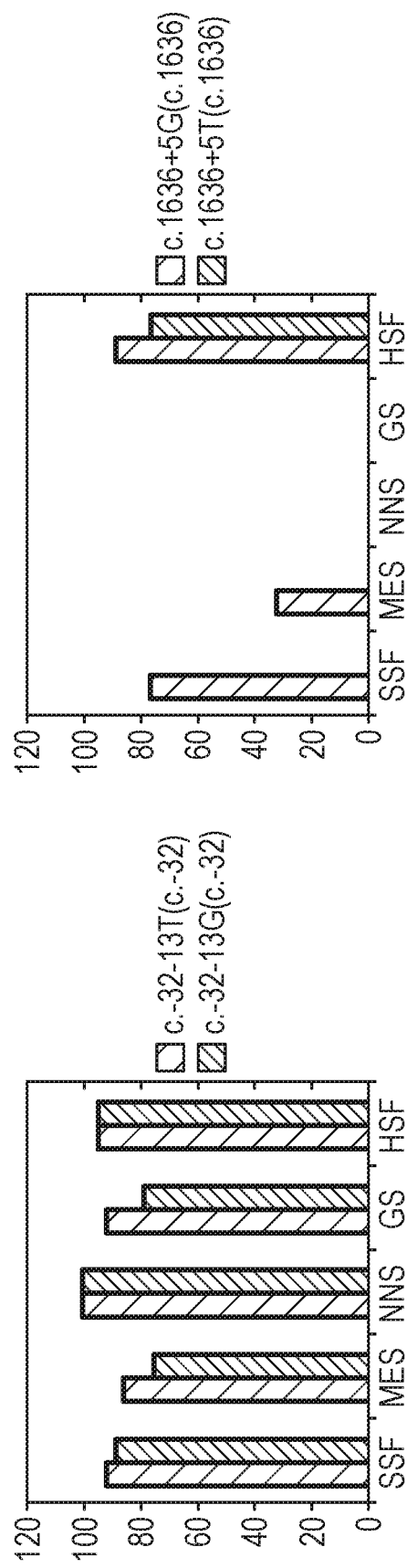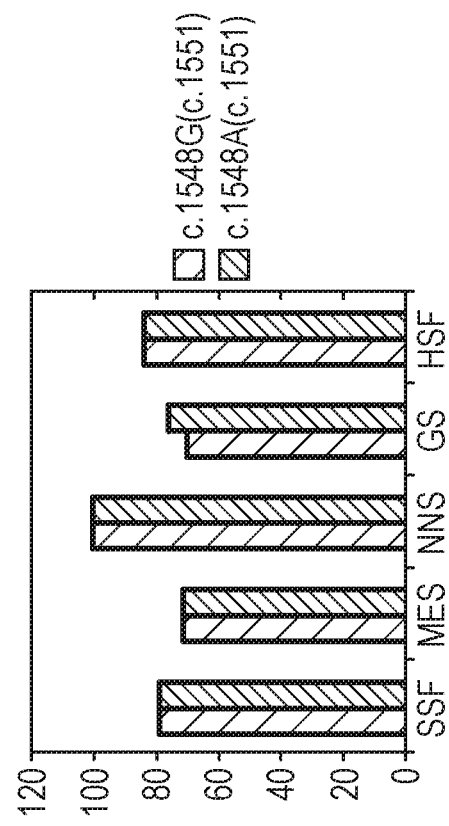
Fig. 14A
Fig. 14B

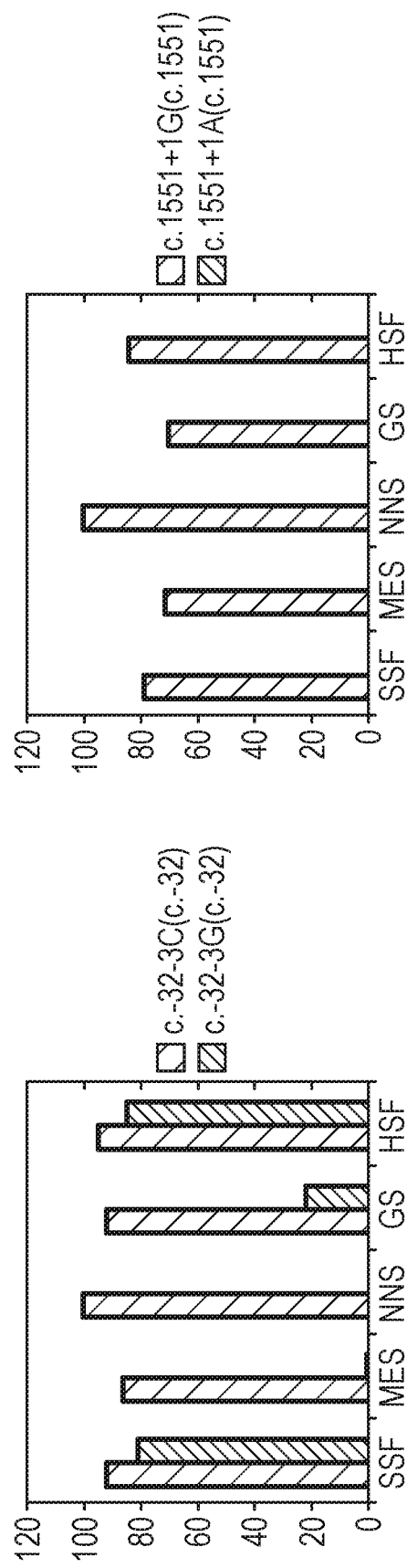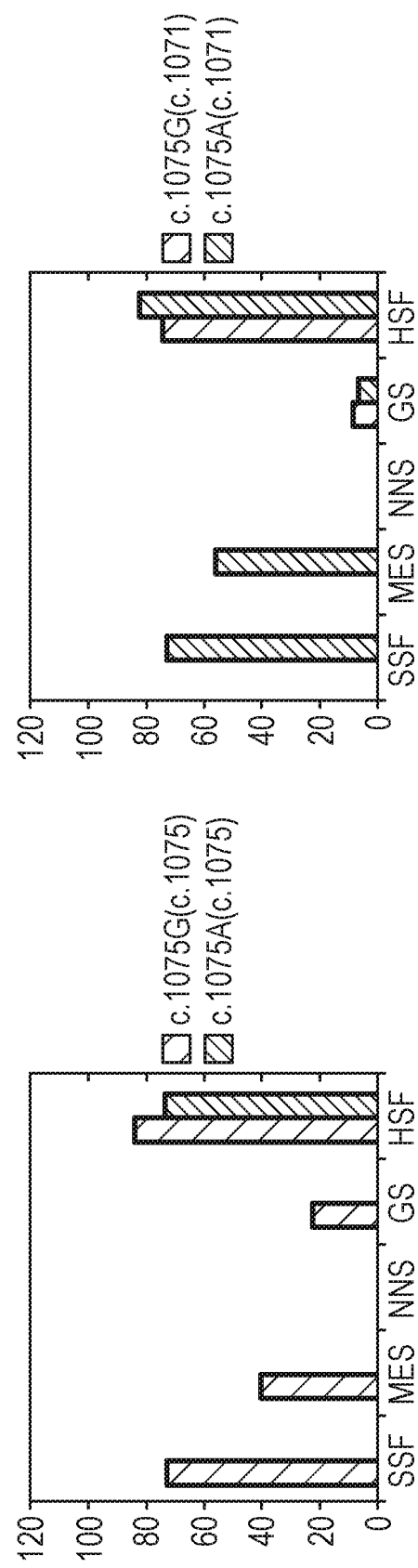

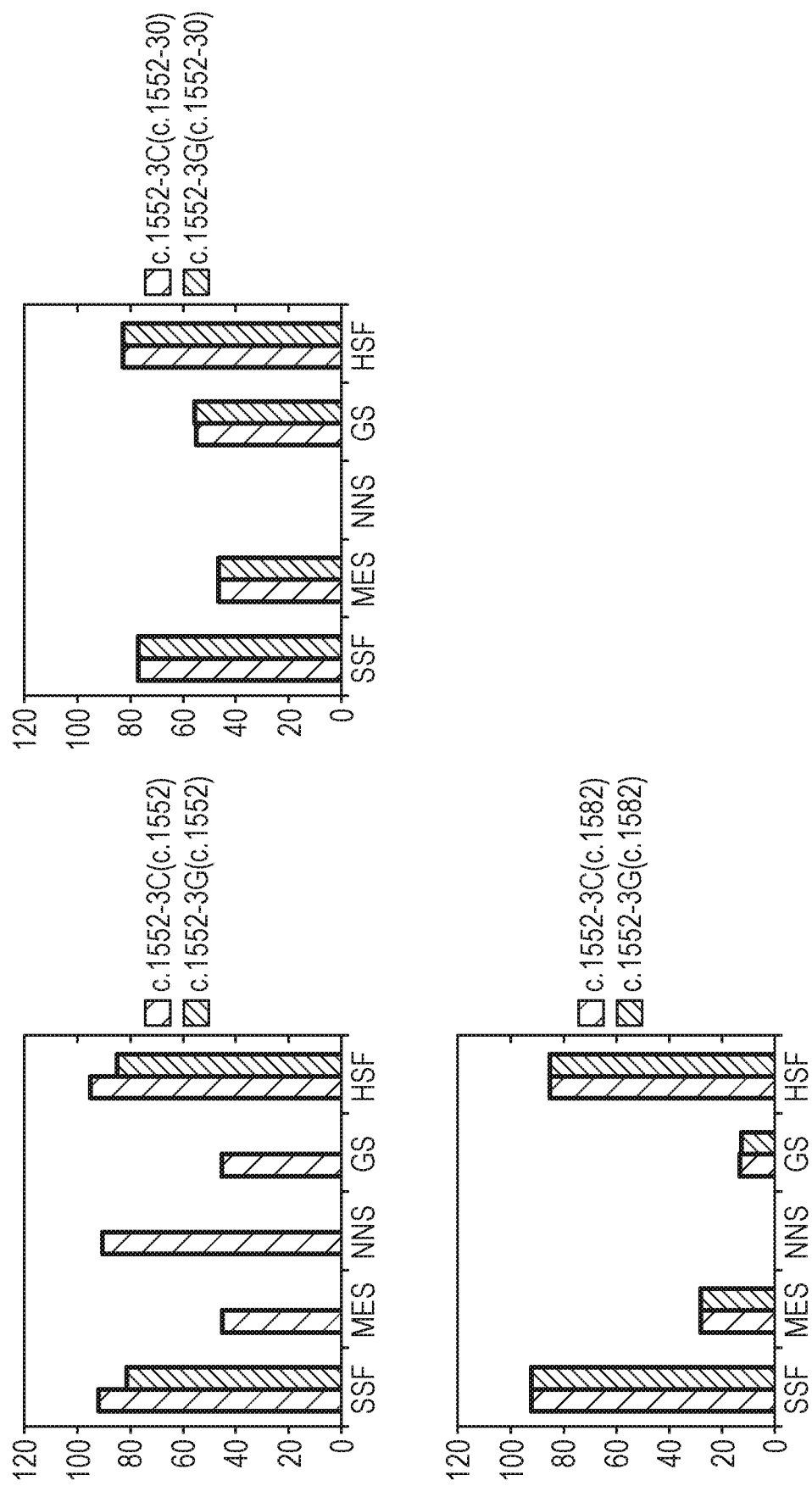

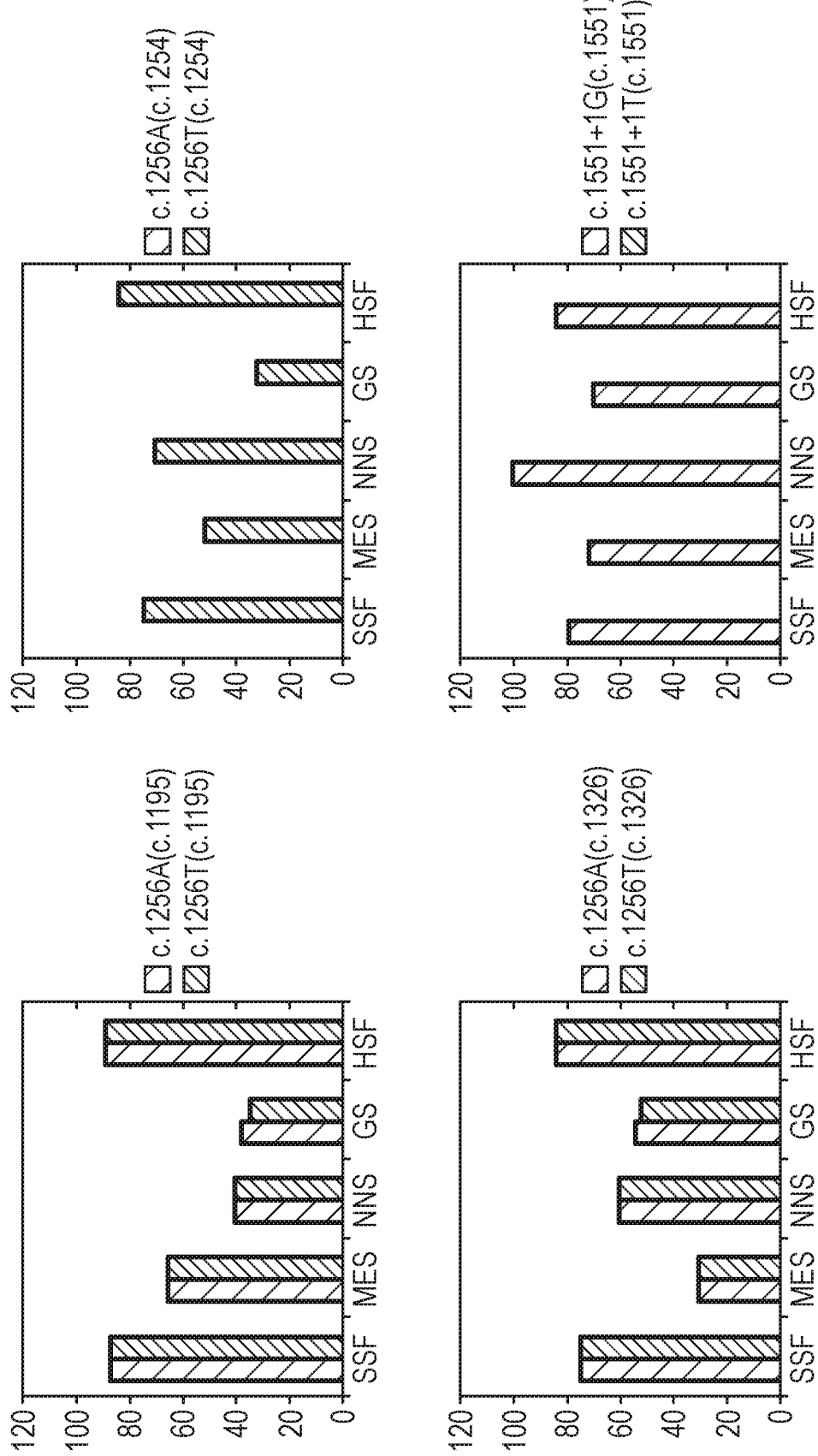

Fig. 15

| Exon tested: | Forward: | Reverse: | Full length Product: | Size Exon: | Skipped Product: |
|---|---|---|---|---|---|
| GAA Exon 2 | AAACTGAGGCACGGAGCG | GAAGGGCTCCTCCGGAGAA | 705 | 578 | 127 |
| GAA Exon 3 | AGTCCTCTGAAATGGGCTACA | GCAAGGTCCCGGTTCCACA | 428 | 146 | 282 |
| GAA Exon 4 | GCTAACAGGCGCTACGAGGT | TGCTGTTTAGCAGGAACACCC | 388 | 166 | 222 |
| GAA Exon 5 | CTGTTCTTTGCGGACCAGTTC | CCACAACGTCCAGGTACTGCT | 361 | 97 | 265 |
| GAA Exon 6 | GGTCTCACCCTTTCTACCTGG | GTGATAGCGGTGGAGGAGTAG | 274 | 120 | 154 |
| GAA Exon 7 | CAGCAGTACCTGGACGTTGTG | AGTCCATGTAGTCCAGGTCGTT | 175 | 119 | 56 |
| GAA Exon 8 | CGTTCATGCCGCCATACT | GGTCTCGTTGGTGATGAAAAC | 335 | 132 | 203 |
| GAA Exon 9 | GACGTCCAGTGGAACGACCT | ACCTGGTCATGGAACTCAGC | 335 | 111 | 224 |
| GAA Exon 10 | GATCCTGCCATCAGCAGCT | TGGGTTCTCCAGTCCATTGT | 297 | 114 | 183 |
| GAA Exon 11 | AGGACATGGTGGCTGAGTTC | CGTAGAGGTTGTGCAGGTTGTA | 228 | 85 | 143 |
| GAA Exon 12 | AACGAGCCTTCCAACTTCATC | GAGCGGGAGATCACAAATGG | 245 | 118 | 127 |
| GAA Exon 13 | CACCAGTTTCTCTCCACACACTA | GTTCCGCATGAAGGGGTAGA | 337 | 134 | 202 |
| GAA Exon 14 | ACACGCCCATTTGTGATCTC | GTGTAGAGGTGGGGAGGAGT | 356 | 152 | 204 |
| GAA Exon 15 | AAATCCTGCAGTTTAACCTGCTG | GCAGGTCGTACCATGTGCC | 438 | 149 | 289 |
| GAA Exon 16 | GAGCCGTACAGCTTCAGCGA | ATGTACCCAGCCCGGAGGT | 422 | 142 | 280 |
| GAA Exon 17 | CCTGGACTGTGGACCACA | CAGGAAGATGACCTGTGTGTAGG | 428 | 150 | 278 |
| GAA Exon 18 | GTGCCAGTAGAGGCCCTTG | GGCTGTAGGTGAAGTTGGAGAC | 457 | 165 | 292 |
| GAA Exon 19 | TCACAACCACAGAGTCCCG | AGAAACTGCTCTCCCATCAACA | 352 | 153 | 199 |

Fig. 16

| | Forward | Reverse |
|---|---|---|
| B-Actin | AACCGCGAGAAGATGACCC | GCCAGAGGCGTACAGGGATAG |
| GAA Exon 2 | AGCTCCTCTGAAATGGGCTACAC | GGTTCTCAGTCTCCATCATCACG |
| GAA Exon 3 | ATCCAGCTAACAGGCGCTAC | GCTCCTCGGAGAACTCCAC |
| GAA Exon 4 | CTGTTCTTTGCGGACCAGTT | CTGAGCATCAGGGGACTGAG |
| GAA Exon 5 | CGAACCTCTACGGGTCTCAC | TGCTGTTTAGCAGGAACACC |
| GAA Exon 6 | CTTAGCTGGAGGTCGACAGG | CACAACGTCCAGGTACTGCT |
| GAA Exon 7 | CGTTCATGCCGCCATACT | GGTCATGTTCTCCACCACCT |
| GAA Exon 8 | GACGTCCAGTGGAACGACCT | GAAGTCCCGGAAGCCATC |
| GAA Exon 9 | ATCCTGCCATCAGCAGCTC | GGTCTCGTTGGTGATGAAAA |
| GAA Exon 10 | CACTGCCTTCCCCGACTT | ACCTGGTCATGGAACTCAGC |
| GAA Exon 11 | ACATGAACGAGCCTTCCAAC | ACGTAGGGTGGGTTCTCCAG |
| GAA Exon 12 | CCTCCAGCCACCAGTTTCTCT | TGTGGGAGGCGATGGCTT |
| GAA Exon 13 | GACACGCCCATTTGTGATCT | CCAGGAGCTCCACACGTC |
| GAA Exon 14 | CTCAGAGGAGCTGTGTGTGC | CAGACTGAGCAGGCTGTTGT |
| GAA Exon 15 | CAGCAGGCCATGAGGAAG | GGCCTGGTGGAACAGTGTG |
| GAA Exon 16 | CCCAAGGACTCTAGCACCTG | CAAGGGGAAGTAGCCAGTCA |
| GAA Exon 17 | GTGCCAGTAGAGGCCCTTG | GAGGTGGACGTTGATGGTGT |
| GAA Exon 18 | GCCTCACAACCACAGAGTCC | TCTCTCCATCGTCCCAGAAC |
| GAA Exon 19 | TGCAGAAGGTGACTGTCCTG | GGGCTGTAGGTGAAGTTGGA |
| GAA Exon 20 | GGGCGGAGTGTGTTAGTCTC | CTCCAGGTGACACATGCAAC |

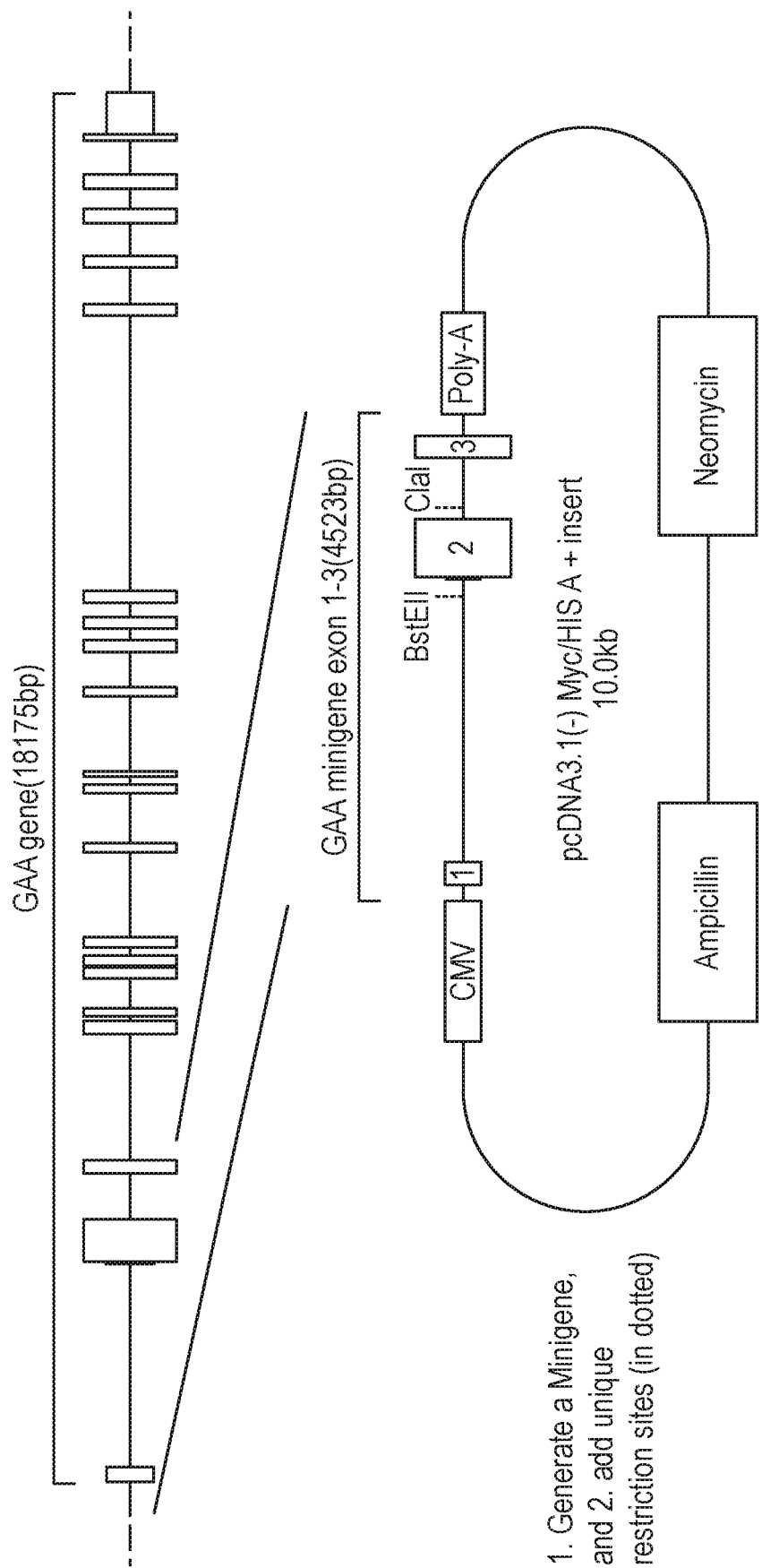

3. Carry out degenerate PCR with the minigene as template

4. Ligate PCR products in vector and generate clones

M = Marker
1 = IVS1 control
2 = Less inclusion
3 = More inclusion

Full length exon 2
Cryptic exon 2
Skipped exon 2

5. Transfect clones in Hek293 cells and analyse RNA for exon 2 inclusion via Exon flanking RT-PCR and exon internal qPCR

CACTTCACGATCAAAGATC (for example) G > A mutation detected

5. Sequence analysis of clone

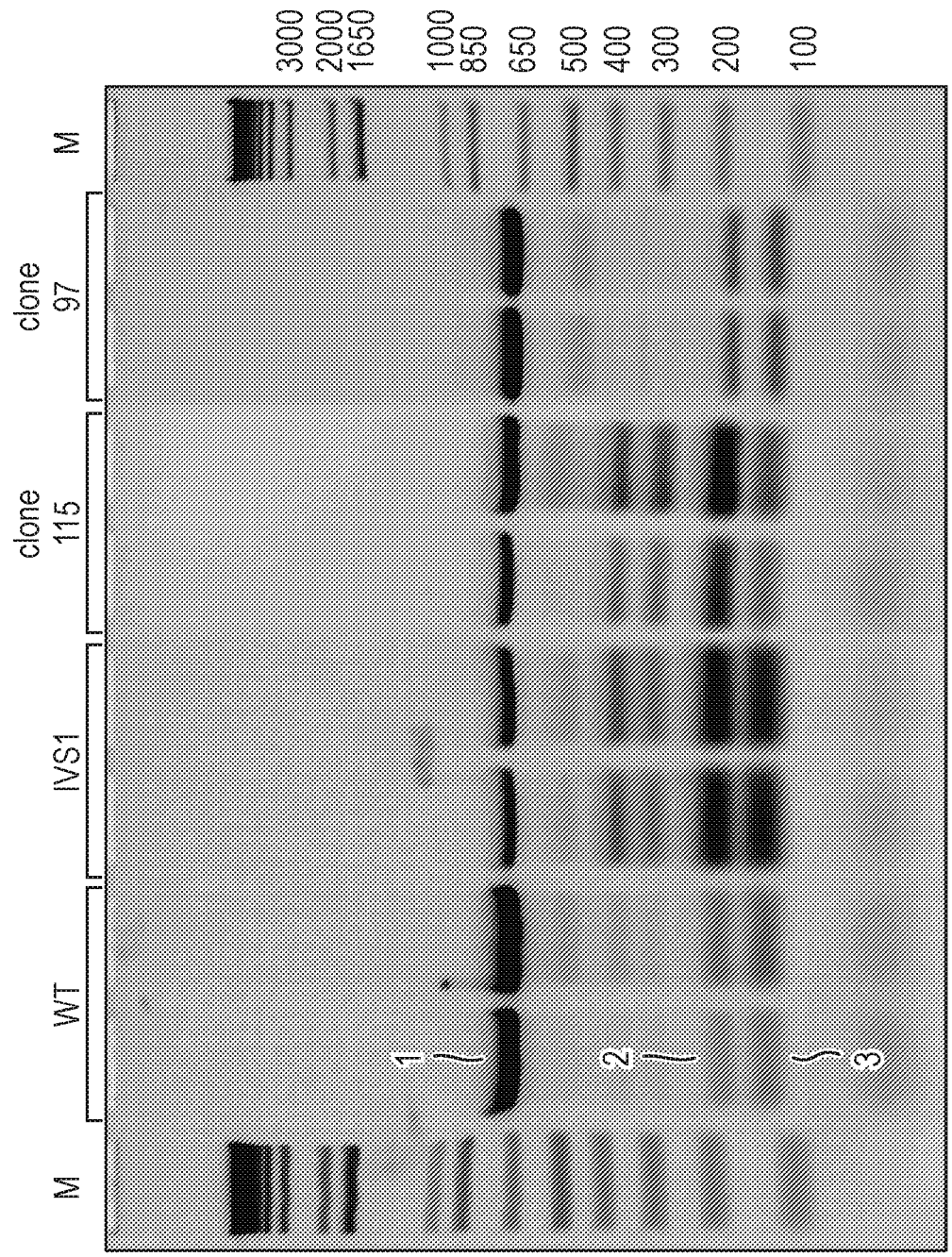

Figure 28:
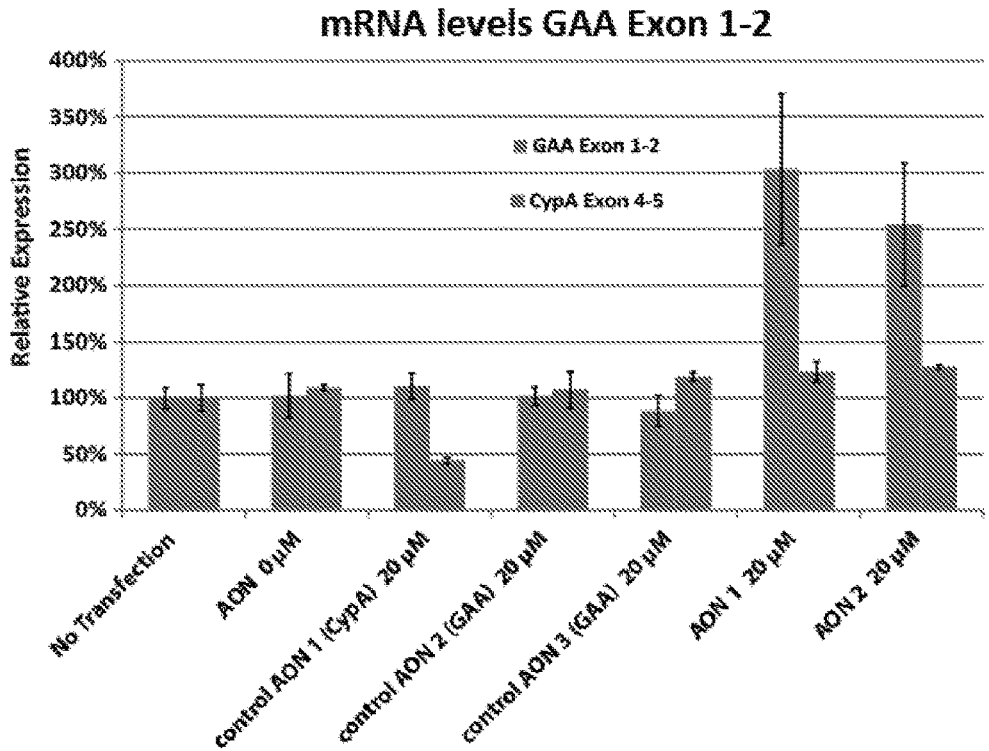
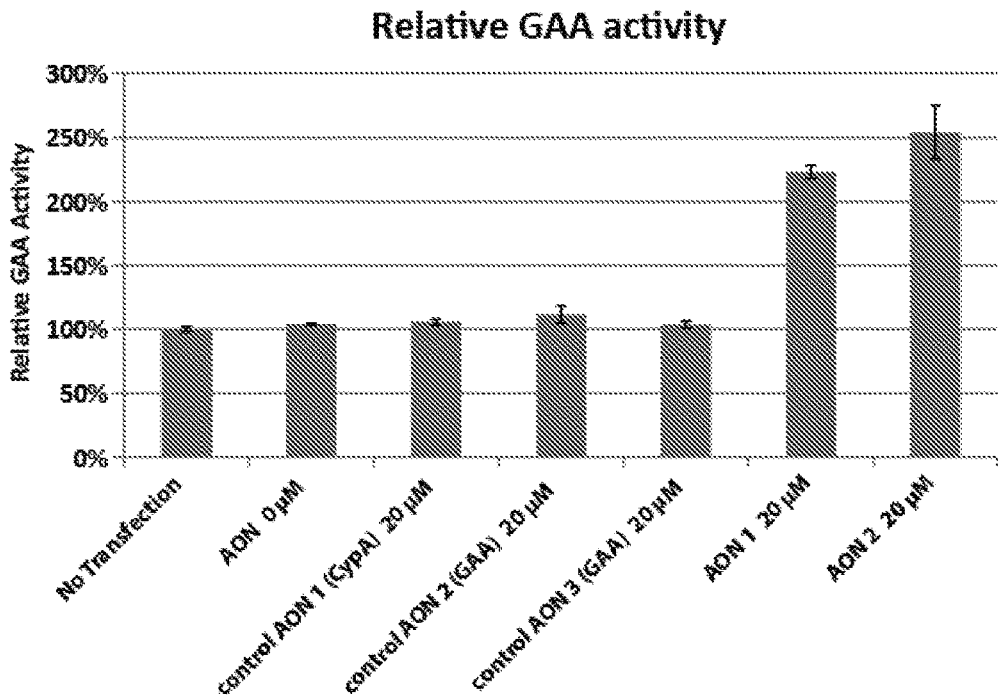

SEQUENCE LISTING

<160> NUMBER OF SEQ ID NOS: 730

<210> SEQ ID NO 1
<211> LENGTH: 55
<212> TYPE: DNA
<213> ORGANISM: Artificial Sequence
<220> FEATURE:
<223> OTHER INFORMATION: target nucleic acid

<400> SEQUENCE: 1
gctctgcact cccctgctgg agcttttctc gcccttcctt ctggccctct cccca        55

<210> SEQ ID NO 2
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 2
tggggagagg gccagaagga agggc                                          25

<210> SEQ ID NO 3
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 3
ggggagaggg ccagaaggaa gggcg                                          25

<210> SEQ ID NO 4
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 4
gggagagggc cagaaggaag ggcga                                          25

<210> SEQ ID NO 5

```
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 5
ggagagggcc agaaggaagg gcgag                                    25

<210> SEQ ID NO 6
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 6
gagagggcca aaggaagggc gaga                                     25

<210> SEQ ID NO 7
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 7
agagggccag aaggaagggc gagaa                                    25

<210> SEQ ID NO 8
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 8
gagggccaga aggaagggcg agaaa                                    25

<210> SEQ ID NO 9
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 9
agggccagaa ggaagggcga gaaaa                                    25

<210> SEQ ID NO 10
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 10
gggccagaag gaagggcgag aaaag                                    25

<210> SEQ ID NO 11
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 11
```
ggccagaagg aagggcgaga aaagc                                      25

<210> SEQ ID NO 12
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 12
gccagaagga agggcgagaa aagct                                      25

<210> SEQ ID NO 13
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 13
ccagaaggaa gggcgagaaa agctc                                      25

<210> SEQ ID NO 14
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 14
cagaaggaag ggcgagaaaa gctcc                                      25

<210> SEQ ID NO 15
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 15
agaaggaagg gcgagaaaag ctcca                                      25

<210> SEQ ID NO 16
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 16
gaaggaaggg cgagaaaagc tccag                                      25

<210> SEQ ID NO 17
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 17
aaggaagggc gagaaaagct ccagc                                      25

<210> SEQ ID NO 18
<211> LENGTH: 25
<212> TYPE: DNA

```
<213> ORGANISM: Artificial Sequence
<220> FEATURE:
<223> OTHER INFORMATION: antisense oligonucleotide compound

<400> SEQUENCE: 18
aggaagggcg agaaaagctc cagca                                          25

<210> SEQ ID NO 19
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 19
ggaagggcga gaaaagctcc agcag                                          25

<210> SEQ ID NO 20
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 20
gaagggcgag aaaagctcca gcagg                                          25

<210> SEQ ID NO 21
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 21
aagggcgaga aaagctccag caggg                                          25

<210> SEQ ID NO 22
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 22
agggcgagaa aagctccagc agggg                                          25

<210> SEQ ID NO 23
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 23
gggcgagaaa agctccagca gggga                                          25

<210> SEQ ID NO 24
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 24
ggcgagaaaa gctccagcag gggag                                          25
```

<210> SEQ ID NO 25
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 25
gcgagaaaag ctccagcagg ggagt                                          25

<210> SEQ ID NO 26
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 26
cgagaaaagc tccagcaggg gagtg                                          25

<210> SEQ ID NO 27
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 27
gagaaaagct ccagcagggg agtgc                                          25

<210> SEQ ID NO 28
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 28
agaaaagctc cagcagggga gtgca                                          25

<210> SEQ ID NO 29
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 29
gaaaagctcc agcagggagt gcag                                           25

<210> SEQ ID NO 30
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 30
aaaagctcca gcagggggagt gcaga                                         25

<210> SEQ ID NO 31
<211> LENGTH: 25
<212> TYPE: DNA
<213> ORGANISM: Artificial Sequence
<220> FEATURE:

<223> OTHER INFORMATION: antisense oligonucleotide compound

<400> SEQUENCE: 31
aaagctccag caggggagtg cagag                                    25

<210> SEQ ID NO 32
<211> LENGTH: 25
<212> TYPE: DNA
<213> ORGANISM: Artificial Sequence
<220> FEATURE:
<223> OTHER INFORMATION: antisense oligonucleotide compound

<400> SEQUENCE: 32
aagctccagc aggggagtgc agagc                                    25

<210> SEQ ID NO 33
<211> LENGTH: 21
<212> TYPE: DNA
<213> ORGANISM: Artificial Sequence
<220> FEATURE:
<223> OTHER INFORMATION: antisense oligonucleotide compound

<400> SEQUENCE: 33
ccagaaggaa gggcgagaaa a                                        21

<210> SEQ ID NO 34
<211> LENGTH: 20
<212> TYPE: DNA
<213> ORGANISM: Artificial Sequence
<220> FEATURE:
<223> OTHER INFORMATION: control AON1

<400> SEQUENCE: 34 tgtacccctta ccactcagtc                                         20

<210> SEQ ID NO 35
<211> LENGTH: 25
<212> TYPE: DNA
<213> ORGANISM: Artificial Sequence
<220> FEATURE:
<223> OTHER INFORMATION: control AON2

<400> SEQUENCE: 35
gagtgcagag cacttgcaca gtctg                                    25

<210> SEQ ID NO 36
<211> LENGTH: 25
<212> TYPE: DNA
<213> ORGANISM: Artificial Sequence
<220> FEATURE:
<223> OTHER INFORMATION: control AON3

<400> SEQUENCE: 36
gagtgcagag cacttgcaca gtctg                                    25

<210> SEQ ID NO 37
<211> LENGTH: 45
<212> TYPE: DNA
<213> ORGANISM: Artificial Sequence
<220> FEATURE:
<223> OTHER INFORMATION: target nucleic acid

<400> SEQUENCE: 37
gctctgcact cccctgctgg agcttttctc gcccttcctt ctggc              45

<210> SEQ ID NO 38
<211> LENGTH: 31
<212> TYPE: DNA
<213> ORGANISM: Artificial Sequence
<220> FEATURE:
<223> OTHER INFORMATION: target nucleic acid

<400> SEQUENCE: 38
tgcactcccc tgctggagct tttctcgccc t                              31

<210> SEQ ID NO 39
<211> LENGTH: 36
<212> TYPE: DNA
<213> ORGANISM: Artificial Sequence
<220> FEATURE:
<223> OTHER INFORMATION: target nucleic acid

<400> SEQUENCE: 39
tgcactcccc tgctggagct tttctcgccc ttcctt                         36

<210> SEQ ID NO 40
<211> LENGTH: 31
<212> TYPE: DNA
<213> ORGANISM: Artificial Sequence
<220> FEATURE:
<223> OTHER INFORMATION: target nucleic acid

<400> SEQUENCE: 40
tcccctgctg gagcttttct cgcccttcct t                              31

<210> SEQ ID NO 41
<211> LENGTH: 20
<212> TYPE: DNA
<213> ORGANISM: Artificial Sequence
<220> FEATURE:
<223> OTHER INFORMATION: antisense sequence

<400> SEQUENCE: 41
ccaaacagct gtcgcctggg                                           20

<210> SEQ ID NO 42
<211> LENGTH: 20
<212> TYPE: DNA
<213> ORGANISM: Artificial Sequence
<220> FEATURE:
<223> OTHER INFORMATION: antisense sequence

<400> SEQUENCE: 42
aggtagacac ttgaaacagg                                           20

<210> SEQ ID NO 43
<211> LENGTH: 20
<212> TYPE: DNA
<213> ORGANISM: Artificial Sequence
<220> FEATURE:
<223> OTHER INFORMATION: antisense sequence

<400> SEQUENCE: 43
cccaggaaga ccagcaaggc                                           20

<210> SEQ ID NO 44
<211> LENGTH: 20
<212> TYPE: DNA
<213> ORGANISM: Artificial Sequence
<220> FEATURE:
<223> OTHER INFORMATION: antisense sequence

```
<400> SEQUENCE: 44
tcaaacacgc ttagaatgtc                                                    20

<210> SEQ ID NO 45
<211> LENGTH: 20
<212> TYPE: DNA
<213> ORGANISM: Artificial Sequence
<220> FEATURE:
<223> OTHER INFORMATION: antisense sequence

<400> SEQUENCE: 45
gtctgctaaa atgttacaaa                                                    20

<210> SEQ ID NO 46
<211> LENGTH: 20
<212> TYPE: DNA
<213> ORGANISM: Artificial Sequence
<220> FEATURE:
<223> OTHER INFORMATION: antisense sequence

<400> SEQUENCE: 46
gagtgcagag cacttgcaca                                                    20

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
cgagaaaagc tccagcaggg                                                    20

<210> SEQ ID NO 48
<211> LENGTH: 20
<212> TYPE: DNA
<213> ORGANISM: Artificial Sequence
<220> FEATURE:
<223> OTHER INFORMATION: antisense sequence

<400> SEQUENCE: 48
gagagggcca gaaggaaggg                                                    20

<210> SEQ ID NO 49
<211> LENGTH: 20
<212> TYPE: DNA
<213> ORGANISM: Artificial Sequence
<220> FEATURE:
<223> OTHER INFORMATION: antisense sequence

<400> SEQUENCE: 49
gccctgctgt ctagactggg                                                    20

<210> SEQ ID NO 50
<211> LENGTH: 20
<212> TYPE: DNA
<213> ORGANISM: Artificial Sequence
<220> FEATURE:
<223> OTHER INFORMATION: antisense sequence

<400> SEQUENCE: 50
aggtggccag ggtgggtgtt                                                    20

<210> SEQ ID NO 51
<211> LENGTH: 20
```

```
<212> TYPE: DNA
<213> ORGANISM: Artificial Sequence
<220> FEATURE:
<223> OTHER INFORMATION: antisense sequence

<400> SEQUENCE: 51
gcacccaggc aggtggggta                                           20

<210> SEQ ID NO 52
<211> LENGTH: 20
<212> TYPE: DNA
<213> ORGANISM: Artificial Sequence
<220> FEATURE:
<223> OTHER INFORMATION: \

<400> SEQUENCE: 52
caaccgcggc tggcactgca                                           20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
tcaaagcagc tctgagacat                                           20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
gggcggcact cacggggctc                                           20

<210> SEQ ID NO 55
<211> LENGTH: 20
<212> TYPE: DNA
<213> ORGANISM: Artificial Sequence
<220> FEATURE:
<223> OTHER INFORMATION: antisense sequence

<400> SEQUENCE: 55
gctcagcagg gaggcgggag                                           20

<210> SEQ ID NO 56
<211> LENGTH: 20
<212> TYPE: DNA
<213> ORGANISM: Artificial Sequence
<220> FEATURE:
<223> OTHER INFORMATION: antisense sequence

<400> SEQUENCE: 56
cctgcgggag aagaaagcgg                                           20

<210> SEQ ID NO 57
<211> LENGTH: 20
<212> TYPE: DNA
<213> ORGANISM: Artificial Sequence
<220> FEATURE:
<223> OTHER INFORMATION: antisense sequence

<400> SEQUENCE: 57
```
gcctggacag ctcctacagg                                                     20

<210> SEQ ID NO 58
<211> LENGTH: 20
<212> TYPE: DNA
<213> ORGANISM: Artificial Sequence
<220> FEATURE:
<223> OTHER INFORMATION: antisense sequence

<400> SEQUENCE: 58
cactcccatg gttggagatg                                                     20

<210> SEQ ID NO 59
<211> LENGTH: 20
<212> TYPE: DNA
<213> ORGANISM: Artificial Sequence
<220> FEATURE:
<223> OTHER INFORMATION: antisense sequence

<400> SEQUENCE: 59
tgggagcagg gcgggtgcct                                                     20

<210> SEQ ID NO 60
<211> LENGTH: 20
<212> TYPE: DNA
<213> ORGANISM: Artificial Sequence
<220> FEATURE:
<223> OTHER INFORMATION: antisense sequence

<400> SEQUENCE: 60
cgcagacggc caggagccgg                                                     20

<210> SEQ ID NO 61
<211> LENGTH: 20
<212> TYPE: DNA
<213> ORGANISM: Artificial Sequence
<220> FEATURE:
<223> OTHER INFORMATION: antisense sequence

<400> SEQUENCE: 61
ggttgccaag gacacgaggg                                                     20

<210> SEQ ID NO 62
<211> LENGTH: 20
<212> TYPE: DNA
<213> ORGANISM: Artificial Sequence
<220> FEATURE:
<223> OTHER INFORMATION: antisense sequence

<400> SEQUENCE: 62
atgtgcccca ggagtgcagc                                                     20

<210> SEQ ID NO 63
<211> LENGTH: 20
<212> TYPE: DNA
<213> ORGANISM: Artificial Sequence
<220> FEATURE:
<223> OTHER INFORMATION: antisense sequence

<400> SEQUENCE: 63
gcaggaaatc atggagtagg                                                     20

<210> SEQ ID NO 64
<211> LENGTH: 20
<212> TYPE: DNA
<213> ORGANISM: Artificial Sequence

```
<220> FEATURE:
<223> OTHER INFORMATION: antisense sequence

<400> SEQUENCE: 64
actcagctct cggggaacca                                              20

<210> SEQ ID NO 65
<211> LENGTH: 20
<212> TYPE: DNA
<213> ORGANISM: Artificial Sequence
<220> FEATURE:
<223> OTHER INFORMATION: antisense sequence

<400> SEQUENCE: 65
tccaggactg gggaggagcc                                              20

<210> SEQ ID NO 66
<211> LENGTH: 20
<212> TYPE: DNA
<213> ORGANISM: Artificial Sequence
<220> FEATURE:
<223> OTHER INFORMATION: antisense sequence

<400> SEQUENCE: 66
ggtgagctgg gtgagtctcc                                              20

<210> SEQ ID NO 67
<211> LENGTH: 20
<212> TYPE: DNA
<213> ORGANISM: Artificial Sequence
<220> FEATURE:
<223> OTHER INFORMATION: antisense sequence

<400> SEQUENCE: 67
tggtctgctg gctccctgct                                              20

<210> SEQ ID NO 68
<211> LENGTH: 20
<212> TYPE: DNA
<213> ORGANISM: Artificial Sequence
<220> FEATURE:
<223> OTHER INFORMATION: antisense sequence

<400> SEQUENCE: 68
gcctgggcat cccggggccc                                              20

<210> SEQ ID NO 69
<211> LENGTH: 20
<212> TYPE: DNA
<213> ORGANISM: Artificial Sequence
<220> FEATURE:
<223> OTHER INFORMATION: antisense sequence

<400> SEQUENCE: 69
ctctgggacg gccggggtgt                                              20

<210> SEQ ID NO 70
<211> LENGTH: 20
<212> TYPE: DNA
<213> ORGANISM: Artificial Sequence
<220> FEATURE:
<223> OTHER INFORMATION: antisense sequence

<400> SEQUENCE: 70
gtcgcactgt gtgggcactg                                              20
```

<210> SEQ ID NO 71
<211> LENGTH: 20
<212> TYPE: DNA
<213> ORGANISM: Artificial Sequence
<220> FEATURE:
<223> OTHER INFORMATION: antisense sequence

<400> SEQUENCE: 71
aagcggctgt tgggggggac                                              20

<210> SEQ ID NO 72
<211> LENGTH: 20
<212> TYPE: DNA
<213> ORGANISM: Artificial Sequence
<220> FEATURE:
<223> OTHER INFORMATION: antisense sequence

<400> SEQUENCE: 72
ccttgtcagg ggcgcaatcg                                              20

<210> SEQ ID NO 73
<211> LENGTH: 20
<212> TYPE: DNA
<213> ORGANISM: Artificial Sequence
<220> FEATURE:
<223> OTHER INFORMATION: antisense sequence

<400> SEQUENCE: 73
gcactgttcc tgggtgatgg                                              20

<210> SEQ ID NO 74
<211> LENGTH: 20
<212> TYPE: DNA
<213> ORGANISM: Artificial Sequence
<220> FEATURE:
<223> OTHER INFORMATION: antisense sequence

<400> SEQUENCE: 74
tagcaacagc cgcgggcctc                                              20

<210> SEQ ID NO 75
<211> LENGTH: 20
<212> TYPE: DNA
<213> ORGANISM: Artificial Sequence
<220> FEATURE:
<223> OTHER INFORMATION: antisense sequence

<400> SEQUENCE: 75
gcccctgctt tgcagggatg                                              20

<210> SEQ ID NO 76
<211> LENGTH: 20
<212> TYPE: DNA
<213> ORGANISM: Artificial Sequence
<220> FEATURE:
<223> OTHER INFORMATION: antisense sequence

<400> SEQUENCE: 76
ccccatctgg gctccctgca                                              20

<210> SEQ ID NO 77
<211> LENGTH: 20
<212> TYPE: DNA
<213> ORGANISM: Artificial Sequence
<220> FEATURE:
<223> OTHER INFORMATION: antisense sequence

```
<400> SEQUENCE: 77
gggaagaagc accagggctg                                              20

<210> SEQ ID NO 78
<211> LENGTH: 20
<212> TYPE: DNA
<213> ORGANISM: Artificial Sequence
<220> FEATURE:
<223> OTHER INFORMATION: antisense sequence

<400> SEQUENCE: 78
tgtagctggg gtagctgggt                                              20

<210> SEQ ID NO 79
<211> LENGTH: 20
<212> TYPE: DNA
<213> ORGANISM: Artificial Sequence
<220> FEATURE:
<223> OTHER INFORMATION: antisense sequence

<400> SEQUENCE: 79
ggagctcagg ttctccagct                                              20

<210> SEQ ID NO 80
<211> LENGTH: 20
<212> TYPE: DNA
<213> ORGANISM: Artificial Sequence
<220> FEATURE:
<223> OTHER INFORMATION: antisense sequence

<400> SEQUENCE: 80
gccgtgtagc ccatttcaga                                              20

<210> SEQ ID NO 81
<211> LENGTH: 20
<212> TYPE: DNA
<213> ORGANISM: Artificial Sequence
<220> FEATURE:
<223> OTHER INFORMATION: antisense sequence

<400> SEQUENCE: 81
gggtggtacg ggtcagggtg                                              20

<210> SEQ ID NO 82
<211> LENGTH: 20
<212> TYPE: DNA
<213> ORGANISM: Artificial Sequence
<220> FEATURE:
<223> OTHER INFORMATION: antisense sequence

<400> SEQUENCE: 82
gtccttgggg aagaaggtgg                                              20

<210> SEQ ID NO 83
<211> LENGTH: 20
<212> TYPE: DNA
<213> ORGANISM: Artificial Sequence
<220> FEATURE:
<223> OTHER INFORMATION: antisense sequence

<400> SEQUENCE: 83
tccagccgca gggtcaggat                                              20

<210> SEQ ID NO 84
```

```
<211> LENGTH: 20
<212> TYPE: DNA
<213> ORGANISM: Artificial Sequence
<220> FEATURE:
<223> OTHER INFORMATION: antisense sequence

<400> SEQUENCE: 84
tctcagtctc catcatcacg                                               20

<210> SEQ ID NO 85
<211> LENGTH: 16
<212> TYPE: DNA
<213> ORGANISM: Artificial Sequence
<220> FEATURE:
<223> OTHER INFORMATION: antisense sequence

<400> SEQUENCE: 85
gtgaagtgga ggcggt                                                   16

<210> SEQ ID NO 86
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 86
agagcacttg cacagtctgc                                               20

<210> SEQ ID NO 87
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 87
gcagagcact tgcacagtct                                               20

<210> SEQ ID NO 88
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 88
gtgcagagca cttgcacagt                                               20

<210> SEQ ID NO 89
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 89
gggagtgcag agcacttgca                                               20

<210> SEQ ID NO 90
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 90
```
aggggagtgc agagcacttg                                              20

<210> SEQ ID NO 91
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 91
gcaggggagt gcagagcact                                              20

<210> SEQ ID NO 92
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 92
gccagaagga agggcgagaa                                              20

<210> SEQ ID NO 93
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 93
gggccagaag gaagggcgag                                              20

<210> SEQ ID NO 94
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 94
gagggccaga aggaagggcg                                              20

<210> SEQ ID NO 95
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 95
gggagagggc cagaaggaag                                              20

<210> SEQ ID NO 96
<211> LENGTH: 20
<212> TYPE: DNA
<213> ORGANISM: Artificial Sequence
<220> FEATURE:
<223> OTHER INFORMATION: antisense oligonucleotide compound

<400> SEQUENCE: 96
tggggagagg gccagaagga                                              20

<210> SEQ ID NO 97
<211> LENGTH: 20
<212> TYPE: DNA

<213> ORGANISM: Artificial Sequence
<220> FEATURE:
<223> OTHER INFORMATION: antisense oligonucleotide compound

<400> SEQUENCE: 97
actggggaga gggccagaag							20

<210> SEQ ID NO 98
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 98
cacccaggca ggtgggtaa ggtgg							25

<210> SEQ ID NO 99
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 99
agcacccagg caggtggggt aaggt							25

<210> SEQ ID NO 100
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 100
gcagcaccca ggcaggtggg gtaag							25

<210> SEQ ID NO 101
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 101
ctgcagcacc caggcaggtg gggta							25

<210> SEQ ID NO 102
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 102
cactgcagca cccaggcagg tgggg							25

<210> SEQ ID NO 103
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 103
ggcactgcag cacccaggca ggtgg							25

<210> SEQ ID NO 104
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 104
ctggcactgc agcacccagg caggt                                          25

<210> SEQ ID NO 105
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 105
ggctggcact gcagcaccca ggcag                                          25

<210> SEQ ID NO 106
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 106
gcggctggca ctgcagcacc caggc                                          25

<210> SEQ ID NO 107
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 107
ccgcggctgg cactgcagca cccag                                          25

<210> SEQ ID NO 108
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 108
tcaaccgcgg ctggcactgc agcac                                          25

<210> SEQ ID NO 109
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 109
acccaggcag gtggggtaag gtggc                                          25

<210> SEQ ID NO 110
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 110
gcacccaggc aggtggggta aggtg                                              25

<210> SEQ ID NO 111
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 111
cagcacccag gcaggtgggg taagg                                              25

<210> SEQ ID NO 112
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 112
tgcagcaccc aggcaggtgg ggtaa                                              25

<210> SEQ ID NO 113
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 113
actgcagcac ccaggcaggt ggggt                                              25

<210> SEQ ID NO 114
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 114
gcactgcagc acccaggcag gtggg                                              25

<210> SEQ ID NO 115
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 115
tggcactgca gcacccaggc aggtg                                              25

<210> SEQ ID NO 116
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 116
gctggcactg cagcacccag gcagg                                              25

```
<210> SEQ ID NO 117
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 117
cggctggcac tgcagcaccc aggca                                          25

<210> SEQ ID NO 118
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 118
cgcggctggc actgcagcac ccagg                                          25

<210> SEQ ID NO 119
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 119
accgcggctg gcactgcagc accca                                          25

<210> SEQ ID NO 120
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 120
caaccgcggc tggcactgca gcacc                                          25

<210> SEQ ID NO 121
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 121
atcaaccgcg gctggcactg cagca                                          25

<210> SEQ ID NO 122
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 122
ggctctcaaa gcagctctga gacat                                          25

<210> SEQ ID NO 123
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 123
ggggctctca aagcagctct gagac                                              25

<210> SEQ ID NO 124
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 124
acggggctct caaagcagct ctgag                                              25

<210> SEQ ID NO 125
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 125
tcacggggct ctcaaagcag ctctg                                              25

<210> SEQ ID NO 126
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 126
actcacgggg ctctcaaagc agctc                                              25

<210> SEQ ID NO 127
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 127
gcactcacgg ggctctcaaa gcagc                                              25

<210> SEQ ID NO 128
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 128
cggcactcac ggggctctca aagca                                              25

<210> SEQ ID NO 129
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 129
ggcggcactc acggggctct caaag                                              25

<210> SEQ ID NO 130
<211> LENGTH: 25
```

-continued

<212> TYPE: DNA
<213> ORGANISM: Artificial Sequence
<220> FEATURE:
<223> OTHER INFORMATION: antisense oligomeric compound

<400> SEQUENCE: 130
ggggcggcac tcacggggct ctcaa                                           25

<210> SEQ ID NO 131
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 131
gaggggcggc actcacgggg ctctc                                           25

<210> SEQ ID NO 132
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 132
gggaggggcg gcactcacgg ggctc                                           25

<210> SEQ ID NO 133
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 133
gcgggagggg cggcactcac ggggc                                           25

<210> SEQ ID NO 134
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 134
aggcgggagg ggcggcactc acggg                                           25

<210> SEQ ID NO 135
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 135
ggaggcggga ggggcggcac tcacg                                           25

<210> SEQ ID NO 136
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 136
agggaggcgg gagggggcggc actca					25

<210> SEQ ID NO 137
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 137
gcagggaggc gggaggggcg gcact					25

<210> SEQ ID NO 138
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 138
cagcagggag gcgggagggg cggca					25

<210> SEQ ID NO 139
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 139
ctcagcaggg aggcgggagg ggcgg					25

<210> SEQ ID NO 140
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 140
ggctcagcag ggaggcggga ggggc					25

<210> SEQ ID NO 141
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 141
cgggctcagc agggaggcgg gaggg					25

<210> SEQ ID NO 142
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 142
agcgggctca gcagggaggc gggag					25

<210> SEQ ID NO 143
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 143
aaagcgggct cagcagggag gcggg                                              25

<210> SEQ ID NO 144
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 144
agaaagcggg ctcagcaggg aggcg                                              25

<210> SEQ ID NO 145
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 145
gaagaaagcg ggctcagcag ggagg                                              25

<210> SEQ ID NO 146
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 146
gagaagaaag cgggctcagc aggga                                              25

<210> SEQ ID NO 147
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 147
gggagaagaa agcgggctca gcagg                                              25

<210> SEQ ID NO 148
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 148
gcgggagaag aaagcggget cagca                                              25

<210> SEQ ID NO 149
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 149
ctgcgggaga agaaagcggg ctcag                                              25
```

```
<210> SEQ ID NO 150
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 150
gcctgcggga gaagaaagcg ggctc                                 25

<210> SEQ ID NO 151
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 151
aggcctgcgg gagaagaaag cgggc                                 25

<210> SEQ ID NO 152
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 152
actcccatgg ttggagatgg cctgg                                 25

<210> SEQ ID NO 153
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 153
tcactcccat ggttggagat ggcct                                 25

<210> SEQ ID NO 154
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 154
cctcactccc atggttggag atggc                                 25

<210> SEQ ID NO 155
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 155
tgcctcactc ccatggttgg agatg                                 25

<210> SEQ ID NO 156
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 156
ggtgcctcac tcccatggtt ggaga                                              25

<210> SEQ ID NO 157
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 157
cgggtgcctc actcccatgg ttgga                                              25

<210> SEQ ID NO 158
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 158
ggcgggtgcc tcactcccat ggttg                                              25

<210> SEQ ID NO 159
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 159
agggcgggtg cctcactccc atggt                                              25

<210> SEQ ID NO 160
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 160
gcagggcggg tgcctcactc ccatg                                              25

<210> SEQ ID NO 161
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 161
gagcagggcg ggtgcctcac tccca                                              25

<210> SEQ ID NO 162
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 162
gggagcaggg cgggtgcctc actcc                                              25

<210> SEQ ID NO 163
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 163
gtgggagcag ggcgggtgcc tcact                                         25

<210> SEQ ID NO 164
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 164
cggtgggagc agggcgggtg cctca                                         25

<210> SEQ ID NO 165
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 165
gccggtggga gcaggcggg tgcct                                          25

<210> SEQ ID NO 166
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 166
gagccggtgg gagcagggcg ggtgc                                         25

<210> SEQ ID NO 167
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 167
aggagccggt gggagcaggg cgggt                                         25

<210> SEQ ID NO 168
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 168
ccaggagccg gtgggagcag ggcgg                                         25

<210> SEQ ID NO 169
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 169
```
ggccaggagc cggtgggagc agggc                                              25

<210> SEQ ID NO 170
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 170
acggccagga gccggtggga gcagg                                              25

<210> SEQ ID NO 171
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 171
agacggccag gagccggtgg gagca                                              25

<210> SEQ ID NO 172
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 172
gcagacggcc aggagccggt gggag                                              25

<210> SEQ ID NO 173
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 173
gcgcagacgg ccaggagccg gtggg                                              25

<210> SEQ ID NO 174
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 174
gggcgcagac ggccaggagc cggtg                                              25

<210> SEQ ID NO 175
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 175
gagggcgcag acggccagga gccgg                                              25

<210> SEQ ID NO 176
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 176
acgagggcgc agacggccag gagcc                                                 25

<210> SEQ ID NO 177
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 177
acacgagggc gcagacggcc aggag                                                 25

<210> SEQ ID NO 178
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 178
ggacacgagg gcgcagacgg ccagg                                                 25

<210> SEQ ID NO 179
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 179
aaggacacga gggcgcagac ggcca                                                 25

<210> SEQ ID NO 180
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 180
ccaaggacac gagggcgcag acggc                                                 25

<210> SEQ ID NO 181
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 181
tgccaaggac acgagggcgc agacg                                                 25

<210> SEQ ID NO 182
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 182
gctctcaaag cagctctgag acatc                                                 25
```

<210> SEQ ID NO 183
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 183
gggctctcaa agcagctctg agaca                                    25

<210> SEQ ID NO 184
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 184
ctcacggggc tctcaaagca gctct                                    25

<210> SEQ ID NO 185
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 185
cactcacggg gctctcaaag cagct                                    25

<210> SEQ ID NO 186
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 186
ggcactcacg gggctctcaa agcag                                    25

<210> SEQ ID NO 187
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 187
gcggcactca cggggctctc aaagc                                    25

<210> SEQ ID NO 188
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 188
gggcggcact cacggggctc tcaaa                                    25

<210> SEQ ID NO 189
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 189
aggggcggca ctcacgggc tctca							25

<210> SEQ ID NO 190
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 190
ggaggggcgg cactcacggg gctct							25

<210> SEQ ID NO 191
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 191
cgggaggggc ggcactcacg gggct							25

<210> SEQ ID NO 192
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 192
ggcgggaggg gcggcactca cgggg							25

<210> SEQ ID NO 193
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 193
gaggcgggag gggcggcact cacgg							25

<210> SEQ ID NO 194
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 194
gggaggcggg aggggcggca ctcac							25

<210> SEQ ID NO 195
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 195
cagggaggcg ggaggggcgg cactc							25

```
<210> SEQ ID NO 196
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 196
agcagggagg cgggaggggc ggcac                                          25

<210> SEQ ID NO 197
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 197
tcagcaggga ggcgggaggg gcggc                                          25

<210> SEQ ID NO 198
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 198
gctcagcagg gaggcgggag gggcg                                          25

<210> SEQ ID NO 199
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 199
gggctcagca gggaggcggg agggg                                          25

<210> SEQ ID NO 200
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 200
gcgggctcag cagggaggcg ggagg                                          25

<210> SEQ ID NO 201
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 201
aagcgggctc agcagggagg cggga                                          25

<210> SEQ ID NO 202
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 202
gaaagcgggc tcagcaggga ggcgg                                           25

<210> SEQ ID NO 203
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 203
aagaaagcgg gctcagcagg gaggc                                           25

<210> SEQ ID NO 204
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 204
agaagaaagc gggctcagca gggag                                           25

<210> SEQ ID NO 205
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 205
ggagaagaaa gcgggctcag caggg                                           25

<210> SEQ ID NO 206
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 206
cgggagaaga aagcgggctc agcag                                           25

<210> SEQ ID NO 207
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 207
tgcgggagaa gaaagcgggc tcagc                                           25

<210> SEQ ID NO 208
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 208
cctgcgggag aagaaagcgg gctca                                           25

<210> SEQ ID NO 209
<211> LENGTH: 25

```
<212> TYPE: DNA
<213> ORGANISM: Artificial Sequence
<220> FEATURE:
<223> OTHER INFORMATION: antisense oligomeric compound

<400> SEQUENCE: 209
ggcctgcggg agaagaaagc gggct                                          25

<210> SEQ ID NO 210
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 210
caggcctgcg ggagaagaaa gcggg                                          25

<210> SEQ ID NO 211
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 211
cggggctctc aaagcagctc tgaga                                          25

<210> SEQ ID NO 212
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 212
cacggggctc tcaaagcagc tctga                                          25

<210> SEQ ID NO 213
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 213
ctcccatggt tggagatggc ctgga                                          25

<210> SEQ ID NO 214
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 214
cactcccatg gttggagatg gcctg                                          25

<210> SEQ ID NO 215
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 215
```
ctcactccca tggttggaga tggcc                                               25

<210> SEQ ID NO 216
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 216
gcctcactcc catggttgga gatgg                                               25

<210> SEQ ID NO 217
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 217
gtgcctcact cccatggttg gagat                                               25

<210> SEQ ID NO 218
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 218
gggtgcctca ctcccatggt tggag                                               25

<210> SEQ ID NO 219
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 219
gcgggtgcct cactcccatg gttgg                                               25

<210> SEQ ID NO 220
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 220
gggcgggtgc ctcactccca tggtt                                               25

<210> SEQ ID NO 221
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 221
cagggcgggt gcctcactcc catgg                                               25

<210> SEQ ID NO 222
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 222
agcagggcgg gtgcctcact cccat                                             25

<210> SEQ ID NO 223
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 223
ggagcagggc gggtgcctca ctccc                                             25

<210> SEQ ID NO 224
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 224
tgggagcagg gcgggtgcct cactc                                             25

<210> SEQ ID NO 225
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 225
ggtgggagca gggcgggtgc ctcac                                             25

<210> SEQ ID NO 226
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 226
ccggtgggag cagggcgggt gcctc                                             25

<210> SEQ ID NO 227
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 227
agccggtggg agcagggcgg gtgcc                                             25

<210> SEQ ID NO 228
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 228
ggagccggtg ggagcagggc gggtg                                             25
```

```
<210> SEQ ID NO 229
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 229
caggagccgg tgggagcagg gcggg                                              25

<210> SEQ ID NO 230
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 230
gccaggagcc ggtgggagca gggcg                                              25

<210> SEQ ID NO 231
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 231
cggccaggag ccggtgggag caggg                                              25

<210> SEQ ID NO 232
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 232
gacggccagg agccggtggg agcag                                              25

<210> SEQ ID NO 233
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 233
cagacggcca ggagccggtg ggagc                                              25

<210> SEQ ID NO 234
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 234
cgcagacggc caggagccgg tggga                                              25

<210> SEQ ID NO 235
<211> LENGTH: 25
<212> TYPE: DNA
<213> ORGANISM: Artificial Sequence
<220> FEATURE:
<223> OTHER INFORMATION: antisense oligomeric compound
```

-continued

```
<400> SEQUENCE: 235
ggcgcagacg gccaggagcc ggtgg                                              25

<210> SEQ ID NO 236
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 236
agggcgcaga cggccaggag ccggt                                              25

<210> SEQ ID NO 237
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 237
cgagggcgca gacggccagg agccg                                              25

<210> SEQ ID NO 238
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 238
cacgagggcg cagacggcca ggagc                                              25

<210> SEQ ID NO 239
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 239
gacacgaggg cgcagacggc cagga                                              25

<210> SEQ ID NO 240
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 240
aggacacgag ggcgcagacg gccag                                              25

<210> SEQ ID NO 241
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 241
caaggacacg agggcgcaga cggcc                                              25

<210> SEQ ID NO 242
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 242
gccaaggaca cgagggcgca gacgg                                          25

<210> SEQ ID NO 243
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 243
ttgccaagga cacgagggcg cagac                                          25

<210> SEQ ID NO 244
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 244
ggatgtgccc caggagtgca gcggt                                          25

<210> SEQ ID NO 245
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 245
taggatgtgc cccaggagtg cagcg                                          25

<210> SEQ ID NO 246
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 246
agtaggatgt gccccaggag tgcag                                          25

<210> SEQ ID NO 247
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 247
ggagtaggat gtgccccagg agtgc                                          25

<210> SEQ ID NO 248
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 248
```

```
atggagtagg atgtgcccca ggagt                                               25

<210> SEQ ID NO 249
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 249
tcatggagta ggatgtgccc cagga                                               25

<210> SEQ ID NO 250
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 250
aatcatggag taggatgtgc cccag                                               25

<210> SEQ ID NO 251
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 251
gaaatcatgg agtaggatgt gcccc                                               25

<210> SEQ ID NO 252
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 252
aggaaatcat ggagtaggat gtgcc                                               25

<210> SEQ ID NO 253
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 253
gcaggaaatc atggagtagg atgtg                                               25

<210> SEQ ID NO 254
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 254
cagcaggaaa tcatggagta ggatg                                               25

<210> SEQ ID NO 255
<211> LENGTH: 25
<212> TYPE: DNA
```

<213> ORGANISM: Artificial Sequence
<220> FEATURE:
<223> OTHER INFORMATION: antisense oligomeric compound

<400> SEQUENCE: 255
accagcagga aatcatggag tagga                                     25

<210> SEQ ID NO 256
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 256
gaaccagcag gaaatcatgg agtag                                     25

<210> SEQ ID NO 257
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 257
gggaaccagc aggaaatcat ggagt                                     25

<210> SEQ ID NO 258
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 258
cggggaacca gcaggaaatc atgga                                     25

<210> SEQ ID NO 259
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 259
ctcggggaac cagcaggaaa tcatg                                     25

<210> SEQ ID NO 260
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 260
ctctcgggga accagcagga aatca                                     25

<210> SEQ ID NO 261
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 261
agctctcggg gaaccagcag gaaat                                     25

<210> SEQ ID NO 262
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 262
tcagctctcg gggaaccagc aggaa                                              25

<210> SEQ ID NO 263
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 263
actcagctct cggggaacca gcagg                                              25

<210> SEQ ID NO 264
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 264
ccactcagct ctcggggaac cagca                                              25

<210> SEQ ID NO 265
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 265
agccactcag ctctcgggga accag                                              25

<210> SEQ ID NO 266
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 266
ggagccactc agctctcggg gaacc                                              25

<210> SEQ ID NO 267
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 267
gaggagccac tcagctctcg gggaa                                              25

<210> SEQ ID NO 268
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 268
gggaggagcc actcagctct cggggg                                              25

<210> SEQ ID NO 269
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 269
tggggaggag ccactcagct ctcgg                                               25

<210> SEQ ID NO 270
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 270
actggggagg agccactcag ctctc                                               25

<210> SEQ ID NO 271
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 271
ggactgggga ggagccactc agctc                                               25

<210> SEQ ID NO 272
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 272
caggactggg gaggagccac tcagc                                               25

<210> SEQ ID NO 273
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 273
tccaggactg gggaggagcc actca                                               25

<210> SEQ ID NO 274
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 274
cctccaggac tggggaggag ccact                                               25

<210> SEQ ID NO 275
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 275
ctcctccagg actggggagg agcca                                       25

<210> SEQ ID NO 276
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 276
gtctcctcca ggactgggga ggagc                                       25

<210> SEQ ID NO 277
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 277
gagtctcctc caggactggg gagga                                       25

<210> SEQ ID NO 278
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 278
gtgagtctcc tccaggactg gggag                                       25

<210> SEQ ID NO 279
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 279
gggtgagtct cctccaggac tgggg                                       25

<210> SEQ ID NO 280
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 280
ctgggtgagt ctcctccagg actgg                                       25

<210> SEQ ID NO 281
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 281
agctgggtga gtctcctcca ggact                                           25

<210> SEQ ID NO 282
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 282
tgagctgggt gagtctcctc cagga                                           25

<210> SEQ ID NO 283
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 283
ggtgagctgg gtgagtctcc tccag                                           25

<210> SEQ ID NO 284
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 284
ctggtgagct gggtgagtct cctcc                                           25

<210> SEQ ID NO 285
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 285
tgctggtgag ctgggtgagt ctcct                                           25

<210> SEQ ID NO 286
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 286
cctgctggtg agctgggtga gtctc                                           25

<210> SEQ ID NO 287
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 287
tccctgctgg tgagctgggt gagtc                                           25

<210> SEQ ID NO 288
<211> LENGTH: 25
```

```
<212> TYPE: DNA
<213> ORGANISM: Artificial Sequence
<220> FEATURE:
<223> OTHER INFORMATION: antisense oligomeric compound

<400> SEQUENCE: 288
gctccctgct ggtgagctgg gtgag                                    25

<210> SEQ ID NO 289
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 289
tggctccctg ctggtgagct gggtg                                    25

<210> SEQ ID NO 290
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 290
gctggctccc tgctggtgag ctggg                                    25

<210> SEQ ID NO 291
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 291
ctgctggctc cctgctggtg agctg                                    25

<210> SEQ ID NO 292
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 292
gtctgctggc tccctgctgg tgagc                                    25

<210> SEQ ID NO 293
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 293
gatgtgcccc aggagtgcag cggtt                                    25

<210> SEQ ID NO 294
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 294
```
aggatgtgcc ccaggagtgc agcgg                                25

<210> SEQ ID NO 295
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 295
gtaggatgtg cccaggagt gcagc                                 25

<210> SEQ ID NO 296
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 296
gagtaggatg tgccccagga gtgca                                25

<210> SEQ ID NO 297
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 297
tggagtagga tgtgccccag gagtg                                25

<210> SEQ ID NO 298
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 298
catggagtag gatgtgcccc aggag                                25

<210> SEQ ID NO 299
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 299
atcatggagt aggatgtgcc ccagg                                25

<210> SEQ ID NO 300
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 300
aaatcatgga gtaggatgtg cccca                                25

<210> SEQ ID NO 301
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 301
ggaaatcatg gagtaggatg tgccc                                              25

<210> SEQ ID NO 302
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 302
caggaaatca tggagtagga tgtgc                                              25

<210> SEQ ID NO 303
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 303
agcaggaaat catggagtag gatgt                                              25

<210> SEQ ID NO 304
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 304
ccagcaggaa atcatggagt aggat                                              25

<210> SEQ ID NO 305
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 305
aaccagcagg aaatcatgga gtagg                                              25

<210> SEQ ID NO 306
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 306
ggaaccagca ggaaatcatg gagta                                              25

<210> SEQ ID NO 307
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 307
ggggaaccag caggaaatca tggag                                              25
```

<210> SEQ ID NO 308
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 308
tcggggaacc agcaggaaat catgg                                              25

<210> SEQ ID NO 309
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 309
tctcggggaa ccagcaggaa atcat                                              25

<210> SEQ ID NO 310
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 310
gctctcgggg aaccagcagg aaatc                                              25

<210> SEQ ID NO 311
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 311
cagctctcgg ggaaccagca ggaaa                                              25

<210> SEQ ID NO 312
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 312
ctcagctctc ggggaaccag cagga                                              25

<210> SEQ ID NO 313
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 313
cactcagctc tcggggaacc agcag                                              25

<210> SEQ ID NO 314
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 314
gccactcagc tctcggggaa ccagc                                            25

<210> SEQ ID NO 315
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 315
gagccactca gctctcgggg aacca                                            25

<210> SEQ ID NO 316
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 316
aggagccact cagctctcgg ggaac                                            25

<210> SEQ ID NO 317
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 317
ggaggagcca ctcagctctc gggga                                            25

<210> SEQ ID NO 318
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 318
ggggaggagc cactcagctc tcggg                                            25

<210> SEQ ID NO 319
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 319
ctggggagga gccactcagc tctcg                                            25

<210> SEQ ID NO 320
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 320
gactggggag gagccactca gctct                                            25

<210> SEQ ID NO 321
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 321
aggactgggg aggagccact cagct                                    25

<210> SEQ ID NO 322
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 322
ccaggactgg ggaggagcca ctcag                                    25

<210> SEQ ID NO 323
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 323
ctccaggact ggggaggagc cactc                                    25

<210> SEQ ID NO 324
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 324
tcctccagga ctggggagga gccac                                    25

<210> SEQ ID NO 325
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 325
tctcctccag gactggggag gagcc                                    25

<210> SEQ ID NO 326
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 326
agtctcctcc aggactgggg aggag                                    25

<210> SEQ ID NO 327
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 327
```
tgagtctcct ccaggactgg ggagg                                             25

<210> SEQ ID NO 328
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 328
ggtgagtctc ctccaggact gggga                                             25

<210> SEQ ID NO 329
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 329
tgggtgagtc tcctccagga ctggg                                             25

<210> SEQ ID NO 330
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 330
gctgggtgag tctcctccag gactg                                             25

<210> SEQ ID NO 331
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 331
gagctgggtg agtctcctcc aggac                                             25

<210> SEQ ID NO 332
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 332
gtgagctggg tgagtctcct ccagg                                             25

<210> SEQ ID NO 333
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 333
tggtgagctg ggtgagtctc ctcca                                             25

<210> SEQ ID NO 334
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 334
gctggtgagc tgggtgagtc tcctc                                              25

<210> SEQ ID NO 335
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 335
ctgctggtga gctgggtgag tctcc                                              25

<210> SEQ ID NO 336
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 336
ccctgctggt gagctgggtg agtct                                              25

<210> SEQ ID NO 337
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 337
ctccctgctg gtgagctggg tgagt                                              25

<210> SEQ ID NO 338
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 338
ggctccctgc tggtgagctg ggtga                                              25

<210> SEQ ID NO 339
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 339
ctggctccct gctggtgagc tgggt                                              25

<210> SEQ ID NO 340
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 340
tgctggctcc ctgctggtga gctgg                                              25
```

```
<210> SEQ ID NO 341
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 341
tctgctggct ccctgctggt gagct                                      25

<210> SEQ ID NO 342
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 342
ggtctgctgg ctccctgctg gtgag                                      25

<210> SEQ ID NO 343
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 343 agccctgct tgcagggat gtagc                                        25

<210> SEQ ID NO 344
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 344
gcagcccctg ctttgcaggg atgta                                      25

<210> SEQ ID NO 345
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 345
ctgcagcccc tgctttgcag ggatg                                      25

<210> SEQ ID NO 346
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 346
ccctgcagcc cctgctttgc aggga                                      25

<210> SEQ ID NO 347
<211> LENGTH: 25
<212> TYPE: DNA
<213> ORGANISM: Artificial Sequence
<220> FEATURE:
```

<223> OTHER INFORMATION: antisense oligomeric compound

<400> SEQUENCE: 347
ctccctgcag ccctgctttt gcagg                               25

<210> SEQ ID NO 348
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 348
ggctccctgc agccctgct ttgca                                25

<210> SEQ ID NO 349
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 349
tgggctccct gcagccctg ctttg                                25

<210> SEQ ID NO 350
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 350
tctgggctcc ctgcagcccc tgctt                               25

<210> SEQ ID NO 351
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 351
catctgggct ccctgcagcc cctgc                               25

<210> SEQ ID NO 352
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 352
cccatctggg ctccctgcag ccct                                25

<210> SEQ ID NO 353
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 353
gccccatctg ggctccctgc agccc                               25

```
<210> SEQ ID NO 354
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 354
ctgccccatc tgggctccct gcagc                                              25

<210> SEQ ID NO 355
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 355
ggctgcccca tctgggctcc ctgca                                              25

<210> SEQ ID NO 356
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 356
agggctgccc catctgggct ccctg                                              25

<210> SEQ ID NO 357
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 357
ccagggctgc cccatctggg ctccc                                              25

<210> SEQ ID NO 358
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 358
caccagggct gccccatctg ggctc                                              25

<210> SEQ ID NO 359
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 359
agcaccaggg ctgccccatc tgggc                                              25

<210> SEQ ID NO 360
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 360
gaagcaccag ggctgcccca tctgg                                                25

<210> SEQ ID NO 361
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 361
aagaagcacc agggctgccc catct                                                25

<210> SEQ ID NO 362
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 362
ggaagaagca ccagggctgc cccat                                                25

<210> SEQ ID NO 363
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 363
tgggaagaag caccagggct gcccc                                                25

<210> SEQ ID NO 364
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 364
ggtgggaaga agcaccaggg ctgcc                                                25

<210> SEQ ID NO 365
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 365
tgggtgggaa gaagcaccag ggctg                                                25

<210> SEQ ID NO 366
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 366
gctgggtggg aagaagcacc agggc                                                25

<210> SEQ ID NO 367
<211> LENGTH: 25

```
<212> TYPE: DNA
<213> ORGANISM: Artificial Sequence
<220> FEATURE:
<223> OTHER INFORMATION: antisense oligomeric compound

<400> SEQUENCE: 367 gccctgctt tgcagggatg tagca                                          25

<210> SEQ ID NO 368
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 368 cagccctgc tttgcaggga tgtag                                          25

<210> SEQ ID NO 369
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 369 tgcagccct gctttgcagg gatgt                                          25

<210> SEQ ID NO 370
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 370
cctgcagccc ctgctttgca gggat                                         25

<210> SEQ ID NO 371
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 371
tccctgcagc ccctgctttg caggg                                         25

<210> SEQ ID NO 372
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 372
gctccctgca gccctgctt tgcag                                          25

<210> SEQ ID NO 373
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 373
```
gggctccctg cagcccctgc tttgc                                          25

<210> SEQ ID NO 374
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 374
ctgggctccc tgcagcccct gcttt                                          25

<210> SEQ ID NO 375
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 375
atctgggctc cctgcagccc ctgct                                          25

<210> SEQ ID NO 376
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 376
ccatctgggc tccctgcagc ccctg                                          25

<210> SEQ ID NO 377
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 377
ccccatctgg gctccctgca gcccc                                          25

<210> SEQ ID NO 378
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 378
tgccccatct gggctccctg cagcc                                          25

<210> SEQ ID NO 379
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 379
gctgccccat ctgggctccc tgcag                                          25

<210> SEQ ID NO 380
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 380
gggctgcccc atctgggctc cctgc                                              25

<210> SEQ ID NO 381
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 381
cagggctgcc ccatctgggc tccct                                              25

<210> SEQ ID NO 382
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 382
accagggctg ccccatctgg gctcc                                              25

<210> SEQ ID NO 383
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 383
gcaccagggc tgccccatct gggct                                              25

<210> SEQ ID NO 384
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 384
aagcaccagg gctgccccat ctggg                                              25

<210> SEQ ID NO 385
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 385
agaagcacca gggctgcccc atctg                                              25

<210> SEQ ID NO 386
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 386
gaagaagcac agggctgcc ccatc                                               25
```

<210> SEQ ID NO 387
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 387
gggaagaagc accagggctg cccca                                             25

<210> SEQ ID NO 388
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 388
gtgggaagaa gcaccagggc tgccc                                             25

<210> SEQ ID NO 389
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 389
gggtgggaag aagcaccagg gctgc                                             25

<210> SEQ ID NO 390
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 390
ctgggtggga agaagcacca gggct                                             25

<210> SEQ ID NO 391
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 391
agctgggtgg gaagaagcac caggg                                             25

<210> SEQ ID NO 392
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 392
cagcttgtag ctggggtagc tgggt                                             25

<210> SEQ ID NO 393
<211> LENGTH: 25
<212> TYPE: DNA
<213> ORGANISM: Artificial Sequence
<220> FEATURE:
<223> OTHER INFORMATION: antisense oligomeric compound

```
<400> SEQUENCE: 393
tccagcttgt agctggggta gctgg                                              25

<210> SEQ ID NO 394
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 394
tctccagctt gtagctgggg tagct                                              25

<210> SEQ ID NO 395
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 395
gttctccagc ttgtagctgg ggtag                                              25

<210> SEQ ID NO 396
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 396
aggttctcca gcttgtagct ggggt                                              25

<210> SEQ ID NO 397
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 397
tcaggttctc cagcttgtag ctggg                                              25

<210> SEQ ID NO 398
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 398
gctcaggttc tccagcttgt agctg                                              25

<210> SEQ ID NO 399
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 399
gagctcaggt tctccagctt gtagc                                              25

<210> SEQ ID NO 400
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 400
aggagctcag gttctccagc ttgta                                    25

<210> SEQ ID NO 401
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 401
agaggagctc aggttctcca gcttg                                    25

<210> SEQ ID NO 402
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 402
tcagaggagc tcaggttctc cagct                                    25

<210> SEQ ID NO 403
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 403
tttcagagga gctcaggttc tccag                                    25

<210> SEQ ID NO 404
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 404
agcttgtagc tggggtagct gggtg                                    25

<210> SEQ ID NO 405
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 405
ccagcttgta gctggggtag ctggg                                    25

<210> SEQ ID NO 406
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 406
```
ctccagcttg tagctggggt agctg                                              25

<210> SEQ ID NO 407
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 407
ttctccagct tgtagctggg gtagc                                              25

<210> SEQ ID NO 408
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 408
ggttctccag cttgtagctg gggta                                              25

<210> SEQ ID NO 409
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 409
caggttctcc agcttgtagc tgggg                                              25

<210> SEQ ID NO 410
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 410
ctcaggttct ccagcttgta gctgg                                              25

<210> SEQ ID NO 411
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 411
agctcaggtt ctccagcttg tagct                                              25

<210> SEQ ID NO 412
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 412
ggagctcagg ttctccagct tgtag                                              25

<210> SEQ ID NO 413
<211> LENGTH: 25
<212> TYPE: DNA

```
<213> ORGANISM: Artificial Sequence
<220> FEATURE:
<223> OTHER INFORMATION: antisense oligomeric compound

<400> SEQUENCE: 413
gaggagctca ggttctccag cttgt                                          25

<210> SEQ ID NO 414
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 414
cagaggagct caggttctcc agctt                                          25

<210> SEQ ID NO 415
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 415
ttcagaggag ctcaggttct ccagc                                          25

<210> SEQ ID NO 416
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 416
atttcagagg agctcaggtt ctcca                                          25

<210> SEQ ID NO 417
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 417
ggggtggtac gggtcagggt ggccg                                          25

<210> SEQ ID NO 418
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 418
tgggggtggt acgggtcagg gtggc                                          25

<210> SEQ ID NO 419
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 419
ggtgggggtg gtacgggtca gggtg                                          25
```

<210> SEQ ID NO 420
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 420
aaggtggggg tggtacgggt caggg                                              25

<210> SEQ ID NO 421
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 421
agaaggtggg ggtggtacgg gtcag                                              25

<210> SEQ ID NO 422
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 422
gaagaaggtg ggggtggtac gggtc                                              25

<210> SEQ ID NO 423
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 423
gggaagaagg tgggggtggt acggg                                              25

<210> SEQ ID NO 424
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 424
tggggaagaa ggtgggggtg gtacg                                              25

<210> SEQ ID NO 425
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 425
cttggggaag aaggtggggg tggta                                              25

<210> SEQ ID NO 426
<211> LENGTH: 25
<212> TYPE: DNA
<213> ORGANISM: Artificial Sequence
<220> FEATURE:

<223> OTHER INFORMATION: antisense oligomeric compound

<400> SEQUENCE: 426
tccttgggga agaaggtggg ggtgg                                    25

<210> SEQ ID NO 427
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 427
tgtccttggg gaagaaggtg ggggt                                    25

<210> SEQ ID NO 428
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 428
gatgtccttg gggaagaagg tgggg                                    25

<210> SEQ ID NO 429
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 429
aggatgtcct tgggaagaa ggtgg                                     25

<210> SEQ ID NO 430
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 430
tcaggatgtc cttggggaag aaggt                                    25

<210> SEQ ID NO 431
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 431
ggtcaggatg tccttgggga agaag                                    25

<210> SEQ ID NO 432
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 432
agggtcagga tgtccttggg gaaga                                    25

-continued

```
<210> SEQ ID NO 433
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 433
gcagggtcag gatgtccttg gggaa                                            25

<210> SEQ ID NO 434
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 434
ccgcagggtc aggatgtcct tgggg                                            25

<210> SEQ ID NO 435
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 435
agccgcaggg tcaggatgtc cttgg                                            25

<210> SEQ ID NO 436
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 436
gggtggtacg ggtcagggtg gccgt                                            25

<210> SEQ ID NO 437
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 437
gggggtggta cgggtcaggg tggcc                                            25

<210> SEQ ID NO 438
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 438
gtgggggtgg tacgggtcag ggtgg                                            25

<210> SEQ ID NO 439
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 439
aggtgggggt ggtacgggtc agggt                                    25

<210> SEQ ID NO 440
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 440
gaaggtgggg gtggtacggg tcagg                                    25

<210> SEQ ID NO 441
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 441
aagaaggtgg gggtggtacg ggtca                                    25

<210> SEQ ID NO 442
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 442
ggaagaaggt gggggtggta cgggt                                    25

<210> SEQ ID NO 443
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 443
ggggaagaag gtgggggtgg tacgg                                    25

<210> SEQ ID NO 444
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 444
ttggggaaga aggtgggggt ggtac                                    25

<210> SEQ ID NO 445
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 445
ccttggggaa gaaggtgggg gtggt                                    25

<210> SEQ ID NO 446
<211> LENGTH: 25

```
<210> SEQ ID NO 446
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 446
gtccttgggg aagaaggtgg gggtg                                              25

<210> SEQ ID NO 447
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 447
atgtccttgg ggaagaaggt ggggg                                              25

<210> SEQ ID NO 448
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 448
ggatgtcctt ggggaagaag gtggg                                              25

<210> SEQ ID NO 449
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 449
caggatgtcc ttggggaaga aggtg                                              25

<210> SEQ ID NO 450
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 450
gtcaggatgt ccttggggaa gaagg                                              25

<210> SEQ ID NO 451
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 451
gggtcaggat gtccttgggg aagaa                                              25

<210> SEQ ID NO 452
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 452
```
cagggtcagg atgtccttgg ggaag                                              25

<210> SEQ ID NO 453
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 453
cgcagggtca ggatgtcctt gggga                                              25

<210> SEQ ID NO 454
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 454
gccgcagggt caggatgtcc ttggg                                              25

<210> SEQ ID NO 455
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 455
cagccgcagg gtcaggatgt ccttg                                              25

<210> SEQ ID NO 456
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 456
cgtccagccg cagggtcagg atgtc                                              25

<210> SEQ ID NO 457
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 457
cacgtccagc cgcagggtca ggatg                                              25

<210> SEQ ID NO 458
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 458
atcacgtcca gccgcagggt cagga                                              25

<210> SEQ ID NO 459
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 459
tcatcacgtc cagccgcagg gtcag                                              25

<210> SEQ ID NO 460
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 460
catcatcacg tccagccgca gggtc                                              25

<210> SEQ ID NO 461
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 461
tccatcatca cgtccagccg caggg                                              25

<210> SEQ ID NO 462
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 462
tctccatcat cacgtccagc cgcag                                              25

<210> SEQ ID NO 463
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 463
agtctccatc atcacgtcca gccgc                                              25

<210> SEQ ID NO 464
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 464
tcagtctcca tcatcacgtc cagcc                                              25

<210> SEQ ID NO 465
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 465
tctcagtctc catcatcacg tccag                                              25
```

```
<210> SEQ ID NO 466
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 466
gttctcagtc tccatcatca cgtcc                                        25

<210> SEQ ID NO 467
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 467
cggttctcag tctccatcat cacgt                                        25

<210> SEQ ID NO 468
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 468
ggcggttctc agtctccatc atcac                                        25

<210> SEQ ID NO 469
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 469
gaggcggttc tcagtctcca tcatc                                        25

<210> SEQ ID NO 470
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 470
tggaggcggt tctcagtctc catca                                        25

<210> SEQ ID NO 471
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 471
agtggaggcg gttctcagtc tccat                                        25

<210> SEQ ID NO 472
<211> LENGTH: 25
<212> TYPE: DNA
<213> ORGANISM: Artificial Sequence
<220> FEATURE:
<223> OTHER INFORMATION: antisense oligomeric compound
```

```
<400> SEQUENCE: 472
gaagtggagg cggttctcag tctcc                                              25

<210> SEQ ID NO 473
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 473
gtccagccgc agggtcagga tgtcc                                              25

<210> SEQ ID NO 474
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 474
acgtccagcc gcagggtcag gatgt                                              25

<210> SEQ ID NO 475
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 475
tcacgtccag ccgcagggtc aggat                                              25

<210> SEQ ID NO 476
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 476
catcacgtcc agccgcaggg tcagg                                              25

<210> SEQ ID NO 477
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 477
atcatcacgt ccagccgcag ggtca                                              25

<210> SEQ ID NO 478
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 478
ccatcatcac gtccagccgc agggt                                              25

<210> SEQ ID NO 479
```

```
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 479
ctccatcatc acgtccagcc gcagg                                              25

<210> SEQ ID NO 480
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 480
gtctccatca tcacgtccag ccgca                                              25

<210> SEQ ID NO 481
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 481
cagtctccat catcacgtcc agccg                                              25

<210> SEQ ID NO 482
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 482
ctcagtctcc atcatcacgt ccagc                                              25

<210> SEQ ID NO 483
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 483
ttctcagtct ccatcatcac gtcca                                              25

<210> SEQ ID NO 484
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 484
ggttctcagt ctccatcatc acgtc                                              25

<210> SEQ ID NO 485
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 485
```

```
gcggttctca gtctccatca tcacg                                          25

<210> SEQ ID NO 486
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 486
aggcggttct cagtctccat catca                                          25

<210> SEQ ID NO 487
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 487
ggaggcggtt ctcagtctcc atcat                                          25

<210> SEQ ID NO 488
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 488
gtggaggcgg ttctcagtct ccatc                                          25

<210> SEQ ID NO 489
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 489
aagtggaggc ggttctcagt ctcca                                          25

<210> SEQ ID NO 490
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 490
tgaagtggag gcggttctca gtctc                                          25

<210> SEQ ID NO 491
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 491
tgccctgccc accgtgaagt ggagg                                          25

<210> SEQ ID NO 492
<211> LENGTH: 25
<212> TYPE: DNA
```

```
<213> ORGANISM: Artificial Sequence
<220> FEATURE:
<223> OTHER INFORMATION: antisense oligomeric compound

<400> SEQUENCE: 492
cctgccctgc ccaccgtgaa gtgga                                  25

<210> SEQ ID NO 493
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 493
cccctgccct gcccaccgtg aagtg                                  25

<210> SEQ ID NO 494
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 494
cgcccctgcc ctgcccaccg tgaag                                  25

<210> SEQ ID NO 495
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 495
cccgcccctg ccctgcccac cgtga                                  25

<210> SEQ ID NO 496
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 496
gccctgccca ccgtgaagtg gaggc                                  25

<210> SEQ ID NO 497
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 497
ctgccctgcc caccgtgaag tggag                                  25

<210> SEQ ID NO 498
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 498
ccctgccctg cccaccgtga agtgg                                  25
```

<210> SEQ ID NO 499
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 499 gccctgccc tgcccaccgt gaagt                                    25

<210> SEQ ID NO 500
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 500
ccgcccctgc cctgcccacc gtgaa                                   25

<210> SEQ ID NO 501
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 501 ccccgccct gccctgccca ccgtg                                    25

<210> SEQ ID NO 502
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 502 gccccgccc ctgccctgcc caccg                                    25

<210> SEQ ID NO 503
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 503 ccgccccgc ccctgccctg cccac                                    25

<210> SEQ ID NO 504
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 504
cgccgccccc gccctgccc tgccc                                    25

<210> SEQ ID NO 505
<211> LENGTH: 25
<212> TYPE: DNA
<213> ORGANISM: Artificial Sequence
<220> FEATURE:

```
<223> OTHER INFORMATION: antisense oligomeric compound

<400> SEQUENCE: 505
gccgccgccc ccgcccctgc cctgc                                              25

<210> SEQ ID NO 506
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 506
tggccgccgc ccccgcccct gccct                                              25

<210> SEQ ID NO 507
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 507
cctggccgcc gccccgccc ctgcc                                               25

<210> SEQ ID NO 508
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 508
gccctggccg ccgccccgc ccctg                                               25

<210> SEQ ID NO 509
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 509
ctgccctggc cgccgccccc gcccc                                              25

<210> SEQ ID NO 510
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 510
ctctgccctg gccgccgccc ccgcc                                              25

<210> SEQ ID NO 511
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 511
ccctctgccc tggccgccgc ccccg                                              25
```

```
<210> SEQ ID NO 512
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 512
caccctctgc cctggccgcc gcccc                                     25

<210> SEQ ID NO 513
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 513
cgcaccctct gccctggccg ccgcc                                     25

<210> SEQ ID NO 514
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 514
cgcgcaccct ctgccctggc cgccg                                     25

<210> SEQ ID NO 515
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 515
cccccgcccc tgccctgccc accgt                                     25

<210> SEQ ID NO 516
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 516
cgcccccgcc cctgccctgc ccacc                                     25

<210> SEQ ID NO 517
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 517
gccgcccccg ccctgccct gccca                                      25

<210> SEQ ID NO 518
<211> LENGTH: 25
<212> TYPE: DNA
<213> ORGANISM: Artificial Sequence
<220> FEATURE:
<223> OTHER INFORMATION: antisense oligomeric compound
```

<400> SEQUENCE: 518
ccgccgcccc cgccctgcc ctgcc                                          25

<210> SEQ ID NO 519
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 519
ggccgccgcc cccgcccctg ccctg                                         25

<210> SEQ ID NO 520
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 520
ctggccgccg ccccgcccc tgccc                                          25

<210> SEQ ID NO 521
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 521
ccctggccgc cgcccccgcc cctgc                                         25

<210> SEQ ID NO 522
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 522
tgccctggcc gccgccccg ccct                                           25

<210> SEQ ID NO 523
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 523
tctgccctgg ccgccgcccc cgccc                                         25

<210> SEQ ID NO 524
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 524
cctctgccct ggccgccgcc cccgc                                         25

<210> SEQ ID NO 525
<211> LENGTH: 25

-continued

```
<212> TYPE: DNA
<213> ORGANISM: Artificial Sequence
<220> FEATURE:
<223> OTHER INFORMATION: antisense oligomeric compound

<400> SEQUENCE: 525
accctctgcc ctggccgccg ccccc                                               25

<210> SEQ ID NO 526
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 526
gcaccctctg ccctggccgc cgccc                                               25

<210> SEQ ID NO 527
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 527
gcgcaccctc tgccctggcc gccgc                                               25

<210> SEQ ID NO 528
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 528
agagatgggg gtttattgat gttcc                                               25

<210> SEQ ID NO 529
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 529
gaagagatgg gggtttattg atgtt                                               25

<210> SEQ ID NO 530
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 530
tagaagagat gggggtttat tgatg                                               25

<210> SEQ ID NO 531
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 531
```
tctagaagag atggggttt attga                                    25

<210> SEQ ID NO 532
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 532
gatctagaag agatggggt ttatt                                    25

<210> SEQ ID NO 533
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 533
ttgatctaga agagatgggg gttta                                   25

<210> SEQ ID NO 534
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 534
ctttgatcta gaagagatgg gggtt                                   25

<210> SEQ ID NO 535
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 535
atctttgatc tagaagagat ggggg                                   25

<210> SEQ ID NO 536
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 536
ggatctttga tctagaagag atggg                                   25

<210> SEQ ID NO 537
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 537
ctggatcttt gatctagaag agatg                                   25

<210> SEQ ID NO 538
<211> LENGTH: 25
<212> TYPE: DNA
<213> ORGANISM: Artificial Sequence

```
<220> FEATURE:
<223> OTHER INFORMATION: antisense oligomeric compound

<400> SEQUENCE: 538
agctggatct tgatctaga agaga                                              25

<210> SEQ ID NO 539
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 539
ttagctggat ctttgatcta gaaga                                             25

<210> SEQ ID NO 540
<211> LENGTH: 25
<212> TYPE: DNA
<213> ORGANISM: Artificial Sequence
<220> FEATURE:
<223> OTHER INFORMATION: antisense oligomeric compound

<400> SEQUENCE: 540
tgttagctgg atctttgatc tagaa                                             25

<210> SEQ ID NO 541
<211> LENGTH: 368
<212> TYPE: DNA
<213> ORGANISM: Artificial Sequence
<220> FEATURE:
<223> OTHER INFORMATION: target nucleic acid

<400> SEQUENCE: 541
aaccccagag ctgcttccct tccagatgtg gtcctgcagc cgagccctgc ccttagctgg       60
aggtcgacag gtgggatcct ggatgtctac atcttcctgg gcccagagcc caagagcgtg     120
gtgcagcagt acctggacgt tgtgggtagg gcctgctccc tggccgcggc ccccgcccca     180
aggctccctc ctccctccct catgaagtcg gcgttggcct gcaggatacc cgttcatgcc     240
gccatactgg ggcctgggct tccacctgtg ccgctggggc tactcctcca ccgctatcac     300
ccgccaggtg gtggagaaca tgaccagggc ccacttcccc ctggtgagtt ggggtggtgg     360
cagggagg                                                              368

<210> SEQ ID NO 542
<211> LENGTH: 74
<212> TYPE: DNA
<213> ORGANISM: Artificial Sequence
<220> FEATURE:
<223> OTHER INFORMATION: target nucleic acid

<400> SEQUENCE: 542
aaccccagag ctgcttccct tccagatgtg gtcctgcagc cgagccctgc ccttagctgg       60
aggtcgacag gtgg                                                        74

<210> SEQ ID NO 543
<211> LENGTH: 74
<212> TYPE: DNA
<213> ORGANISM: Artificial Sequence
<220> FEATURE:
<223> OTHER INFORMATION: target nucleic acid

<400> SEQUENCE: 543
```

```
gatcctggat gtctacatct tcctgggccc agagcccaag agcgtggtgc agcagtacct    60
ggacgttgtg ggta                                                     74

<210> SEQ ID NO 544
<211> LENGTH: 74
<212> TYPE: DNA
<213> ORGANISM: Artificial Sequence
<220> FEATURE:
<223> OTHER INFORMATION: target nucleic acid

<400> SEQUENCE: 544
gggcctgctc cctggccgcg gcccccgccc caaggctccc tcctccctcc ctcatgaagt    60
cggcgttggc ctgc                                                     74

<210> SEQ ID NO 545
<211> LENGTH: 74
<212> TYPE: DNA
<213> ORGANISM: Artificial Sequence
<220> FEATURE:
<223> OTHER INFORMATION: target nucleic acid

<400> SEQUENCE: 545
aggatacccg ttcatgccgc catactgggg cctgggcttc cacctgtgcc gctggggcta    60
ctcctccacc gcta                                                     74

<210> SEQ ID NO 546
<211> LENGTH: 72
<212> TYPE: DNA
<213> ORGANISM: Artificial Sequence
<220> FEATURE:
<223> OTHER INFORMATION: target nucleic acid

<400> SEQUENCE: 546
tcacccgcca ggtggtggag aacatgacca gggcccactt ccccctggtg agttggggtg    60
gtggcagggg ag                                                       72

<210> SEQ ID NO 547
<211> LENGTH: 23
<212> TYPE: DNA
<213> ORGANISM: Artificial Sequence
<220> FEATURE:
<223> OTHER INFORMATION: primer

<400> SEQUENCE: 547
agctcctctg aaatgggcta cac                                           23

<210> SEQ ID NO 548
<211> LENGTH: 20
<212> TYPE: DNA
<213> ORGANISM: Artificial Sequence
<220> FEATURE:
<223> OTHER INFORMATION: primer

<400> SEQUENCE: 548
atccagctaa caggcgctac                                               20

<210> SEQ ID NO 549
<211> LENGTH: 20
<212> TYPE: DNA
<213> ORGANISM: Artificial Sequence
<220> FEATURE:
<223> OTHER INFORMATION: primer

<400> SEQUENCE: 549
```
ctgttctttg cggaccagtt                                                    20

<210> SEQ ID NO 550
<211> LENGTH: 20
<212> TYPE: DNA
<213> ORGANISM: Artificial Sequence
<220> FEATURE:
<223> OTHER INFORMATION: primer

<400> SEQUENCE: 550
cgaacctcta cgggtctcac                                                    20

<210> SEQ ID NO 551
<211> LENGTH: 20
<212> TYPE: DNA
<213> ORGANISM: Artificial Sequence
<220> FEATURE:
<223> OTHER INFORMATION: primer

<400> SEQUENCE: 551
cttagctgga ggtcgacagg                                                    20

<210> SEQ ID NO 552
<211> LENGTH: 18
<212> TYPE: DNA
<213> ORGANISM: Artificial Sequence
<220> FEATURE:
<223> OTHER INFORMATION: primer

<400> SEQUENCE: 552
cgttcatgcc gccatact                                                      18

<210> SEQ ID NO 553
<211> LENGTH: 20
<212> TYPE: DNA
<213> ORGANISM: Artificial Sequence
<220> FEATURE:
<223> OTHER INFORMATION: primer

<400> SEQUENCE: 553
gacgtccagt ggaacgacct                                                    20

<210> SEQ ID NO 554
<211> LENGTH: 19
<212> TYPE: DNA
<213> ORGANISM: Artificial Sequence
<220> FEATURE:
<223> OTHER INFORMATION: primer

<400> SEQUENCE: 554
atcctgccat cagcagctc                                                     19

<210> SEQ ID NO 555
<211> LENGTH: 18
<212> TYPE: DNA
<213> ORGANISM: Artificial Sequence
<220> FEATURE:
<223> OTHER INFORMATION: primer

<400> SEQUENCE: 555
cactgccttc cccgactt                                                      18

<210> SEQ ID NO 556
<211> LENGTH: 20
<212> TYPE: DNA

```
<213> ORGANISM: Artificial Sequence
<220> FEATURE:
<223> OTHER INFORMATION: primer

<400> SEQUENCE: 556
acatgaacga gccttccaac                                               20

<210> SEQ ID NO 557
<211> LENGTH: 21
<212> TYPE: DNA
<213> ORGANISM: Artificial Sequence
<220> FEATURE:
<223> OTHER INFORMATION: primer

<400> SEQUENCE: 557
cctccagcca ccagtttctc t                                             21

<210> SEQ ID NO 558
<211> LENGTH: 20
<212> TYPE: DNA
<213> ORGANISM: Artificial Sequence
<220> FEATURE:
<223> OTHER INFORMATION: primer

<400> SEQUENCE: 558
gacacgccca tttgtgatct                                               20

<210> SEQ ID NO 559
<211> LENGTH: 20
<212> TYPE: DNA
<213> ORGANISM: Artificial Sequence
<220> FEATURE:
<223> OTHER INFORMATION: primer

<400> SEQUENCE: 559
ctcagaggag ctgtgtgtgc                                               20

<210> SEQ ID NO 560
<211> LENGTH: 18
<212> TYPE: DNA
<213> ORGANISM: Artificial Sequence
<220> FEATURE:
<223> OTHER INFORMATION: primer

<400> SEQUENCE: 560
cagcaggcca tgaggaag                                                 18

<210> SEQ ID NO 561
<211> LENGTH: 20
<212> TYPE: DNA
<213> ORGANISM: Artificial Sequence
<220> FEATURE:
<223> OTHER INFORMATION: primer

<400> SEQUENCE: 561
cccaaggact ctagcacctg                                               20

<210> SEQ ID NO 562
<211> LENGTH: 19
<212> TYPE: DNA
<213> ORGANISM: Artificial Sequence
<220> FEATURE:
<223> OTHER INFORMATION: primer

<400> SEQUENCE: 562
gtgccagtag aggcccttg                                                19
```

<210> SEQ ID NO 563
<211> LENGTH: 20
<212> TYPE: DNA
<213> ORGANISM: Artificial Sequence
<220> FEATURE:
<223> OTHER INFORMATION: primer

<400> SEQUENCE: 563
gcctcacaac cacagagtcc                                               20

<210> SEQ ID NO 564
<211> LENGTH: 20
<212> TYPE: DNA
<213> ORGANISM: Artificial Sequence
<220> FEATURE:
<223> OTHER INFORMATION: primer

<400> SEQUENCE: 564
tgcagaaggt gactgtcctg                                               20

<210> SEQ ID NO 565
<211> LENGTH: 20
<212> TYPE: DNA
<213> ORGANISM: Artificial Sequence
<220> FEATURE:
<223> OTHER INFORMATION: primer

<400> SEQUENCE: 565
gggcggagtg tgttagtctc                                               20

<210> SEQ ID NO 566
<211> LENGTH: 18
<212> TYPE: DNA
<213> ORGANISM: Artificial Sequence
<220> FEATURE:
<223> OTHER INFORMATION: primer

<400> SEQUENCE: 566
aaactgaggc acggagcg                                                 18

<210> SEQ ID NO 567
<211> LENGTH: 16
<212> TYPE: DNA
<213> ORGANISM: Artificial Sequence
<220> FEATURE:
<223> OTHER INFORMATION: primer

<400> SEQUENCE: 567
ggcacggagc gggaca                                                   16

<210> SEQ ID NO 568
<211> LENGTH: 18
<212> TYPE: DNA
<213> ORGANISM: Artificial Sequence
<220> FEATURE:
<223> OTHER INFORMATION: primer

<400> SEQUENCE: 568
aggcacggag cgggatca                                                 18

<210> SEQ ID NO 569
<211> LENGTH: 23
<212> TYPE: DNA
<213> ORGANISM: Artificial Sequence
<220> FEATURE:

```
<223> OTHER INFORMATION: primer

<400> SEQUENCE: 569
ggttctcagt ctccatcatc acg                                            23

<210> SEQ ID NO 570
<211> LENGTH: 19
<212> TYPE: DNA
<213> ORGANISM: Artificial Sequence
<220> FEATURE:
<223> OTHER INFORMATION: primer

<400> SEQUENCE: 570
gctcctcgga gaactccac                                                 19

<210> SEQ ID NO 571
<211> LENGTH: 20
<212> TYPE: DNA
<213> ORGANISM: Artificial Sequence
<220> FEATURE:
<223> OTHER INFORMATION: primer

<400> SEQUENCE: 571
ctgagcatca ggggactgag                                                20

<210> SEQ ID NO 572
<211> LENGTH: 20
<212> TYPE: DNA
<213> ORGANISM: Artificial Sequence
<220> FEATURE:
<223> OTHER INFORMATION: primer

<400> SEQUENCE: 572
tgctgtttag caggaacacc                                                20

<210> SEQ ID NO 573
<211> LENGTH: 20
<212> TYPE: DNA
<213> ORGANISM: Artificial Sequence
<220> FEATURE:
<223> OTHER INFORMATION: primer

<400> SEQUENCE: 573
cacaacgtcc aggtactgct                                                20

<210> SEQ ID NO 574
<211> LENGTH: 20
<212> TYPE: DNA
<213> ORGANISM: Artificial Sequence
<220> FEATURE:
<223> OTHER INFORMATION: primer

<400> SEQUENCE: 574
ggtcatgttc tccaccacct                                                20

<210> SEQ ID NO 575
<211> LENGTH: 18
<212> TYPE: DNA
<213> ORGANISM: Artificial Sequence
<220> FEATURE:
<223> OTHER INFORMATION: primer

<400> SEQUENCE: 575
gaagtcccgg aagccatc                                                  18
```

```
<210> SEQ ID NO 576
<211> LENGTH: 20
<212> TYPE: DNA
<213> ORGANISM: Artificial Sequence
<220> FEATURE:
<223> OTHER INFORMATION: primer

<400> SEQUENCE: 576
ggtctcgttg gtgatgaaaa                                         20

<210> SEQ ID NO 577
<211> LENGTH: 20
<212> TYPE: DNA
<213> ORGANISM: Artificial Sequence
<220> FEATURE:
<223> OTHER INFORMATION: primer

<400> SEQUENCE: 577
acctggtcat ggaactcagc                                         20

<210> SEQ ID NO 578
<211> LENGTH: 20
<212> TYPE: DNA
<213> ORGANISM: Artificial Sequence
<220> FEATURE:
<223> OTHER INFORMATION: primer

<400> SEQUENCE: 578
acgtagggtg ggttctccag                                         20

<210> SEQ ID NO 579
<211> LENGTH: 18
<212> TYPE: DNA
<213> ORGANISM: Artificial Sequence
<220> FEATURE:
<223> OTHER INFORMATION: primer

<400> SEQUENCE: 579
tgtgggaggc gatggctt                                           18

<210> SEQ ID NO 580
<211> LENGTH: 18
<212> TYPE: DNA
<213> ORGANISM: Artificial Sequence
<220> FEATURE:
<223> OTHER INFORMATION: primer

<400> SEQUENCE: 580
ccaggagctc cacacgtc                                           18

<210> SEQ ID NO 581
<211> LENGTH: 20
<212> TYPE: DNA
<213> ORGANISM: Artificial Sequence
<220> FEATURE:
<223> OTHER INFORMATION: primer

<400> SEQUENCE: 581
cagactgagc aggctgttgt                                         20

<210> SEQ ID NO 582
<211> LENGTH: 19
<212> TYPE: DNA
<213> ORGANISM: Artificial Sequence
<220> FEATURE:
<223> OTHER INFORMATION: primer
```

<400> SEQUENCE: 582
ggcctggtgg aacagtgtg                                                19

<210> SEQ ID NO 583
<211> LENGTH: 20
<212> TYPE: DNA
<213> ORGANISM: Artificial Sequence
<220> FEATURE:
<223> OTHER INFORMATION: primer

<400> SEQUENCE: 583
caaggggaag tagccagtca                                               20

<210> SEQ ID NO 584
<211> LENGTH: 20
<212> TYPE: DNA
<213> ORGANISM: Artificial Sequence
<220> FEATURE:
<223> OTHER INFORMATION: primer

<400> SEQUENCE: 584
gaggtggacg ttgatggtgt                                               20

<210> SEQ ID NO 585
<211> LENGTH: 20
<212> TYPE: DNA
<213> ORGANISM: Artificial Sequence
<220> FEATURE:
<223> OTHER INFORMATION: primer

<400> SEQUENCE: 585
tctctccatc gtcccagaac                                               20

<210> SEQ ID NO 586
<211> LENGTH: 20
<212> TYPE: DNA
<213> ORGANISM: Artificial Sequence
<220> FEATURE:
<223> OTHER INFORMATION: primer

<400> SEQUENCE: 586
gggctgtagg tgaagttgga                                               20

<210> SEQ ID NO 587
<211> LENGTH: 20
<212> TYPE: DNA
<213> ORGANISM: Artificial Sequence
<220> FEATURE:
<223> OTHER INFORMATION: primer

<400> SEQUENCE: 587
ctccaggtga cacatgcaac                                               20

<210> SEQ ID NO 588
<211> LENGTH: 18
<212> TYPE: DNA
<213> ORGANISM: Artificial Sequence
<220> FEATURE:
<223> OTHER INFORMATION: primer

<400> SEQUENCE: 588
gagtgcagcg gttgccaa                                                 18

<210> SEQ ID NO 589
<211> LENGTH: 24

```
<212> TYPE: DNA
<213> ORGANISM: Artificial Sequence
<220> FEATURE:
<223> OTHER INFORMATION: primer

<400> SEQUENCE: 589
ctgttagctg gatctttgat cgtg                                       24

<210> SEQ ID NO 590
<211> LENGTH: 20
<212> TYPE: DNA
<213> ORGANISM: Artificial Sequence
<220> FEATURE:
<223> OTHER INFORMATION: primer

<400> SEQUENCE: 590
tcggagaact ccacgctgta                                            20

<210> SEQ ID NO 591
<211> LENGTH: 20
<212> TYPE: DNA
<213> ORGANISM: Artificial Sequence
<220> FEATURE:
<223> OTHER INFORMATION: primer

<400> SEQUENCE: 591
gggtgctcct ggacaactac                                            20

<210> SEQ ID NO 592
<211> LENGTH: 20
<212> TYPE: DNA
<213> ORGANISM: Artificial Sequence
<220> FEATURE:
<223> OTHER INFORMATION: primer

<400> SEQUENCE: 592
cctgttgcaa cttcttcgcc                                            20

<210> SEQ ID NO 593
<211> LENGTH: 20
<212> TYPE: DNA
<213> ORGANISM: Artificial Sequence
<220> FEATURE:
<223> OTHER INFORMATION: primer

<400> SEQUENCE: 593
atggcacctg ggaatgtacc                                            20

<210> SEQ ID NO 594
<211> LENGTH: 20
<212> TYPE: DNA
<213> ORGANISM: Artificial Sequence
<220> FEATURE:
<223> OTHER INFORMATION: primer

<400> SEQUENCE: 594
gtgttgttcc agagcccact                                            20

<210> SEQ ID NO 595
<211> LENGTH: 20
<212> TYPE: DNA
<213> ORGANISM: Artificial Sequence
<220> FEATURE:
<223> OTHER INFORMATION: primer

<400> SEQUENCE: 595
```
acgctctgaa tgtcacacga                                              20

<210> SEQ ID NO 596
<211> LENGTH: 20
<212> TYPE: DNA
<213> ORGANISM: Artificial Sequence
<220> FEATURE:
<223> OTHER INFORMATION: primer

<400> SEQUENCE: 596
gttggcagcc agtcagagat                                              20

<210> SEQ ID NO 597
<211> LENGTH: 20
<212> TYPE: DNA
<213> ORGANISM: Artificial Sequence
<220> FEATURE:
<223> OTHER INFORMATION: primer

<400> SEQUENCE: 597
aaaaagcagt gggctctgga                                              20

<210> SEQ ID NO 598
<211> LENGTH: 20
<212> TYPE: DNA
<213> ORGANISM: Artificial Sequence
<220> FEATURE:
<223> OTHER INFORMATION: primer

<400> SEQUENCE: 598
cggtgaagag tccacgaagt                                              20

<210> SEQ ID NO 599
<211> LENGTH: 20
<212> TYPE: DNA
<213> ORGANISM: Artificial Sequence
<220> FEATURE:
<223> OTHER INFORMATION: primer

<400> SEQUENCE: 599
cagaagggcg tgaagaaccg                                              20

<210> SEQ ID NO 600
<211> LENGTH: 22
<212> TYPE: DNA
<213> ORGANISM: Artificial Sequence
<220> FEATURE:
<223> OTHER INFORMATION: primer

<400> SEQUENCE: 600
cccgtgagga gtttccaatt tc                                           22

<210> SEQ ID NO 601
<211> LENGTH: 20
<212> TYPE: DNA
<213> ORGANISM: Artificial Sequence
<220> FEATURE:
<223> OTHER INFORMATION: primer

<400> SEQUENCE: 601
acttcgtgga ctcttcaccg                                              20

<210> SEQ ID NO 602
<211> LENGTH: 20
<212> TYPE: DNA
<213> ORGANISM: Artificial Sequence

```
<220> FEATURE:
<223> OTHER INFORMATION: primer

<400> SEQUENCE: 602
agtacacggg gactgagtgt                                              20

<210> SEQ ID NO 603
<211> LENGTH: 29
<212> TYPE: DNA
<213> ORGANISM: Artificial Sequence
<220> FEATURE:
<223> OTHER INFORMATION: primer

<400> SEQUENCE: 603
gcgcctgcag taacaacata ggagctgtg                                    29

<210> SEQ ID NO 604
<211> LENGTH: 30
<212> TYPE: DNA
<213> ORGANISM: Artificial Sequence
<220> FEATURE:
<223> OTHER INFORMATION: primer

<400> SEQUENCE: 604
gcgcgtcgac cagatacgcg tttcctagga                                   30

<210> SEQ ID NO 605
<211> LENGTH: 38
<212> TYPE: DNA
<213> ORGANISM: Artificial Sequence
<220> FEATURE:
<223> OTHER INFORMATION: primer

<400> SEQUENCE: 605
gctcttttag aatttttgga gcaggttttc tgacttcg                          38

<210> SEQ ID NO 606
<211> LENGTH: 38
<212> TYPE: DNA
<213> ORGANISM: Artificial Sequence
<220> FEATURE:
<223> OTHER INFORMATION: primer

<400> SEQUENCE: 606
cgaagtcaga aaacctgctc caaaaattct aaaagagc                          38

<210> SEQ ID NO 607
<211> LENGTH: 39
<212> TYPE: DNA
<213> ORGANISM: Artificial Sequence
<220> FEATURE:
<223> OTHER INFORMATION: primer

<400> SEQUENCE: 607
cctggctcgc tacagaggcc tttccgcaag tgttacagc                         39

<210> SEQ ID NO 608
<211> LENGTH: 39
<212> TYPE: DNA
<213> ORGANISM: Artificial Sequence
<220> FEATURE:
<223> OTHER INFORMATION: primer

<400> SEQUENCE: 608
gctgtaacac ttgcggaaag gcctctgtag cgagccagg                         39
```

<210> SEQ ID NO 609
<211> LENGTH: 16
<212> TYPE: DNA
<213> ORGANISM: Artificial Sequence
<220> FEATURE:
<223> OTHER INFORMATION: primer

<400> SEQUENCE: 609
gtaaaacgac ggccag                                                      16

<210> SEQ ID NO 610
<211> LENGTH: 17
<212> TYPE: DNA
<213> ORGANISM: Artificial Sequence
<220> FEATURE:
<223> OTHER INFORMATION: primer

<400> SEQUENCE: 610
caggaaacag ctatgac                                                     17

<210> SEQ ID NO 611
<211> LENGTH: 37
<212> TYPE: DNA
<213> ORGANISM: Artificial Sequence
<220> FEATURE:
<223> OTHER INFORMATION: primer

<400> SEQUENCE: 611
cctggctcgc tacagatgca taggaggacg gaggacg                               37

<210> SEQ ID NO 612
<211> LENGTH: 37
<212> TYPE: DNA
<213> ORGANISM: Artificial Sequence
<220> FEATURE:
<223> OTHER INFORMATION: primer

<400> SEQUENCE: 612
cgtcctccgt cctcctatgc atctgtagcg agccagg                               37

<210> SEQ ID NO 613
<211> LENGTH: 10
<212> TYPE: DNA
<213> ORGANISM: Artificial Sequence
<220> FEATURE:
<223> OTHER INFORMATION: primer first part before antisense insert

<400> SEQUENCE: 613
gcgcatgcat                                                             10

<210> SEQ ID NO 614
<211> LENGTH: 30
<212> TYPE: DNA
<213> ORGANISM: Artificial Sequence
<220> FEATURE:
<223> OTHER INFORMATION: primer

<400> SEQUENCE: 614
gcgcgtcgac cagatacgcg tttcctagga                                       30

<210> SEQ ID NO 615
<211> LENGTH: 16
<212> TYPE: DNA
<213> ORGANISM: Artificial Sequence
<220> FEATURE:
<223> OTHER INFORMATION: exemplary U7 hairpin sequence

```
<400> SEQUENCE: 615
ggctcttttc agagcc                                                       16

<210> SEQ ID NO 616
<211> LENGTH: 16
<212> TYPE: DNA
<213> ORGANISM: Artificial Sequence
<220> FEATURE:
<223> OTHER INFORMATION: conserved exemplary U7 hairpin sequence

<400> SEQUENCE: 616 ggcyctttm agrgcc                                                        16

<210> SEQ ID NO 617
<211> LENGTH: 10
<212> TYPE: DNA
<213> ORGANISM: Artificial Sequence
<220> FEATURE:
<223> OTHER INFORMATION: primer SEQ 613) second part after antisense
      insert

<400> SEQUENCE: 617
ttggagcagg                                                              10

<210> SEQ ID NO 618
<211> LENGTH: 20
<212> TYPE: DNA
<213> ORGANISM: Artificial Sequence
<220> FEATURE:
<223> OTHER INFORMATION: Fig. 1 example

<400> SEQUENCE: 618
ggccaggaat aacacgatcg                                                   20

<210> SEQ ID NO 619
<211> LENGTH: 20
<212> TYPE: DNA
<213> ORGANISM: Artificial Sequence
<220> FEATURE:
<223> OTHER INFORMATION: Fig. 9 product 1

<400> SEQUENCE: 619
cacggagcgg gcctgtagga                                                   20

<210> SEQ ID NO 620
<211> LENGTH: 19
<212> TYPE: DNA
<213> ORGANISM: Artificial Sequence
<220> FEATURE:
<223> OTHER INFORMATION: Fig. 9 Product 1

<400> SEQUENCE: 620
cacttcacga tcaaagatc                                                    19

<210> SEQ ID NO 621
<211> LENGTH: 19
<212> TYPE: DNA
<213> ORGANISM: Artificial Sequence
<220> FEATURE:
<223> OTHER INFORMATION: Fig. 9 Product 2

<400> SEQUENCE: 621
cacggacggg acatcctga                                                    19
```

```
<210> SEQ ID NO 622
<211> LENGTH: 20
<212> TYPE: DNA
<213> ORGANISM: Artificial Sequence
<220> FEATURE:
<223> OTHER INFORMATION: Fig. 9 Product 3

<400> SEQUENCE: 622
cacggagcgg atcaaagatc                                              20

<210> SEQ ID NO 623
<211> LENGTH: 20
<212> TYPE: DNA
<213> ORGANISM: Artificial Sequence
<220> FEATURE:
<223> OTHER INFORMATION: Fig. 10 product 4

<400> SEQUENCE: 623 cccectgcag ggccctggcc                                              20

<210> SEQ ID NO 624
<211> LENGTH: 20
<212> TYPE: DNA
<213> ORGANISM: Artificial Sequence
<220> FEATURE:
<223> OTHER INFORMATION: Fig. 10 Product 4

<400> SEQUENCE: 624
ggccaggaat aacacgatcg                                              20

<210> SEQ ID NO 625
<211> LENGTH: 20
<212> TYPE: DNA
<213> ORGANISM: Artificial Sequence
<220> FEATURE:
<223> OTHER INFORMATION: Fig. 10 Product 5

<400> SEQUENCE: 625 cccectgcag aacacgatcg                                              20

<210> SEQ ID NO 626
<211> LENGTH: 20
<212> TYPE: DNA
<213> ORGANISM: Artificial Sequence
<220> FEATURE:
<223> OTHER INFORMATION: Fig. 10 Product 6

<400> SEQUENCE: 626
cacggagcgg gcctgtagga                                              20

<210> SEQ ID NO 627
<211> LENGTH: 19
<212> TYPE: DNA
<213> ORGANISM: Artificial Sequence
<220> FEATURE:
<223> OTHER INFORMATION: Fig. 10 Product 6

<400> SEQUENCE: 627
cacttcacga tcaaagatc                                               19

<210> SEQ ID NO 628
<211> LENGTH: 20
<212> TYPE: DNA
<213> ORGANISM: Artificial Sequence
<220> FEATURE:
<223> OTHER INFORMATION: Fig. 10 Product 7
```

-continued

<400> SEQUENCE: 628
cacggagcgg gacatcctga                                          20

<210> SEQ ID NO 629
<211> LENGTH: 20
<212> TYPE: DNA
<213> ORGANISM: Artificial Sequence
<220> FEATURE:
<223> OTHER INFORMATION: Fig. 10 Product 8

<400> SEQUENCE: 629
cacggagcgg atcaaagatc                                          20

<210> SEQ ID NO 630
<211> LENGTH: 21
<212> TYPE: DNA
<213> ORGANISM: Artificial Sequence
<220> FEATURE:
<223> OTHER INFORMATION: Fig. 10 Product 9

<400> SEQUENCE: 630
gattgggaaa ggtatggccc g                                        21

<210> SEQ ID NO 631
<211> LENGTH: 20
<212> TYPE: DNA
<213> ORGANISM: Artificial Sequence
<220> FEATURE:
<223> OTHER INFORMATION: Fig. 10 Product 9

<400> SEQUENCE: 631
catgtggatt gacatgaacg                                          20

<210> SEQ ID NO 632
<211> LENGTH: 20
<212> TYPE: DNA
<213> ORGANISM: Artificial Sequence
<220> FEATURE:
<223> OTHER INFORMATION: Fig. 10 Product 10

<400> SEQUENCE: 632
gattgggaag gacatgaacg                                          20

Figure 11B:
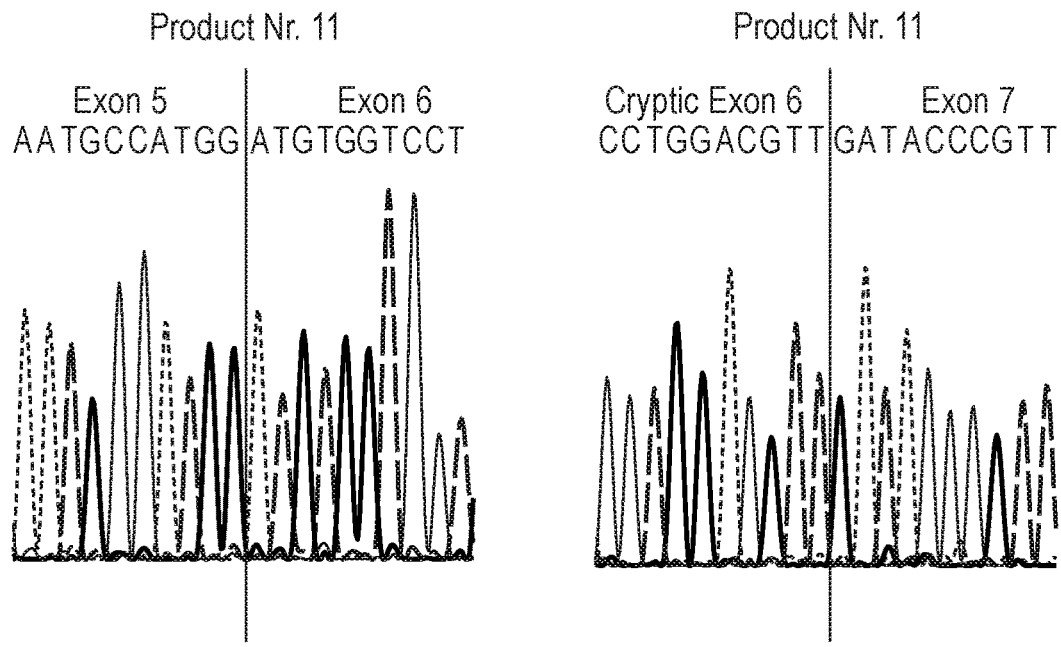

<210> SEQ ID NO 633
<211> LENGTH: 20
<212> TYPE: DNA
<213> ORGANISM: Artificial Sequence
<220> FEATURE:
<223> OTHER INFORMATION: Fig. 11 Product 11

<400> SEQUENCE: 633
aatgccatgg atgtggtcct                                          20

<210> SEQ ID NO 634
<211> LENGTH: 21
<212> TYPE: DNA
<213> ORGANISM: Artificial Sequence
<220> FEATURE:
<223> OTHER INFORMATION: Fig. 11 Product 11

<400> SEQUENCE: 634
cctggacgtt gatacccgtt g                                        21

<210> SEQ ID NO 635
<211> LENGTH: 20

-continued

```
<212> TYPE: DNA
<213> ORGANISM: Artificial Sequence
<220> FEATURE:
<223> OTHER INFORMATION: Fig. 11 product 12

<400> SEQUENCE: 635
gattgggaag gtatggcccg                                               20

<210> SEQ ID NO 636
<211> LENGTH: 20
<212> TYPE: DNA
<213> ORGANISM: Artificial Sequence
<220> FEATURE:
<223> OTHER INFORMATION: Fig. 11 product 12

<400> SEQUENCE: 636
catgtggatt gtaagtgtgg                                               20

<210> SEQ ID NO 637
<211> LENGTH: 20
<212> TYPE: DNA
<213> ORGANISM: Artificial Sequence
<220> FEATURE:
<223> OTHER INFORMATION: Fig. 11 Product 12

<400> SEQUENCE: 637
tctcttggag gacatgaacg                                               20

<210> SEQ ID NO 638
<211> LENGTH: 20
<212> TYPE: DNA
<213> ORGANISM: Artificial Sequence
<220> FEATURE:
<223> OTHER INFORMATION: Fig. 11 Product 13

<400> SEQUENCE: 638
catgtggatt gacatgaacg                                               20

<210> SEQ ID NO 639
<211> LENGTH: 20
<212> TYPE: DNA
<213> ORGANISM: Artificial Sequence
<220> FEATURE:
<223> OTHER INFORMATION: Fig. 11 product 14

<400> SEQUENCE: 639
gattgggaag agtcacctac                                               20

<210> SEQ ID NO 640
<211> LENGTH: 20
<212> TYPE: DNA
<213> ORGANISM: Artificial Sequence
<220> FEATURE:
<223> OTHER INFORMATION: Fig. 11 Product 15

<400> SEQUENCE: 640
gatcatcgtg gatcctgcca                                               20

<210> SEQ ID NO 641
<211> LENGTH: 20
<212> TYPE: DNA
<213> ORGANISM: Artificial Sequence
<220> FEATURE:
<223> OTHER INFORMATION: Fig. 11 Product 15

<400> SEQUENCE: 641
```
gattgggaag gtatggcccg                                           20

<210> SEQ ID NO 642
<211> LENGTH: 20
<212> TYPE: DNA
<213> ORGANISM: Artificial Sequence
<220> FEATURE:
<223> OTHER INFORMATION: Fig. 11 Product 16

<400> SEQUENCE: 642
gatcatcgtg gtatggcccg                                           20

<210> SEQ ID NO 643
<211> LENGTH: 20
<212> TYPE: DNA
<213> ORGANISM: Artificial Sequence
<220> FEATURE:
<223> OTHER INFORMATION: Fig. 12 Product 17

<400> SEQUENCE: 643 cttcccctg gacgtccaat                                            20

<210> SEQ ID NO 644
<211> LENGTH: 20
<212> TYPE: DNA
<213> ORGANISM: Artificial Sequence
<220> FEATURE:
<223> OTHER INFORMATION: Fig. 12 Product 17

<400> SEQUENCE: 644
gatcatcgtg gatcctgcca                                           20

<210> SEQ ID NO 645
<211> LENGTH: 20
<212> TYPE: DNA
<213> ORGANISM: Artificial Sequence
<220> FEATURE:
<223> OTHER INFORMATION: Fig. 12 Product 18

<400> SEQUENCE: 645
gttcaacaag gatcctgcca                                           20

<210> SEQ ID NO 646
<211> LENGTH: 20
<212> TYPE: DNA
<213> ORGANISM: Artificial Sequence
<220> FEATURE:
<223> OTHER INFORMATION: Fig. 12 product 19

<400> SEQUENCE: 646
gattgggaag gtatggcccg                                           20

<210> SEQ ID NO 647
<211> LENGTH: 20
<212> TYPE: DNA
<213> ORGANISM: Artificial Sequence
<220> FEATURE:
<223> OTHER INFORMATION: Fig. 12 Product 21

<400> SEQUENCE: 647
catgtggatt gacatgaacg                                           20

<210> SEQ ID NO 648
<211> LENGTH: 20
<212> TYPE: DNA
<213> ORGANISM: Artificial Sequence
<220> FEATURE:
<223> OTHER INFORMATION: Fig. 12 Product 22

<400> SEQUENCE: 648
gattgggaag gacatgaacg                                        20

<210> SEQ ID NO 649
<211> LENGTH: 18
<212> TYPE: DNA
<213> ORGANISM: Artificial Sequence
<220> FEATURE:
<223> OTHER INFORMATION: primer

<400> SEQUENCE: 649
aaactgaggc acggagcg                                          18

<210> SEQ ID NO 650
<211> LENGTH: 18
<212> TYPE: DNA
<213> ORGANISM: Artificial Sequence
<220> FEATURE:
<223> OTHER INFORMATION: primer

<400> SEQUENCE: 650
gaagggctcc tcggagaa                                          18

<210> SEQ ID NO 651
<211> LENGTH: 22
<212> TYPE: DNA
<213> ORGANISM: Artificial Sequence
<220> FEATURE:
<223> OTHER INFORMATION: primer

<400> SEQUENCE: 651
agctcctctg aaatgggcta ca                                     22

<210> SEQ ID NO 652
<211> LENGTH: 19
<212> TYPE: DNA
<213> ORGANISM: Artificial Sequence
<220> FEATURE:
<223> OTHER INFORMATION: primer

<400> SEQUENCE: 652
gcaaggtccc ggttccaca                                         19

<210> SEQ ID NO 653
<211> LENGTH: 20
<212> TYPE: DNA
<213> ORGANISM: Artificial Sequence
<220> FEATURE:
<223> OTHER INFORMATION: primer

<400> SEQUENCE: 653
gctaacaggc gctacgaggt                                        20

<210> SEQ ID NO 654
<211> LENGTH: 21
<212> TYPE: DNA
<213> ORGANISM: Artificial Sequence
<220> FEATURE:
<223> OTHER INFORMATION: primer

<400> SEQUENCE: 654
tgctgtttag caggaacacc c                                      21

<210> SEQ ID NO 655
<211> LENGTH: 21
<212> TYPE: DNA
<213> ORGANISM: Artificial Sequence
<220> FEATURE:
<223> OTHER INFORMATION: primer

<400> SEQUENCE: 655
ctgttctttg cggaccagtt c                                    21

<210> SEQ ID NO 656
<211> LENGTH: 21
<212> TYPE: DNA
<213> ORGANISM: Artificial Sequence
<220> FEATURE:
<223> OTHER INFORMATION: primer

<400> SEQUENCE: 656
ccacaacgtc caggtactgc t                                    21

<210> SEQ ID NO 657
<211> LENGTH: 21
<212> TYPE: DNA
<213> ORGANISM: Artificial Sequence
<220> FEATURE:
<223> OTHER INFORMATION: primer

<400> SEQUENCE: 657
ggtctcaccc tttctacctg g                                    21

<210> SEQ ID NO 658
<211> LENGTH: 21
<212> TYPE: DNA
<213> ORGANISM: Artificial Sequence
<220> FEATURE:
<223> OTHER INFORMATION: primer

<400> SEQUENCE: 658
gtgatagcgg tggaggagta g                                    21

<210> SEQ ID NO 659
<211> LENGTH: 21
<212> TYPE: DNA
<213> ORGANISM: Artificial Sequence
<220> FEATURE:
<223> OTHER INFORMATION: primer

<400> SEQUENCE: 659
cagcagtacc tggacgttgt g                                    21

<210> SEQ ID NO 660
<211> LENGTH: 22
<212> TYPE: DNA
<213> ORGANISM: Artificial Sequence
<220> FEATURE:
<223> OTHER INFORMATION: primer

<400> SEQUENCE: 660
agtccatgta gtccaggtcg tt                                   22

<210> SEQ ID NO 661
<211> LENGTH: 18
<212> TYPE: DNA
<213> ORGANISM: Artificial Sequence
<220> FEATURE:
<223> OTHER INFORMATION: primer -continued

<400> SEQUENCE: 661
cgttcatgcc gccatact                                                    18

<210> SEQ ID NO 662
<211> LENGTH: 21
<212> TYPE: DNA
<213> ORGANISM: Artificial Sequence
<220> FEATURE:
<223> OTHER INFORMATION: primer

<400> SEQUENCE: 662
ggtctcgttg gtgatgaaaa c                                                21

<210> SEQ ID NO 663
<211> LENGTH: 20
<212> TYPE: DNA
<213> ORGANISM: Artificial Sequence
<220> FEATURE:
<223> OTHER INFORMATION: primer

<400> SEQUENCE: 663
gacgtccagt ggaacgacct                                                  20

<210> SEQ ID NO 664
<211> LENGTH: 20
<212> TYPE: DNA
<213> ORGANISM: Artificial Sequence
<220> FEATURE:
<223> OTHER INFORMATION: primer

<400> SEQUENCE: 664
acctggtcat ggaactcagc                                                  20

<210> SEQ ID NO 665
<211> LENGTH: 19
<212> TYPE: DNA
<213> ORGANISM: Artificial Sequence
<220> FEATURE:
<223> OTHER INFORMATION: primer

<400> SEQUENCE: 665
gatcctgcca tcagcagct                                                   19

<210> SEQ ID NO 666
<211> LENGTH: 20
<212> TYPE: DNA
<213> ORGANISM: Artificial Sequence
<220> FEATURE:
<223> OTHER INFORMATION: primer

<400> SEQUENCE: 666
tgggttctcc agctcattgt                                                  20

<210> SEQ ID NO 667
<211> LENGTH: 20
<212> TYPE: DNA
<213> ORGANISM: Artificial Sequence
<220> FEATURE:
<223> OTHER INFORMATION: primer

<400> SEQUENCE: 667
aggacatggt ggctgagttc                                                  20

<210> SEQ ID NO 668

```
<211> LENGTH: 22
<212> TYPE: DNA
<213> ORGANISM: Artificial Sequence
<220> FEATURE:
<223> OTHER INFORMATION: primer

<400> SEQUENCE: 668
cgtagaggtt gtgcaggttg ta                                              22

<210> SEQ ID NO 669
<211> LENGTH: 21
<212> TYPE: DNA
<213> ORGANISM: Artificial Sequence
<220> FEATURE:
<223> OTHER INFORMATION: primer

<400> SEQUENCE: 669
aacgagcctt ccaacttcat c                                               21

<210> SEQ ID NO 670
<211> LENGTH: 20
<212> TYPE: DNA
<213> ORGANISM: Artificial Sequence
<220> FEATURE:
<223> OTHER INFORMATION: primer

<400> SEQUENCE: 670
gagcgggaga tcacaaatgg                                                 20

<210> SEQ ID NO 671
<211> LENGTH: 23
<212> TYPE: DNA
<213> ORGANISM: Artificial Sequence
<220> FEATURE:
<223> OTHER INFORMATION: primer

<400> SEQUENCE: 671
caccagtttc tctccacaca cta                                             23

<210> SEQ ID NO 672
<211> LENGTH: 20
<212> TYPE: DNA
<213> ORGANISM: Artificial Sequence
<220> FEATURE:
<223> OTHER INFORMATION: primer

<400> SEQUENCE: 672
gttccgcatg aagggtaga                                                  20

<210> SEQ ID NO 673
<211> LENGTH: 20
<212> TYPE: DNA
<213> ORGANISM: Artificial Sequence
<220> FEATURE:
<223> OTHER INFORMATION: primer

<400> SEQUENCE: 673
acacgcccat ttgtgatctc                                                 20

<210> SEQ ID NO 674
<211> LENGTH: 21
<212> TYPE: DNA
<213> ORGANISM: Artificial Sequence
<220> FEATURE:
<223> OTHER INFORMATION: primer

<400> SEQUENCE: 674
```
gtgtagaggt gggggaggag t                                    21

<210> SEQ ID NO 675
<211> LENGTH: 23
<212> TYPE: DNA
<213> ORGANISM: Artificial Sequence
<220> FEATURE:
<223> OTHER INFORMATION: primer

<400> SEQUENCE: 675
aaatcctgca gtttaacctg ctg                                  23

<210> SEQ ID NO 676
<211> LENGTH: 19
<212> TYPE: DNA
<213> ORGANISM: Artificial Sequence
<220> FEATURE:
<223> OTHER INFORMATION: primer

<400> SEQUENCE: 676
gcaggtcgta ccatgtgcc                                       19

<210> SEQ ID NO 677
<211> LENGTH: 20
<212> TYPE: DNA
<213> ORGANISM: Artificial Sequence
<220> FEATURE:
<223> OTHER INFORMATION: primer

<400> SEQUENCE: 677
gagccgtaca gcttcagcga                                      20

<210> SEQ ID NO 678
<211> LENGTH: 19
<212> TYPE: DNA
<213> ORGANISM: Artificial Sequence
<220> FEATURE:
<223> OTHER INFORMATION: primer

<400> SEQUENCE: 678
atgtacccag cccggaggt                                       19

<210> SEQ ID NO 679
<211> LENGTH: 19
<212> TYPE: DNA
<213> ORGANISM: Artificial Sequence
<220> FEATURE:
<223> OTHER INFORMATION: primer

<400> SEQUENCE: 679
cctggactgt ggaccacca                                       19

<210> SEQ ID NO 680
<211> LENGTH: 23
<212> TYPE: DNA
<213> ORGANISM: Artificial Sequence
<220> FEATURE:
<223> OTHER INFORMATION: primer

<400> SEQUENCE: 680
caggaagatg acctgtgtgt agg                                  23

<210> SEQ ID NO 681
<211> LENGTH: 19
<212> TYPE: DNA

```
<213> ORGANISM: Artificial Sequence
<220> FEATURE:
<223> OTHER INFORMATION: primer

<400> SEQUENCE: 681
gtgccagtag aggcccttg                                               19

<210> SEQ ID NO 682
<211> LENGTH: 22
<212> TYPE: DNA
<213> ORGANISM: Artificial Sequence
<220> FEATURE:
<223> OTHER INFORMATION: primer

<400> SEQUENCE: 682
ggctgtaggt gaagttggag ac                                           22

<210> SEQ ID NO 683
<211> LENGTH: 19
<212> TYPE: DNA
<213> ORGANISM: Artificial Sequence
<220> FEATURE:
<223> OTHER INFORMATION: primer

<400> SEQUENCE: 683
tcacaaccac agagtcccg                                               19

<210> SEQ ID NO 684
<211> LENGTH: 22
<212> TYPE: DNA
<213> ORGANISM: Artificial Sequence
<220> FEATURE:
<223> OTHER INFORMATION: primer

<400> SEQUENCE: 684
agaaactgct ctcccatcaa ca                                           22

<210> SEQ ID NO 685
<211> LENGTH: 19
<212> TYPE: DNA
<213> ORGANISM: Artificial Sequence
<220> FEATURE:
<223> OTHER INFORMATION: primer

<400> SEQUENCE: 685
aaccgcgaga agatgaccc                                               19

<210> SEQ ID NO 686
<211> LENGTH: 21
<212> TYPE: DNA
<213> ORGANISM: Artificial Sequence
<220> FEATURE:
<223> OTHER INFORMATION: primer

<400> SEQUENCE: 686
gccagaggcg tacagggata g                                            21

<210> SEQ ID NO 687
<211> LENGTH: 23
<212> TYPE: DNA
<213> ORGANISM: Artificial Sequence
<220> FEATURE:
<223> OTHER INFORMATION: primer

<400> SEQUENCE: 687
agctcctctg aaatgggcta cac                                          23
```

<210> SEQ ID NO 688
<211> LENGTH: 23
<212> TYPE: DNA
<213> ORGANISM: Artificial Sequence
<220> FEATURE:
<223> OTHER INFORMATION: primer

<400> SEQUENCE: 688
ggttctcagt ctccatcatc acg                                          23

<210> SEQ ID NO 689
<211> LENGTH: 20
<212> TYPE: DNA
<213> ORGANISM: Artificial Sequence
<220> FEATURE:
<223> OTHER INFORMATION: primer

<400> SEQUENCE: 689
atccagctaa caggcgctac                                              20

<210> SEQ ID NO 690
<211> LENGTH: 19
<212> TYPE: DNA
<213> ORGANISM: Artificial Sequence
<220> FEATURE:
<223> OTHER INFORMATION: primer

<400> SEQUENCE: 690
gctcctcgga gaactccac                                               19

<210> SEQ ID NO 691
<211> LENGTH: 20
<212> TYPE: DNA
<213> ORGANISM: Artificial Sequence
<220> FEATURE:
<223> OTHER INFORMATION: primer

<400> SEQUENCE: 691
ctgttctttg cggaccagtt                                              20

<210> SEQ ID NO 692
<211> LENGTH: 20
<212> TYPE: DNA
<213> ORGANISM: Artificial Sequence
<220> FEATURE:
<223> OTHER INFORMATION: primer

<400> SEQUENCE: 692
ctgagcatca ggggactgag                                              20

<210> SEQ ID NO 693
<211> LENGTH: 20
<212> TYPE: DNA
<213> ORGANISM: Artificial Sequence
<220> FEATURE:
<223> OTHER INFORMATION: primer

<400> SEQUENCE: 693
cgaacctcta cgggtctcac                                              20

<210> SEQ ID NO 694
<211> LENGTH: 20
<212> TYPE: DNA
<213> ORGANISM: Artificial Sequence
<220> FEATURE:

<223> OTHER INFORMATION: primer

<400> SEQUENCE: 694
tgctgtttag caggaacacc                                               20

<210> SEQ ID NO 695
<211> LENGTH: 20
<212> TYPE: DNA
<213> ORGANISM: Artificial Sequence
<220> FEATURE:
<223> OTHER INFORMATION: primer

<400> SEQUENCE: 695
cttagctgga ggtcgacagg                                               20

<210> SEQ ID NO 696
<211> LENGTH: 20
<212> TYPE: DNA
<213> ORGANISM: Artificial Sequence
<220> FEATURE:
<223> OTHER INFORMATION: primer

<400> SEQUENCE: 696
cacaacgtcc aggtactgct                                               20

<210> SEQ ID NO 697
<211> LENGTH: 18
<212> TYPE: DNA
<213> ORGANISM: Artificial Sequence
<220> FEATURE:
<223> OTHER INFORMATION: primer

<400> SEQUENCE: 697
cgttcatgcc gccatact                                                 18

<210> SEQ ID NO 698
<211> LENGTH: 20
<212> TYPE: DNA
<213> ORGANISM: Artificial Sequence
<220> FEATURE:
<223> OTHER INFORMATION: primer

<400> SEQUENCE: 698
ggtcatgttc tccaccacct                                               20

<210> SEQ ID NO 699
<211> LENGTH: 20
<212> TYPE: DNA
<213> ORGANISM: Artificial Sequence
<220> FEATURE:
<223> OTHER INFORMATION: primer

<400> SEQUENCE: 699
gacgtccagt ggaacgacct                                               20

<210> SEQ ID NO 700
<211> LENGTH: 18
<212> TYPE: DNA
<213> ORGANISM: Artificial Sequence
<220> FEATURE:
<223> OTHER INFORMATION: primer

<400> SEQUENCE: 700
gaagtcccgg aagccatc                                                 18

```
<210> SEQ ID NO 701
<211> LENGTH: 19
<212> TYPE: DNA
<213> ORGANISM: Artificial Sequence
<220> FEATURE:
<223> OTHER INFORMATION: primer

<400> SEQUENCE: 701
atcctgccat cagcagctc                                                    19

<210> SEQ ID NO 702
<211> LENGTH: 20
<212> TYPE: DNA
<213> ORGANISM: Artificial Sequence
<220> FEATURE:
<223> OTHER INFORMATION: primer

<400> SEQUENCE: 702
ggtctcgttg gtgatgaaaa                                                   20

<210> SEQ ID NO 703
<211> LENGTH: 18
<212> TYPE: DNA
<213> ORGANISM: Artificial Sequence
<220> FEATURE:
<223> OTHER INFORMATION: primer

<400> SEQUENCE: 703
cactgccttc cccgactt                                                     18

<210> SEQ ID NO 704
<211> LENGTH: 20
<212> TYPE: DNA
<213> ORGANISM: Artificial Sequence
<220> FEATURE:
<223> OTHER INFORMATION: primer

<400> SEQUENCE: 704
acctggtcat ggaactcagc                                                   20

<210> SEQ ID NO 705
<211> LENGTH: 20
<212> TYPE: DNA
<213> ORGANISM: Artificial Sequence
<220> FEATURE:
<223> OTHER INFORMATION: primer

<400> SEQUENCE: 705
acatgaacga gccttccaac                                                   20

<210> SEQ ID NO 706
<211> LENGTH: 20
<212> TYPE: DNA
<213> ORGANISM: Artificial Sequence
<220> FEATURE:
<223> OTHER INFORMATION: primer

<400> SEQUENCE: 706
acgtagggtg ggttctccag                                                   20

<210> SEQ ID NO 707
<211> LENGTH: 21
<212> TYPE: DNA
<213> ORGANISM: Artificial Sequence
<220> FEATURE:
<223> OTHER INFORMATION: primer
```

```
<400> SEQUENCE: 707
cctccagcca ccagtttctc t                                               21

<210> SEQ ID NO 708
<211> LENGTH: 18
<212> TYPE: DNA
<213> ORGANISM: Artificial Sequence
<220> FEATURE:
<223> OTHER INFORMATION: primer

<400> SEQUENCE: 708
tgtgggaggc gatggctt                                                   18

<210> SEQ ID NO 709
<211> LENGTH: 20
<212> TYPE: DNA
<213> ORGANISM: Artificial Sequence
<220> FEATURE:
<223> OTHER INFORMATION: primer

<400> SEQUENCE: 709
gacacgccca tttgtgatct                                                 20

<210> SEQ ID NO 710
<211> LENGTH: 18
<212> TYPE: DNA
<213> ORGANISM: Artificial Sequence
<220> FEATURE:
<223> OTHER INFORMATION: primer

<400> SEQUENCE: 710
ccaggagctc cacacgtc                                                   18

<210> SEQ ID NO 711
<211> LENGTH: 20
<212> TYPE: DNA
<213> ORGANISM: Artificial Sequence
<220> FEATURE:
<223> OTHER INFORMATION: primer

<400> SEQUENCE: 711
ctcagaggag ctgtgtgtgc                                                 20

<210> SEQ ID NO 712
<211> LENGTH: 20
<212> TYPE: DNA
<213> ORGANISM: Artificial Sequence
<220> FEATURE:
<223> OTHER INFORMATION: primer

<400> SEQUENCE: 712
cagactgagc aggctgttgt                                                 20

<210> SEQ ID NO 713
<211> LENGTH: 18
<212> TYPE: DNA
<213> ORGANISM: Artificial Sequence
<220> FEATURE:
<223> OTHER INFORMATION: primer

<400> SEQUENCE: 713
cagcaggcca tgaggaag                                                   18

<210> SEQ ID NO 714
<211> LENGTH: 19
```

```
<212> TYPE: DNA
<213> ORGANISM: Artificial Sequence
<220> FEATURE:
<223> OTHER INFORMATION: primer

<400> SEQUENCE: 714
ggcctggtgg aacagtgtg                                                   19

<210> SEQ ID NO 715
<211> LENGTH: 20
<212> TYPE: DNA
<213> ORGANISM: Artificial Sequence
<220> FEATURE:
<223> OTHER INFORMATION: primer

<400> SEQUENCE: 715
cccaaggact ctagcacctg                                                  20

<210> SEQ ID NO 716
<211> LENGTH: 20
<212> TYPE: DNA
<213> ORGANISM: Artificial Sequence
<220> FEATURE:
<223> OTHER INFORMATION: primer

<400> SEQUENCE: 716 caagggaag tagccagtca                                                   20

<210> SEQ ID NO 717
<211> LENGTH: 19
<212> TYPE: DNA
<213> ORGANISM: Artificial Sequence
<220> FEATURE:
<223> OTHER INFORMATION: primer

<400> SEQUENCE: 717
gtgccagtag aggcccttg                                                   19

<210> SEQ ID NO 718
<211> LENGTH: 20
<212> TYPE: DNA
<213> ORGANISM: Artificial Sequence
<220> FEATURE:
<223> OTHER INFORMATION: primer

<400> SEQUENCE: 718
gaggtggacg ttgatggtgt                                                  20

<210> SEQ ID NO 719
<211> LENGTH: 20
<212> TYPE: DNA
<213> ORGANISM: Artificial Sequence
<220> FEATURE:
<223> OTHER INFORMATION: primer

<400> SEQUENCE: 719
gcctcacaac cacagagtcc                                                  20

<210> SEQ ID NO 720
<211> LENGTH: 20
<212> TYPE: DNA
<213> ORGANISM: Artificial Sequence
<220> FEATURE:
<223> OTHER INFORMATION: primer

<400> SEQUENCE: 720
```
tctctccatc gtcccagaac        20

<210> SEQ ID NO 721
<211> LENGTH: 20
<212> TYPE: DNA
<213> ORGANISM: Artificial Sequence
<220> FEATURE:
<223> OTHER INFORMATION: primer

<400> SEQUENCE: 721
tgcagaaggt gactgtcctg        20

<210> SEQ ID NO 722
<211> LENGTH: 20
<212> TYPE: DNA
<213> ORGANISM: Artificial Sequence
<220> FEATURE:
<223> OTHER INFORMATION: primer

<400> SEQUENCE: 722
gggctgtagg tgaagttgga        20

<210> SEQ ID NO 723
<211> LENGTH: 20
<212> TYPE: DNA
<213> ORGANISM: Artificial Sequence
<220> FEATURE:
<223> OTHER INFORMATION: primer

<400> SEQUENCE: 723
gggcggagtg tgttagtctc        20

<210> SEQ ID NO 724
<211> LENGTH: 20
<212> TYPE: DNA
<213> ORGANISM: Artificial Sequence
<220> FEATURE:
<223> OTHER INFORMATION: primer

<400> SEQUENCE: 724
ctccaggtga cacatgcaac        20

<210> SEQ ID NO 725
<211> LENGTH: 40
<212> TYPE: DNA
<213> ORGANISM: Homo sapiens

<400> SEQUENCE: 725
gcttttctcg cccttccttc tggccctctc cccagtctag        40

<210> SEQ ID NO 726
<211> LENGTH: 19
<212> TYPE: DNA
<213> ORGANISM: Artificial Sequence
<220> FEATURE:
<223> OTHER INFORMATION: part of minigene construct

<400> SEQUENCE: 726
cacttcacga tcaaagatc        19

<210> SEQ ID NO 727
<211> LENGTH: 55
<212> TYPE: DNA
<213> ORGANISM: Homo sapiens

<400> SEQUENCE: 727

```
gctctgcact ccactgctgg agcttttctc gccattcctt ctggccctct cccca          55

<210> SEQ ID NO 728
<211> LENGTH: 25
<212> TYPE: DNA
<213> ORGANISM: Artificial Sequence
<220> FEATURE:
<223> OTHER INFORMATION: AON

<400> SEQUENCE: 728
gccagaagga agggcgagaa aagct                                           25

<210> SEQ ID NO 729
<211> LENGTH: 21
<212> TYPE: DNA
<213> ORGANISM: Artificial Sequence
<220> FEATURE:
<223> OTHER INFORMATION: AON

<400> SEQUENCE: 729
ccagaaggaa gggcgagaaa a                                               21

<210> SEQ ID NO 730
<211> LENGTH: 368
<212> TYPE: DNA
<213> ORGANISM: Homo sapiens

<400> SEQUENCE: 730
aaccccagag ctgcttccct tccagatgtg gtcctgcagc cgagccctgc ccttagctgg     60
aggtcgacag gtgggatcct ggatgtctac atcttcctgg gcccagagcc caagagcgtg   120
gtgcagcagt acctggacgt tgtgggtagg gcctgctccc tggccgcggc ccccgcccca   180
aggctccctc ctccctccct catgaagtcg gcgttggcct gcaggatacc cgttcatgcc   240
gccatactgg ggcctgggct tccacctgtg ccgctggggc tactcctcca ccgctatcac   300
ccgccaggtg gtggagaaca tgaccagggc ccacttcccc ctggtgagtt ggggtggtgg   360
caggggag                                                            368
```

METHODS FOR CHARACTERIZING ALTERNATIVELY OR ABERRANTLY SPLICED MRNA ISOFORMS

CROSS REFERENCE TO RELATED APPLICATIONS

This application is the U.S. National Stage of International Patent Application No. PCT/NL2015/050420, filed Jun. 10, 2015, published in English, which claims priority to International Patent Application No. PCT/NL2014/050375, filed Jun. 10, 2014, and priority to European Patent Application No. 14183623.9, filed Sep. 4, 2014.

SEQUENCE LISTING

This application contains a Sequence Listing which has been submitted electronically in ASCII format and which is incorporated by reference in its entirety. Said ASCII file is named P104578US10seqlistcorrected_ST25.txt, is 146,205 bytes in size and was created on Jun. 20, 2017.

FIELD OF THE INVENTION

The disclosure provides method and kits for characterizing spliced mRNA isoforms. The disclosure also provides methods of screening for mutations and oligonucleotides that modulate splicing.

BACKGROUND OF THE INVENTION

Pre-mRNA splicing is the process in eukaryotes in which newly transcribed RNA is processed to remove intronic sequences. Splicing is highly regulated and enables the production of different mRNAs and proteins from the same gene. This is important to provide increased complexity during evolution. Alternative splicing is regulated by proteins (i.e., trans-acting proteins) which bind to regulator elements (i.e., cis-acting elements). Cis-acting elements may be located either close to or more distant from the splice sites. These include the polypyrimidine tract, branchpoints, and loosely defined regulatory elements present in either exons (exonic splicing enhancers (ESEs) and exon splicing silencers ESSs) or introns (intronic splicing enhancers (ISEs) and intronic splicing silencers (ISSs)) (reviewed in [2]). In many human genetic diseases, DNA mutations can cause aberrant splicing resulting in partial or complete disruption of protein function. Various consequences of splicing mutations can be envisioned including exon skipping, exon inclusion, intron retention, utilization of a nearby cryptic splice site, or generation of a novel splice site.

Alternative splicing often leads to more than one species of mRNA being produced from a single genetic allele. In addition to the "alternatively/aberrantly spliced" variant being produced, there is often a small amount of the wild-type mRNA produced, which is termed leaky wild-type splicing. The extent of this leaky wild-type splicing can have a predictive factor for the disease severity resulting from a splicing mutant.

Mutations and polymorphisms affecting pre-mRNA splicing are difficult to predict due to the complex mechanism of splicing regulation. Many DNA mutations are known, however the effect of these mutations on splicing is largely unknown. A number of splicing prediction programs exists [3-6], but they may produce different predictions for the same mutation or polymorphism, obscuring data interpretation. Furthermore, when weakening of a splice site is likely from in silico predictions, the effect on splicing is even more difficult to predict. Diagnostic methods often involve sequencing of the exons and a small part of the introns only. This may lead to the detection of a mutation in an intron that may affect splicing. Exonic mutations are often investigated only for their effect on protein translation. However, certain exonic mutations may also affect splicing. Sequencing of the remaining part of the introns is often not performed, also because introns can be very large in size. Intronic mutations can affect splicing, even at large distances. For example, they can create a cryptic splice site, affect RNA structure, or affect ISSs or ISEs. Promoters and UTRs are also not sequenced in diagnostics. Mutations in promoters may affect mRNA expression by changing the efficiency of RNA polymerase II-directed transcription. Mutations in UTRs may affect mRNA stability, polyadenylation, and they may interfere with regulation by micro RNAs. Exonic mutations can be studied by introducing the mutation in a cDNA and testing the effect on protein activity in a transient transfection assay, however this requires prior knowledge of the mutation. If such mutation is unknown, one cannot perform the functional assay. Effects on splicing can be determined after identification of a mutation, followed by region-specific PCR analysis. However, this requires prior identification of the mutation. This approach falls short if the mutation is not found (e.g. because it lies outside the regions normally analyzed by sequencing). In addition, it is very difficult to predict whether a mutation will affect splicing, and if so, what the outcome will be.

For example, perfect skipping of an exon while the reading frame is unchanged may generate a truncated protein with significant residual activity, while a change of the reading frame results in a premature termination codon leading to mRNA degradation via the Nonsense Mediated Decay (NMD) pathway.

Therefore, a need exists for a generic assay to systemically identify and characterize the effects of sequence variants on splicing also in the absence of mutational data. Furthermore, there is a need for an assay that may identify and characterise mutations affecting splicing and mRNA expression. In addition there is a need for method for identifying sequences that affect pre-mRNA splicing for therapeutic use.

SUMMARY OF THE INVENTION

In a first aspect the invention is directed to a method for characterizing an alternatively or aberrantly spliced isoform of an mRNA, comprising
providing a biological sample comprising said mRNA isoform,
performing flanking exon PCR on each internal exon corresponding to the mRNA to obtain one or more flanking exon amplification products, and detecting the presence and length of the said flanking exon amplification products,
determining the quantity of each protein encoding exon of said mRNA,
wherein said alternatively or aberrantly spliced mRNA isoform is characterized based on the presence and/or size of said flanking exon amplification products and from the quantity of each protein encoding exon.

In a second aspect the invention is directed to a method for quantifying an alternatively or aberrantly spliced isoform of an mRNA, comprising
providing a biological sample comprising said mRNA isoform, determining the quantity of the alternatively or aberrantly spliced isoform by PCR by using at least one primer that hybridizes to at least one nucleotide downstream of the alternative splice ligation site and to at least one nucleotide upstream of the alternative splice ligation site and wherein the primer is at least 15 nucleotides long.

In preferred embodiments of aspects and/or embodiments of the invention, the method further comprises a method for quantifying an alternatively or aberrantly spliced isoform of an mRNA, according to the second aspect of the invention.

In preferred embodiments of aspects and/or embodiments of the invention, the method further comprises determining at least part of the sequence of at least one flanking exon amplification product. In preferred embodiments of aspects and/or embodiments of the invention, the method further comprises determining at least part of the sequence of at least one flanking exon amplification product that is alternatively spliced. In preferred embodiments of aspects and/or embodiments of the invention, the method further comprises determining the sequence of more than one flanking exon amplification product. In preferred embodiments of aspects and/or embodiments of the invention, the method further comprises determining the sequence of all internal exons. In preferred embodiments of aspects and/or embodiments of the invention, the method further comprises determining the sequence of all exons. In preferred embodiments of aspects and/or embodiments of the invention, the method further comprises determining the sequence of said mRNA.

In preferred embodiments of aspects and/or embodiments of the invention, the method further comprises determining the quantity of each exon of said mRNA.

In preferred embodiments of aspects and/or embodiments of the invention, the quantity of each exon is determined using quantitative PCR (qPCR), preferably wherein the quantitative PCR is RT-qPCR.

In preferred embodiments of aspects and/or embodiments of the invention the biological sample comprises tissue from an individual. In preferred embodiments of aspects and/or embodiments of the invention the biological sample comprises primary or transformed or otherwise modified cells from an individual. In preferred embodiments of aspects and/or embodiments of the invention the individual is diagnosed or suspected to have a disease. In preferred embodiments of aspects and/or embodiments of the invention the disease is a disease which involves alternative splicing. In preferred embodiments of aspects and/or embodiments of the invention the disease is Pompe disease. In preferred embodiments of aspects and/or embodiments of the invention the cells are primary fibroblast cells.

In preferred embodiments of aspects and/or embodiments of the invention the flanking exon PCR comprises performing RT-PCR amplification with primers that flank the internal exons.

In preferred embodiments of aspects and/or embodiments of the invention, the method further comprises the step of detecting a mutation. In preferred embodiments of aspects and/or embodiments of the invention, the method further comprises a step of linking the mutation to the alternatively or aberrantly spliced mRNA isoform.

In a third aspect, the invention is directed to a kit-of-parts for characterizing an alternatively or aberrantly spliced isoform of an mRNA, the kit comprising
  a) multiple primer pairs for performing flanking exon PCR for each internal exon of the mRNA, wherein each primer pair is for performing flanking exon PCR for a different internal exon,
  b) multiple primer pairs for performing quantitative PCR for each protein encoding exon of the mRNA, wherein each primer pair is for performing quantitative PCR on a different internal exon,
  c) Detection probes for determining the quantity of each protein encoding exon of said mRNA, wherein each probe is specific for a different protein encoding exon.
  d) sequencing primers for determining the sequence of the product of the flanking exon PCR.

In preferred embodiments of aspects and/or embodiments of the invention, at least one primer of each primer pair for performing quantitative PCR is the detection probe.

In a fourth aspect, the invention is directed to a method for identifying a mutation in a pre-mRNA that modulates splicing of said pre-mRNA in a cell comprising
  providing a control minigene construct comprising a contiguous genomic sequence, wherein the genomic sequence comprises
    a) at least the 5' donor splice site of a first (upstream) exon,
    b) a second exon,
    c) and at least the 3' acceptor splice site of a third (downstream) exon from the pre-mRNA,
  introducing mutations into the genomic sequences of said control minigene construct to produce a library of mutant minigene constructs,
  providing the mutant minigene constructs and the control minigene construct in an expression vector,
  contacting cells with each member of the library of mutant minigene constructs in said expression vector and contacting said cells with the control minigene construct in said expression vector independently, such that splicing of said minigene constructs can occur,
  detecting the splicing of said constructs, and
  identifying one or more mutant minigene constructs having a splicing pattern altered from the control gene construct splicing pattern.

In preferred embodiments of aspects and/or embodiments of the invention the detecting of the splicing of said constructs is performed with RT-PCR, flanking exon PCR, or the method of according to the first aspect of the invention and/or embodiments thereof.

In preferred embodiments of aspects and/or embodiments of the invention the minigene construct comprises unique restriction sites.

In preferred embodiments of aspects and/or embodiments of the invention at least part of the sequence of the genomic sequence of the mutant minigene constructs having a splicing pattern altered is determined. In preferred embodiments of aspects and/or embodiments of the invention the complete sequence of the genomic sequence of the mutant minigene construct is determined. In preferred embodiments of aspects and/or embodiments of the invention the sequence of the mutant minigene construct is compared to the control minigene construct to identify at least one mutation.

In preferred embodiments of aspects and/or embodiments of the invention the control minigene construct comprises a genomic sequence from a healthy individual or from a patient, wherein the genomic sequence carries a mutation, preferably a pathogenic mutation, or has no mutation.

In a fifth aspect, the invention is directed to a library of mutant minigene constructs comprising a multitude of expression vectors each comprising a mutant minigene construct, wherein the mutant minigene construct comprises a contiguous genomic sequence, wherein the genomic sequence comprises a) at least the 5' donor splice site of a first exon, b) a second exon, c) and at least the 3' acceptor splice site of a third exon from the pre-mRNA, and wherein the genomic sequence comprises at least one random or deliberate mutation.

In preferred embodiments of aspects and/or embodiments of the invention, the mutant minigene construct comprises unique restriction sites, preferably at the 3'-end and the 5'-end of the genomic sequence.

In preferred embodiments of aspects and/or embodiments of the fourth aspect of the invention and/or embodiments thereof, the multitude of expression vectors are each separately present in separate containers, preferably the containers are wells in a micro well plate.

In a sixth aspect, the invention is directed to a method for screening for compounds that modulate the splicing of a pre-mRNA in a cell comprising, identifying a mutation in a pre-mRNA that modulates splicing according to the methods according to the first and third aspect of the invention;

making a mutant minigene construct with the identified mutation;

contacting the mutant minigene construct with the identified mutation with a compound that is able to bind to RNA;

identify the compound that modulates splicing of the mRNA

In preferred embodiments of aspects and/or embodiments of the invention, the method comprises providing the mutant minigene construct with the identified mutation in an expression vector, contacting cells with the mutant minigene construct with the identified mutation in said expression vector, such that splicing of said minigene constructs can occur, detecting the splicing of said constructs, and identifying one or compounds that provide a splicing pattern altered from the control without added compound that is able to bind to RNA.

In a seventh aspect the invention is directed to a method for making an antisense oligonucleotide (AON) for modulating the splicing of a pre-mRNA in a cell comprising, identifying a mutation in a pre-mRNA that modulates splicing according to the first and/or third aspect of the invention and/or embodiments thereof, making an AON that is complementary to at least a part of said pre-mRNA, wherein the AON binds to the region of the pre-mRNA comprising the mutation and modulates splicing of the pre-mRNA.

In preferred embodiments of aspects and/or embodiments of the invention, said splicing is modulated to promote the inclusion of an exon into the mRNA of said pre-mRNA.

In a eighth aspect the invention is directed to a method for screening a library of antisense oligonucleotides (AONs) for oligonucleotides that modulate splicing of a pre-mRNA in a cell comprising contacting cells, preferably primary cells, which express said pre-mRNA with the library of AONs, wherein the library comprises a collection of expression vectors, each vector comprising a modified U7 snRNA and a different AON that is complementary to at least a part of said pre-mRNA, and identifying one or more AONs that modulates the splicing of said pre-mRNA.

In preferred embodiments of aspects and/or embodiments of the invention said vector is selected from an eukaryotic expression plasmid, a lentiviral vector, retroviral vector, an adenoviral vector, an SV40 virus-based vector, a Sendai virus vector, or an adeno-associated viral vector.

In preferred embodiments of aspects and/or embodiments of the invention said vector comprises two unique restriction sites.

In preferred embodiments of aspects and/or embodiments of the invention said AON promotes exon inclusion.

In preferred embodiments of aspects and/or embodiments of the invention the collection of expression vectors are each separately present in separate containers, preferably the containers are wells in a micro well plate.

In a ninth aspect the invention is directed to a library of antisense oligonucleotides (AONs) comprising a multitude of expression vectors, each vector comprising a modified U7 snRNA and a different AON that is complementary to at least a part of said pre-mRNA.

In preferred embodiments of aspects and/or embodiments of the invention, unique restriction sites are present, preferably at the 3'-end and the 5'-end of the antisense sequence.

In preferred embodiments of aspects and/or embodiments of the invention the multitude of expression vectors are each separately present in separate containers, preferably the containers are wells in a micro well plate.

BRIEF DESCRIPTION OF THE DRAWINGS

FIG. 6: Table 1 Laboratory diagnosis of Pompe patients used in this study.

FIG. 7: Table 2. Summary of splicing events resulting from the mutations studied. Patients 1-3 (in blue) have been characterized previously and served for validation of the assay. Patients 4-8 (in red) have been investigated in this study and all patients revealed novel splicing events.

FIG. 13. Cartoon of exons in patient 8 and the locations of PCR primers used for flanking exon PCR analysis. Only those primer pairs are shown that anneal to exons affected by the splicing mutations.

FIG. 15: Flanking exon PCR primers used in Example 1. GAA Exon 2: Forward: SEQ ID NO: 649; Reverse: SEQ ID NO: 650; GAA Exon 3: Forward: SEQ ID NO: 651; Reverse: SEQ ID NO: 652; GAA Exon 4: Forward: SEQ ID NO: 653; Reverse: SEQ ID NO: 654; GAA Exon 5: Forward: SEQ ID NO: 655; Reverse: SEQ ID NO: 656; GAA Exon 6: Forward: SEQ ID NO: 657; Reverse: SEQ ID NO: 658; GAA Exon 7: Forward: SEQ ID NO: 659; Reverse: SEQ ID NO: 660; GAA Exon 8: Forward: SEQ ID NO: 661; Reverse: SEQ ID NO: 662; GAA Exon 9: Forward: SEQ ID NO: 663; Reverse: SEQ ID NO: 664; GAA Exon 10: Forward: SEQ ID NO: 665; Reverse: SEQ ID NO: 666; GAA Exon 11: Forward: SEQ ID NO: 667; Reverse: SEQ ID NO: 668; GAA Exon 12: Forward: SEQ ID NO: 669; Reverse: SEQ ID NO: 670; GAA Exon 13: Forward: SEQ ID NO: 671; Reverse: SEQ ID NO: 672; GAA Exon 14: Forward: SEQ ID NO: 673; Reverse: SEQ ID NO: 674; GAA Exon 15: Forward: SEQ ID NO: 675; Reverse: SEQ ID NO: 676; GAA Exon 16: Forward: SEQ ID NO: 677; Reverse: SEQ ID NO: 678; GAA Exon 17: Forward: SEQ ID NO: 679; Reverse: SEQ ID NO: 680; GAA Exon 18: Forward: SEQ ID NO: 681; Reverse: SEQ ID NO: 682; GAA Exon 19: Forward: SEQ ID NO: 683; Reverse: SEQ ID NO: 684.

FIG. 16: Exon-internal qPCR primers used in Example 1. B-Actin: Forward: SEQ ID NO: 685; Reverse: SEQ ID NO: 686; GAA Exon 2: Forward: SEQ ID NO: 687; Reverse: SEQ ID NO: 688; GAA Exon 3: Forward: SEQ ID NO: 689; Reverse: SEQ ID NO: 690; GAA Exon 4: Forward: SEQ ID NO: 691; Reverse: SEQ ID NO: 692; GAA Exon 5: Forward: SEQ ID NO: 693; Reverse: SEQ ID NO: 694; GAA Exon 6: Forward: SEQ ID NO: 965; Reverse: SEQ ID NO: 696; GAA Exon 7: Forward: SEQ ID NO: 697; Reverse: SEQ ID NO: 698; GAA Exon 8: Forward: SEQ ID NO: 699; Reverse: SEQ ID NO: 700; GAA Exon 9: Forward: SEQ ID NO: 701; Reverse: SEQ ID NO: 702; GAA Exon 10: Forward: SEQ ID NO: 703; Reverse: SEQ ID NO: 704; GAA Exon 11: Forward: SEQ ID NO: 705; Reverse: SEQ ID NO: 706; GAA Exon 12: Forward: SEQ ID NO: 707; Reverse: SEQ ID NO: 708; GAA Exon 13: Forward: SEQ ID NO: 709; Reverse: SEQ ID NO: 710; GAA Exon 14: Forward: SEQ ID NO: 711; Reverse: SEQ ID NO: 712: GAA Exon 15: Forward: SEQ ID NO: 713: Reverse: SEQ ID NO: 714; GAA Exon 16: Forward: SEQ ID NO: 715; Reverse: SEQ ID NO: 716; GAA Exon 17: Forward: SEQ ID NO: 717; Reverse: SEQ ID NO: 718; GAA Exon 18: Forward: SEQ ID NO: 719; Reverse: SEQ ID NO: 720; GAA Exon 19: Forward: SEQ ID NO: 721; Reverse: SEQ ID NO: 722; GAA Exon 20: Forward: SEQ ID NO: 723; Reverse: SEQ ID NO: 724.

FIG. 28. Specificity of antisense oligomeric compounds. AON1 (SEQ ID NO: 12) and AON33 (SEQ ID NO: 33) for promoting exon 2 inclusion at the mRNA level (FIG. 28A) and at the protein level (FIG. 28B).

DETAILED DESCRIPTION OF THE DISCLOSED EMBODIMENTS

Definitions

Figure 1:
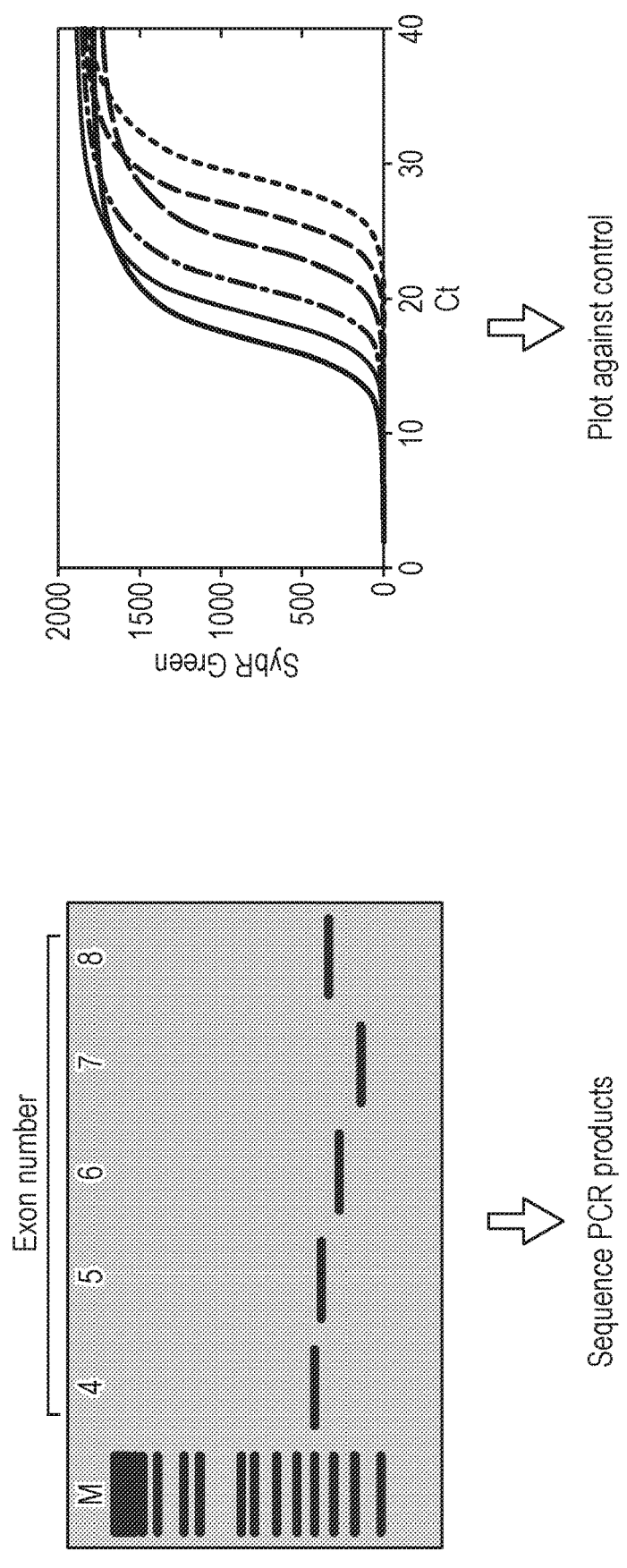
FIG. 1. Workflow for the generic analysis of splice site mutations. Changes in splice site usage are detected by PCR using primers annealing to the flanking exons (flanking exon PCR), followed by sequencing (left part). Aberrant splice products are quantified using primers annealing within each exon (exon-internal qPCR; right part).

As used herein, "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article.

The terms "individual", "patient", and "subject" are used interchangeably herein and refer to mammals, in particular primates and preferably humans.

The term "exon" refers to a portion of a gene that is present in the mature form of mRNA. Exons include the ORF (open reading frame), i.e., the sequence which encodes protein, as well as the 5' and 3' UTRs (untranslated regions). The UTRs are important for translation of the protein. Algorithms and computer programs are available for predicting exons in DNA sequences (Grail, Grail 2 and Genscan and US 20040219522 for determining an exon-intron junctions).

As used herein, the term "protein coding exon" refers to an exon which codes (or at least partially codes) for a protein (or part of a protein). The first protein coding exon in an mRNA is the exon which contains the start codon. The last protein encoding exon in an mRNA is the exon which contains the stop codon. The start and stop codons can be predicted using any number of well-known programs in the art.

As used herein, the term "internal exon" refers to an exon that is flanked on both its 5' and 3' end by another exon. For an mRNA comprising n exons, exon 2 to exon (n−1) are the internal exons. The first and last exons of an mRNA are referred to herein as "external exons".

The term "intron" refers to a portion of a gene that is not translated into protein and while present in genomic DNA and pre-mRNA, it is removed in the formation of mature mRNA.

The term "messenger RNA" or "mRNA" refers to RNA that is transcribed from genomic DNA and that carries the coding sequence for protein synthesis. Pre-mRNA (precursor mRNA) is transcribed from genomic DNA. In eukaryotes, pre-mRNA is processed into mRNA, which includes removal of the introns, i.e., "splicing", and modifications to the 5' and 3' end (e.g., polyadenylation). mRNA typically comprises from 5' to 3'; a 5'cap (modified guanine nucleotide), 5' UTR (untranslated region), the coding sequence (beginning with a start codon and ending with a stop codon), the 3' UTR, and the poly(A) tail.

The term "nucleic acid sequence" or "nucleic acid molecule" or polynucleotide are used interchangeably and refer to a DNA or RNA molecule in single or double stranded form. An "isolated nucleic acid sequence" refers to a nucleic acid sequence which is no longer in the natural environment from which it was isolated, e.g. the nucleic acid sequence in a cell.

A "mutation" in a nucleic acid molecule is a change of one or more nucleotides compared to the wild type sequence, e.g. by replacement, deletion or insertion of one or more nucleotides. A "point mutation" is the replacement of a single nucleotide, or the insertion or deletion of a single nucleotide.

Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximising the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS (http://www.ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 70%, 75%, 80%, 85%, 90%, 95%, 98%, 99% or more, preferably 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'variants' herein, e.g. other variants of antisense oligomeric compounds. It should be understood that sequence with substantial sequence identity do not necessarily have the same length and may differ in length. For example sequences that have the same nucleotide sequence but of which one has additional nucleotides on the 3'- and/or 5'-side are 100% identical.

The term "hybridisation" as used herein is generally used to mean hybridisation of nucleic acids at appropriate conditions of stringency as would be readily evident to those skilled in the art depending upon the nature of the probe sequence and target sequences. Conditions of hybridisation and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1×Denhardt's solution and 0.5% SOS. hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature (TM) of the duplex. The TM is known to be a function of the G-C content and duplex length as well as the ionic strength of the solution.

As used herein, the phrase "hybridizes" to a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridisation under appropriate conditions. For example a 25 nucleotide long sequence in the antisense orientation of GAA_c.-32-190_-166 will recognize and hybridize to a approximately 25 nucleotide long sequence in the GAA_c.-32-190_-166 gene so long as there is about 70% or more sequence similarity between the two sequences. It is to be understood that the size of the corresponding portion will allow for some mismatches in hybridisation such that the corresponding portion may be smaller or larger than the molecule which hybridizes to it, for example 20-30% larger or smaller, preferably no more than about 12-15% larger or smaller.

The term "allele(s)" means any of one or more alternative forms of a gene at a particular locus, all of which alleles relate to one trait or characteristic at a specific locus. One allele is present on each chromosome of the pair of homologous chromosomes. These may be identical alleles of the gene (homozygous) or two different alleles (heterozygous).

Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different conformation, being targeted to a different sub-cellular compartment, having a modified catalytic domain, having a modified binding activity to nucleic acids or proteins, etc, it may also lead to a different splicing event.

A "fragment" of the gene or nucleotide sequence or antisense oligomeric compound refers to any subset of the molecule, e.g., a shorter polynucleotide or oligonucleotide.

A "variant" refers to a molecule substantially similar to the antisense oligomeric compound or a fragment thereof, such as a nucleotide substitution variant having one or more substituted nucleotides, but which maintains the ability to hybridize with the particular gene. Preferably the variant comprises the mutations as identified by the invention. Variants also include longer sequences.

An "analogue" refers to a non-natural molecule substantially similar to or functioning in relation to either the entire molecule, a variant or a fragment thereof.

Sequences in the description are depicted as DNA molecules. The U7snRNA constructs and the minigene constructs are DNA molecules, that are transcribed as RNA molecules by the vector. The U7snRNA constructs and the minigene constructs are DNA molecules that are cloned into a vector, wherein the vector is subsequently introduced into a cell, wherein the RNA form of the U7snRNA constructs and the minigene constructs are transcribed. It is to be understood that the present invention covers RNA sequences as well. All sequences depicted in the present description may also be RNA sequences wherein the T is U.

It was found that 15% of point mutants that result in human genetic disease disrupted splicing (Krawczak et al. 1992; *Hum. Genet.* 90:41-54.). This is likely to be an underestimate because the analysis was limited to mutations in the classical splice-site sequences, the only splicing elements widely recognized at the time. It is now known that widespread aberrant splicing is also caused by mutations that disrupt exonic splicing elements (ESEs and ESSs). Given recent predictions that the majority of human exons contain ESEs (Liu et al. 2001; *Nat. Genet.* 27:55-58; Fairbrother et al. 2002; *Mol. Cell. Biol.* 20:6816-6825), one striking realization is that a significant fraction of exonic mutations that cause disease are unrecognized splicing mutations (for review, see Cooper and Mattox 1997; *Am. J. Hum. Genet.* 61:259-266; Caceres and Kornblihtt 2002 *Trends Genet.* 18:186-193; Cartegni et al. 2002; *Nat. Genet.* 30:377-384).

In principle any diseases affected by splicing may be the subject of the methods of the present invention. The human gene mutation database (http://www.hgmd.org/) contains a list of diseases affected by genetic mutations including mutations affecting splicing. The methods of the present invention may also identify hitherto unknown alternative splicing events that cause diseases. It is to be understood that all these diseases are covered and may be the subject of the present invention. The method of the present invention is able to rapidly identify the effect on splicing events in an unbiased way, thus without prior knowledge of a mutation. The methods of the present invention are able to identify the effect on splicing, and the effect of the aberrant splicing on the resulting mRNA, e.g. a truncated form, or non-sense mediated decay, or leaky wild-type splicing. In addition, the methods of the present invention are able to identify the parts of the pre-mRNA that are responsible for the aberrant or alternative splicing, enabling the finding of a possible treatment. Furthermore, the methods of the present invention may also directly provide antisense sequences that may be used to alleviate the aberrant or alternative splicing and may be used for treatment of the disease.

The methods of the present invention and/or embodiments thereof are thus directed to mRNA or pre-MRNA from genes that are involved in a disease wherein the pre-mRNA is or may be alternatively spliced. Many of such genes and diseases are known, see e.g. the human gene mutation database (http://www.hgmd.org/) and the SpliceDisease database (http://cmbi.bjmu.edu.cn/sdisease). In preferred embodiments the mRNA or pre-mRNA may be from any gene identified in the human gene mutation database or the SpliceDisease database wherein the mutation causes alternative or aberrant splicing.

The following table exemplifies diseases and the effected protein. The diseases are referenced with the Online Mendelian Inheritance in Man (OMIM) number, see http://www.omim.org/:

| diseases | OMIM number | gene involved |
|---|---|---|
| Glycogenosis I (Von Gierke) | 232200 | Glucose-6-phosphatase L |
| Glycogenosis II (Pompe) | 232300 | α-Glucosidase BF |
| Glycogenosis III (Cori) | 232400 | Debranching enzyme B (F) |
| Debranching enzyme deficiency | 232400 | Debranching enzyme B (F) |
| Glycogenosis IV (Andersen) | 232500 | Branching enzyme BF |
| Branching enzyme deficiency | 232500 | Branching enzyme BF |
| Glycogenosis V (McArdle) | 232600 | Phosphorylase Muscle S |
| Muscle phosphorylase deficiency | 232600 | Phosphorylase Muscle S |
| Glycogenosis VI (Hers) | 232700 | Phosphorylase liver L |
| Liver phosphorylase deficiency | 232700 | Phosphorylase liver L |
| Glycogenosis VII (Tarui) | 232800 | Phosphofructokinase (PFK) S |
| Muscle PFK deficiency | 232800 | Phosphofructokinase (PFK) S |
| Glycogenosis IX | 306000 | Phosphorylase kinase BSL |
| Phosphorylase kinase deficiency | 306000 | Phosphorylase kinase BSL |
| Glycogenosis 0 | 240600 | Glycogen synthetase L |
| Glycogen synthetase deficiency | 240600 | Glycogen synthetase L |
| Fabry | 301500 | α-Galactosidase BF |
| Farber | 228000 | Ceramidase BF |
| Gaucher | 230800 | β-Glucosidase BF |
| GM1 - gangliosidosis | 230500 | β-Galactosidase BF |
| GM2 - gangliosidosis (Sandhoff) | 268800 | β-Hexosaminidase A + B BF |
| GM2 - gangliosidosis (Tay-Sachs) | 272800 | β-Hexosaminidase A BF |
| Jansky-Bielschowsky(LINCL) | 204500 | Tripeptidyl-peptidase 1 BF |
| Krabbe | 245200 | Cerebroside-β-galactosidase BF |
| Metachromatic Leukodystrophy (MLD) | 250100 | Arylsulphatase A BF |
| Neuronal ceroid lipofuscinosis (CLN-1) | 256730 | Palmitoyl-protein thioesterase BF |
| Neuronal ceroid lipofuscinosis (CLN-2) | 204500 | Tripeptidyl-peptidase 1 BF |
| Niemann-Pick A + B | 257200 | Sphingomyelinase BF |
| Niemann-Pick C | 257220 | Cholesterol storage F |
| Santavuori-Haltia (INCL) | 256730 | Palmitoyl-protein thioesterase BF |
| α-Mannosidosis | 609458 | α-Mannosidase BF |
| α-NAGA deficiency (Schindler) | 609241 | α-N-acetyl-galactosaminidase BF |
| β-Mannosidosis | 248510 | β-Mannosidase BF |

| diseases | OMIM number | gene involved |
| --- | --- | --- |
| Aspartylglucosaminuria | 208400 | Aspartylglucosaminidase BF |
| Fucosidosis | 230000 | α-Fucosidase BF |
| Galactosialidosis | 256540 | Cathepsin A FB |
| Mucolipidosis I (Sialidosis) | 256550 | α-N-acetyl-neuraminidase F |
| Mucolipidosis II + III (I-cell disease) | 252500 | Several lysosomal hydrolases BF |
| Hunter (MPS II) | 309900 | Iduronate sulphatase BF |
| Hurler/Scheie (MPS I) | 252800 | α-L-iduronidase BF |
| Maroteaux-Lamy (MPS VI) | 253200 | Arylsulphatase B BF |
| Morquio A (MPS IVA) | 253000 | Galactose-6S sulphatase BF |
| Morquio B (MPS IVB) | 253010 | β-Galactosidase BF |
| Sanfilippo A (MPS IIIA) | 252900 | Heparan sulphamidase BF |
| Sanfilippo B (MPS IIIB) | 252920 | α-N-acetylglucosaminidase BF |
| Sanfilippo C (MPS IIIC) | 252930 | Acetyl-CoA:glucosamine N-acetyltransferase BF |
| Sanfilippo D (MPS IIID) | 252940 | N-Acetylglucosamine-6-S-sulphatase BF |
| Sly (MPS VII) | 253220 | β-Glucuronidase BF |
| Cystinosis | 606272 | Cystine transporter F |
| Papillon-Lefevre (Cathepsine C def.) | 245000 | Cathepsin C BF |
| Pompe (GSD II) | 232300 | α-Glucosidase BF |
| Sialic acid storage disease (Salla) | 604369 | Sialic acid transport F |
| Wolman disease and CESD | 278000 | Acid lipase BF |
| 3-Methylcrotonoyl-CoA deficiency | 210200 | 3-methyl crotonoyl CoA carboxylase FL |
| Arginino succinuria | 207900 | Arginino succinate lyase F |
| Biotinidase deficiency | 253260 | Biotinidase B |
| Citrullinemia | 215700 | Arginino succinate synthetase F |
| CPS deficiency | 237300 | Carbamoyl phosphate synthetase L |
| Cystinosis | 606272 | Cysteine F |
| Isovaleric academia | 243500 | Isovaleryl-CoA dehydrogenase F |
| Malonacidemie | 248360 | Malonyl-CoA decarboxylase F |
| Maple Syrup Urine disease | 248600 | α-ketoisocaproate dehydrogenase F |
| Methylmalonacidemia | 251000 | Methylmalonyl-CoA mutase F |
| OTC deficiency | 311250 | Ornithine transcarbamylase (OTC) L |
| Prolidase deficiency | 170100 | Prolidase BF |
| Propion academia | 606054 | Propionyl-CoA carboxylase BFL |
| Pyruvate carboxylase deficiency | 266150 | Pyruvate carboxylase FL |
| CDG 1a | 212065 | Phosphomannomutase B |
| CDG 1b | 602579 | Phosphomannose isomerase B |
| Aldolase A deficiency | 103850 | Fructose-1,6-biphosphate aldolase L |
| Enolase deficiency | 131370 | Enolase S |
| Fructose-1,6-biphosphatase deficiency | 229700 | Fructose-1,6-biphosphatase BL |
| Galactokinase deficiency | 230200 | Galactokinase B |
| Galactosemia (Classic) | 230400 | Galactose-1-phosphate uridyltransferase BF |
| Glucose-6-phosphate dehydrogenase deficiency | 305900 | Glucose-6-phosphate dehydrogenase B |
| Glycerolkinase deficiency | 307030 | Glycerolkinase F |
| Hereditary Fructose intolerance(Aldolase B) | 229600 | Fructose-1-phosphate aldolase L |
| Hexokinase deficiency | 601125 | Hexokinase S |
| Lactate dehydrogenase deficiency M-type | 150000 | Lactate dehydrogenase S |
| Phosphoenolpyruvate carboxykinase deficiency | 261650 | Phosphoenolpyruvate carboxykinase FL |
| Phosphoglucoisomerase deficiency | 172400 | Phospho-glucose isomerase S |
| Phosphoglucomutase deficiency | 171900 | Phospho-glucose-mutase S |
| Phosphoglycerate kinase deficiency | 311800 | Phosphoglycerate kinase S |
| Phospoglycerate mutase deficiency | 261670 | Phospoglycerate mutase S |
| Pyruvate kinase deficiency | 266200 | Pyruvate kinase S |
| Triosephosphate isomerase deficiency | 190450 | Triosephosphate isomerase S |
| UDP-Galactose-4-epimerase deficiency | 230350 | UDP-Galactose-4-epimerase B |
| APRT deficiency type 1 | 102600 | Adenine phosphoribosyltransferase (APRT) B(F) |
| Lesch-Nyhan | 300322 | Hypoxanthine phosphoribosyltransferase B(F) |
| Muscle AMP deaminase deficiency | 102770 | Adenosinemonophosphate deaminase S |
| Muscle AMP deaminase deficiency | 102770 | Myoadenylate deaminase S |
| Purine nucleoside phosphorylase deficiency | 164050 | Purine nucleoside phosphorylase (PNP) BF |
| Severe Combined Immunodeficiency (ADA deficiency) | 102700 | Adenosine deaminase (ADA) B(F) |

| diseases | OMIM number | gene involved |
|---|---|---|
| Ataxia telangiectasia | 208920 | Radioresistant DNA synthesis F |
| Cerebro oculo facial skeletal syndrome (COFS) | 216400 | DNA-synthesis UV recovery F |
| Cockayne syndrome | 216400 | DNA-synthesis UV recovery F |
| Nijmegen breakage syndrome | 251260 | Radioresistant DNA synthesis F |
| Trichothiodystrophy | 278730 | DNA UV survival/synthesis F |
| Xeroderma pigmentosum | 278700 | DNA-repair synthesis F |
| α-Ketoglutarate dehydrogenase deficiency | 203740 | α-Ketoglutarate dehydrogenase BF |
| Complex I deficiency | 252010 | Complex I (NADH-Coenzyme Q reductase) SLF |
| Complex II deficiency | 252011 | Complex II (Succinate-Coenzyme Q reduct.) SLF |
| Complex III deficiency | 124000 | Complex III (Ubichinol cytochrome c reduct.) SLF |
| Complex IV deficiency | 220110 | Complex IV (Cytochrome c oxidase) SLF |
| Complex V deficiency | 516060 | Complex V (ATP synthetase) SLF |
| CPT-1 deficiency | 255120 | Carnitine palmitoyltransferase I BSF |
| CPT-2 deficiency | 255110 | Carnitine palmitoyltransferase 2 BSF |
| Oxidative phosphorylation defect | 251900 | ADP dependent oxygen consumption SLF |
| Pyruvate dehydrogenase deficiency | 312170 | Pyruvate dehydrogenase F |

Exemplary diseases are Familial isolated growth hormone deficiency type II (IGHD II), Frasier syndrome, Frontotemporal dementia and Parkinsonism linked to Chromosome 17 (FTDP-17), cystic fibrosis, Retinitis pigmentosa, Spinal muscular atrophy, Myotonic dystrophy, neoplasia and malignancy, Becker muscular dystrophy, Deficiency of the MCAD enzyme, Familial Dysautonomia, Menke disease, Occipital horn syndrome, Pyruvate dehydrogenase deficiency, Retinitis pigmentosa, Sandhoff disease, Hutchinson-Gilford Progeria Syndrome, Breast cancer, Fragile X syndrome, Facioscapulohumeral Muscular Dystrophy (FSHD), Gastric cancer, Giant cell tumors of bones, Growth hormone deficiency type II, Head and neck squamous cell carcinoma, Lung cancer, Lymphoma, Melanoma, Neoplasia, Neurofibromatosis type II, Oral and oropharyngeal cancers, Ovarian cancer, Papillary thyroid cancer, Prader Willi syndrome, Prostate cancer, Renal and urothelial cancers, Wilms tumour, Fascioscapulohumeral muscular dystrophy (FSHD), 6-thalassemia, Duchenne Muscular Dystrophy, Glycogen storage disease type II (also called Pompe disease), and Mucopolycaccharidosis type VI (Maroteaux-Lamy syndrome).

Exemplary genes are Growth Hormone gene (HG gene), Wilms tumor suppressor gene (WT1), MAPTgene encoding tau, cystic fibrosis transmembrane conductance regulator (CFTR) gene, PRPF31, HPRP3, PRPC8, survivor of motor neuron gene (SMN1), DM protein kinase (DMPK) gene, ZNF9 gene, CD44 gene, fibroblast growth factor receptor 1 (FGFR1) gene, BRCA1 gene, MCAD gene, FRG1, SMN2 gene, CASP-2 gene, Bcl-X gene, Clk1 gene, Tau gene, CASP-9 gene, SR gene, Insulin receptor gene, Stress axis-regulated (STREX) gene, Ania-6, L-type Ca2+ channel, IKBKAP, GAA gene, DMD gene, arylsulfatase B gene (ARSB).

In preferred embodiments, the disease or gene is selected from the group comprising:

| | | | |
|---|---|---|---|
| Glycogenosis I (Von Gierke) | 232200 | Glucose-6-phosphatase L |
| Glycogenosis II (Pompe) | 232300 | α-Glucosidase BF |
| Glycogenosis III (Cori) | 232400 | Debranching enzyme B(F) |
| Debranching enzyme deficiency | 232400 | Debranching enzyme B(F) |
| Glycogenosis IV (Andersen) | 232500 | Branching enzyme BF |
| Branching enzyme deficiency | 232500 | Branching enzyme BF |
| Glycogenosis V (McArdle) | 232600 | Phosphorylase Muscle S |
| Muscle phosphorylase deficiency | 232600 | Phosphorylase Muscle S |
| Glycogenosis VI (Hers) | 232700 | Phosphorylase liver L |
| Liver phosphorylase deficiency | 232700 | Phosphorylase liver L |
| Glycogenosis VII (Tarui) | 232800 | Phosphofructokinase(PFK) S |
| Muscle PFK deficiency | 232800 | Phosphofructokinase(PFK) S |
| Glycogenosis IX | 306000 | Phosphorylase kinase BSL |
| Phosphorylase kinase deficiency | 306000 | Phosphorylase kinase BSL |
| Glycogenosis 0 | 240600 | Glycogen synthetase L |
| Glycogen synthetase deficiency | 240600 | Glycogen synthetase L |
| Fabry | 301500 | α-Galactosidase BF |
| Farber | 228000 | Ceramidase BF |
| Gaucher | 230800 | β-Glucosidase BF |
| GM1 - gangliosidosis | 230500 | β-Galactosidase BF |
| GM2 - gangliosidosis (Sandhoff) | 268800 | β-Hexosaminidase A + B BF |
| GM2 - gangliosidosis (Tay-Sachs) | 272800 | β-Hexosaminidase A BF |
| Jansky-Bielschowsky(LINCL) | 204500 | Tripeptidyl-peptidase 1 BF |

-continued

| | | |
|---|---|---|
| Krabbe | 245200 | Cerebroside-β-galactosidase BF |
| Metachromatic Leukodystrophy(MLD) | 250100 | Arylsulphatase A BF |
| Neuronal ceroid lipofuscinosis(CLN-1) | 256730 | Palmitoyl-protein thioesterase BF |
| Neuronal ceroid lipofuscinosis(CLN-2) | 204500 | Tripeptidyl-peptidase 1 BF |
| Niemann-Pick A + B | 257200 | Sphingomyelinase BF |
| Niemann-Pick C | 257220 | Cholesterol storage F |
| Santavuori-Haltia (INCL) | 256730 | Palmitoyl-protein thioesterase BF |
| α-Mannosidosis | 609458 | α-Mannosidase BF |
| α-NAGA deficiency (Schindler) | 609241 | α-N-acetyl-galactosaminidase BF |
| β-Mannosidosis | 248510 | β-Mannosidase BF |

In another preferred embodiment, the disease is selected from the group comprising Mucopolisaccaridosis (MPS) I, MPS II, MPS VI, Cystic fibrosis, Myotonic dystrophy, Becker muscular dystrophy, Fragile X syndrome, Facioscapulohumeral Muscular Dystrophy (FSHD), Duchenne Muscular Dystrophy, tuberous sclerosis, Parkinson Disease, Parkinsonism, Hirschsprung disease, congenital diaphragmatic hernia, esophageal atresia, Short Bowel Syndrome, (OMIM): SPG50, also called AP-4 syndrome (OMIM 612936); MEDS, microcephaly-epilepsy-diabetes syndrome (OMIM 614231); POREN2, familial porencephaly type 2 (OMIM 614483) and PMGYS, polymicrogyria with seizures syndrome (OMIM 614833), fragile X associated tremor/ataxia syndrome (FXTAS), Pompe disease.

In another preferred embodiment, the disease is selected from the group comprising MPS I, MPS II, MPS VI, tuberous sclerosis, cystic fibrosis, Pompe disease.

Preferably the disease is Pompe disease and the de gene is the GAA gene.

In preferred embodiments, the mRNA or pre-mRNA described herein is acid-alpha glucosidase (GAA) mRNA or GAA pre-mRNA. Mutations of GAA result in Pompe disease, an autosomal recessive monogenic disease caused by the failure to degrade lysosomal glycogen, resulting in glycogen accumulation that is particularly harmful for cardiac and skeletal muscle cells. Severe mutations that completely abrogate GAA enzyme activity cause a classic infantile disease course with hypertrophic cardiomyopathy, general skeletal muscle weakness, and respiratory failure and result in death within 1.5 years of life. Milder mutations leave partial GAA enzyme activity resulting in a milder phenotype with onset varying from childhood to adult.

The IVS1 mutation (c.-32-13T>G) is located in intron 1 of the GAA gene and causes skipping of exon 2 resulting in deletion of the translation start codon and absence of a protein product from these exon 2-skipped mRNAs. It was found by the new splicing assay that the IVS1 mutation allows a low level of leaky wild type splicing, which is the reason that patient can survive to adulthood.

In preferred embodiments, the mRNA or pre-mRNA described herein is N-acetylgalactosamine 4-sulfatase (arylsulfatase B; ARSB)mRNA or ARSB pre-mRNA. Mucopolycaccharidosis type VI (Maroteaux-Lamy syndrome) is a autosomal recessive monogenic disorder caused by defects in the gene coding for N-acetylgalactosamine 4-sulfatase (arylsulfatase B; ARSB). ARSB variant c.1142+2T>C. has been described previously in Brands et al. (Orphanet J Rare Dis. 2013 Apr. 4; 8:51), however it was unknown what the effect of the mutation was on splicing. The new splicing assay of the present invention showed that a shorter product of exon 5 was produced which indicated that exon 5 was skipped, and a deletion of 244 nucleotides in the mRNA.

Pre-mRNA splicing is the process in eukaryotes in which newly transcribed RNA is processed to remove intronic sequences. Splicing is highly regulated and enables the production of different mRNAs and proteins from the same gene. This is important to provide increased complexity during evolution. Splicing of a pre-mRNA occurs by, firstly, the 2'OH of a specific branch-point nucleotide within an intron performs a nucleophilic attack on the first nucleotide of the intron at the 5' splice site forming the lariat intermediate. Second, the 3'OH of the released 5' exon then performs a nucleophilic attack at the last nucleotide of the intron at the 3' splice site thus joining the exons and releasing the intron lariat. The 5' and 3' splice sites contain consensus sequences, which can be used to predict the exon-intron boundaries.

Alternative splicing or aberrant splicing is a regulated process during gene expression that results in a single gene coding for multiple proteins. In this process, particular exons of a gene may be included within, or excluded from, the final, processed messenger RNA (mRNA) produced from that gene. Consequently the proteins translated from alternatively spliced mRNAs will contain differences in their amino acid sequence and, often, in their biological functions. Alternative splicing allows the human genome to direct the synthesis of many more proteins than would be expected from its ~20,000 protein-coding genes. Alternative splicing occurs as a normal phenomenon in eukaryotes, where it greatly increases the biodiversity of proteins that can be encoded by the genome; in humans, ~95% of multiexonic genes are alternatively spliced. There are numerous modes of alternative splicing observed, of which the most common is exon skipping. In this mode, a particular exon may be included in mRNAs under some conditions or in particular tissues, and omitted from the mRNA in others. The production of alternatively spliced mRNAs is regulated by a system of trans-acting proteins and RNAs that bind to cis-acting sites on the primary transcript itself. Such proteins include splicing activators that promote the usage of a particular splice site, and splicing repressors that reduce the usage of a particular site. Abnormal variations in splicing or aberrant splicing are implicated in disease; a significant proportion of human genetic disorders result from splicing variants. Abnormal or aberrant splicing variants are also thought to contribute to the development of cancer, Pompe disease, Duchenne muscular dystrophy (DMD), Spinal muscular atrophy (SMA), Familial dysautonomia, frontotemporal dementia and parkinsonism linked to chromosome 17 (FTDP-17), amyotrophic lateral sclerosis (ALS), Hutchinson-Gilford progeria syndrome, Medium-chain acyl-CoA dehydrogenase (MCAD) deficiency, Myotonic dystrophy, Prader-Willi syndrome, cystic fibrosis (CF), beta-thalassemia, Alport syndrome, congenital cataracts facial dysmorphism neuropathy syndrome, and mucopolysaccharidosis type VII. See also the human gene mutation database and the SpliceDisease database. Alternative splicing or aberrant splicing can be caused by exon skipping, intron inclusion, cryptic splice site usage, alternative splice site usage, and combination thereof. For the purpose of the present invention, alternative splicing also includes pathogenic alternative splicing, or aberrant splicing.

Splicing of pre-mRNA can be modulated by e.g., providing compounds that bind pre-mRNA such as antisense oligonucleotides (AON), antibiotics (gentamicin, chloramphenicol, and tetracycline) HDAC inhibitors, kinase inhibitors, phosphatase inhibitors, cAMP antagonist and cAMP agonists. A list of compounds that modulate mRNA splicing can be found on http://www.stamms-lab.net/cpds.htm. Identified splicing modulators are, sodium butyrate, valproic acid, sodium 4-phenylbutyrate, N-hydroxyl-7-(4-(dimethylamino)benzoyl)aminoheptanamide (M344), suberoylanilide hydroxamic acid (SAHA), aclarubicin, camptothecin, 6-N-formylamino-12,13-Topo I dihydro-1,11-dihydroxy-13-(β-D-glucopyranosyl)5H-indolo[2,3-a]pyrrolo[3,4-c]carbazole-5,7 (6H)-dione (NB-506), isodiospyrin, (Z)-1-(3-ethyl-5-methoxy-2, 3-dihydrobenzothiazol-2-ylidene) propan-2-one (TG003), N-(4-methoxybenzyl)-N'-(5-nitro-1,3-thiazol-2-yl) urea (AR-A014418, lithium chloride, sodium orthovanadate, N-(hexanoyl)sphingosine (C6-ceramide), tautomycin, cantharidin, rac-2-[4-(1-oxo-2-isoindolinyl)phenyl]propionic acid (indoprofen), 2-(tert-butylamino)-1-(4-hydroxy-3-hydroxymethylphenyl) ethanol sulfate (salbutamol), 10-chloro-2,6-dimethyl-2H-pyrido[3',4':4,5]pyrrolo[2,3-g]isoquinoline (IDC16), dexamethasone, dihydroepiandrosterone (DHEA), steroid hormones, 5-(N-ethyl-N-isopropyl) amiloride (EIPA), glutamate, hydroxyurea, ethanol, dimethyl sulfoxide (DMSO), 6-furfuryladenine (kinetin), etoposide (VP16), epigallocatechin gallate (EGCG), cucurmin, resveratrol.

Splicing of pre-mRNA can also be modulated by introducing mutations into the pre-mRNA sequence. As used herein, "modulating splicing" refers to changing the splicing pattern of a particular mRNA and includes promoting or inhibiting exon skipping, exon inclusion, intron inclusion, utilization of a nearby cryptic splice site, or generation of a novel splice site. The alteration of the splicing pattern need not be 100%, i.e., it is understood that promoting and inhibiting refer to increasing and decreasing the frequency that a particular splicing event occurs (or does not occur) relative to the frequency in the original pre-mRNA (without mutation or without compound treatment).

Antisense oligonucleotides (AONs) are single strands of DNA or RNA that are complementary to a target sequence. RNaseH dependent AONs exhibit an effect via the RNaseH enzyme, i.e. the RNA strand of a RNA/DNA duplex is hydrolysed resulting in the degradation of targeted mRNA. RNaseH independent AONs include oligonucleotides that exert their effect by binding to mRNA and presumably block other interactions. The effect of exon-skipping AONs is RNaseH independent. Methods for designing exon-skipping oligonucleotides have been described herein, as well as in the art (see, e.g., Aartsma-Rus et al., 2005 Oligonucleotides 15:284-297; Aartsma-Rus et al., 2008 Guidelines for Antisense AON Design and Insight Into Splice-modulating Mechanisms. Mol Ther, and PCT Publication Nos. WO2006/000057 and WO2007/135105).

cDNA (complementary DNA) refers to a DNA synthesized from a mRNA template. cDNA is prepared using the process of reverse transcription, which is catalyzed by a nucleic acid polymerase with reverse transcriptase activity.

Reverse transcription polymerase chain reaction (RT-PCR) is a variant of polymerase chain reaction (PCR), wherein an RNA strand is first reverse transcribed into cDNA followed by amplification using PCR. cDNA can be generated using an oligo(T) primer or using random primers to generate a library of essentially all mRNA transcripts in a sample. Alternatively, a sequence specific primer can be used to prepare cDNA from a particular mRNA.

The term "amplification reaction" refers to a chemical reaction which results in increased copies of a template nucleic acid sequence. Preferably, the amplification reaction is PCR. PCR refers to the method of amplifying DNA and generally uses a DNA template (the target DNA), a set of DNA primers, deoxyribonucleotides, a suitable buffer solution (preferably comprising a divalent metal cation) and an enzyme capable of DNA-directed DNA synthesis such as a heat-stable DNA polymerase, (e.g., Taq polymerase). A typical PCR cycle involves a denaturing phase where the target dsDNA is melted, a primer annealing phase where the temperature optimal for the primers to bind to the now-single-stranded target, and a chain elongation phase where the temperature is optimal for DNA polymerase to function.

The products of an amplification reaction, i.e., the amplification products, can be detected by any number of methods known to the skilled person. Gel electrophoresis is commonly used as a simple method to separate nucleic acid fragments based on size. The size of the fragments on the gel corresponds to their length and can be deduced using size standards, i.e., "DNA ladders". The composition of the gels (amounts of, e.g., agarose or polyacrylamide) can be modified to obtain the best resolution of size differences. Alternatively, the amplification products can be sequenced (either directly or after cloning into a vector.

A primer is an oligonucleotide (preferably single-stranded), typically from 6 to 50 nucleotides, preferably from 15-35 nucleotides in length. A forward primer refers to a primer that is capable of hybridizing to a region of DNA along the coding strand of DNA, whereas a reverse primer is capable of hybridizing to a region of DNA along the non-coding strand of DNA. A primer pair refers to a specific combination of a forward primer and a reverse primer and may be used in a PCR reaction to generate a specific PCR product or "amplification product".

DNA primers are "specific" for a DNA template if they hybridize primarily only to the DNA template under sufficiently stringent conditions. A skilled person is able to determine the optimum conditions (e.g., temperature, salt conditions, primer sequence) for a particular PCR reaction. The design of specific primers is familiar to those of skill in the art. Programs useful for such design include, Sequencher (Gene Codes, Ann Arbor, Mich.) and DNAStar (DNAStar, Inc., Madison, Wis.).

Error prone PCR is a form of PCR in which conditions are used which introduce random copying errors. Conditions which lead to error prone PCR include increasing the $MgCl_2$ in the reaction, adding $MnCl_2$, using unequal concentrations of each nucleotide, or using limiting concentrations of nucleotides.

Quantitative polymerase chain reaction (qPCR) or real-time polymerase chain reaction refers to a well-known method for simultaneously amplifying (using PCR) and quantifying targeted DNA molecules. Amplification uses two DNA primers and quantification is performed using a qPCR probe, usually fluorescent dyes that intercalate with double-stranded DNA or modified DNA oligonucleotide probes that fluoresce upon binding to complementary DNA. Generally, qPCR is performed in a PCR thermocycler which has a suitable optical system for detecting the qPCR probe (usually a fluorometer). In some embodiments, one or both of the DNA primers is also the qPCR probe. Suitable qPCR probes do not significantly inhibit the rate of amplification.

Suitable qPCR methods are described in U.S. Pat. No. 5,994,056. RT-pPCR refers to qPCR in which the substrate is RNA and a first strand of cDNA is prepared using reverse transcriptase.

Quantify and quantification may be used interchangeably, and refer to a process of determining the quantity of a substance in a sample (e.g., a biomarker). Quantity can refer to the abundance or concentration of a substance. It may also be an absolute or relative amount. For example, quantification of DNA and RNA may be determined by methods including but not limited to, micro-array analysis, qRT-PCR, band intensity on a Northern blot, or by various other methods know in the art. Absolute quantification can be performed with qPCR using the "digital PCR method" or "the standard curve method" where the absolute quantities in the standard curve are known.

As used herein, the term gene preferably refers to a eurokaryotic gene. More preferably a mammalian, in particular a human gene. In preferred embodiments the gene is the GAA gene.

As used herein, a mutation is the change in the nucleotide sequence in the genome that is present at a frequency of less than 1% of a population. A change in the splicing pattern of a pre-mRNA which is due to a mutation is referred to as aberrant splicing.

Genetic polymorphism refers to the presence of at least two alleles of the same gene in a population. An allele which is present with a frequency of at least 1% in the population is generally considered a polymorphism. A common type of polymorphism is a single nucleotide polymorphism (SNP). Certain polymorphisms are known to affect alternative splicing.

Wild-type or wild-type allele refers to the non-mutated form of a gene (or its corresponding mRNA or protein product). In the case that more than one allele of a particular gene are frequently present in nature, then the wild-type allele refers to the allele with the highest gene frequency.

A primary cell is a cell that is derived directly from an organism such as human. In most cases, these cells have a limited life span, although certain cells such as embryonic stem cells have a strongly enhanced capacity for survival and proliferation in vitro. For example fibroblasts isolated from skin biopsies can be grown for at least 30 passages and are an excellent source of primary cells to test splicing.

In one embodiment the present invention is directed to a method to identify splicing events. Identification of mutations involved in human inherited disease is an ongoing effort. Detection of mutations may be missed in diagnostic settings that involve sequencing of the exons only. This would exclude detection of mutations in promoters, UTRs, or introns, which may affect gene expression, RNA stability, or pre-mRNA splicing. Even if mutations are found, it is still not known what the effect of the mutation on these processes is. Performing only flanking exon PCR to a dedicated mutation may miss nonsense mediated decay because the detection assay is semi quantitative. In addition, the prior art techniques require prior knowledge of a mutation, meaning that first the whole sequence needs to be determined, compared with a wild type sequence to detect the mutation. The present invention provides for a method that does not require the knowledge of mutations, meaning that the method can be performed without mutational knowledge. The method of invention however provides unbiased structural and functional information on splicing of the whole mRNA, such as mRNA abundance/expression levels. The methods and kits of the invention also provide information on mRNA stability which may indicate nonsense mediated decay. Furthermore, the present methods and kits of the invention allow for detection of leaky wild type splicing. Although prior art techniques may also determine leaky wild type splicing, the present methods and kits of the invention provide such information with the same method, thereby skipping the need to perform dedicated and separate testing for leaky wild type splicing, which are also usually designed for a particular mutation The present method and kit of the invention is also not limited to specific splicing events. Whereas certain prior art techniques can perfectly detect exon-skipping, other splicing events are much more difficult to detect such as weakening of splice sites. Moreover, the present method and kit of the present invention is not limited to certain diseases. The present invention provides thus a reliable diagnostic tool for detecting splicing events, mutations causing alternative splicing, the effect of the alternative splicing, nonsense mediated decay and leaky wild type splicing. All this information is extremely important for the clinical outcome of a disease and the choice of treatment. The present invention provides for the first time all this information from one assay, without requiring prior mutational data.

One aspect of the disclosure provides a method for characterizing a spliced isoform of an mRNA encoded by a gene. The method comprises
   providing a biological sample comprising said mRNA isoform,
   performing flanking exon PCR on each internal exon corresponding to the mRNA to obtain one or more flanking exon amplification products,
   detecting the presence and length of the flanking exon amplification products,
   determining the quantity of each protein encoding exon of said mRNA,
   wherein said alternatively or aberrantly spliced mRNA isoform is characterized based on the presence and size of the flanking exon amplification products obtained from flanking exon PCR and from the quantity of each protein coding exon.

The present invention allows the characterisation of spliced isoforms and to see whether the isoform is alternatively or aberrantly spliced. It may determine whether exon skipping, intron inclusion, alternative splicing sites, nonsense mediated decay or other splicing events are present.

The method of the invention comprises the combination of an exon flanking PCR and determining the quantity of the protein encoding exons of a mRNA.

The flanking exon PCR is performed on each internal exon. This means that each internal exon is investigated. When a mRNA comprises n total exons, it comprises n−2 internal exons; the flanking exon PCR is then performed on every n−2 internal exons, thus on exon 2 and exon n−1 and all exons in between exon 2 and exon n−1. For example an mRNA comprising 18 exons in the wild type sequence comprises 16 internal exons, namely exon 2-17 and on exon 2-17 an flanking exon PCR is performed.

The quantity of each protein encoding exon of said mRNA is determined. The protein coding exon" refers to an exon which codes (or at least partially codes) for a protein (or part of a protein). The first protein coding exon in an mRNA is the exon which contains the start codon. The last protein encoding exon in an mRNA is the exon which contains the stop codon. The start and stop codons can be predicted using any number of well-known programs in the art. In the method of the invention for a given mRNA the quantity of all the protein encoding exons are determined, for each protein encoding exon separately so that for every single protein encoding exon the quantity is determined.

The quantity of the protein encoding exon may be expressed as abundance or concentration. For example a synthetic control may be used to spike a sample so that a absolute quantity may be determined. Also relative abundance or concentration is suitable, for example relative to the abundance or concentration of protein encoding exons of a healthy control, or relative to the average abundance of a pool of healthy controls. As is well known to a skilled person, normalisation of the levels RNA can be done to a variety of housekeeping genes such as GAPDH, beta-actin, cyclophilin A and others. As well as non-coding RNA, ribosomal RNA, or a pool of genes, or added synthetic RNA.

The alternatively/aberrantly spliced isoform can be characterized both structurally and functionally. For example, the isoform may be characterized structurally e.g. by sequence analysis as, e.g., lacking a predicted exon (exon-skipping), lacking a part of an exon (partial exon-skipping), or including (part of) an intron (intron inclusion). The structural characterization can be used together with the quantity of each exon to predict the functional effect of the isoform as compared to wild-type splicing. For example, exon-skipping can lead to a dysfunctional protein. However, a certain level of leaky wild type splicing may be present that allows a low but significant level of residual protein activity. It may also be that the skipping of a certain exon leaves the reading frame intact and that the remaining (truncated) protein contains residual activity. For these reasons, characterization of the splicing products (identity of splice junctions) combined with quantitative analysis of the splice products is preferred to determine to total outcome of a particular pathogenic mutation.

The method, in particular, characterizes the effect of a mutation or polymorphism in a gene on the corresponding mRNA molecule.

After the identification of the aberrant or alternative splicing, one may sequence the affected area or the whole mRNA or pre-mRNA for a mutation. In some embodiments, the method characterizes the mutation as a pathogenic mutation (i.e., a mutation that causes a disease or disorder). The method can thus be used as a diagnostic tool to aid in determining a) whether a patient is afflicted with a particular disorder and b) the severity (or predicted severity) of said disorder, as well as to identify a mutation causing the aberrant splicing. For example, the amount of leaky wild-type expression provides an indication of the severity (e.g., age on onset) of a disease.

An advantage of the method is that altered splicing products can be detected in an unbiased and functional manner. This expands the options for detecting splice site mutations as current human mutation analysis is based on prior knowledge and often involves sequence analysis of exons. While the methods may be performed on mRNA with known mutations, they are also useful for characterizing mRNA isoforms when the presence or type of mutation is unknown. Quantitative information on mRNA expression and stability, and on the level of leaky wild type splicing is also provided by the method. Mutations present in regulatory regions like promoters and the UTRs which affect splicing are also detected using the methods.

In preferred embodiments, the method comprises providing a biological sample comprising RNA and obtaining the corresponding cDNA (e.g., by performing a reverse transcriptase reaction). The resulting cDNA is then used as the template for flanking exon PCR. The cDNA call also be used to determine the quantity of the relevant exons (e.g., by qPCR). In other preferred embodiments, a biological sample is provided and RT-PCR is performed on the RNA using primers that flank the exons of interest (i.e., the preparation of cDNA and flanking exon PCR is performed in one step). Similarly, in preferred embodiments, a biological sample is provided and RT-qPCR is performed.

Suitable biological samples include blood and other biological fluids and tissue (e.g., healthy, diseased, cancerous). Preferably, the biological sample is derived from primary cells. Primary blood cell which can be used in the present invention include fibroblasts, leukocytes, granulocytes, monocytes, macrophages, lymphocytes, immature forms of each of the previous cells (as well as immature erythroblasts) ($CD_{34}+$ cells) and totipotent, adult or embryonic stem cells including pluripotent, multipotent, oligopotent, or unipotent stem cells or their derivatives, myoblast cells, skin cells, tooth cells, hair cells, muscle cells, induced pluripotent stem cells or their derivatives, liver cells, intestinal cells, neuronal cells. oral or nasal mucosa cellsPrimary cells can be transformed e.g. using adenovirus genes or SV40 T antigen to grow indefinitely. Transformed cells can also be derived from a tumor, these cells have been transformed naturally and can also form a valuable source to study splicing. Splicing and potential therapies can also be studied in such cells after transient or stable transfection of a minigene construct.

Preferably, the cells are obtained from an individual afflicted with a disorder, e.g., Pompe disease. The cells do not necessarily have to be cells that are afflicted by the disorder, as the pre-mRNA may be expressed in other cells as well. As long as the pre-mRNA that is alternatively spliced is expressed in a cell, such a cell is suitable for the method of the invention. Preferably a cell is chosen wherein the pre-mRNA is expressed and which cell is obtained and easily cultured. It is known that splicing is cell-dependent, and thus that splicing can vary between cells. Therefore in a preferred embodiment, the relevant cells are used to screen. Relevant cells are cells that express the pre-mRNA and preferably have the same splicing patterns as cells that are causing the disorder. For example in the case of Pompe disease glycogen is accumulated in the lysosome due to a deficiency of the acid alpha glucosidase to breakdown the excess of glycogen. Heart muscles, skeletal muscles, liver and nervous system are the tissues that are most affected by the accumulation of glycogen. However, other cells, such as fibroblast are also affected by the alternative splicing, but the effect of alternative splicing is in these cells is not so much as in muscle cells. Fibroblast are easier to culture than primary muscle cells, and thus are more suitable for screening. A skilled person is able to select the most suitable cell type for screening, depending on the disease, the affected cells, cells with alternative splicing, and ease of culturing patient cells.

The biological samples may be obtained from healthy individuals in order to identify and characterize alternatively spliced isoforms, e.g., those caused by polymorphisms in the gene encoding the relevant mRNA or by polymorphisms in genes which regulate and direct splicing. The biological samples may be obtained from individuals having or are suspected of having a disorder in order to, e.g., identify and characterize the effect of a mutation on splicing, i.e., aberrant splicing. In a preferred embodiment the individual is diagnosed with or is suspected to have a disorder selected from the group comprising cancer, Pompe disease, Duchenne muscular dystrophy (DMD), Spinal muscular atrophy (SMA), Familial dysautonomia, frontotemporal dementia and parkinsonism linked to chromosome 17 (FTDP-17), amyotrophic lateral sclerosis (ALS), Hutchinson-Gilford progeria syndrome, Medium-chain acyl-CoA dehydrogenase (MCAD) deficiency, Myotonic dystrophy, Prader-Willi syndrome, cystic fibrosis (CF), beta-thalassemia, Alport syndrome, congenital cataracts facial dysmorphism neuropathy syndrome, and mucopolysaccharidosis type VII. In preferred embodiments, the individual has Pompe disease.

In preferred embodiments, at least part of the DNA sequence corresponding to at least one flanking exon amplification product is also determined, preferably the sequence corresponding to the entire flanking exon amplification product is sequenced. Although the amplification product itself can be sequenced, it is understood that sequencing the cDNA corresponding to the amplification product is also encompassed by this embodiment. A skilled person can recognize which sequences are useful to determine. For example, if one of the amplification products is shorter than predicted, this product or the corresponding sequence in cDNA can be sequenced to determine precisely which sequences are missing. In preferred embodiments all of the flanking exon amplification products are sequenced, or the exon flanking amplification product which is different than expected and the exon flanking amplification products corresponding to the exons flanking the exon of the exon flanking amplification product which is different than expected.

The quantity of each predicted protein encoding exon of said mRNA can be determined using any number of assays known to a skilled person. These assays quantify the amount of alternative splicing preferably relative to a healthy control (e.g., the amount of exon skipping or intron inclusion) and indicate the amount of mRNA expression, and leaky-wild type splicing. For example such as for the IVS1 mutation, exon 2 is skipped, this does not only lead to the fact that exon 2 is not included in the mature mRNA. The present method shows it also leads to very low expression of all exons. Because skipping of exon 2 removes the natural translation start codon (as derived from determining the precise splice junction by sequence analysis), the mRNA cannot be properly translated while utilization of alternative start codons will result in a premature stop codon. This triggers the nonsense mediated decay pathway, resulting in mRNA degradation explaining the low expression of all exons. It is the combination of structural information from the exon-flanking PCR and the quantitative information from the quantification of the protein encoding exons that enables one to deduce direct functional and clinically relevant conclusion on the splicing event. Sequencing then provides a direct link of found mutations to the observed splicing event.

Preferably, the quantity is determined using qPCR. Other suitable methods include DNA microarrays, RNA-seq (i.e., RNA Deep Sequencing which determines both the abundance and sequence of an RNA fragment), differential display and Northern blotting. Preferably, the quantity is a relative concentration. Preferably, the quantity of all exons including and following the start-codon containing exon is determined. For example, if an mRNA contains 10 exons and the start codon is in exon 2 and the stop codon in exon 9 then the quantity is determined for exons 2 to 10, or even for exons 1 to 10. Preferably, the quantity of all exons is determined.

The quantification of exons involves techniques using sequences, primers and/or probes that are directed to sequences of the exon itself and not directed to sequences of other part of the mRNA, such as flanking exons. However, it is also possible to design primers that amplify splice junctions, but the interpretation of the effects of unknown splicing mutations can be more complicated.

Figure 24B:
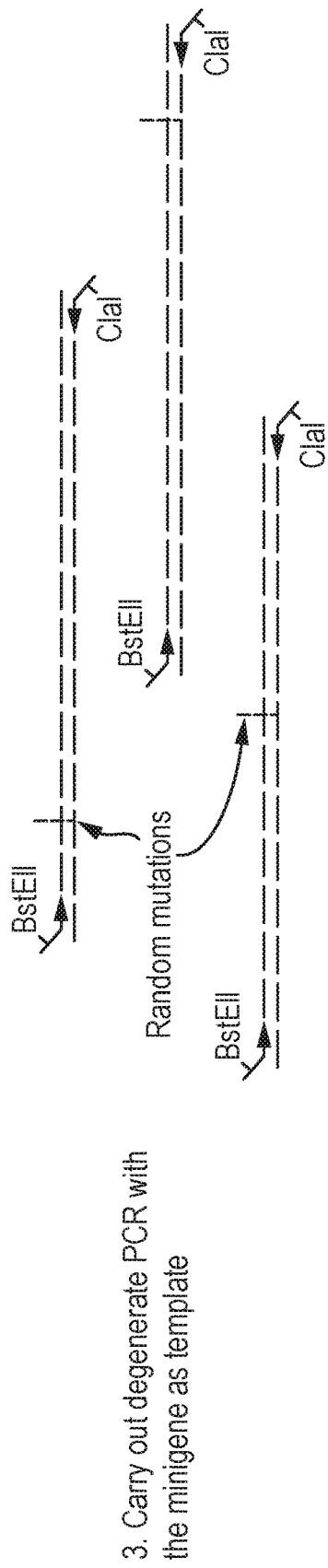
FIG. 24. Minigene construct and method to identify sequences that affect mRNA splicing. A. Generate a Minigene and add unique restriction sites (in red); B Carry out degenerate PCR with minigene as template; C. Ligate PCR products in vector and generate clones; D. Transfect clones in HEK293 cells and analyse RNa for exon 2 inclusion via Exon flanking RT-PCR and exon internal qPCR; E Sequence analysis of clone.
Figure 24C:
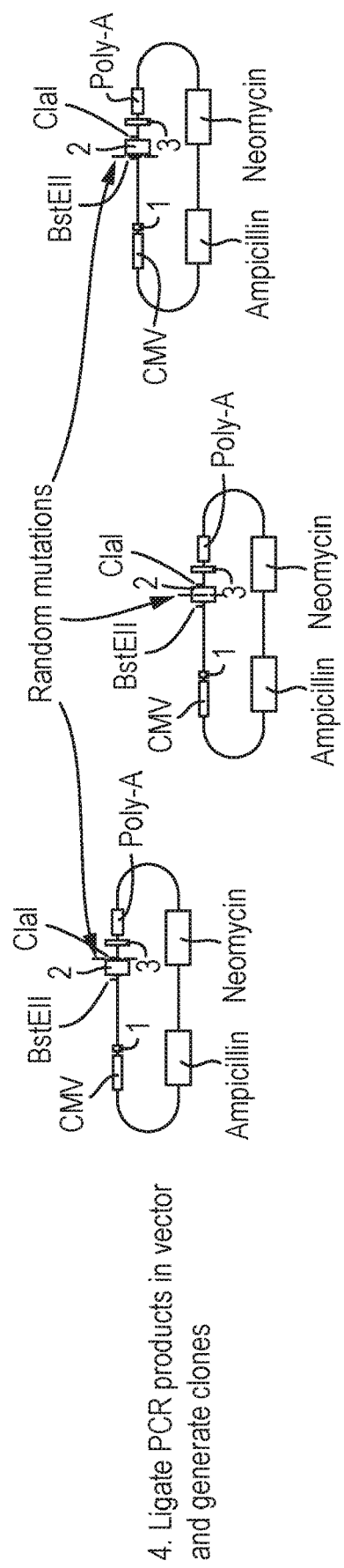
Figure 24D:
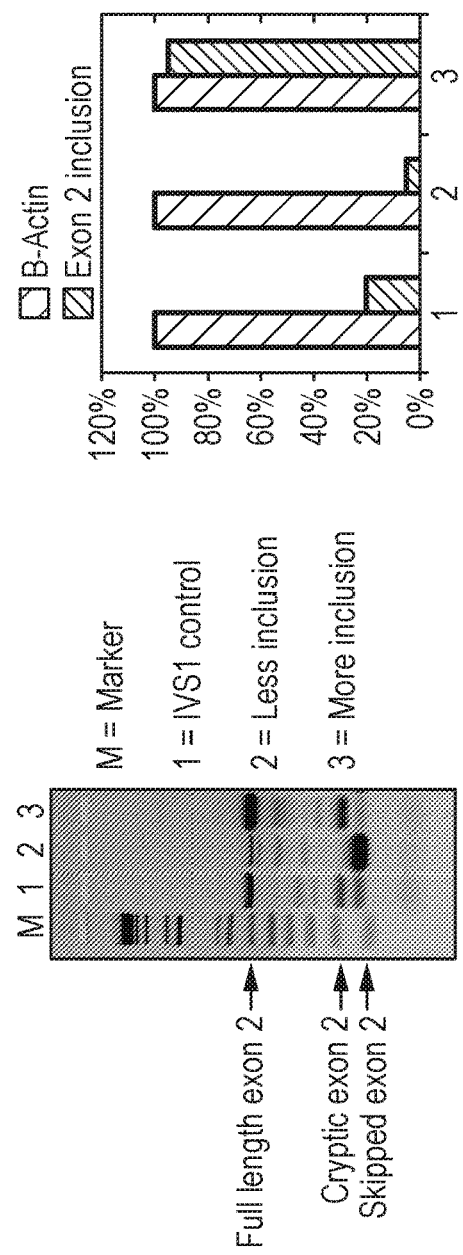
Figure 24E:
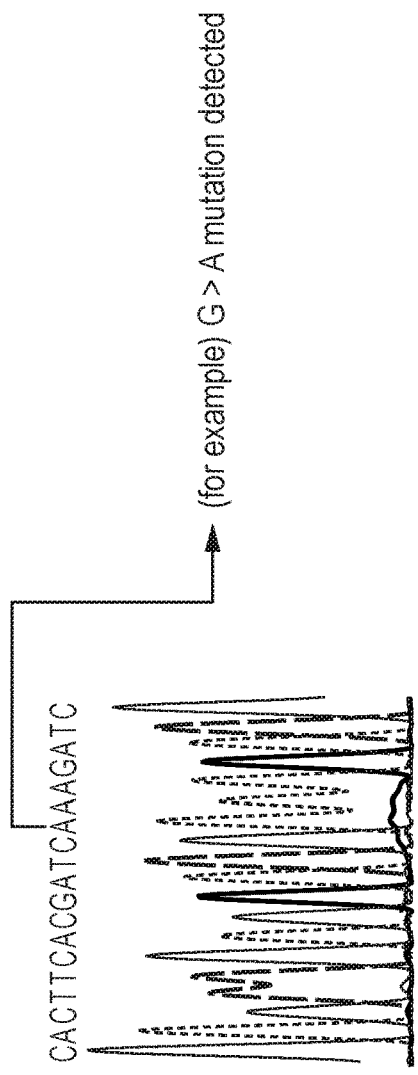

The present invention is also directed to a method for quantifying an alternatively or aberrantly spliced isoform of an mRNA as an embodiment of the invention and/or as an aspect of the invention. The method for quantifying an alternatively or aberrantly spliced isoform comprises primers that amplify splice junctions. It is not uncommon that more than one aberrantly or alternatively spliced isoforms occur. Information on the amount of each specific isoform is important. In order to quantify specific isoforms the method comprises using at least one primer that hybridizes to at least one nucleotide downstream of the alternative splice ligation site and to at least one nucleotide upstream of the alternative splice ligation site and wherein the primer is at least 15 nucleotides long. The primer thus spans over a splice ligation site, i.e. the site where two exons are ligated to each other. For example in exon skipping, two exons are joined that are not consecutive in the normal splicing event. For example if exon 2 is skipped, exon 1 and 3 are ligated. A primer spanning this ligation site, thus comprising at least 1 nucleotide of the 3'-site of exon 1 and at least 1 nucleotide of the 5'-site exon 3, is specific for an isoform RNA with a skipped exon. Examples of specific primers are shown in FIG. 24E. Also with an cryptic splice site, the non-canonical splice site is ligated to another splice. A primer spanning this alternative splice ligation site has at least one nucleotide of the cryptic splice site and 1 nucleotide of the exon ligated to this cryptic splice site. For example the cryptic splice acceptor site at c.486 results in that the preRNA is spliced at a different site, and a fragment wherein exon 1 is ligated to the cryptic splice acceptor site at c.486 and sequences of exon 2 upstream of this splice site, see FIGS. 24B and E. A primer spanning this alternative splice junction, or splice ligation site will only amply this particular splice form. Preferably the primer comprises at least 2, more preferably at least 3, more preferably at least 4, more preferably at least 5, more preferably at least 6, more preferably at least 7, more preferably at least 8, more preferably at least 9, more preferably at least 10, more preferably at least 12, more preferably at least 14 nucleotide downstream of the alternative splice ligation site. Preferably the primer comprises at least 2, more preferably at least 3, more preferably at least 4, more preferably at least 5, more preferably at least 6, more preferably at least 7, more preferably at least 8, more preferably at least 9, more preferably at least 10, more preferably at least 12, more preferably at least 14 nucleotide upstream of the alternative splice ligation site. Preferably, the primer is at least 15 nucleotide, more preferably at 16, more preferably at 17, more preferably at 18, more preferably at 19, more preferably at 20, more preferably at 21, more preferably at 22, more preferably at 23, more preferably at 24, more preferably at 25, more preferably at 26, more preferably at 27, more preferably at 28, more preferably at 29, more preferably at 30 nucleotides long. It is to be understood that the primer spans the alternative splice ligation site having at least one nucleotide upstream and one nucleotide downstream of the alternative splice ligation site.

The methods also comprise amplifying each predicted internal exon. This can be performed using, e.g., "flanking exon PCR". Flanking exon PCR is performed by contacting cDNA with a primers that "flank" the exon, i.e., a primer that is specific to the cDNA upstream of the exon and a primer that is specific to the cDNA downstream of the exon and performing an amplification reaction with at least one enzyme capable of DNA synthesis. Flanking exon PCR is a well-known method and the design of the appropriate primers is within the purview of a skilled person. Usually, the upstream (or forward) primer is designed to bind to the 3' region of the exon located 5' to the relevant exon and the downstream (or reverse) primer is designed to bind to the 5' region of the exon located 3' to the relevant exon. For example, for exon 3, one primer is designed to exon 2 (usually the 3'end of exon 2) and another primer is designed to exon 4 (usually the 5'end of exon 4). More in general, for exon n, primers are used that correspond to and are able to bind to sequences present in exon n−1 and exon n+1. If the exons are very short and/or the exon sequence is not favourable to the design of a specific primer, then the primer (e.g., the downstream primer) could be directed to another part of the same exon, or to an exon even further downstream, e.g., exon 5, or more in general to exon n+2, or exon n−2, or even exon n+3 or exon n−3. A skilled person may vary the sequence of the primers to optimise the method. The primers for the flanking PCR may be chosen to anneal where it is convenient, either to see only one exon, or to see more exons, e.g. to check for a skipped exon. It is also possible to select primers that anneal within the exon if this would be more suitable for the situation, e.g. forward primer on exon 1 and reverse primer on exon 2, to detect the presence of exon 1. If no mutation and/or no information is known on a splicing event, a skilled person may select from the wild-type sequence of the mRNA suitable sequence for primers, to perform a first flanking exon PCR. For example if the method shows that a certain exon flanking amplification product is not present a skilled person knows that he may check whether this is caused because the exon is skipped or because one or both of the primers used is directed to a sequence in the flanking exon that may be polymorphic, mutated, or (partially) removed by splicing, e.g. by activation of a cryptic splice site causing the primer not to bind to the flanking exon and hence no amplification product is obtained. An alternative exon flanking primer pair for that specific exon may be used to verify whether the exon is skipped or not. Alternatively, primers for exons further down-stream or up-stream may be used so that exon flanking amplification products spanning more than one exon may be obtained. This is all within the skills of a skilled person. It is also clear for a skilled person that the primer pairs will vary depending on the mRNA to be studied. However from the known sequence of the mRNA, for example the wild-type sequence or a known mutation, a skilled person is able to identify the predicted exons and from there the primer pairs for the flanking exon PCR. This makes the methods of the present invention suitable for many different diseases affected by splicing.

As described above, flanking exon PCR can be performed on cDNA (e.g., total cDNA from a cell) or one of the flanking exon PCR primers can be used first in a reverse transcriptase reaction to generate a cDNA strand.

Amplification using the flanking exon primers generally results in the production of one or more amplification products for each predicted exon. These products (and their corresponding lengths) are detected by standard methods such as gel electrophoresis.

It is understood that the "internal exons" and "protein encoding exons" referred to in the methods are the predicted internal and protein encoding exons of said gene. Preferably, the wild-type form of the gene. Alternatively/aberrantly spliced isoforms may have different internal exons or different protein coding exons due to alternative splicing.

Preferably, the amplification products from flanking exon PCR are compared to the amplification products obtained when a "control" cDNA is used for amplification. A control cDNA is preferably the cDNA corresponding to the wild-type sequence of a gene or to a sequence as obtained from a healthy control. A change in the length or presence or absence of an amplification product as compared to the amplification product in a control indicates alternative or aberrant splicing. Alternatively, a control cDNA may correspond to a known splicing mutation or polymorphism.

FIG. 2 of the present disclosure describes an example of an exon-skipping event. Specifically, the IVS1 mutation results in three different mRNA products; wild-type splicing, fully skipped exon 2 (product 3 of FIG. 2C), and partially skipped exon 2 (product 2 of FIG. 2C). The relative concentration of the exons was determined to be similar for all exons as determined by exon-internal qPCR analysis. The results from FIG. 2 indicate that the IVS1 mutation allows for leaky wild-type expression, while the exon 2-skipped products are degraded by non-sense mediated decay. Importantly, the five splicing prediction programs which were used in the examples failed to detect the effect of the IVS1 mutation on splicing.

Amplification using flanking exon PCR can also lead to the absence of an amplification product. If, for example, one of the flanking primers is specific for an exon (or part of an exon) that is skipped, no product will be amplified. See, for example, patient 5 in the examples in which the patient has a homozygous mutation in exon 6 of the GAA gene. Specifically, 4 nucleotides of exon 6 are deleted. These 4 nucleotides are part of the primer binding site for exon 7, resulting in no amplification product for exon 7. The quantification of the exon will also show this.

The methods of the present invention are used to confirm known mutations and to link these mutation to specific splicing events and the functional result of the splicing event. For example, the known mutation of IVS1, is shown here to result in nonsense mediated decay but also shows leaky wild type splicing, explaining the later onset of the disease. The methods of the present invention have also shown to be able to identify novel mutations. For example a novel mutation was found in intron 1 c.-32-3C>G close to the splice acceptor site of exon 2 of the GAA mRNA and causes a skipping of exon 2. Splicing prediction programs were ambivalent in predicting the outcome of the splicing as some indicated a weakening of the splice site where others did not. Furthermore a known mutation c.1551+1G>A which is located in intron 10 of GAA mRNA but for which no characterization existed, was identified and characterized in methods of the present invention. Splicing predicting programs predicted a complete loss of the splice donor site of exon 10. It was therefore expected that the loss or weakening of the splice donor site would result in a failure to remove intron 10. The present methods however showed that the contrary had happed, namely a complete skipping of exon 10 mRNA.

The disclosure also provides a kit-of-parts for characterizing an alternatively/aberrantly spliced isoform of an mRNA. The kit comprises multiple primer pairs for performing flanking exon PCR for each internal exon of the mRNA, wherein each primer pair is for performing flanking exon PCR for a different internal exon. The kit also comprises multiple primer pairs for performing qPCR for each protein encoding exon, wherein each primer pair is for performing qPCR for a different exon, and multiple qPCR probes for determining the quantity of each protein encoding exon of said mRNA, wherein each probe is specific for a different protein encoding exon. Preferably, the qPCR probe is also a primer. The kit-of-parts may further comprise other reagents useful for performing qPCR, such as suitable buffers, dNTPs, MgCl$_2$, and a heat stable DNA polymerase.

In another aspect, the present invention is to a screen using minigene constructs for detecting mutations.

Modification of mRNA splicing has great therapeutic potential. For example, exon-skipping is a technique used for restructuring mRNA. Specifically, at least one exon of an mRNA is skipped resulting in an altered protein. This can be beneficial when the skipped exon contains, e.g., a nonsense mutation. Antisense oligonucleotides (AONs) are currently being tested in clinical trials for their ability to modulate splicing. A classical example is Duchenne muscular dystrophy. In this disease, mutation hotspots are present in certain exons. Using AONs, the mutated exon is skipped and the mutation is bypassed. This results in a slightly shorter protein that is still partially functional.

In contrast to exon-skipping, it is very difficult to induce exon inclusion because it relies on targeting a splicing repressor sequence, which cannot be reliably predicted. For example, the IVS1 mutation in Pompe disease causes the skipping of exon 2. Promotion of the inclusion of exon 2 would offer a treatment of the disease. Targeting repressor sequences that cause the skipping of the exon would include the exon again. It is known that such repressor sequences may be present anywhere in the gene, either in an exon (exonic splicing silencer or ESS) or in an intron (intronic splicing silencer or ISS). The challenge is finding the sequence to be targeted.

The disclosure provides a method for identifying sequences that affect pre-mRNA splicing using a library of mutant minigene constructs. Minigenes having known mutations have been used to study the affect of a particular mutation on splicing. The present disclosure provides for libraries of randomly mutagenized minigene constructs which can be used in a screen to identify sequences that affect pre-mRNA splicing. Since the mutations are essentially random, the screen can identify sequences that are not predicted (or cannot be predicted due to a lack of prediction programs) to have a role in splicing regulation. Minigene vectors such as the pSPL3 Exon Trapping vector are commercially available for cloning exonic sequences (Life Technologies). These exon trapping vectors use the 5' and 3' splice sites in the vector to determine whether the exonic sequence can be spliced into the final transcript. Importantly, the methods disclosed herein use minigenes in which the 5' and 3' splice sites are from the pre-mRNA of interest and are in the context of being spatially separated by the corresponding intron. This construction offers the advantage of placing potential regulatory elements in a biologically relevant configuration. For the purpose of this invention, it is important to include the genomic sequence that may affect splicing of a particular exon. This includes the neighbouring introns and exons on both sides. Shorter genomic sequences, e.g. containing only the exon of interest and short flanking intron sequences, may also be tested, but these may miss the splicing mutation as the mutation itself may lie further away from the affected exon. In addition, the splicing can be influenced by the strength of the neighbouring splice sites, and by silencing or activating sequences in the introns, also when these are located at far distance from the exon. It is therefore advisable to include at least one upstream exon and intron, and one downstream intron and exon. It is important to realise that minigenes have been used to study the effect of a known mutation in splicing. The present method however uses a library of randomly mutated minigene constructs to identify sequences that have an effect on splicing. The present method allows detection of repressor sequences.

None of the prior art techniques is able to do this. It is also important to realise that the present method does not require prior knowledge of mutations but can be used in a generic unbiased way for screening for sequences that have an effect on splicing and may be used as targets for therapy.

In a one aspect, the disclosure provides a method for identifying a mutation in a pre-mRNA that modulates splicing of said pre-mRNA in a cell comprising
 providing a control minigene construct comprising a contiguous genomic sequence, wherein the genomic sequence comprises
 a) at least the 5' donor splice site of a first exon,
 b) a second exon,
 c) and at least the 3' acceptor splice site of a third exon
from the pre-mRNA, introducing mutations, preferably random mutations into said minigene construct to produce a library of mutant minigene constructs contacting cells with each member of the library of mutant minigene constructs and also contacting the cells with the control minigene construct independently, such that splicing of said minigene constructs can occur, wherein each member of the library of mutant minigene constructs and the control minigene construct is provided in an expression vector,
 detecting the splicing of said constructs, and
 identifying one or more mutant minigene constructs having a splicing pattern altered from the control minigene construct splicing pattern.

The introduction of mutation may also suitably performed by site directed mutagenesis. In a preferred embodiment, unique restriction sites are introduced into the region of interest, enabling the removal of the region of interest by restriction enzyme mediated digestion via the unique restriction sites. The region of interest is thereafter mutated, preferably by random mutations, and the mutated region of interest is ligated back into the minigene construct thereby producing a mutant minigene construct. The invention thus explicitly provides the possibility to only create mutations in a part of the minigene construct, e.g. in only one of the three consecutive exon, or even in only a part of one of the three consecutive exons, or in an intron, or in both. In this way several specific libraries may be obtained, to study one particular regions, but also completely random libraries may be obtained to screen unbiased for mutations.

In a preferred embodiment, the disclosure provides a method for identifying a mutation in a pre-mRNA that modulates splicing of said pre-mRNA in a cell comprising
 providing a control minigene construct comprising a contiguous genomic sequence, wherein the genomic sequence comprises
 a) at least the 5' donor splice site of a first exon,
 b) a second exon,
 c) and at least the 3' acceptor splice site of a third exon
from the pre-mRNA,
 introducing mutations, preferably random mutations, into said minigene construct to produce a library of mutant minigene constructs contacting cells with each member of the library of mutant minigene constructs and also contacting the cells with the control minigene construct independently, such that splicing of said minigene constructs can occur, wherein each member of the library of mutant minigene constructs and the control minigene construct is provided in an expression vector,
 detecting the splicing of said constructs,
 identifying one or more mutant minigene constructs having a splicing pattern altered from the control minigene construct splicing pattern, sequencing at least part of the mutant minigene construct, preferably the mutant minigene constructs having a splicing pattern altered from the control minigene construct splicing pattern.

In a preferred embodiment, the disclosure provides a method for identifying a mutation in a pre-mRNA that modulates splicing of said pre-mRNA in a cell comprising
providing an expression vector comprising a control minigene construct wherein the minigene construct comprises at least three consecutive exons and the intervening intronic sequences between these at least three consecutive exons,
introducing mutations, preferably random mutations into said minigene construct using error prone PCR and introducing restriction sites at the 5' and 3' ends of the PCR products via the PCR primers,
ligating each mutant minigene construct into an expression vector, thus producing a library of expression vectors comprising mutant minigene constructs,
transfecting individual members of the library of expression vectors comprising mutant minigene constructs and the control minigene construct expression vector into cells,
detecting the splicing of said constructs, and
identifying one or more mutant minigene constructs having a splicing pattern altered from the control gene construct splicing pattern.
optionally performing exon flanking RT-PCR and quantification of internal exon of the identified mutant minigene construct,
sequencing the mutant minigene construct.

In a preferred embodiment, the disclosure provides a method for identifying a mutation in a pre-mRNA that modulates splicing of said pre-mRNA in a cell comprising
providing a control minigene construct comprising a contiguous genomic sequence, wherein the genomic sequence comprises
a) at least the 5' donor splice site of a first exon,
b) a second exon,
c) and at least the 3' acceptor splice site of a third exon
from the pre-mRNA,
introducing unique restrictions sites in the minigene construct,
digestion of the minigene construct by restriction enzymes via the unique restriction sites to provide a region of interest
introducing mutations, preferably random mutations into said region of interest,
ligating the mutated region of interest back into said minigene construct to produce a library of mutant minigene constructs
contacting cells with each member of the library of mutant minigene constructs and also contacting the cells with the control minigene construct independently, such that splicing of said minigene constructs can occur, wherein each member of the library of mutant minigene constructs and the control minigene construct is provided in an expression vector,
detecting the splicing of said constructs, and
identifying one or more mutant minigene constructs having a splicing pattern altered from the control minigene construct splicing pattern.

In an alternative embodiment, the minigene construct only comprises the contiguous genomic sequence of one control exon with (part of) flanking introns. Mutations, preferably random mutations, are introduced in the minigene construct and the mutated minigene construct with the mutated exon is ligated into an expression vector that already contains the exon upstream and downstream of the control exon. This method works fast and is suitable if large exons and/or introns are present. It also ensure that only the exon and flanking intronic sequences are mutated. Sequences than only needs to be done on the control exon. It is to be understood that in the description when it is referred to minigene construct, it may also mean a vector comprising a minigene construct, wherein the minigene comprises one exon of interest and the vector comprises the exon upstream or down-stream. It is however preferred to have a contiguous genomic sequence of at three continuous exons present as a minigene construct. In this way also sequences further up- or downstream are part of the assay and the influence thereof.

Preferably, the method further comprises sequencing at least part of the mutant minigene construct, preferably the mutant minigene constructs having a splicing pattern altered from the control minigene construct splicing pattern. In a preferred method, a mutation is identified. Preferably, the method further comprises correlating a mutation in a minigene construct with an altered splicing pattern. In a preferred embodiment the genomic sequence of the mutant minigene construct is sequenced. If an altered splice patterns is identified, the vector with the mutant minigene construct is identified at least part of the genomic sequence, more preferably all of the genomic sequence in the mutant minigene construct is determined to identify one or more mutations.

In a preferred embodiment a library of mutant minigene constructs is screened for splicing patterns altered from control minigene construct splicing patterns. The sequences of the minigene construct having a splicing pattern altered from the control minigene construct splicing pattern is determined and the mutation, or more than one mutation is identified. When one mutation is identified, the mutation may be correlated to the altered splicing pattern. If more than one mutation is identified, the identified mutations may be individually analysed by creating mutant minigene construct each containing a single identified mutation, by e.g. site-directed mutagenis. The mutant minigene contructs each with one of the identified mutation is transfected into the cell to identify the splicing products and identifying one or more mutant minigene constructs with one of the identified mutations having a splicing pattern altered from the control gene construct splicing pattern. Alternatively, combinations of more than one identified mutations may be checked by creating mutant minigene construct having two or more identified mutations, e.g. by site-directed mutagenis, whereafter the mutant minigene construct having two or more identified mutations is transfected and checked for splicing variation.

The splicing pattern altered from the control gene construct splicing pattern may be an increased expression of mRNA or a decreased expression of mRNA. The splicing pattern altered from the control gene construct splicing pattern maybe the inclusion of an exon, or the exclusion of an exon, or the inclusion of an intron or the exclusion of an intron, or the use of an abberant splice site, or the use of the canonical splice site. It is to be understood that the present method may be able to detect new mutations, creating an aberrant or alternatively spliced mRNA or it may detect mutations that lead to wild type splicing, or to an increase in wild type splicing. The present method is very suitable to detect mutations that increase wild type splicing, for example in known mutations. For example a library with the IVS-1 mutation may be created with additional, random mutations in minigene construct, and one identifies mutations that increase the inclusion of exon 2, that is normally skipped with IVS1 mutation. In a preferred embodiment, the method identifies an increase in wild type splicing pattern. The region containing the identified mutation may be a splicing repressor, and targeting the region with a antisense oligonucleotide may repress the splicing repressor thereby enhancing the correct splicing event.

A control minigene construct comprises a contiguous genomic sequence comprising
  a) at least the 5' donor splice site of a first exon,
  b) a second exon,
  c) and at least the 3' acceptor splice site of a third exon The minigene comprises genomic sequence and thus also contains the intronic segments separating the first and second exon and the second and third exon of the minigene construct. Preferably, the minigene comprises at least three complete exons. The three exons may be selected from any three contiguous exons of the gene. Preferably, a mutation is identified which results in the skipping of the second exon of the minigene. Preferably, a mutation is identified which results in an increase in the inclusion of the second exon. The control construct may comprise the genomic sequence corresponding to any pre-mRNA. The control genomic sequence includes a wild-type allele or a polymorphic variant of a gene, as well as a mutation, e.g., a mutation that affects splicing. Preferably, the control genomic sequence corresponds to the sequence of a disease causing mutation. In preferred embodiments, the genomic sequence corresponds to the genomic sequence of an individual. The individual may a healthy individual, an individual diagnosed with a disorder or an individual suspected to have a disorder, or an individual with a known or unknown mutation. In an exemplary embodiment, the relevant genomic sequence is obtained by PCR amplification of a genomic template. Preferably unique restriction sites are introduced at the 5' and 3' end of the minigene construct (e.g., by the PCR primers) for cloning into an appropriate vector. The unique restriction sites are unique in the sense that the unique restriction site is not present in the genomic sequence of the minigene construct nor in the sequences of the expression vector. The unique restriction sites at the 5'end and 3'end of the minigene construct may be the same or different.

Site-directed mutagenesis can be used to introduce a particular mutant or variant in the minigene construct, if necessary or desired. Making a minigene construct is well within the skills of a skilled person.

Random mutations can be introduced into the minigene construct by any number of known methods. For example, the minigene construct can be cloned into a "mutator strain", such as an *E. coli* strain having a deficiency in primary DNA repair pathways. Replication of the plasmid carrying the minigene will usually introduce mutations. Alternatively, insertion mutagenesis can be used to randomly introduce a short nucleic acid sequences. Chemical mutagenesis can be performed with, e.g., ethyl methanesulfonate or nitrous acid. Preferably, the mutations are introduced using error prone PCR. The conditions of mutagenesis can be optimized such that, on average, each member of the library has at least one mutation (i.e., at least one nucleotide difference from the control construct). It is understood by a skilled person that each mutant construct may have more than one mutation. Preferably, the mutant minigene construct is sequenced in order to identify the precise mutation(s) introduced. Preferably, the library of mutant minigene constructs comprises at least 10 different constructs, more preferably, at least 20 different constructs, more preferably at least 30 different constructs, more preferably at least 40 different constructs. In preferred embodiments, the library comprises mutant minigene constructs that comprise on average 1 mutation per 10 nucleotides. The conditions of the random mutagenis may be selected in such a way that on average 1, 2, or 3 or even more mutations per minigene construct are introduced. It is to be understood that on average 1 mutation per minigene construct means that most minigene constructs have one mutation but that there are also mingene construct present that have more than one mutation and minigene construct that do not have mutations.

Depending on the average of the mutations per minigene construct, and on the length of the genomic sequence in the minigene construct, one is able select the number of mutant minigene construct so as to have a library wherein mutant minigene constructs are present that represent on average 1 mutation per 10 nucleotides. Libraries with on average one mutation per 5 nucleotides, or 1 mutation per 10 nucleotide or 1 mutation per 150 nucleotides, or 1 mutation per 20 nucleotides are very suitable especially for a first screen. Once mutant minigene construct with altered splicing pattern is observed and the mutation is identified, a further screen may be performed. The further screen may make use of a library of mutant minigene constructs wherein specific mutations of the nucleotides surrounding the identified mutation are introduced thereby providing specific mutant minigene, e.g. by site-directed mutagenesis. In preferred embodiments, on average each nucleotide is mutated, and preferably with all the alternative nucleotides. For example, a G nucleotide in the original sequence is mutated into a C, A and T. In preferred embodiments the library of mutant minigenes contains mutant minigene constructs that on average are mutated every nucleotide, preferably every 2 nucleotide, preferably every 3 nucleotides, preferably every 4 nucleotides, preferably every 5 nucleotides, preferably every 6 nucleotides, preferably every 7 nucleotides, preferably every 8 nucleotides, preferably every 9 nucleotides, preferably every 10 nucleotides. In preferred embodiments in the library of mutant minigene, the constructs comprise mutant mini genes wherein each mutated nucleotide is on average mutated into, 1, preferably 2, preferably 3 alternative nucleotides. In preferred embodiments the library of mutant minigene constructs comprises mutant minigene constructs of at least two or more internal exons, more preferably mutant minigene constructs of each of the internal exons. In another preferred embodiment, separate libraries of mutant minigene constructs are provided for each internal exon separately. The minigene construct of an exon of interest comprises a contiguous genomic sequence comprising at least the 5' donor splice site of the exon upstream of the exon of interest, the exon of interest and at least the 3' acceptor splice site of the exon downstream of the exon of interest. Or more generally, the minigene construct of exon n comprises a contiguous genomic sequence comprising at least the 5' donor splice site exon n−1, the exon of interest, and at least the 3' acceptor splice site of exon n+1. In a preferred embodiment the library of mutant minigene constructs comprises at least one mutant minigene construct of at least one internal exon, preferably at least one mutant minigene constructs of at least 2 internal exons, more preferably at least one mutant minigene constructs of at least 5 n internal exons, more preferably at least one mutant minigene constructs of at least 7 internal exon, more preferably at least one mutant minigene constructs of at least 10, 12, 14, internal exon, most preferably at least one minigene construct of all internal exons. In a preferred embodiment the library of mutant minigene constructs comprises at least 2 mutant minigene construct of at least one internal exon, preferably at least 5 minigene constructs of at least one internal exon, more preferably at least 10 minigene constructs of at least one internal exon, more preferably at least 20 minigene constructs of at least one internal exon, more preferably at least 30, 40, 50, or even 60 minigene constructs of at least one internal exon. More preferably the library comprises between 2-60 minigene constructs of each internal exon, more preferably between 5-40 minigene construct of each internal exon, more preferably between 10-30 minigene construct of each internal exon, more preferably between 15-20 minigene construct of each internal exon.

The constructs are cloned into an appropriate expression vector. In a preferred embodiment, unique restriction sites are introduced by site directed mutagenesis at the region of interest of the minigene construct. The unique restriction sites are unique in the sense that they are not present in the sequence of the expression vector or already present in the genomic sequence of the minigene construct In this way the mutant minigene constructs are easily cloned into the expression vector. Alternatively, unique restriction sites may already be present in the genomic region of interest and these can then be employed to clone mutated fragments. In suitable embodiments, a check is performed whether the introduction of unique restriction sites has an influence on the splicing of the minigene construct. This is done by analysing splicing e.g. by using RT-(q)PCR of minigenes containing or lacking the introduced restriction site. The control minigene construct with the restriction sites may be checked for alternative splicing pattern. If the control minigene construct with the restriction sites shows an alternative splicing pattern, the restriction sites influence the splicing and other restriction sites are suitably chosen.

A skilled person can select a suitable vector. The term "vector" includes both viral and nonviral means for introducing the nucleic acid into a cell and directing mRNA transcription. Viral vectors include lentivirus, retrovirus, adeno-associated virus, pox, baculovirus, vaccinia, herpes simplex, Epstein-Barr, SV40, Sendai, and adenovirus vectors.

Suitable vectors comprise an origin of replication, the necessary regulatory elements for transcription (e.g., promoter elements, transcriptional start and stop sequences, polyA) and preferably a selectable marker (e.g., an antibiotic resistance gene). A promoter sequence is a nucleic acid sequence capable of initiating transcription. Promoters may be constitutive wherein the transcription level is constant and unaffected by modulators of promoter activity, e.g., CMV. Promoters may also be inducible. Selectable markers are preferably present if one desires selection in bacteria. Markers may in addition be present for selection in eukaryotic cells to generate cell lines that stably express a minigene construct. The vector may also comprise a multiple cloning site. These multiple cloning sites are compatible with restriction sites which are introduced at the 5' and 3' end of the minigene for cloning into a suitable vector. Alternative ways to clone mutated fragments in a minigene may be by site-specific recombination in eukaryotes using flp/flpe and FRT sites, Cre and loxP sites, or in vitro using Gateway cloning (Invitrogen).

The cells are preferably eukaryotic cells, in particular mammalian cells such as a HeLa cell, a CHO cell, a human embryonic kidney cell (e.g., HEK 293), HT-29, MCF-7 A549, or another cell, preferably a cancer cell. Preferably, a cell is chosen which normally expresses the mRNA of interest. For example, for liver specific genes the HepG2 cell line can be used. In a preferred embodiment the cells are human cells.

The examples demonstrate the identification of mutations that increase exon 2 inclusion in a minigene containing the genomic region from exon 1 to include exon 3 and in which a known splicing mutation causing Pompe disease (c.-32-13T>G (IVS1)) is present.

Transfection of the vectors into cells can be mediated by a variety of chemicals including liposomes, DEAE-dextran, polybrene, and phosphazenes or phosphazene derivatives (WO97/07226), endoporter, or polyehthylene imine (PEI). The vectors can also be delivered to cells by physical means, e.g., by electroporation, lipids, cationic lipids, liposomes, DNA gun, calcium phosphate precipitation, or injection. The methods further comprise allowing pre-mRNA splicing to occur. It is clear to a skilled person the conditions which are necessary (e.g., time, temperature) to allow the splicing machinery in a cell to perform its function on pre-mRNA.

Cell-screening assays can be performed in a multi-test format. In certain embodiments the assay is carried out in a 12 well format, 24 well format, a 96 well format, a 384 well format, or a 1536 well format. The cell culture can be a 2-D or 3-D cell culture. Preferably, each minigene construct is contacted with cells that are spatially separated from each other, e.g., a different construct is tested in each well of a microwell plate.

Detection of mRNA splicing can be determined, e.g., by performing S1 nuclease protection or RNase protections. Preferably, splicing is measured using RT-PCR (e.g., flanking exon PCR) and/or qPCR of separate exons. qPCR is especially useful if the modulation in splicing results in a quantitative difference of, e.g., exon inclusion. Preferably, the spliced minigene construct is sequenced. The splicing pattern of each member of the mutant minigene constructs is compared to the splicing pattern of the control minigene construct. If the mutant minigene construct comprises several mutations and it is not readily clear which mutation is responsible for the effect on splicing, then additional constructs can be prepared each comprising a single mutation, e.g. by site directed mutagenesis.

In an exemplary embodiment, the method comprises introducing restriction sites by site directed mutagenesis in the genomic sequence of the minigene; performing error prone PCR of the relevant sequence using limiting dNTP concentrations to obtain on average 1 mutation per PCR fragment; cloning the pool of mutated PCR fragments into a vector; transfecting cells with the original minigene (=control minigene construct) and the mutated constructs, and then performing splicing analysis (screening for clones that show increased exon inclusion) followed by sequence analysis of the clone of interest. The examples demonstrate mutant constructs that increase GAA exon 2 inclusion in the IVS1 or wild type (for the IVS1 mutation) minigene. The increase in exon 2 inclusion indicates that the mutation in the minigene construct is in an element that plays a role in repressing the splicing of the second exon. The method thus identifies a target for the development of AONs or other compounds for GAA that can block splicing repressor activity resulting in increased exon 2 inclusion.

Accordingly, the disclosure further provides a method for making an antisense oligonucleotide (AON) for modulating the splicing of a pre-mRNA in a cell comprising,
identifying a mutation in a pre-mRNA that modulates splicing according to the method described herein,
making an AON that is complementary to at least a part of said pre-mRNA, wherein the AON binds to the region of the pre-mRNA comprising the mutation and modulates splicing of the pre-mRNA.

The AON and the pre-mRNA are complementary to each other when a sufficient number of corresponding positions in each molecule are occupied by nucleotides which can hydrogen bond with each other. Thus, "complementary" indicates a sufficient degree of complementarity or precise pairing such that stable and specific binding occurs between the oligonucleotide and the RNA target. It is understood in the art that the sequence of an antisense molecule need not be 100% complementary to that of its target sequence to be specifically hybridisable, but rather, the oligonucleotide can be complementary to at least a part of the pre-mRNA.

The term complementarity is used herein to refer to a stretch of nucleic acids, i.e., contiguous nucleic acids, which can hybridise to another stretch of nucleic acids under physiological conditions. In some embodiments, a complementary part comprises at least 3, 4, 5, 10, 15, or 20 or more consecutive nucleotides. It is clear that oligonucleotides comprising mismatches in the region of complementarity but that retain the capacity to hybridise to the targeted region in the pre-mRNA can be used.

It is thought that higher hybridization strengths, (i.e. increasing number of interactions with the opposing strand) are favorable in increasing the efficiency of the process of interfering with the splicing machinery of the system. In some embodiments, the complementarity is between 90 and 100%. In general, this allows for approximately 1 or 2 mismatch(es) in an oligonucleotide of around 20 nucleotides. Preferably, an AON described herein is at least 90% complementary to 20 consecutive nucleotides of a pre-mRNA.

Generally, the AON will be from about 10 nucleotides in length up to about 50 nucleotides in length. It will be appreciated however that any length of nucleotides within this range may be used in the method. Preferably, an AON is complementary to between 15 and 40 nucleotides of pre-mRNA and has less than 10, 8, 6, or preferably 4 mismatches with the pre-mRNA.

Importantly, the AON binds the region of the pre-mRNA comprising the mutation identified as involved in splice modulation. It is clear to a skilled person that several AON sequences can be designed to bind to a region comprising the mutation and that by shifting the binding (regions of complementarity) either 5' or 3' the effects on splicing may be enhanced.

Amino acid and polynucleotide alignments, percentage sequence identity, and degree of complementarity may be determined for purposes using the ClustalW algorithm using standard settings: see the world wide web at ebi.ac.uk/emboss/align/index.html, Method: EMBOSS::water (local): Gap Open=10.0, Gap extend=0.5, using Blosum 62 (protein), or DNAfull for nucleotide/nucleobase sequences.

As is clear to a skilled person, such AONs are useful as a therapeutic. In order to increase stability/half-life, the AONs can include any number of known AON modifications. Preferably, the AONs comprise a modification increasing nuclease resistance (for example to RNaseH).

Preferably, the AON comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, 2'-O-methyl modification, and phosphorthioate backbone and amide backbones and combinations of modifications to the backbone. For example phosphorodiamidate morpholino oligomers are modified backbone oligonucleotides that have previously been investigated as antisense agents, e.g. eteplirsen for Duchenne Muscular Dystrophy. Morpholino oligonucleotides have an uncharged backbone in which the deoxyribose sugar of DNA is replaced by a six membered ring and the phosphodiester linkage is replaced by a phosphorodiamidate linkage. Another suitable modification is 2'-O-methyl deoxyribose in a phosphorthioate backbone.

Preferably, the AON comprises one or more sugar moieties that are mono- or disubstituted at the 2', 3' and/or 5' position. The sugar moiety can be a pyranose or derivative thereof, or a deoxypyranose or derivative thereof, preferably a ribose or a derivative thereof, or a deoxyribose or a derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. Other substitutions which increase nuclease resistance are known to a skilled person. A suitable modification of the sugar moiety is 2'-O-methyl deoxyribose, or morpholino.

Suitably, the AON is checked for its effect on splicing. The effect of the AON on splicing may be checked by any method known to measure an effect of compounds or AON on splicing. Suitably the method to measure the effect on splicing of the AON is with a U7 constructs.

In yet another aspect the disclosure further provides a method for screening for compounds that modulate the splicing of a pre-mRNA in a cell comprising, identifying a mutation in a pre-mRNA that modulates splicing according to the methods described herein;

making a mutant minigene construct with the identified mutation;

contacting the mutant minigene construct with the identified mutation with a compound that is able to bind to RNA;

identify the compound that modulates splicing of the mRNA.

The mutant minigene construct with the identified mutation preferably results in an alternative or aberrant splicing, or in a non-wild type splicing. The compound that modulates the splicing is preferably the compound that modulates splicing in such a way that at least some of the alternative splicing, aberrant splicing or non-wild type splicing is reduced and/or at least the wild type splicing is increased.

In preferred embodiments, the method for screening of compounds that modulate the splicing of a pre-mRNA in a cell comprising further providing the mutant minigene construct with the identified mutation in an expression vector. In preferred embodiments, the method for screening of compounds that modulate the splicing of a pre-mRNA in a cell comprising further contacting cells with the mutant minigene construct with the identified mutation in said expression vector, preferably such that splicing of said minigene constructs can occur, In preferred embodiments, the method for screening of compounds that modulate the splicing of a pre-mRNA in a cell comprising further detecting the splicing of said constructs. In preferred embodiments, the method for screening of compounds that modulate the splicing of a pre-mRNA in a cell comprising further identifying one or more mutant minigene constructs having a splicing pattern altered from the control without added compound that is able to bind to RNA. The control is a mutant minigene construct with the identified mutation preferably in a expression vector. The control splice pattern is the pattern of the mutant minigene construct with the identified mutation without added compound.

In a suitable embodiment the description provides a method for screening for a compound that modulates the splicing of a pre-mRNA in a cell comprising,
  identifying a mutation in a pre-mRNA that modulates splicing according to the methods described herein;
  making a mutant minigene construct with the identified mutation;
  providing the mutant minigene construct with the identified mutation in an expression vector
  contacting cells with the mutant minigene construct with the identified mutation in an expression vector
  contacting cells with said compound
  allowing splicing to occur
  identifying one or more mutant minigene constructs having a splicing pattern altered from the control without added compound that is able to bind to RNA.

The contacting of the cells with the expression vector and compound may be done simultaneously, or sequentially, either with contacting the cells with the expression vector first or with the compound first.

A skilled person can select a suitable vector. The term "vector" includes both viral and nonviral means for introducing the nucleic acid into a cell and directing mRNA transcription. Viral vectors include retrovirus, adeno-associated virus, pox, baculovirus, vaccinia, herpes simplex, Epstein-Barr and adenovirus vectors.

Suitable vectors comprise an origin of replication, the necessary regulatory elements for transcription (e.g., promoter elements, transcriptional start and stop sequences, polyA) and preferably a selectable marker (e.g., an antibiotic resistance gene). A promoter sequence is a nucleic acid sequence capable of initiating transcription. Promoters may be constitutive wherein the transcription level is constant and unaffected by modulators of promoter activity, e.g., CMV. Promoters may also be inducible. Selectable markers are preferably present if one desires selection in bacteria. Markers may in addition be present for selection in eukaryotic cells to generate cell lines that stably express a minigene construct. The vector may also comprise a multiple cloning site. These multiple cloning sites are compatible with restriction sites which are introduced at the 5' and 3' end of the minigene for cloning into a suitable vector. Alternative ways to clone mutated fragments in a minigene may be by site-specific recombination in eukaryotes using flp/flpe and FRT sites, Cre and loxP sites, or in vitro using Gateway cloning (Invitrogen).

The cells are preferably eukaryotic cells, in particular mammalian cells such as a HeLa cell, a CHO cell, a human embryonic kidney cell (e.g., HEK 293), HT-29, MCF-7 A549, or another cell, preferably a cancer cell. Preferably, a cell is chosen which normally expresses the mRNA of interest. For example, for liver specific genes the HepG2 cell line can be used. In a preferred embodiment the cells are human cells. Primary cells can also be used. Preferably, cells are used that are derived from the species in which the pathogenic mutation has been detected. This is preferred because splicing regulation may be species specific. In principle, any cell can be used to test splicing. Preferably, the biological sample is derived from primary cells. Primary blood cell which can be used in the present invention include fibroblasts, leukocytes, granulocytes, monocytes, macrophages, lymphocytes, immature forms of each of the previous cells (as well as immature erythroblasts) ($CD_{34}$+ cells) and totipotent, adult or embryonic stem cells including pluripotent, multipotent, oligopotent, or unipotent stem cells or their derivatives, myoblast cells, skin cells, tooth cells, hair cells, muscle cells, induced pluripotent stem cells or their derivatives, liver cells, intestinal cells, neuronal cells. oral or nasal mucosa cells. Primary cells can be transformed e.g. using adenovirus genes or SV40 T antigen to grow indefinitely. Transformed cells can also be derived from a tumor, these cells have been transformed naturally and can also form a valuable source to study splicing. Splicing and potential therapies can also be studied in such cells after transient or stable transfection of a minigene construct.

Preferably, the cells are obtained from an individual afflicted with a disorder, e.g., Pompe disease. The cells do not necessarily have to be cells that are afflicted by the disorder, as the pre-mRNA may be expressed in other cells as well. As long as the pre-mRNA that is alternatively spliced is expressed in a cell, such a cell is suitable for the method of the invention. Preferably a cell is chosen wherein the pre-mRNA is expressed and which cell is obtained and easily cultured. It is known that splicing is cell-dependent, and thus that splicing can vary between cells. Therefore in a preferred embodiment, the relevant cells are used to screen. Relevant cells are cells that express the pre-mRNA and preferably have the same splicing patterns as cells that are causing the disorder. For example in the case of Pompe disease glycogen is accumulated in the lysosome due to a deficiency of the acid alpha glucosidase to breakdown the excess of glycogen. Heart muscles, skeletal muscles, liver and nervous system are the tissues that are most affected by the accumulation of glycogen. However, other cells, such as fibroblast are also affected by the alternative splicing, but the effect of alternative splicing is in these cells is not so much as in muscle cells. Fibroblast are easier to culture than primary muscle cells, and thus are more suitable for screening. A skilled person is able to select the most suitable cell type for screening, depending on the disease, the affected cells, cells with alternative splicing, and ease of culturing patient cells.

Transfection of the vectors into cells can be mediated by a variety of chemicals including liposomes, DEAE-dextran, polybrene, and phosphazenes or phosphazene derivatives (WO97/07226), endoporter, or polyehthylene imine (PEI). The vectors can also be delivered to cells by physical means, e.g., by electroporation, lipids, cationic lipids, liposomes, DNA gun, calcium phosphate precipitation, or injection. The methods further comprise allowing pre-mRNA splicing to occur. It is clear to a skilled person the conditions which are necessary (e.g., time, temperature) to allow the splicing machinery in a cell to perform its function on pre-mRNA.

Cell-screening assays can be performed in a multi-test format. In certain embodiments the assay is carried out in a 12 well format, 24 well format, a 96 well format, a 384 well format, or a 1536 well format. The cell culture can be a 2-D or 3-D cell culture. Preferably, each compound is contacted with cells that are spatially separated from each other, e.g., a different compound is tested in each well of a microwell plate.

Detection of mRNA splicing can be determined, e.g, by performing S1 nuclease protection or RNase protections. Preferably, splicing is measured using RT-PCR (e.g., flanking exon PCR) and/or qPCR of separate exons. qPCR is especially useful if the modulation in splicing results in a quantitative difference of, e.g., exon inclusion. Preferably, the spliced minigene construct is sequenced. The splicing pattern of each member of the mutant minigene constructs is compared to the splicing pattern of the control minigene construct. If the mutant minigene construct comprises several mutations and it is not readily clear which mutation is responsible for the effect on splicing, then additional constructs can be prepared each comprising a single mutation, e.g. by site directed mutagenesis.

Another aspect of the invention is directed toward a mutant minigene library comprising a multitude of mutant minigene constructs of a pre-mRNA which may be alternatively spliced. Preferably the library is for use in method to identify a mutation in said pre-mRNA that modulates splicing. The mutant minigene constructs comprise a contiguous genomic sequence, wherein the genomic sequence comprises a) at least the 5' donor splice site of a first exon,
b) a second exon,
c) and at least the 3' acceptor splice site of a third exon from the pre-mRNA, and wherein the genomic sequence comprises a random or deliberate mutation.

In a preferred embodiment the mutant minigene construct is provided in an expression vector. Preferably the library of mutant minigene constructs comprises a multitude of expression vector each comprising a mutant minigene construct wherein the minigene construct comprises at least three consecutive exons and the intervening intronic sequences between these at least three consecutive exons, Preferably the mutant minigene construct comprises unique restriction sites at the 3'-end and the 5'-end of the genomic sequence.

In a suitable embodiment, the library of mutant minigene constructs comprises a multitude of expression vectors each comprising a mutant minigene construct, wherein the mutant minigene construct comprises a contiguous genomic sequence, wherein the genomic sequence comprises a) at least the 5' donor splice site of a first exon,
b) a second exon,
c) and at least the 3' acceptor splice site of a third exon from the pre-mRNA, and wherein the genomic sequence comprises a random or deliberate mutation, and wherein unique restriction sites are present at the 3'-end and the 5'-end of the genomic sequence.

The minigene comprises a genomic sequence that also contains the intronic segments separating the first and second exon and the second and third exon. Preferably, the minigene comprises three complete exons. The three exons may be selected from any three contiguous exons of the gene, e.g. 1-3, 5-7, 2-4, etc.

The mutation may be present in the exons, and/or introns. The mutation may be random or deliberate. Random mutation means that one does not know which mutation is present in the library as they have been introduced randomly. Deliberate mutation means that it is known which mutation is present as these mutations have been introduced deliberately. A preferred library comprises mutant minigene constructs with random mutations. Yet another preferred library comprises mutant minigene construct with deliberate mutations. For a first screen, the random library is suitably to find mutations. Once a mutation is found, a deliberate library may be made with mutations surrounding the identified mutation to fine tune the mutation, and find the effect of the mutation on splicing.

Random mutations can be introduced into the minigene construct by any number of known methods. For example, the minigene construct can be cloned into a "mutator strain", such as an *E. coli* strain having a deficiency in primary DNA repair pathways. Replication of the plasmid carrying the minigene will usually introduce mutations. Alternatively, insertion mutagenesis can be used to randomly introduce a short nucleic acid sequences. Chemical mutagenesis can be performed with, e.g., ethyl methanesulfonate or nitrous acid. Preferably, the mutations are introduced using error prone PCR. The conditions of mutagenesis can be optimized such that, on average, each member of the library has at least one mutation (i.e., at least one nucleotide difference from the control construct). It is understood by a skilled person that each mutant construct may have more than one mutation.

Site-directed mutagenesis can be used to introduce a deliberate mutation.

Preferably, the library of mutant minigene constructs comprises at least 10 different constructs, more preferably, at least 20 different constructs, more preferably at least 30 different constructs, more preferably at least 40 different constructs. In preferred embodiments, the library comprises mutant minigene constructs that comprise on average 1 mutation per 10 nucleotides of the pre-mRNA or the genomic sequence. The conditions of the random mutagenis may be selected in such a way that on average 1, 2, or 3 or even more mutations per minigene construct are introduced. It is to be understood that on average 1 mutation per minigene construct means that most minigene constructs have one mutation but that there are also mingene construct present that have more than one mutation and minigene construct that do not have mutations.

Depending on the average of the mutations per minigene construct, and on the length of the genomic sequence in the minigene construct, one is able select the number of mutant minigene construct so as to have a library wherein mutant minigene constructs are present that represent on average 1 mutation per 10 nucleotides. Libraries with on average one mutation per 5 nucleotides, or 1 mutation per 10 nucleotide or 1 mutation per 150 nucleotides, or 1 mutation per 20 nucleotides are very suitable especially for a first screen. Once mutant minigene construct with altered splicing pattern is observed and the mutation is identified, a further screen may be performed. The further screen may make use of a library of mutant minigene constructs wherein specific mutation of the nucleotides of surrounding the identified mutation are introduced thereby providing specific mutant minigene, e.g. by site-directed mutagenis. In preferred embodiments, on average each nucleotide is mutated, and preferably with all the alternative nucleotides. For example, a G nucleotide in the original sequence is mutated into a C, A and T. In preferred embodiments the library of mutant minigenes contains mutant minigene constructs that on average are mutated every nucleotide, preferably every 2 nucleotide, preferably every 3 nucleotides, preferably every 4 nucleotides, preferably every 5 nucleotides, preferably every 6 nucleotides, preferably every 7 nucleotides, preferably every 8 nucleotides, preferably every 9 nucleotides, preferably every 10 nucleotides. In preferred embodiments in the library of mutant minigene, the constructs comprise mutant mini genes wherein each mutated nucleotide is on average mutated into, 1, preferably 2, preferably 3 alternative nucleotides.

In preferred embodiments the library of mutant minigene constructs comprises mutant minigene constructs of at least two or more internal exons, more preferably mutant minigene constructs of each of the internal exons. In another preferred embodiment, separate libraries of mutant minigene constructs are provided for each internal exon separately. The minigene construct of an exon of interest comprises a contiguous genomic sequence comprising at least the 5' donor splice site of the exon upstream of the exon of interest, the exon of interest and at least the 3' acceptor splice site of the exon downstream of the exon of interest. Or more generally, the minigene construct of exon n comprises a contiguous genomic sequence comprising at least the 5' donor splice site exon n−1, the exon of interest, and at least the 3' acceptor splice site of exon n+1. In a preferred embodiment the library of mutant minigene constructs comprises at least one mutant minigene construct of at least one internal exon, preferably at least one mutant minigene constructs of at least 2 internal exons, more preferably at least one mutant minigene constructs of at least 5 n internal exons, more preferably at least one mutant minigene constructs of at least 7 internal exon, more preferably at least one mutant minigene constructs of at least 10, 12, 14, internal exon, most preferably at least one minigene construct of all internal exons. In a preferred embodiment the library of mutant minigene constructs comprises at least 2 mutant minigene construct of at least one internal exon, preferably at least 5 minigene constructs of at least one internal exon, more preferably at least 10 minigene constructs of at least one internal exon, more preferably at least 20 minigene constructs of at least one internal exon, more preferably at least 30, 40, 50, or even 60 minigene constructs of at least one internal exon. More preferably the library comprises between 2-60 minigene construct of each internal exon, more preferably between 5-40 minigene construct of each internal exon, more preferably between 10-30 minigene construct of each internal exon, more preferably between 15-20 minigene construct of each internal exon. The library preferably comprises at least 20, more preferably at least 40, more preferably at least 50, more preferably at least 80, more preferably at least 100, more preferably at least 120, more preferably at least 150, more preferably at least 180, more preferably at least 200, more preferably at least 220, more preferably at least 250, more preferably at least 300, more preferably at least 350, more preferably at least 400, more preferably at least 500, more preferably at least 600, more preferably at least 700, more preferably at least 800, more preferably at least 900, more preferably at least 1000, more preferably at least 1100, more preferably at least 1300, more preferably at least 1500, more preferably at least 1800, more preferably at least 2000, more preferably at least 2500, more preferably at least 3000, more preferably at least 3500, more preferably at least 4000, more preferably at least 5000 minigene construct. The minigene constructs of the library are preferably mutant minigene construct. A skilled person will understand that in random mutagenesis, some mutations may occur more than one time.

In preferred embodiments, the library comprises expression vectors comprising the mutant minigene constructs. A skilled person can select a suitable vector. The term "vector" includes both viral and nonviral means for introducing the nucleic acid into a cell and directing mRNA transcription. Viral vectors include retrovirus, adeno-associated virus, pox, baculovirus, vaccinia, herpes simplex, Epstein-Barr and adenovirus vectors.

Suitable vectors comprise an origin of replication, the necessary regulatory elements for transcription (e.g., promoter elements, transcriptional start and stop sequences, polyA) and preferably a selectable marker (e.g., an antibiotic resistance gene). A promoter sequence is a nucleic acid sequence capable of initiating transcription. Promoters may be constitutive wherein the transcription level is constant and unaffected by modulators of promoter activity, e.g., CMV. Promoters may also be inducible. Selectable markers are preferably present if one desires selection in bacteria. Markers may in addition be present for selection in eukaryotic cells to generate cell lines that stably express a minigene construct. The vector may also comprise a multiple cloning site. These multiple cloning sites are compatible with restriction sites which are introduced at the 5' and 3' end of the minigene for cloning into a suitable vector. Alternative ways to clone mutated fragments in a minigene may be by site-specific recombination in eukaryotes using flp/flpe and FRT sites, Cre and loxP sites, or in vitro using Gateway cloning (Invitrogen).

Preferably the library is present in a multi-test format. In certain embodiments the library is present in a 12 well format, 24 well format, a 96 well format, a 384 well format, or a 1536 well format. In preferred embodiment each mutant minigene construct is present in separate containers. It means that each container contains mutant minigene construct or a vector comprising a mutant minigene construct carrying the same genomic sequence or mutated genomic sequence. A skilled person is well aware of methods to make a library of mutated constructs and provide each member of the library in separate containers. Preferably the containers are well from a multiwell plate.

It is to be understood that preferred embodiments for the method for identifying a mutation in a pre-mRNA that modulates splicing of said pre-mRNA in a cell are also preferred embodiments for the library of mutant minigene constructs, and for the method of screening for compounds and for the method for making an antisense oligonucleotide (AON) for modulating the splicing of a pre-mRNA in a cell. It is to be understood that preferred embodiments for the library of mutant minigene constructs are also preferred embodiments for the method for identifying a mutation in a pre-mRNA that modulates splicing of said pre-mRNA in a cell, and for the method of screening for compounds and for the method for making an antisense oligonucleotide (AON) for modulating the splicing of a pre-mRNA in a cell.

The minigene assay of the present provided information to construct antisense oligomeric compounds with SEQ ID NO: 98-540.

In a further aspect, the present disclosure provides for methods for identifying antisense oligonucleotide (AON) sequences that modulate splicing by screening a library of AON constructs. These AONs can be used as therapeutics for treating various disorders. Preferably, the AONs are used to treat Pompe disease.

Although it is possible to regulate splicing with AONs, a challenge exists in identifying specific AON sequences which have the desired effect on splicing. It has been especially difficult to identify AONs that block splicing repressor sequences, i.e., splicing silencers. Blocking such repressor sequences may promote exon inclusion and would therefore be useful as treatments for disorders which result from exon skipping. These splicing repressor sequences may be present in the exons, in the UTR's and in the introns. In addition, these splicing repressor sequences cannot reliably be predicted. Also even if the mutation or splicing repressor sequence is found, one still needs to design a suitable sequence or compounds that is able to effectively block the repressor sequence and promote exon inclusion. The present invention provides for a method that can directly and in an unbiased manner identify AONs that effectively modulate splicing.

In one aspect the disclosure provides a method for screening a library of antisense oligonucleotides (AONs) for oligonucleotides that modulate splicing of a pre-mRNA in a cell comprising
    contacting cells, preferably primary cells, which express said pre-mRNA with a library of AONs, wherein the library comprises a collection of vectors, each vector comprising a modified U7 snRNA, comprising each a different AON that is complementary to at least a part of said pre-mRNA and identifying one or more AONs that modulates the splicing of said pre-mRNA.

In another aspect the invention provides for a library comprising a collection of vectors comprising antisense oligonucleotides (AONs) for oligonucleotides that modulate splicing of a pre-mRNA in a cell, each vector comprising a modified U7 snRNA, comprising each a different AON that is complementary to at least a part of said pre-mRNA. Preferably the vector comprises unique restriction sites flanking the antisense sequence and the U7 snRNA.

A collection of modified U7 snRNA vectors is understood to be a multitude of vectors comprising a modified U7 snRNA, comprising each a different AON that is complementary to at least a part of said pre-mRNA.

In a preferred embodiment the invention provides a method for screening a library comprising of antisense oligonucleotides (AONs) for oligonucleotides that modulate splicing of a pre-mRNA in a cell comprising I) preparing a library comprising a multitude of AONs, wherein the preparation of said library comprises a) generating or providing a modified U7 snRNA vector comprising the U7 promoter and a modified U7snRNA, b) introducing unique restrictions sites in the U7 antisense construct c) PCR with primers having the sequence of said antisense oligonucleotide thereby obtaining a U7 antisense construct c) cloning the U7 antisense construct into an appropriate vector thereby obtaining a U7 antisense vector the method of screening further comprising:

II) contacting cells, preferably primary cells, which express said pre-mRNA, with the library of AONs, wherein the library comprises a collection of vectors, each vector comprising a modified U7 snRNA, and comprising a different AON that is complementary to at least a part of said pre-mRNA, and III) identifying one or more AONs that modulates the splicing of said pre-mRNA.

The cells that express said pre-mRNA may also be cells that comprise a minigene construct which has been introduced by transient or stable transfection, or a cell wherein a mutation of interest is present or introduced. The mutation may be introduced by any means known to the skilled person including gene editing techniques such as TALEN, ZFN, Meganucleases or CRISPR/cas9.

In preferred embodiments step b) and c) wherein the sequence of the antisense nucleotides and the unique restrictions sites are introduced, are performed in one step by primers comprising the sequence of said antisense oligonucleotide and a unique restriction site. The unique restriction site is unique in the sense that the restriction site sequence is not present in the sequence of the vector, or the antisense sequence, and only once in the U7 snRNA.

Figure 17:
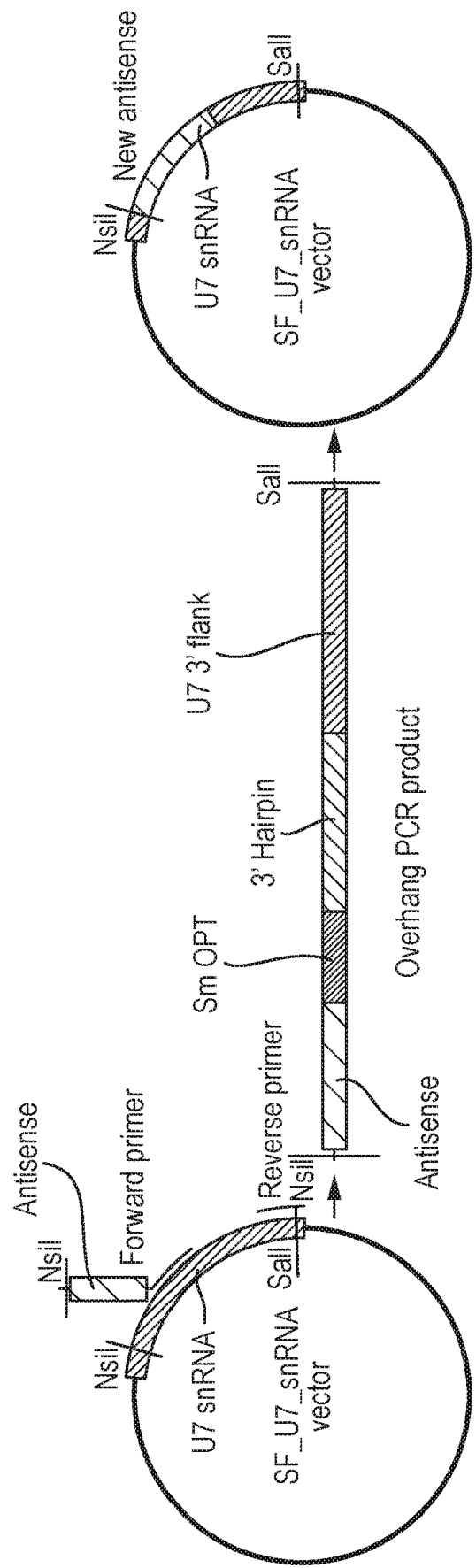
FIG. 17 The modified U7 snRNA which is used with overhang PCR to quickly generate a new U7 snRNA vector with antisense sequence.
Figure 18:
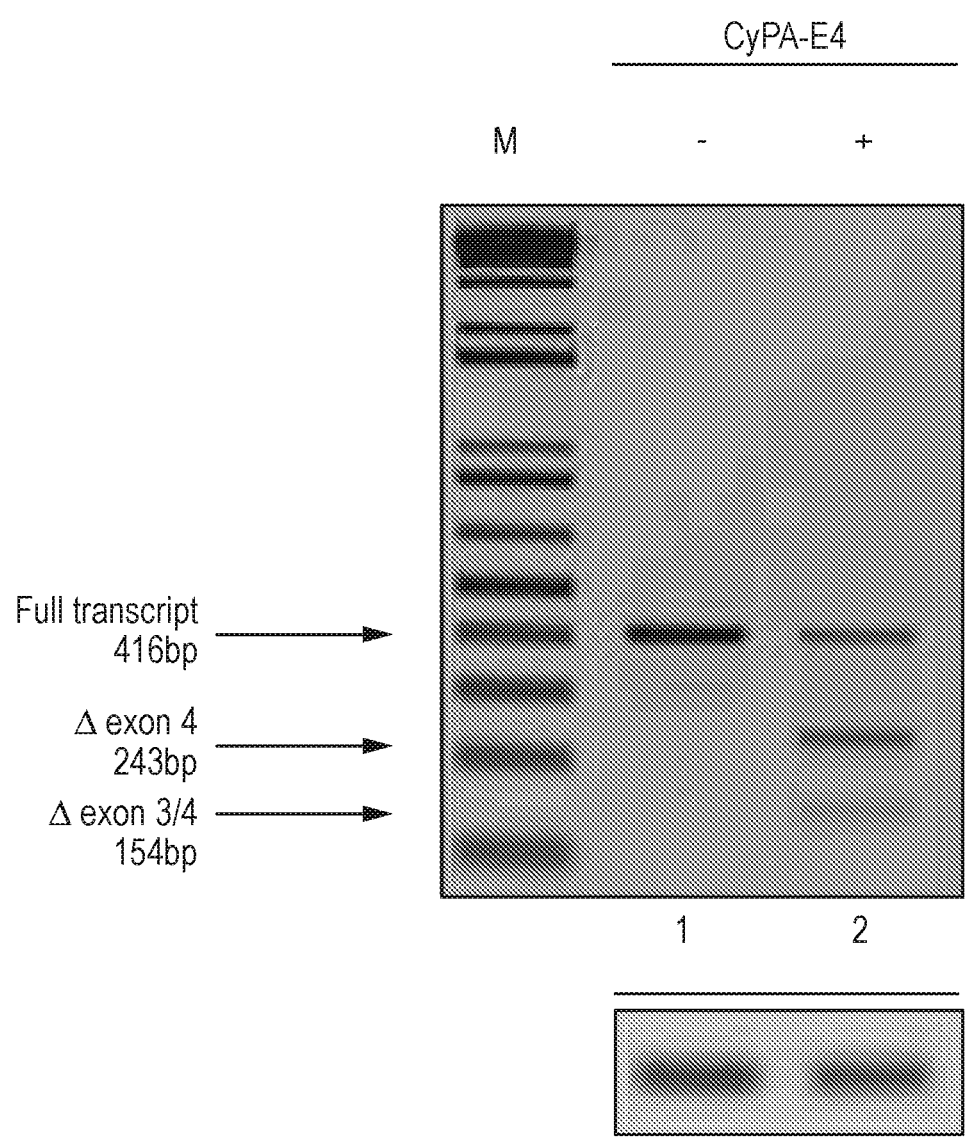
FIG. 18. The modified U7 snRNA lentiviral system is capable of interfering with splicing of CyPA as published previously [Liu, S., et al., Inhibition of HIV-1 multiplication by antisense U7 snRNAs and siRNAs targeting cyclophilin A. Nucleic Acids Res, 2004. 32(12): p. 3752-9]. Upper figure: RT-PCR analysis of exon 4 of cyclophilin A (CyPA- E4).-(lane 1): untransduced HeLa cells.+(lane 2): HeLa cells transduced with modified U7 snRNA lentiviruses (described in FIG. 18) expressing the U7/E4 antisense sequence as described in FIG. 1B of Liu et al. Below: beta actin mRNA. M: molecular weight DNA marker.

In preferred embodiments of aspects of the invention, the vector comprises the following elements;

U7 promoter
A first unique restriction site
Antisense sequence
U7 sm sequence, preferably sm OPT sequence
3'hairpin sequence
U7 3'-flanking sequence
A second unique restriction site Preferably the elements are in the order as indicated above however the order may be different as long as the promoter is first. For example the hairpin sequence may be on the 5' or on the 3'site of the antisense sequence. In addition, the unique restriction sites may flank the antisense sequence, or a third unique restriction site may be present, two of them flanking the anti sense sequence. The first and second, and optionally third unique restriction site may be the same or different as long as the restriction site is not present in the sequence of the rest of the vector or in the antisense sequence or in the U7 sequences. FIG. 17 shows a preferred method of making the AON U7snRNA construct and a preferred AON U7snRNA construct.

To effectively modify splicing with antisense RNAs, accumulation must take place in the nucleoplasm, where splicing occurs [Kathrin Meyer, D. S., Antisense Derivatives of U7 Small Nuclear RNA as Modulators of Pre-mRNA Splicing, in Alternative pre-mRNA Splicing: Theory and Protocols, C.W.J.S.a.R.L.E. S. Stamm, Editor. 2012, Wiley-VCH Verlag GmbH & Co. KGaA: Weinheim, Germany. p. 482-494]. The vectors of the library produce AONs that are linked to a hairpin derived from a U7 snRNA. This constitution stabilizes the AON and delivers it to the nucleus.

Antisense U7 snRNAs accumulate as a stable small nuclear ribonucleoprotein (snRNP), which is normally involved in histone 3'-end processing [Soldati, D. and D. Schumperli, Structural and functional characterization of mouse U7 small nuclear RNA active in 3' processing of histone pre-mRNA. Mol Cell Biol, 1988. 8(4): p. 1518-24]. The U7 snRNA comprises a hairpin, which makes it chemically stable, and an antisense sequence to target specific sequences [Groebe, D. R. and O. C. Uhlenbeck, Nucleic Acids Res, 1988. 16(24): p. 11725-35]. The AON replaces the 5' end of the U7 snRNA moiety which binds to the histone downstream element (HDE).

The U7 hairpin sequences comprise of a 6-base-pair stem and a 4-base loop and is present in many species, such as human, mouse, *Drosophila*, zebrafish, sea urchins. An exemplary U7 hairpin sequence is for example: GGCTCT TTTCAGAGCC (SEQ ID NO: 58), the loop nucleotides are underlined. The hairpin sequence is well conserved and may be depicted by GGCYCTTTTMAGRGCC (SEQ ID NO: 59) wherein Y is a pyrimidine (C or T), M stands for A or C, and R stands for a purine (G or A).

Preferably, the AON sequences are introduced into the U7 construct by performing PCR on the U7 snRNA, in which at least one of the primers preferably both primers, contains the AON sequence to be introduced. Preferably, the U7 construct comprises two or three unique restriction sites. These restriction sites enable rapid 1-step cloning of candidate AON sequences via conventional cloning. In a preferred embodiment, the primer comprising the AON sequence also comprises the unique restriction site sequence.

Preferably, the U7 snRNA comprises a modified Sm OPT sequence Normally, the Sm sequence can bind five Sm proteins also found in spliceosomal snRNPs and two U7 specific proteins (Lsm10 and Lsm11) to effectively process histone RNA [Pillai, R. S., et al., Purified U7 snRNPs lack the Sm proteins D1 and D2 but contain Lsm10, a new 14 kDa Sm D1-like protein. Embo j, 2001. 20(19): p. 5470-9]. By modifying Sm binding site into Sm Opt the function of histone mRNA processing is abolished. In addition, the modified sequence also leads to more efficient accumulation as a nuclear snRNP than unmodified, wild-type U7 snRNA [Schumperli, D et al., The special Sm core structure of the U7 snRNP: farreaching significance of a small nuclear ribonucleoprotein. Cell Mol Life Sci. 2004 October; 61(19-20):2560-70. Schumperli, D. and R. S. Pillai]. Additionally, the U7 snRNA can carry an optional tail, which can be any desired sequence. Depending on function, the sequence can consist of enhancer or silencer elements.

The U7 snRNA construct may comprise U7 3'-flanking sequence. These 3'-lanking sequences may be any kind of sequence and may comprise sequences that modulate splicing such as exon splicing enhancer (ESE), intron splicing enhancer (ISE), exon splicing silencer (ESS) and intron splicing silencer (ISS) sequences, polypyrimidine tract sequences, binding sites for splicing regulators, but also cell penetrating sequences.

The AONs and the pre-mRNA are complementary to each other when a sufficient number of corresponding positions in each molecule are occupied by nucleotides which can hydrogen bond with each other, as described herein. Generally, the AON will be from about 10 nucleotides in length up to about 50 nucleotides in length. Preferably, a AON is complementary to between 15 and 40 nucleotides of pre-mRNA and has less than 10, 8, 6, or preferably less than 4 mismatches with the pre-mRNA. Preferably, the AON is at least 90% complementary to 20 consecutive nucleotides of a pre-mRNA.

In preferred embodiments the U7 snRNA construct comprises more than one AON. These AON may be targeted to different parts of the pre-mRNA.

It is to be understood that the U7 snRNa construct when present in a vector is a DNA sequence, that transcribes the AON-hairpin-3'sequence as a RNA molecule. The U7 snRNA construct is made as a DNA molecule so that it can be cloned into a vector.

Preferably, said library comprises at least 10 different AONs, more preferably at least 20 AONs, more preferably at least 30, preferably at least 40, preferably at least 50, preferably at least 60, preferably at least 70, preferably at least 80, preferably at least 90, preferably at least 100. The sequence of the AON to be tested may be selected based on predictions that it is part of a splicing regulatory element. Sequences may also be selected essentially randomly, e.g., tiled AONs which cover a specific region of a pre-mRNA. Tiled AONs which bind a region surrounding a pathogenic mutation, or identified mutation according to the present invention can also be tested. In preferred embodiments, the library of AONs are complementary to a region of the pre-mRNA comprising a mutation that affects splicing, preferably wherein the mutation is identified in a method as disclosed herein. The AONs to be tested may be partially overlapping or non-overlapping. Preferably the AONs overlap for at least a part, preferably the AONs overlap for about 1-15 nucleotides, more preferably the AONs overlap for about 2-12 nucleotides, more preferably the AONs overlap for about 3-10 nucleotides, more preferably the AONs overlap for about 4-8 nucleotides, more preferably the AONs overlap for about 5-7 nucleotides.

Each member of the library is introduced into a cell, preferably a primary cell that expresses said pre-mRNA. In principle, any cell may be used to test splicing. Primary cells may be transformed e.g. using adenovirus genes or SV40 T antigen to grow indefinitely. Transformed cells may also be derived from a tumor, these cells have been transformed naturally and can also form a valuable source to study splicing. Splicing and potential therapies can also be studied in such cells after transient or stable transfection of a minigene construct.

Introduction of the U7snRNA construct may be by infection, e.g. with a virus, or by transfection, e.g. by expressions plasmids. A skilled person is well aware of the several possibilities to introduce the U7snRNA construct.

Preferably each U7snRNA construct with an AON is introduced into a cell separately. This means that each AON is introduced into a cell in a separate chamber. Thus in a preferred embodiment, the library of AON is present in a multitude of chambers, each chamber comprising a different AON construct. Preferably each chamber comprises a single AON construct, meaning each chamber comprises one or more vectors having the same AON sequence. It means that each chamber may have more than one vectors, however each vector within a chamber comprises vectors having the same AON sequence. In other preferred embodiments each chamber comprises vectors with 2 different AON sequence, or 2-10 different AON sequences, preferably 2-8 different AON sequences, more preferably 3-7 different AON sequences, more preferably 4-6 different AON sequences, more preferably 5 different AON sequences. Suitably, the containers are wells in a micro well plate.

The methods are not directed to determining the effect of a single AON on pre-mRNA splicing, but rather to a method of screening a collection (library) of AONs.

U7 snRNA gene was prepared as described by Suter et al, 1999. However the described system by Suter et al is not suitable for high throughput screening of primary cells such as fibroblast cells as it is difficult to transfect such cells with the system of Suter. Preferably, the vector containing the U7 snRNA-AON is a viral vector, preferably a vector that is able to transfect primary cells. Preferred viral vectors are adenovirus, adeno-associated virus vector (AAV), see U.S. Pat. Nos. 5,139,941 and 4,797,368, and a retroviral vector such as a lentivirus vector (Goyenvalle A, et al. Science 2004; 306(5702):1796-9 and U.S. Pat. No. 5,399,346), SV40, or any other viral vector. A skilled person is able to select a suitable viral vector.

FIG. 17 shows a schematic overview of the U7 snRNA construct with the AON sequences. The U7 snRNA construct with the AON comprises a promoter, the AON, SmOPT sequence, the 3'hairpin and a u7-3'flanking sequence. In preferred embodiments, the AON-U7snRNA, comprising the SmOPT-3'hairpin-U7 3'flanking sequence, comprises unique restrictions sites for ease of cloning. In an exemplary embodiment, the AON library was prepared using a lentiviral vector. This lentiviral contained a second StuI restriction site and therefore the StuI restriction site of the U7 snRNA gene was replaced with an NsiI restriction site for rapid insertion of new antisense sequences by overhang PCR. With this system we were capable of inserting new antisense sequences with a high cloning efficiency (>70%).

The cells are preferably eukaryotic cells, in particular mammalian cells such as a HeLa cell, a CHO cell, a human embryonic kidney cell (e.g., HEK 293), transformed cells, or a cancer cell. The transformed cells may suitably comprise a minigene construct comprising the mutation of interest, the mutated gene of interest or carry a mutation in an endogenous gene. Preferably, the cells are human cells. More preferably the cells are primary cells, such as primary fibroblast cells, primary blood cells, primary leukocytes, Primary blood cell which can be used in the present invention include fibroblasts, leukocytes, granulocytes, monocytes, macrophages, lymphocytes, immature forms of each of the previous cells (as well as immature erythroblasts) ($CD_{34}$+ cells) and totipotent, adult or embryonic stem cells including pluripotent, multipotent, oligopotent, or unipotent stem cells or their derivatives, myoblast cells, skin cells, tooth cells, hair cells, muscle cells, induced pluripotent stem cells or their derivatives, liver cells, intestinal cells, neuronal cells, oral or nasal mucosa cells. The primary cells may have been immortalised by e.g. SV40 T antigen expression or any other method to immortalise cells. Preferably, the cells are obtained from an individual afflicted with a disorder, e.g., Pompe disease. The cells do not necessarily have to be cells that are afflicted by the disorder, as the pre-mRNA may be expressed in other cells as well. As long as the pre-mRNA that is alternatively spliced is expressed in a cell, such a cell is suitable for the method of the invention. Preferably a cell is chosen wherein the pre-mRNA is expressed and which cell is obtained and easily cultured. It is known that splicing is cell-dependent, and thus that splicing can vary between cells. Therefore in a preferred embodiment, the relevant cells are used to screen. Relevant cells are cells that express the pre-mRNA and preferably have the same splicing patterns as cells that are causing the disorder. For example in the case of Pompe disease glycogen is accumulated in the lysosome due to a deficiency of the acid alpha glucosidase to breakdown the excess of glycogen. Heart muscles, skeletal muscles, liver and nervous system are the tissues that are most affected by the accumulation of glycogen. However, other cells, such as fibroblast are also affected by the alternative splicing, but the effect of alternative splicing is in these cells is not so much as in muscle cells. Fibroblast are easier to culture than primary muscle cells, and thus are more suitable for screening. A skilled person is able to select the most suitable cell type for screening, depending on the disease, the affected cells, cells with alternative splicing, and ease of culturing patient cells. The screening method has the advantage that AONs can be identified with direct therapeutic potential for the patient and patients with similar disease causing mutations. The advantage of performing the screen or using the library directly on primary cells obtained from patients is that directly potentially AON may be identified, that need no further or minimal optimisation.

Cell-screening assays can be performed in a multi-test format as described herein. Preferably, each AON is contacted with cells that are spatially separated from each other, e.g., a different AON is tested in a separate container, for example a different AON is tested in each well of a microwell plate.

Cells are contacted with a library of AONs such that the AONs are delivered inside the cell by infection with virus (preferred) and splicing of the pre-mRNA is allowed to take place. Alternatively, constructs can be delivered by transfection. Transfection of the vectors into cells can be mediated by a variety of chemicals including liposomes, DEAE-dextran, polybrene, and phosphazenes, phosphazene derivatives (WO97/07226) or polyetheyleneimine (PEI). The vectors can also be delivered to cells by physical means, e.g., by electroporation, lipids, cationic lipids, liposomes, DNA gun, calcium phosphate precipitation, or injection. Preferred vectors are viruses, preferably a retrovirus, preferably a lentivirus. The advantage of using viruses is that close to 100% of cells including primary cells can be infected resulting in high expression levels in nearly all cells. Any transfection method that delivers the vector into the cell of interest, preferably a cell from a patient, and that leads to a expression of the AON is suitable for the present invention. The methods further comprise allowing pre-mRNA splicing to occur. It is clear to a skilled person the conditions which are necessary (e.g., time, temperature) to allow the splicing machinery to perform its function on pre-mRNA.

AONs that modulate splicing of the pre-mRNA may be identified directly or indirectly. In a direct measurement, the splicing of the pre-mRNA is determined, e.g., by performing S1 nuclease protection or RNase protections. Preferably, splicing is measured by using RT-PCR, preferably flanking exon PCR and/or qPCR for at least one exon as described herein. Splicing may also be measured indirectly, e.g., by protein expression levels (e.g., Western blot) or functional assays of protein activity. Preferably, the effect of the AON on splicing is determined by the method for characterizing alternatively or aberrantly spliced isoforms of an mRNA as described herein. Alternatively, a construct is made wherein at least part of the exon of interest is replaced by a fluorescent marker, such as a fluorescent protein such as GFP, constructs wherein such a fluorescent marker is inserted next to the exon of interest or part of the exon of interest. Proper splicing is then shown by the expression of the fluorescence marker, and fluorescence values may be used to determine a correct splicing event, such as inclusion of the exon of interest. Also if skipping of an intron is desired, a fluorescent marker, such as a fluorescent protein such as GFP, is cloned as part of the construct, either replacing at least a part of the intron to be skipped, or next to the intron or part of the intron to be skipped. Correct skipping of the intron will reduce the fluorescence whereas aberrant inclusion of the intron increases fluorescence.

The test AON may promote exon-skipping or the use of a cryptic splice site. Preferably the test AON promotes intron exclusion, inhibition of the use of a cryptic splice site, exon inclusion, or inhibition of splicing repressor sequences. Preferably, the test AON promotes exon inclusion.

Once an AON is identified which has an effect on splicing, further AONs based on this sequence can be prepared and tested, e.g., shifting the regions of complementarity with the target mRNA a few bases in the 5' or 3' direction in order to optimize the AON sequence. In a preferred embodiment, one may add regulatory sequences to the AON. These include sequences known to regulate splicing such as exon splicing enhancer (ESE), intron splicing enhancer (ISE), exon splicing silencer (ESS) and intron splicing silencer (ISS) sequences, polypyrimidine tract sequences, known binding sites for splicing regulators, sequences that induce a particular secondary structure involved in regulation of splicing, RNA expression, RNA stability, protein translation, but also cell penetrating sequences.

Interfering with splicing using U7 snRNA's is suitable for broad range of splicing diseases. However, screening for potential antisense sequences in an unbiased way on large parts of genomic DNA is currently labour intensive and expensive. The present disclosure provides an efficient high throughput screening system for identifying splice-modulating AONs.

The present invention provided the target sequence for enhanced inclusion of GAA exon 2, SEQ ID 1, 37-40.

The present invention provided the target sequence for enhanced exclusion of GAA intron 6, SEQ ID 541-546.

The present invention provided the following antisense oligomeric compounds SEQ ID NO: 41-97.

All patent and literature references cited in the present specification are hereby incorporated by reference in their entirety.

The invention is further explained in the following examples. These examples do not limit the scope of the invention, but merely serve to clarify the invention.

EXAMPLES

Example 1

Mutations affecting pre-mRNA splicing are difficult to predict due to the complex mechanism of splicing regulation. A generic approach to systemically detect and characterize effects of sequence variants on splicing would improve current diagnostic practice. Here, we show that such approach is feasible by combining flanking exon RT-PCR, sequence analysis of PCR products, and exon-internal quantitative RT-PCR for all coding exons. It has been applied to uncharacterized mutations in the acid-alpha glucosidase gene causing Pompe disease, a monogenic autosomal recessive disease. Effects on splicing included cryptic splice site usage, intron retention and exon skipping. These differed from in silico predictions, highlighting the need for experimental testing. Quantification of the extent of leaky wild type splicing correlated with disease severity.

Materials and Methods

Patients and Healthy Control

Patients were diagnosed with Pompe disease based on clinical symptoms and GAA enzyme activity. All patients and the healthy control provided informed consent for molecular analysis.

Nomenclature

The positions of the mutations described are aligned against Ensembl GAA cDNA association number ENST00000302262.3. c.1 indicates the first nucleotide of the coding region of GAA mRNA. Further numbering is according to HGVS standards [14].

Cell Culture and cDNA Preparation

Fibroblasts were isolated from skin biopsies of patients and a healthy individual. Cells were cultured in DMEM High Glucose (Lonza)+10% Fetal bovine serum (HyClone, Thermo Scientific)+1% penicillin/streptomycin (Lonza). RNA was isolated using the RNAeasy miniprep kit (Qiagen). 800 ng of RNA was used for generation of cDNA using the iScript cDNA synthesis kit (Biorad). cDNA was diluted 10 times before use.

Flanking Exon PCR Analysis cDNA was amplified using FastStart Taq Polymerase (Roche). Primers were used at a final concentration of 0.333 µM each, dNTPs at 0.333 mM each. The PCR program was performed on a Biorad s1000 thermal cycler (96° C. for 4 min., 35× [96° C. 20 sec., 60° C. 30 sec., 72° C. 1 min.], 72° C. 5 min.) 5 µl of each PCR reaction was run on a 1.5% agarose gel containing ethidium bromide. Gel were photographed on a Typhoon FLA 9000 gel imager (G&E Healthcare). The primers used are listed in FIG. 15.

Exon-Internal qPCR Analysis

To determine the relative concentration of each sample, 4 µl of each cDNA sample (10 times diluted in H2O) was processed in a 15 µl PCR reaction containing IQ Mastermix (Biorad) and 0.333 µM of each primer. To account for the efficiency of each specific primer set, all samples were related to a standard curve from the healthy control sample. All samples were measured in triplicate. The primers used are listed in FIG. 16.

Sanger Sequencing

Genomic DNA mutations were identified at the diagnostic department of Clinical Genetics at the Erasmus MC, Rotterdam, The Netherlands. Direct sequencing of flanking exon PCR products was performed using the Big Dye Terminator kit v3.1 (Applied Biosystems). To obtain pure DNA samples, PCR products visible on gel in the splicing assay were stabbed with a 20 µl pipet tip and DNA on the tip was resuspended in 10 µl H2O. 1 µl was subsequently used in a new PCR (as described in the splicing assay) to obtain DNA from a single template. Excess primers and dNTPs were removed using FastAP Thermosensitive Alkaline Phosphatase (Thermo Scientific), according to the manufacturer's protocol. Samples were purified with sephadex G-50 (GE Healthcare) and the sequence was determined on an AB3130 Genetic Analyzer (Applied Biosystems, Hitachi).

GAA Enzyme Activity

The activity of GAA in fibroblasts was measured with 4-methylumbelliferyl-α-gluocpyranoside (4-MU) or with glycogen as substrate as described [15].

Results

Generic Assay to Detect Splicing Mutations

The approach consists of two parts. First (FIG. 1, left), a generic RT-PCR is performed of the mRNA of interest using standard primers that flank each individual canonical exon (flanking exon PCR). The products are separated by agarose gel electrophoresis. Changes in product size are indicative of alternative/aberrant splicing. Splicing junctions can be precisely determined using sequencing of products isolated from gel or by direct sequencing of the PCR reaction. Second (FIG. 1, right), a standard qPCR is performed to quantify each individual exon (exon-internal qPCR). Primers that anneal within each exon are used. Results are normalized for beta-actin mRNA and for expression in a healthy control. The results quantify exon skipping/inclusion, and may also indicate whether a splicing mutation allows leaky wild type splicing.

Development and Validation of the Assay

Healthy Control

Figure 2A:
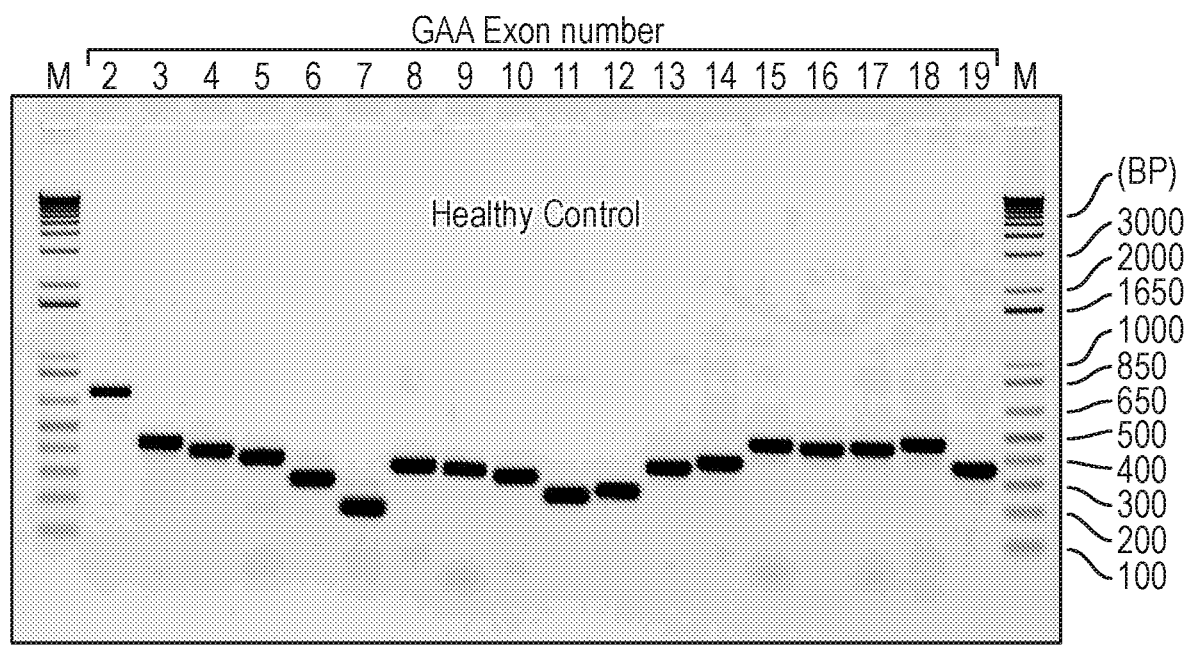
FIG. 2. Splicing analysis of a healthy control and a Pompe patient harboring the common IVS1 splice site mutation. A) Flanking exon PCR analysis of a healthy control. Exon numbers are indicated above the lanes. PCR products were separated by electrophoresis on an agarose gel. B) As A), but for Pompe patient 1 carrying the IVS1 mutation. Numbers besides the bands refer to the products analyzed in further detail (see below). C) Cartoon of the major splicing variants detected for patient 1. The upper cartoon represents the genomic DNA, in which the mutation is indicated. The lower cartoons refer to the splicing variants detected in this study. The translation start site is indicated as c.1. Exons are indicated as boxes. Non-coding exons are in brown, coding exons in green. Introns are depicted as lines. A broken line is used to indicate that the intron is longer than in this drawing. An alternative splice site is indicated. D) Exon-internal qPCR analysis. Beta-actin was used for normalization. Values obtained from the healthy control were set to 100%. Error bars indicate SD (n=3).
Figure 2B:
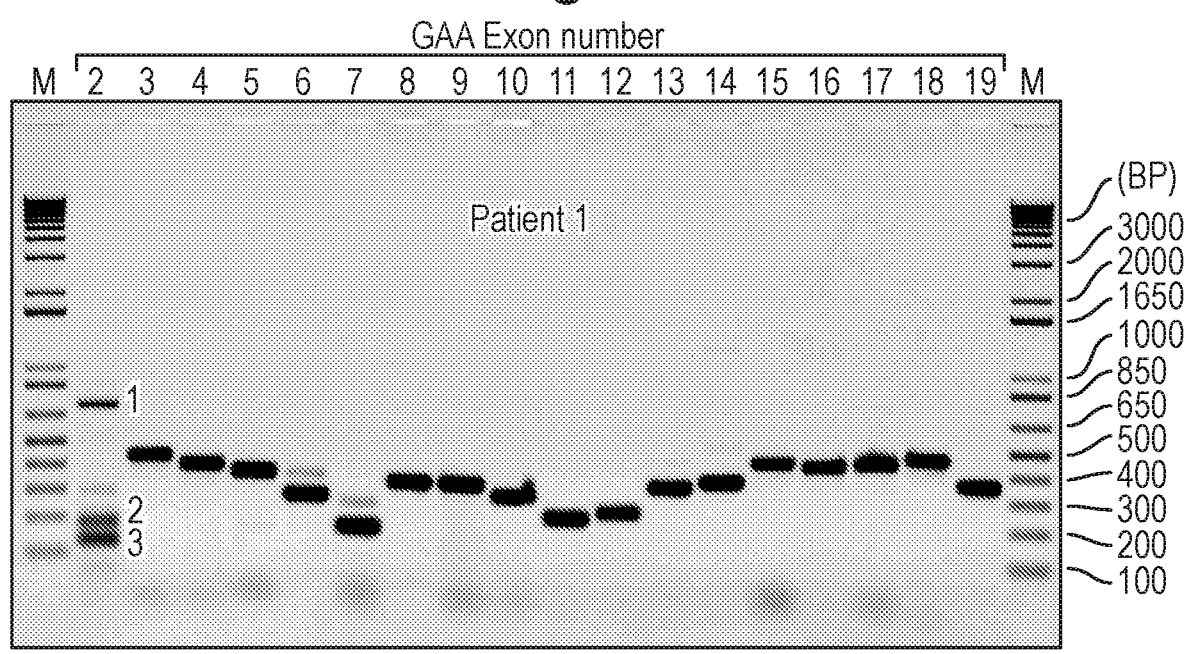
Figure 2C:
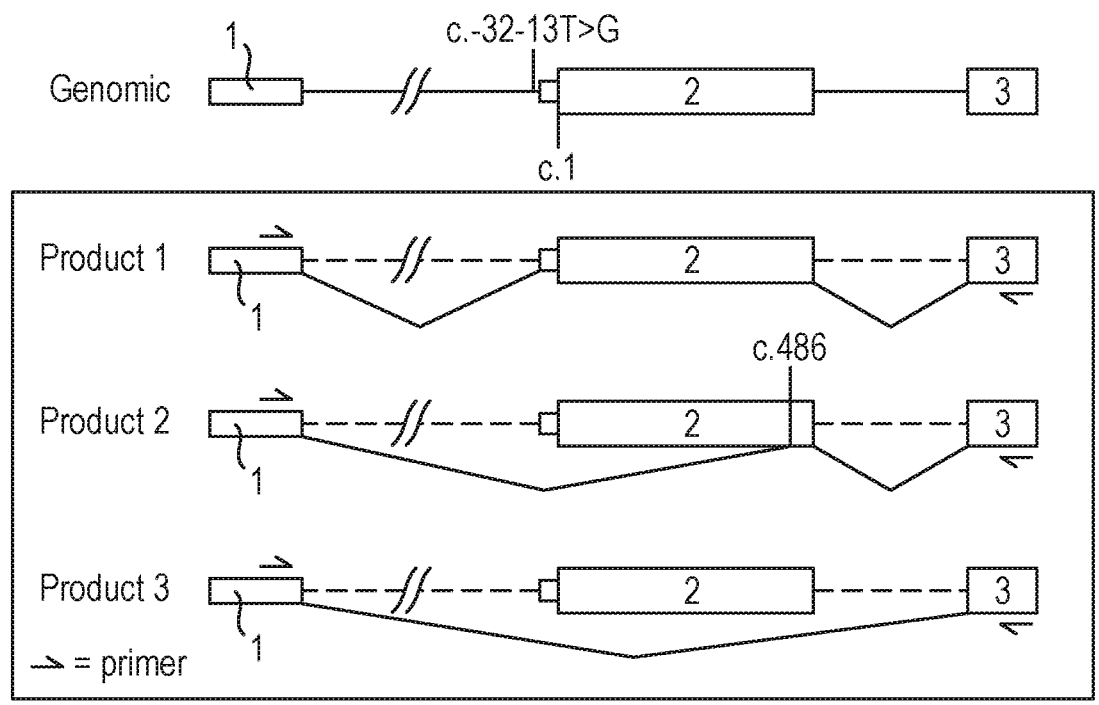

The assay was developed using a healthy control. To detect splicing junctions and exon sizes, flanking exon PCR analysis was performed on cDNA prepared from primary fibroblasts using primers that annealed to flanking exons (FIG. 2A). Gel electrophoresis and ethidium bromide staining showed the correct molecular weight products in all cases. This indicated canonical splicing for all exons in these cells. Some additional products were observed in at minor amounts, notably, just above exon 6 and 7. Sequence analysis indicated that these represent products in which intron 6 was retained. The products were observed in this healthy control and in many Pompe patients and may indicate noisy aberrant splicing, which is a known phenomenon [16]. Individual exons were quantified using exon-internal qPCR (FIG. 1B). Values were normalized for 6-actin expression (as measured by qPCR analysis), and were then ready to use for normalization of test samples.

Patient 1

This patient was used to validate whether a well described splicing mutation could be accurately detected in primary fibroblasts using the assay described above. The c.-32-13G>T (IVS1) mutation was chosen because it is a frequent mutation causing juvenile/adult onset of Pompe disease. It is located in intron 1 close to the splice acceptor site of exon 2, and it causes aberrant splicing of exon 2 but also allows leaky wild type splicing [17, 18]. The second allele is known to be expressed at very low levels due to NMD [19]. This is caused by the c.1636+5G>T mutation, which leads to intron 11 inclusion and a premature termination codon. For this reason, the allele containing the IVS1 mutation dominates in the splicing assay described below.

Figure 9:
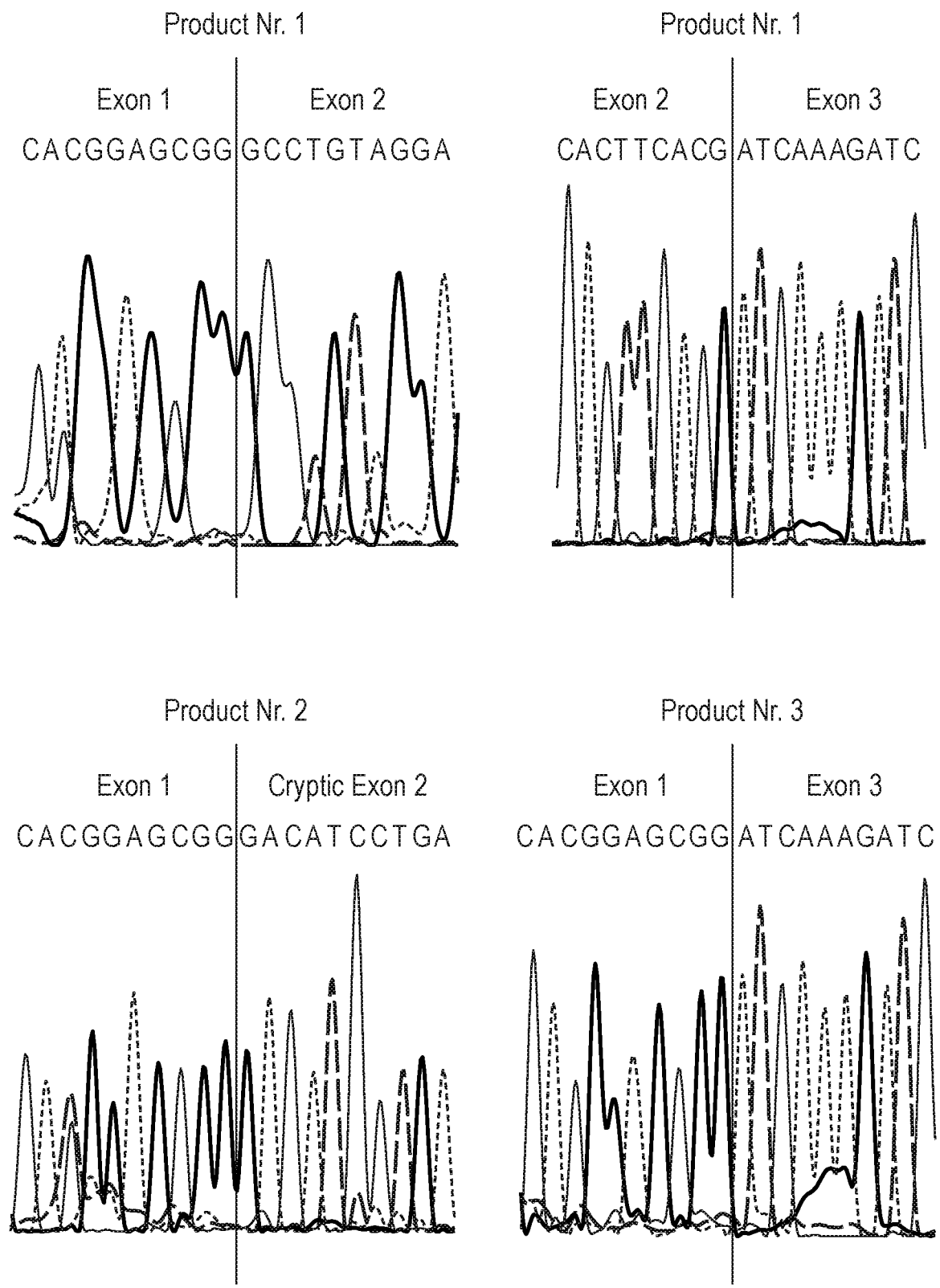
FIG. 9. Sequence analysis of patient 1. Product Nr. 1 Exon 1-Exon 2: SEQ ID NO: 619; Product Nr. 1 Exon 2-Exon 3: SEQ ID NO: 620; Product Nr. 2 Exon 1-Cryptic Exon 2: SEQ ID NO: 621; Product Nr. 3 Exon 1-Exon 3: SEQ ID NO: 622.

Flanking exon PCR analysis yielded three major products from exon 2 amplification (FIG. 2A). These products were analyzed by DNA sequencing, which indicated that product 1 represented full exon 2 with canonical splicing junctions (FIG. 9). Product 2 contained partially skipped exon 2 due to the utilization of a cryptic splice acceptor site at c.486 while product 3 represented fully skipped exon 2 (FIGS. 2A and S2). These products correspond to the major splicing variants reported for the IVS1 mutation, namely normal (N) (product 1), splicing variant (SV) 1 (product 2) and SV2 (product 3) [18].

Exon-internal qPCR analysis showed 10-15% expression of exon 2 and all other exons (FIG. 2). This can be explained as follows. The IVS1 mutation allows leaky wild type splicing of exon 2 (product 1 in FIG. 2A) yielding a normal mRNA containing all exons, as noted previously ([18, 20]. The 2 other major products 2 and 3 both result in the deletion of the canonical start of translation, which is located in exon 2. This leads to in mRNA degradation, resulting in minor contribution in the quantitative exon-internal qPCR assay, and predominant detection of the leaky wild type GAA mRNA from the IVS1 allele. In conclusion, the known effects of the IVS1 mutation on splicing were faithfully detected using the generic splicing assay for GAA. Leaky wild type splicing were 10-15% of healthy control levels and explained the juvenile/adult onset of Pompe disease. It is of note that all five splicing prediction programs used here (SpliceSiteFinder-like (SSF), MaxEntScan (MES), NNSplice (NNS), GeneSplicer (GS) and Human Splicing Finder (HSF)) failed to detect an effect of the IVS1 mutation on splicing (FIG. 14A).

Patient 2

Figure 8A:
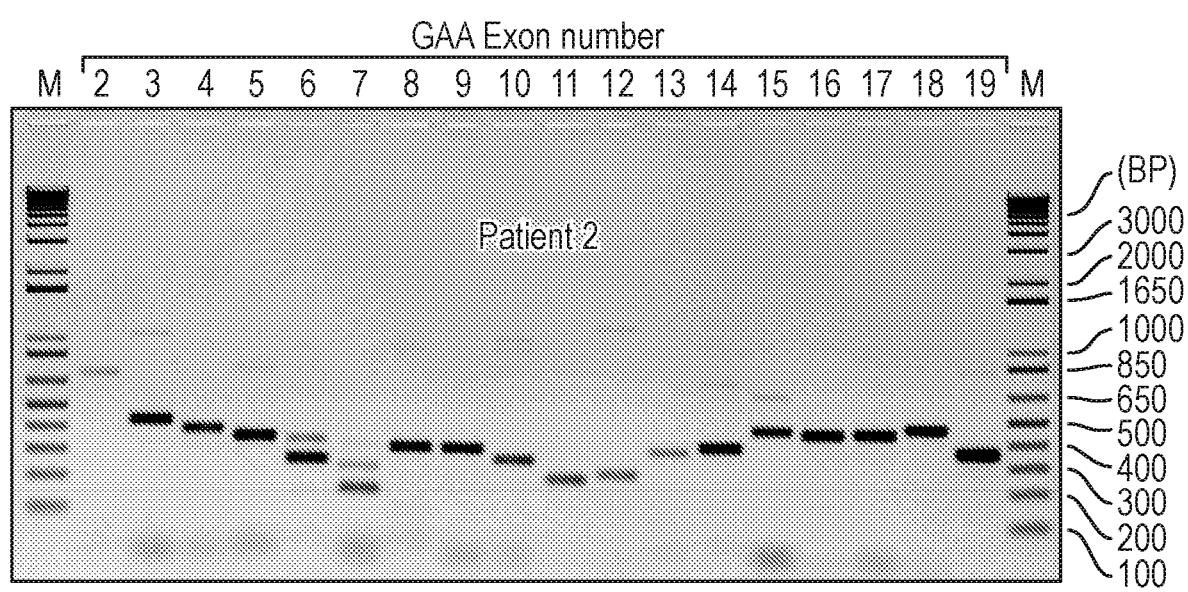
FIG. 8. Splicing analysis of patient 2. A) Flanking exon PCR analysis. B) Exon-internal PCR analysis.

This patient was chosen to test the sensitivity of the assay. Due to a homozygous c.525delT mutation, GAA mRNA expression is very low due to NMD [21]. Surprisingly, flanking exon PCR analysis showed that all exons could still be detected at the correct sizes, although at reduced levels (FIG. 8). Higher molecular weight products were also observed at even lower levels. These may represent unspliced pre-mRNA species, amplified due to the reduced abundance of competing spliced mRNA in the PCR reaction. To quantify the amount of residual mRNA, exon-internal qPCR was performed and showed 5-10% expression of all exons relative to the healthy control (FIG. 8B). In conclusion, the generic splicing assays for GAA allow analysis and quantification of very low mRNA expression. This is particularly relevant for mRNAs that are subject to degradation as the result of reading frame alterations.

Patient 3

A third validation was performed on a patient carrying a well-known deletion removing the entire exon 18 plus its flanking sequences (del ex18, or c.2481+102_2646+31del) (FIG. 2A). This case is interesting because the splice sites of exon 18 are removed. Previous work has shown that a new mRNA is formed in which exon 17 is neatly spliced to exon 19 via canonical splice sites [17]. The translation reading frame of the resulting mRNA remains intact, suggesting that this mRNA is not susceptible to degradation via the NMD pathway (FIG. 7-Table 2). The second mutation in this patient, c.1548G>A, generates a termination codon in exon 10 [22]. Its effects on mRNA expression have not been reported so far. The premature termination codon is likely to result in low mRNA abundance from this allele.

Figure 3A:
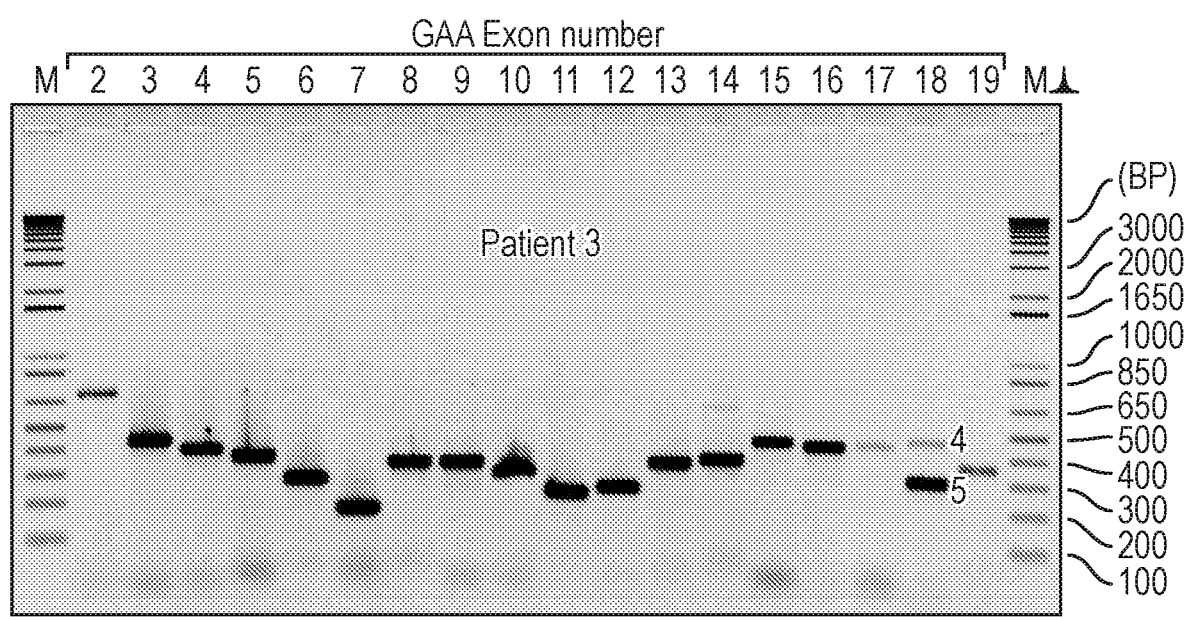
FIG. 3. Splicing analysis of Pompe patients 3 and 4 carrying heterozygous mutations/deletions. A) Flanking exon PCR analysis of patient 3. B) Cartoon of the major splicing variants detected for patient 3. C) Flanking exon PCR analysis of patient 4. D) Cartoon of the major splicing variants detected in patient 4 from allele 1. E) As D) but now for patient 4, allele 2. F) Exon-internal qPCR analysis of patients 3 and 4. Error bars indicate SD (n=3).
Figure 3B:
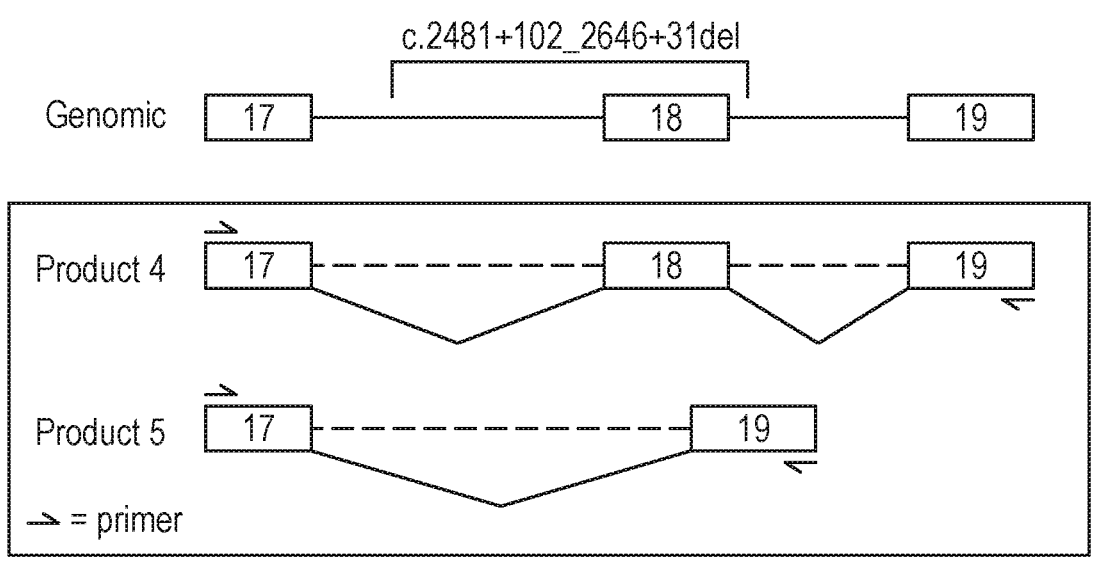

Flanking exon PCR indicated changes for amplification of exons 17, 18, and 19 (FIG. 3A). Exon 18 amplification yielded two products instead of one. Sequence analysis indicated that the highest MW product (number 4) represented wild type spliced exon 18, while the lower MW product (number 5) lacked the entire exon 18, and exon 17 and exon 19 were joined via their canonical splice sites (FIG. S3A). Amplification of exons 17 and 19 yielded lower amounts of the correct products compared to the healthy control. The primers used for their amplification anneal to exon 18, indicating that their detection could not be derived from the delex18 allele but must have come from the c.1548G>A allele. This indicates that the c.1548G>A allele is expressed to some extent, and it explains the detection of moderate levels of wild type spliced exon 18 by flanking exon PCR.

Figure 3C:
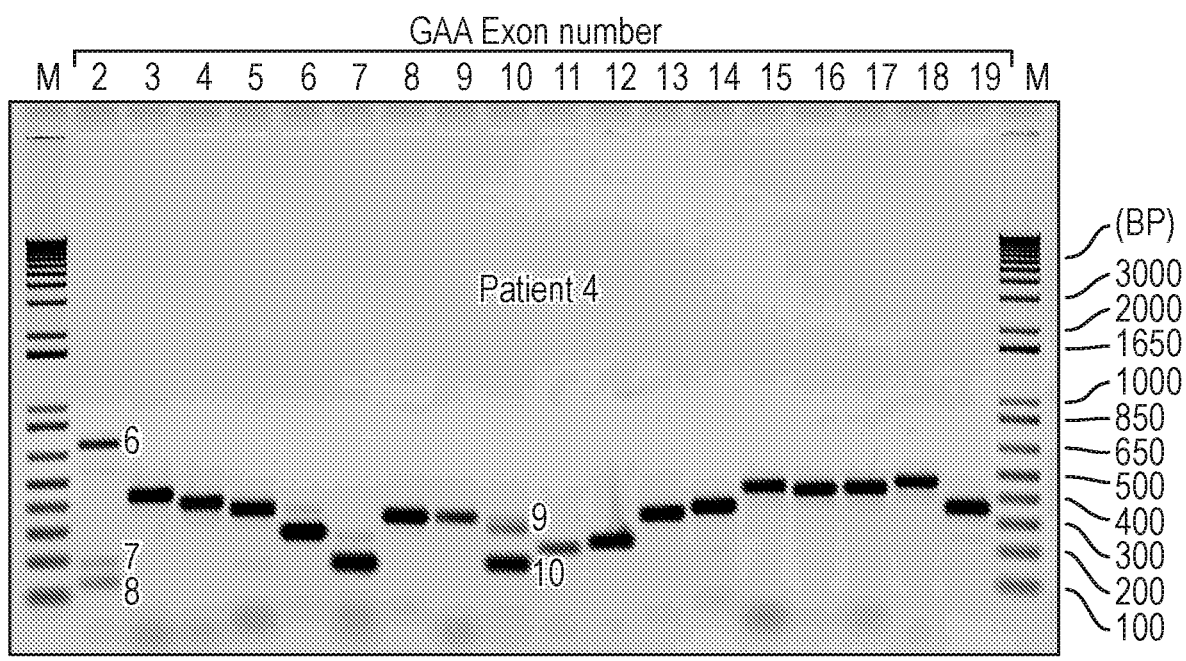
Figure 3D:
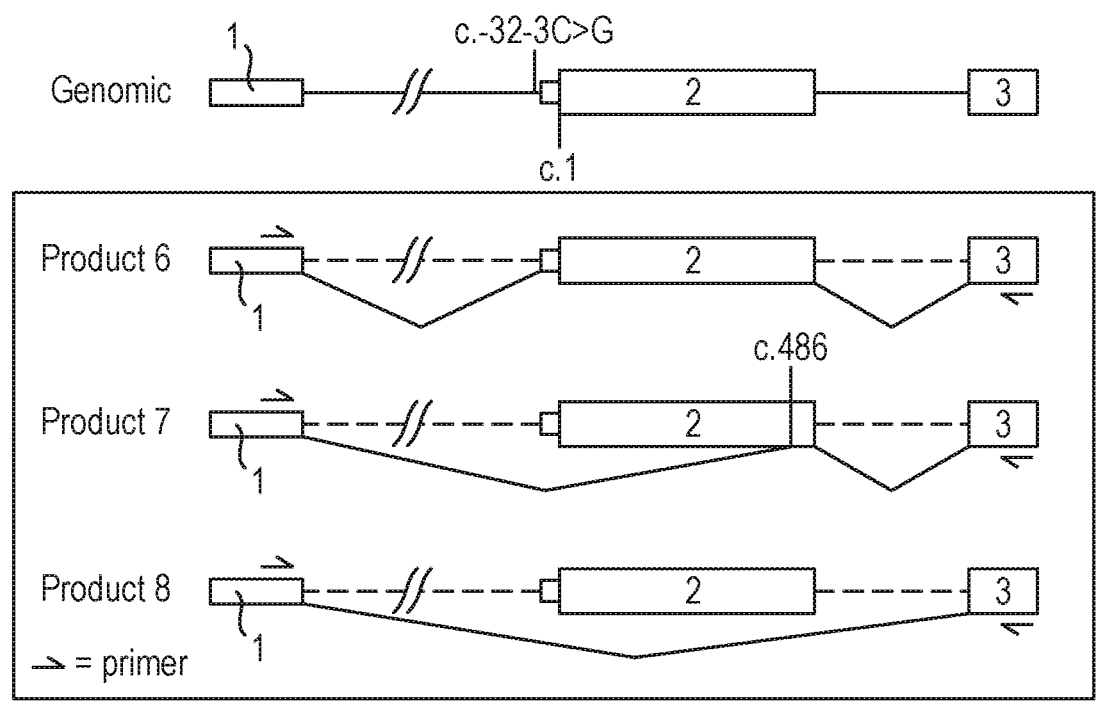
Figure 3E:
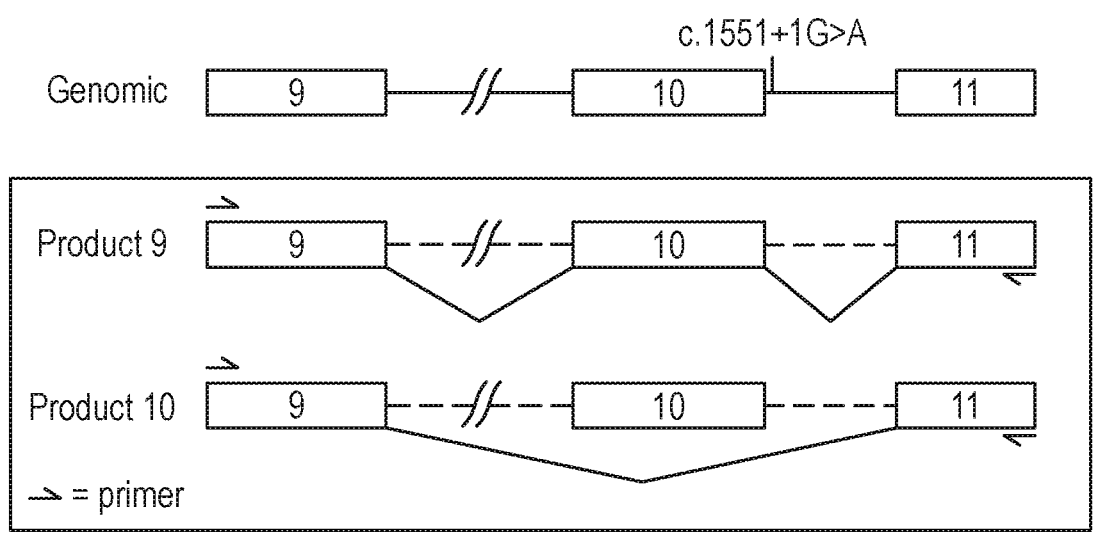
Figure 3F:
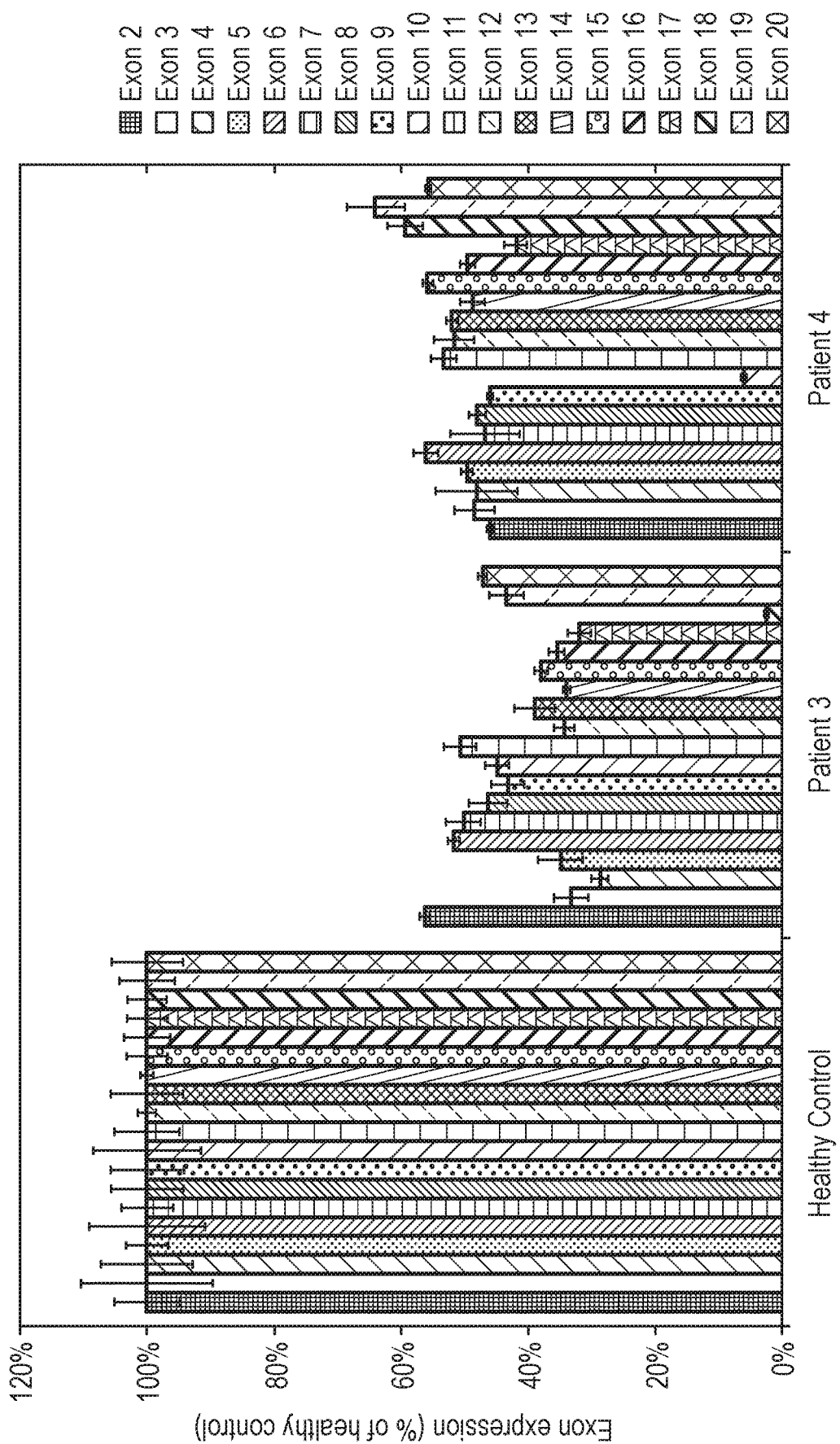

To quantify expression from the c.1548G>A allele, exon-internal qPCR was performed and indicated 3% expression of exon 18, while all other exons were expressed at ~40-50% of healthy control levels (FIG. 3F). This shows that the c.1548G>A mutation results in very low mRNA expression, as measured by the low level of exon 18 detection. Expression of all other exons is derived from the delex18 allele, which produces a stable mRNA in which exon 18 is precisely deleted.

In summary, the generic splicing assay also allows detection and characterization of exonic deletions. A dissection can be made between two alleles by comparing the results of the flanking exon PCR and the exon-internal qPCR assays.

Characterization of Novel Splicing Mutations

Next, a number of patients were analyzed that contained partially characterized or uncharacterized mutations.

Patient 4

Patient 4 contained a novel mutation at c.-32-3C>G located in intron 1 close to the splice acceptor site of exon 2 (FIG. 3D). This mutation is suspected to affect splicing of exon 2 based on its similarity to the published c.-32-3C>A mutation [19]. In this study, a perfect skip of exon 2 was reported. Splicing prediction programs indicated that the c.-32-3C>G mutation weakens the splice acceptor site of exon 2 for some but not all programs (FIG. 14C). The second allele contained a previously reported [23] but uncharacterized mutation at c.1551+1G>A which is located in intron 10 close to the splice donor site of exon 10 (FIG. 3E). Based on the similarity to the published c.1551+1G>C mutation [17, 24], the c.1551+1G>A mutation is suspected to affect exon 10 splicing. Splicing prediction programs indicated loss of the splice donor site of exon 10 (FIG. 14C).

Figure 10B:
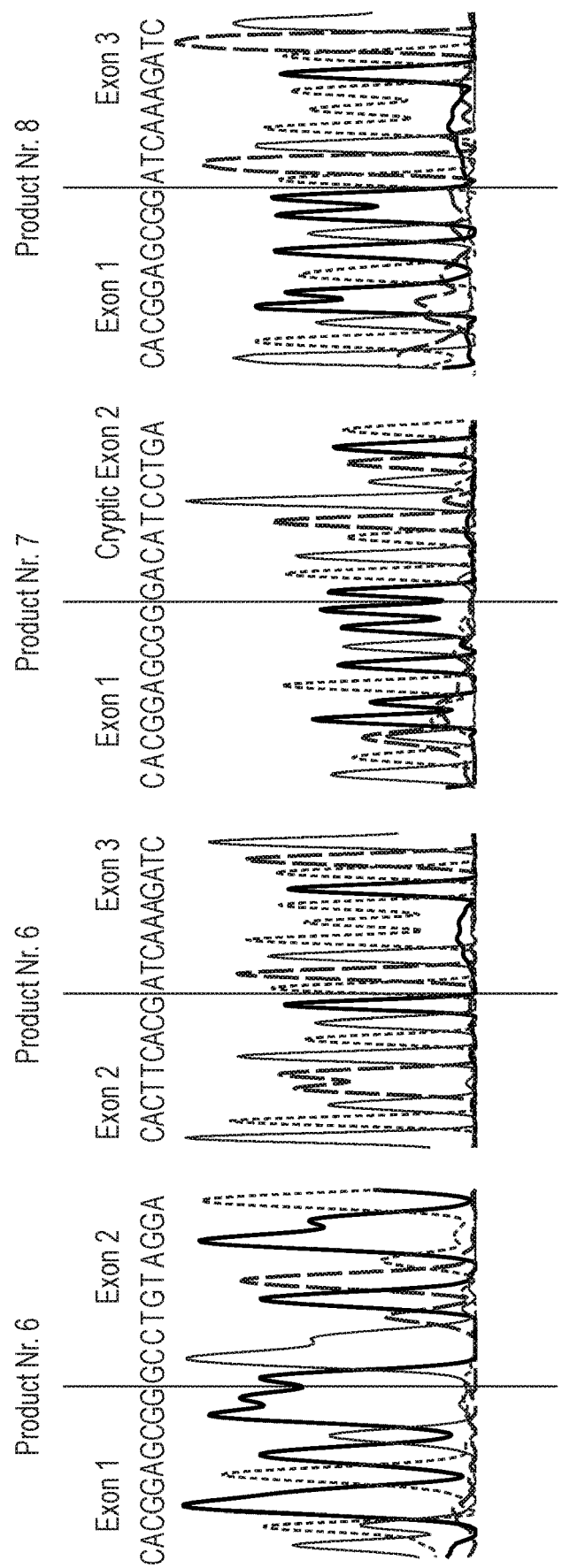
FIG. 10. Sequence analysis of patients 3 (A) and 4 (B-C). Product Nr. 4 Exon 17-Exon 18: SEQ ID NO: 623; Product Nr. 4 Exon 18-Exon 19: SEQ ID NO: 624; Product Nr. 5 Exon 17-Exon 19: SEQ ID NO: 625; Product Nr. 6 Exon 1-Exon 2: SEQ ID NO: 626; Product Nr. 6 Exon 2-Exon 3: SEQ ID NO: 627; Product Nr. 7 Exon 1-Cryptic Exon 2: SEQ ID NO: 628; Product Nr. 8 Exon 1-Exon 3: SEQ ID NO: 629; Product Nr. 9 Exon 9-Exon 10: SEQ ID NO: 630; Product Nr. 9 Exon 10-Exon 11: SEQ ID NO: 631; Product Nr. 10 Exon 9-Exon 11: SEQ ID NO: 632.
Figure 10C:
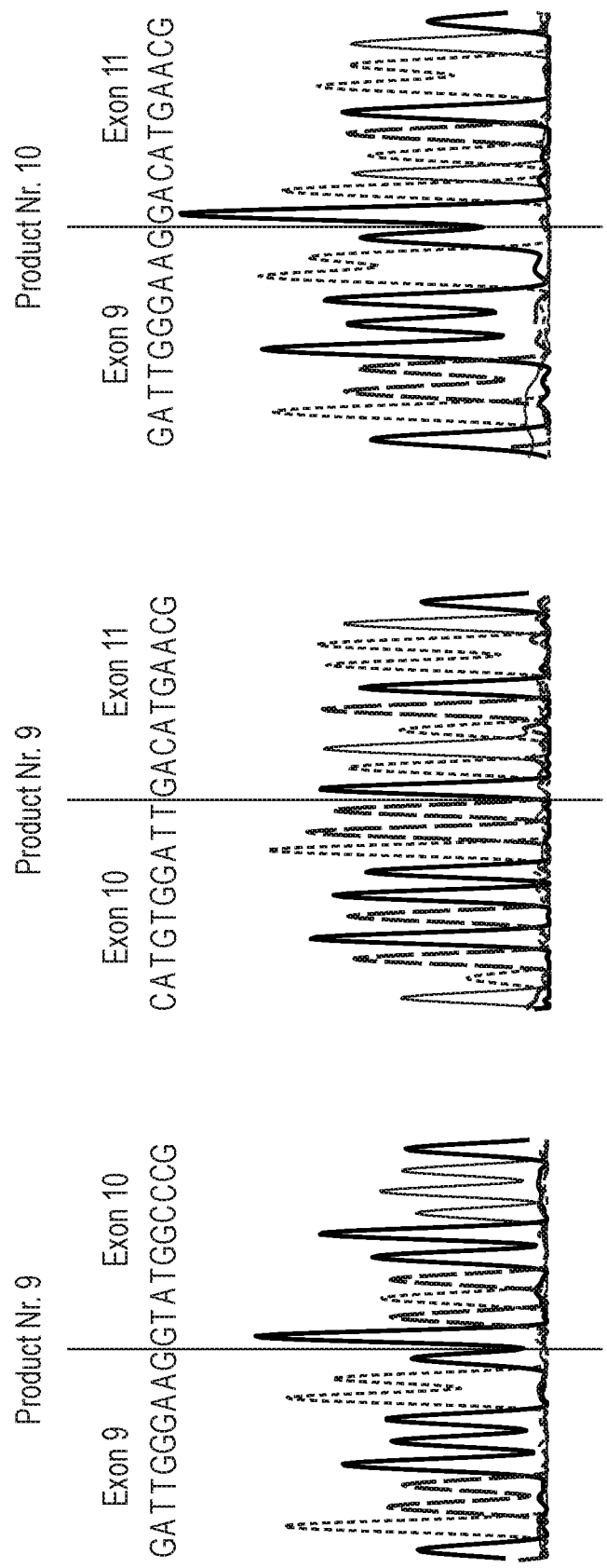

The results of the flanking exon PCR analysis indicated aberrant splicing of two exons: exon 2 and exon 10 (FIG. 3C). Amplification of exon 2 resulted in 3 major products, number 6-8, and sequence analysis indicated that these products included wild type splicing, partial skipping of exon 2 via the cryptic splice acceptor site at c.486 in exon 2, and perfect skipping of exon 2, respectively (FIG. 3D and FIG. 10B). This indicates that two independent mutations in intron 1, namely c.-32-13T>G, which is located in the polypyrimidine tract, and c.-32-3C>G, located near the splice acceptor site, have the same qualitative outcome with respect to exon 2 splicing. Splicing prediction programs were insufficient to accurately predict this outcome. Flanking exon PCR amplification of exon 10 resulted in two major products, 9 and 10 (FIG. 3C). Sequence analysis showed that product 9 contained wild type junctions between exons 9, 10, and 11, and that product 10 represented precise skipping of exon 10 mRNA (FIG. 3E and FIG. 10C) in which the reading frame remains intact. This was surprising because the most straightforward result of a weakening of the splice donor site of exon 10 would be a failure to remove intron 10 rather than a skipping of exon 10.

Figure 2D:
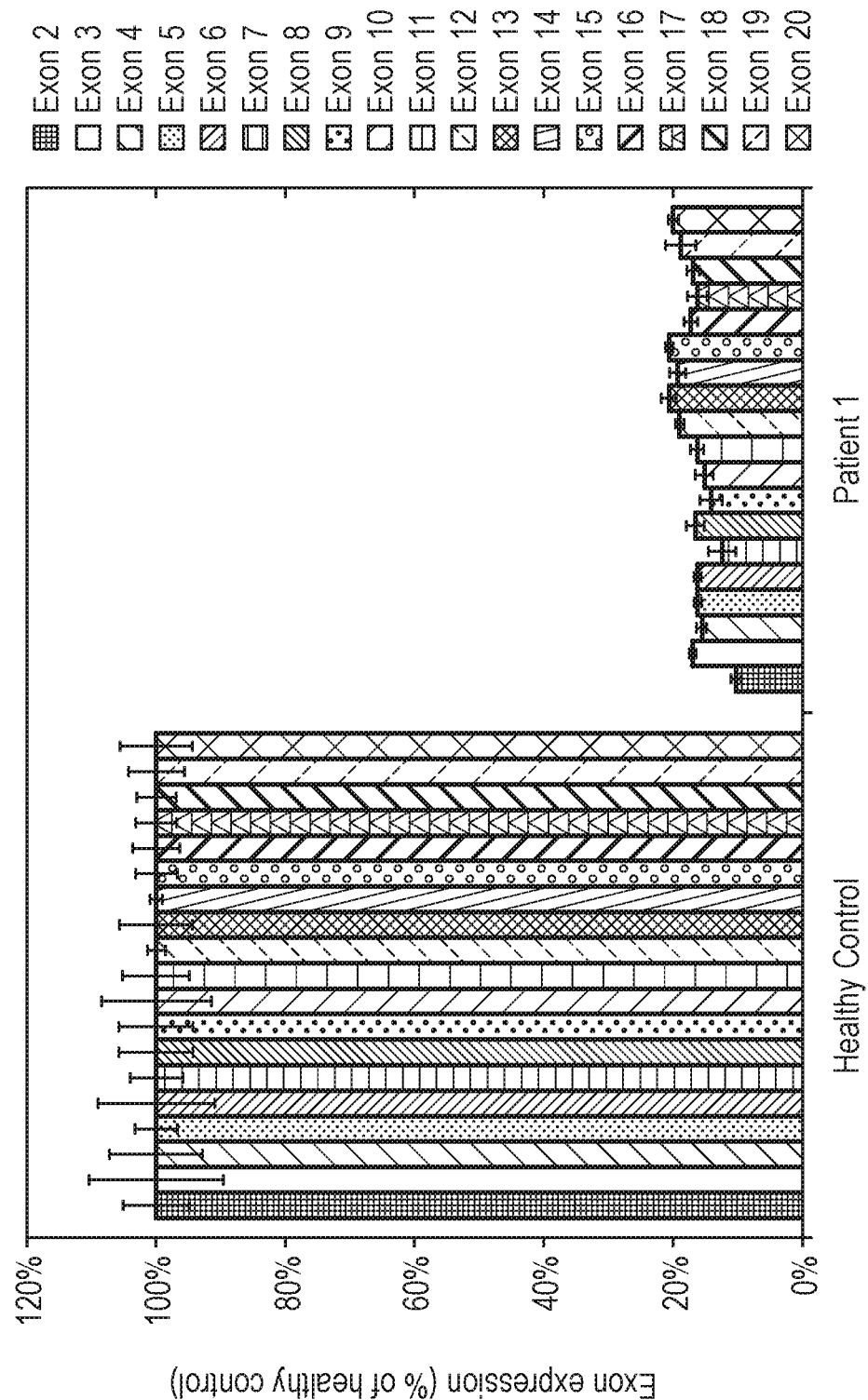

To determine the extent of splicing defects, exon-internal qPCR was performed. Exon 10 was expressed at ~6%, while all other exons were expressed at ~50% of healthy control levels (FIG. 3F). This is consistent with the idea that the majority of mRNA is derived from the c.1551+1G>A allele in which exon 10 is skipped. The shorter product has an unchanged reading frame and is expected to be stable. In contrast, the c.-32-3C>G allele results in (partial) exon 2 skipping, which is known to result in mRNA degradation analogous to the IVS1 mutation. The c.-32-3C>G allele has only a minor contribution to the exon-internal qPCR results. Its contribution can be judged from exon 10 expression, which can result from leaky wild type splicing of the c.-32-3C>G mutation. However, an alternative source for exon 10 expression is leaky wild type expression of the c.1551+1G>A allele. The very low level of exon 10 expression indicates that both the c.-32-3C>G and the c.1551+1G>A have low or absent levels of leaky wild type expression. This indicates that the c.-32-3C>G mutation may be more severe compared to the IVS1 mutation, as the IVS1 mutation allows a higher level of wild type splicing of 10-15% (FIG. 2D). The clinical course of Pompe disease indicates a juvenile onset for this patient, consistent with a low level of wild type GAA expression and GAA enzyme activity levels that were lower compared to adult onset patients (FIG. 6-Table 1).

Patient 5

Patient 5 was homozygous for c.1075G>A, which is a p.Gly359Arg missense mutation located at the last basepair of exon 6 (FIG. 4B) [25]. This mutation has been classified as presumably nonpathogenic with possible effects on splicing [26]. It is located near the splice donor site of exon 6, and splicing prediction analysis indicated weakening of this site and strengthening of a cryptic splice donor site 4 nucleotides upstream (FIG. 14D).

Figure 4A:
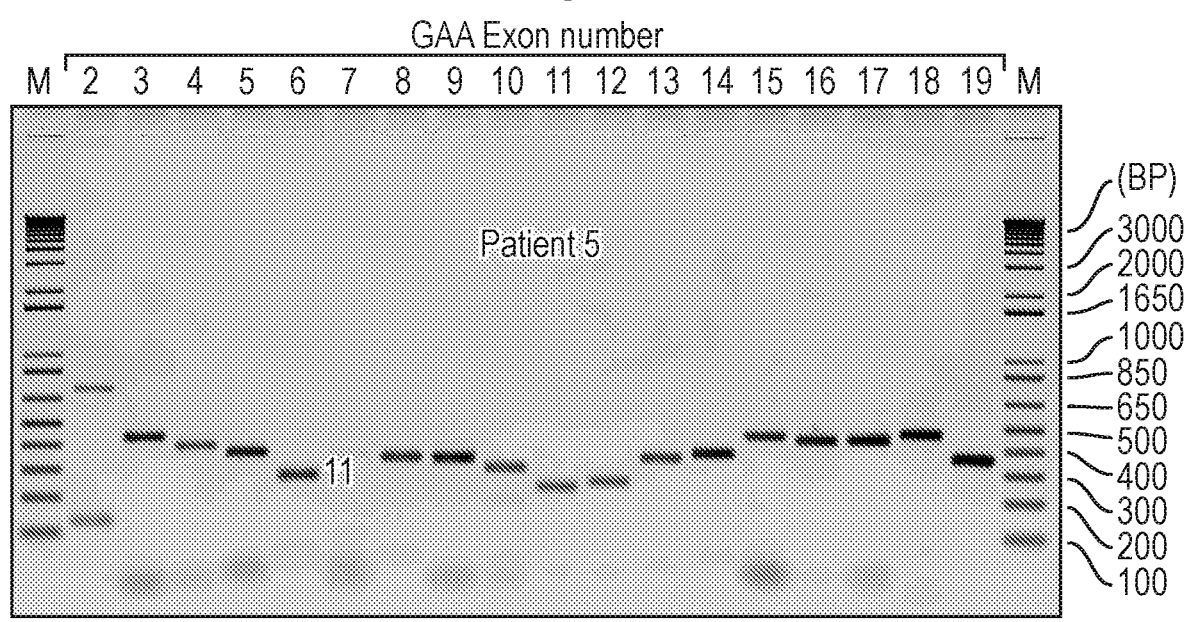
FIG. 4. Splicing analysis of Pompe patients carrying homozygous mutations. A) Flanking exon PCR analysis of patient 5. B) Cartoon of the splicing variant detected for patient 5. C) Flanking exon PCR analysis of patient 6. D) Cartoon of the splicing variants detected for patient 6. E) Flanking exon PCR analysis of patient 7. F) Cartoon of the splicing variant detected for patient 7. G) Exon-internal qPCR analysis of patients 5, 6, and 7. Error bars indicate SD (n=3).
Figure 4B:
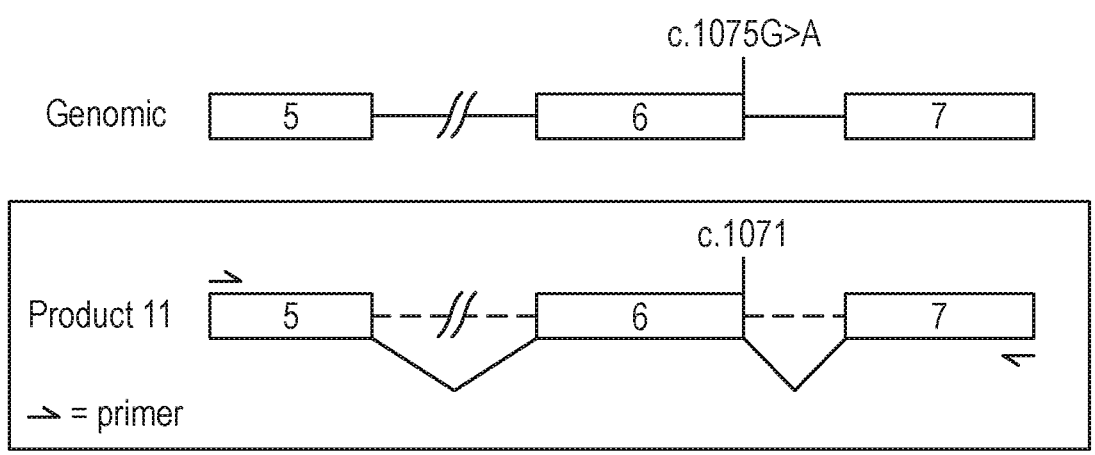
Figure 4C:
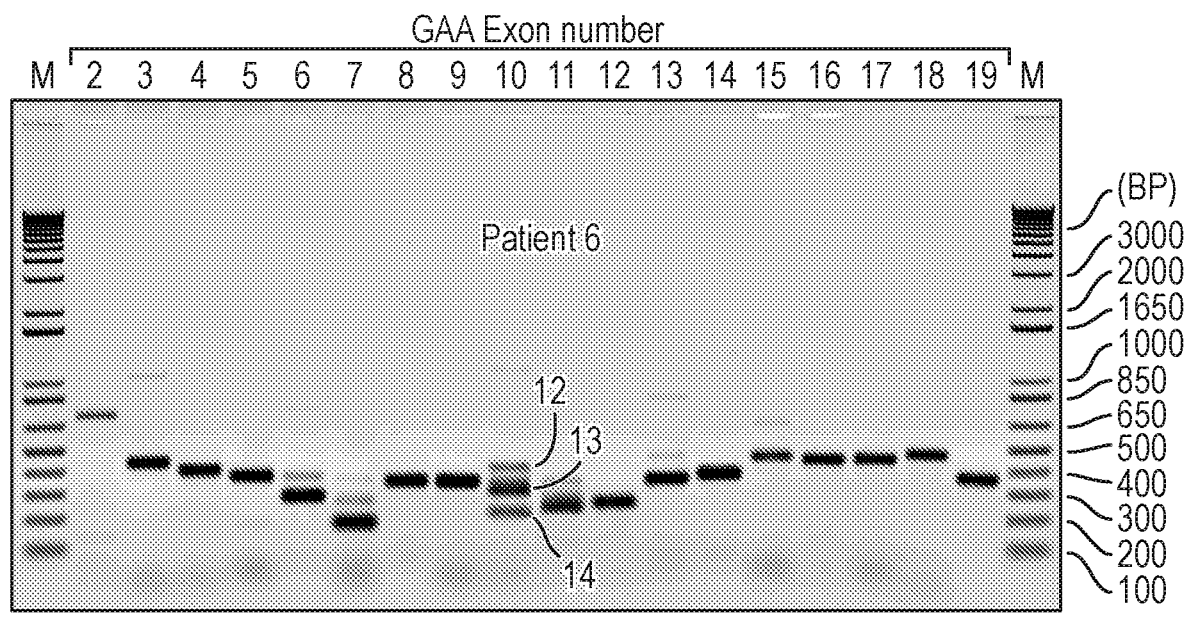
Figure 11A:
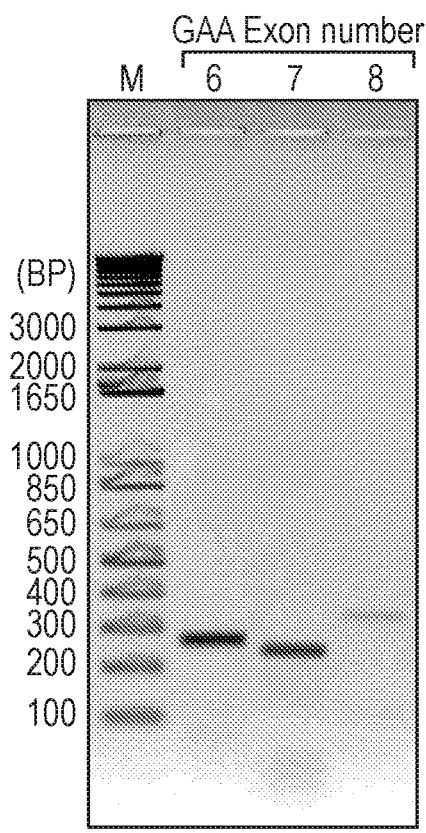
FIG. 11. A) Flanking exon PCR analysis of patient 5 for exon 7 using a forward primer that anneals to exon 5 and a reverse primer that anneals to exon 8. For comparison, standard flanking exon PCR reactions of exons 6 and 8 are shown. Note that GAA mRNA levels in this patient are low due to NMD. B). Sequence analysis of patient 5. C) Sequence analysis of patient 6. D) Sequence analysis of patient 7. Product Nr. 11 Exon 5-Exon 6: SEQ ID NO: 633; Product Nr. 11 Exon 6-Exon 7: SEQ ID NO: 634; Product Nr. 12 Exon 9-Exon 10: SEQ ID NO: 635; Product Nr. 12 Exon 10-Exon 10: SEQ ID NO: 636; Product Nr. 12 Exon 10-Exon 11: SEQ ID NO: 637; Product Nr. 13 Exon 10-Exon 11: SEQ ID NO: 638; Product Nr. 14 Exon 9-Cryptic Exon 10: SEQ ID NO: 639; Product Nr. 15 Exon 8-Exon 10: SEQ ID NO: 640; Product Nr. 15 Exon 9-Exon 10: SEQ ID NO: 641; Product Nr. 16 Exon 8-Exon 10: SEQ ID NO: 642.

Flanking exon PCR analysis showed absence of a product for exon 7, low levels of the other exons, and a low level of a low MW product for exon 2 (FIG. 4A). Based on the predictions and on the location of this mutation in exon 6, we suspected that splicing junctions around exon 6 and 7 may be altered. In agreement, sequencing of the exon 6 PCR product (product 11) showed that the cryptic splice donor site in exon 6 located 4 nucleotides upstream at c.1071 was used instead (FIG. 4B and FIG. S4B). This explains the absence of a product for exon 7, as the forward primer for exon 7 amplification has 4 mismatches due to the changed splice donor site. Remarkably, the flanking exon PCR assay failed to detect leaky wild type splicing for this mutation. This would have resulted in the presence of a wild type band for exon 7 amplification, which was not observed. To further investigate splicing of exon 7, an alternative forward primer located in exon 5 was used. The expected product was now obtained, and showed splicing from c.1071 in exon 6 to the canonical splice acceptor site of exon 7 (FIG. 11A), as was observed for sequence analysis of product 11. The reading frame of the resulting mRNA has been changed leading to a premature termination codon (Table 2). The low MW product obtained with exon 2 amplification has not been pursued further. It may be caused by a yet unidentified intronic mutation. Alternatively, wild type GAA mRNA is known to have leaky exon 2 skipping, the product of which may be preferentially amplified because of mRNA degradation due to the c.1071 mutation.

Figure 4D:
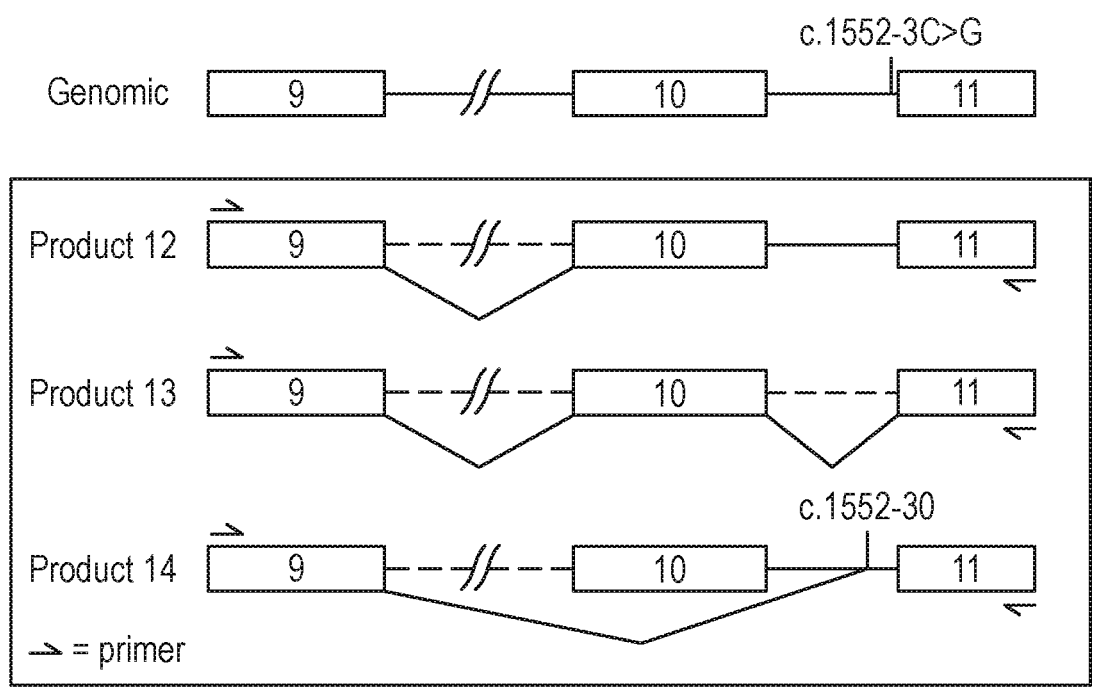
Figure 4E:
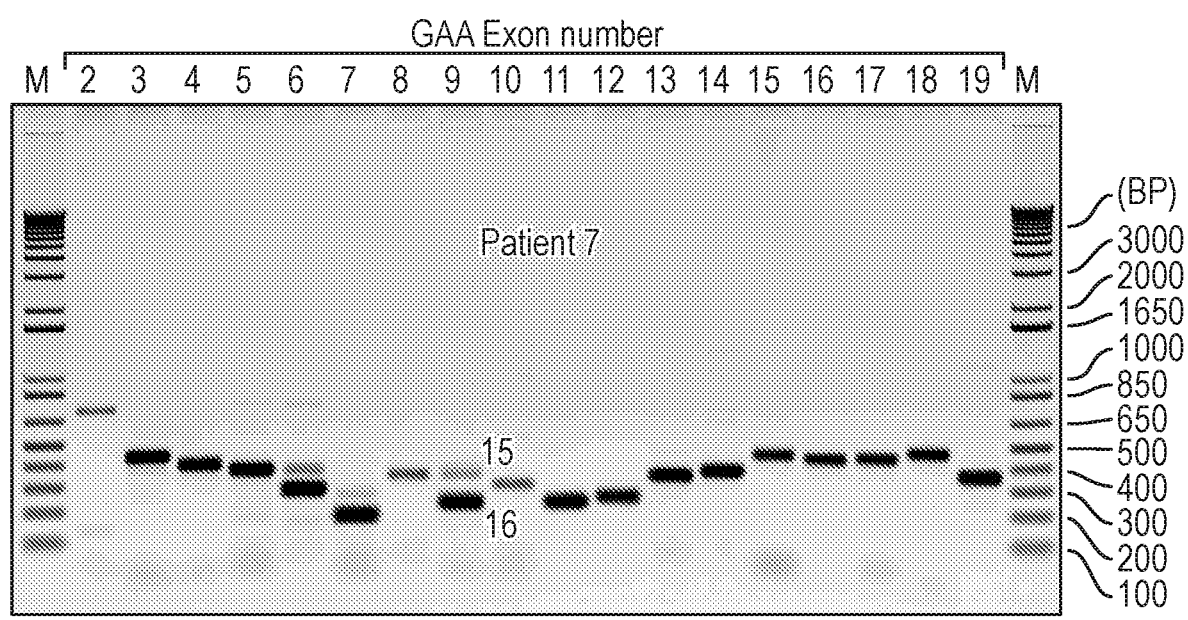
Figure 4F:
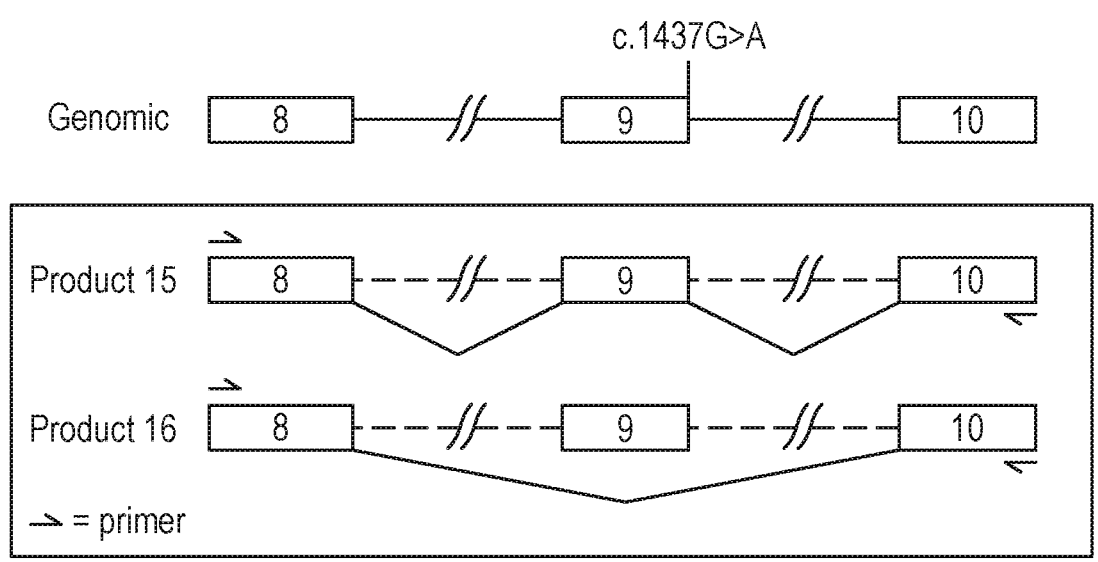
Figure 4G:
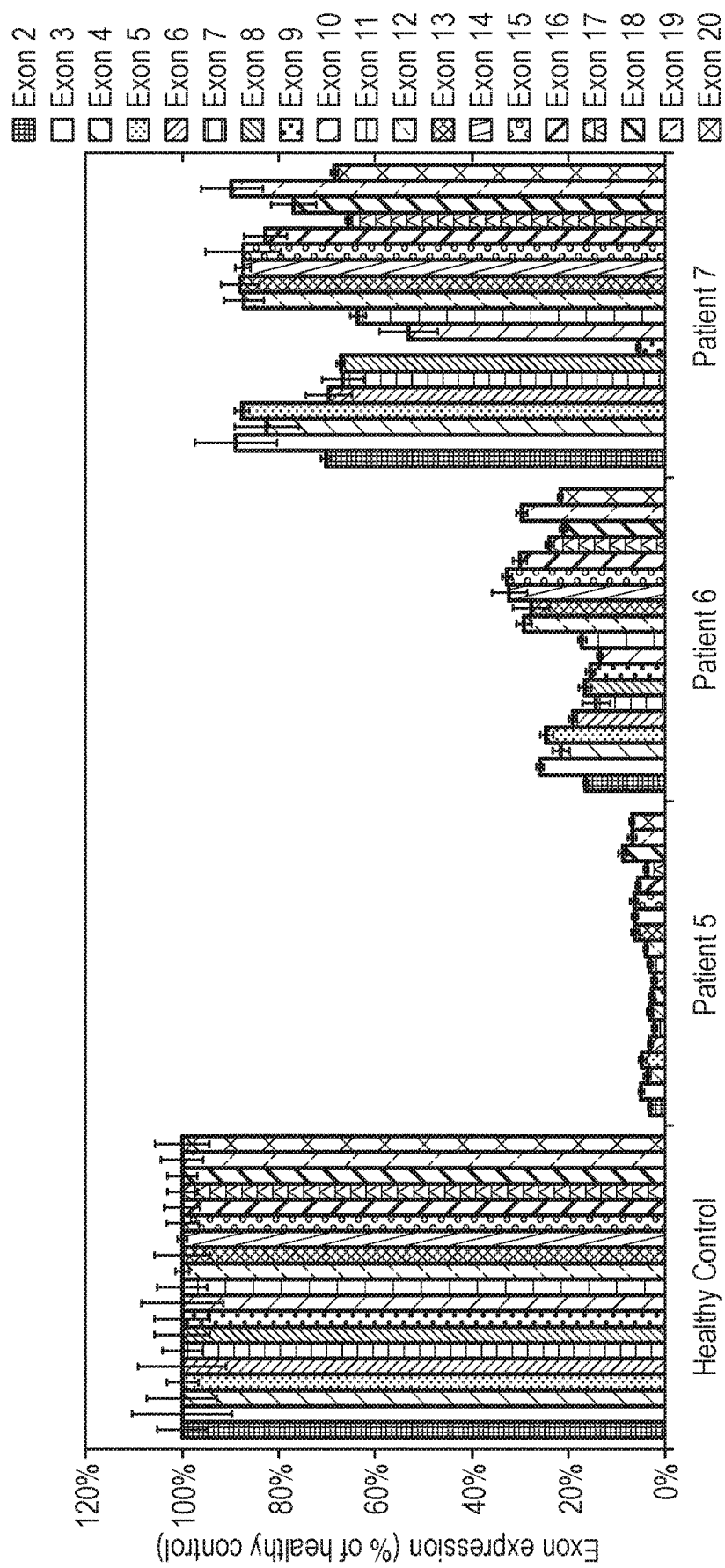

Quantification of GAA mRNA expression using the exon-internal qPCR assay showed that all GAA exons were expressed at very low levels, well below levels observed for the IVS1 mutation but just above the levels observed for the c.525delT mutation (FIG. 4G). This confirmed the notion that leaky wild type splicing levels in this patient are very low or absent, while the majority of the mRNA is unstable. In agreement, very low GAA activity in fibroblasts was measured and the diagnosis of this patient was the most severe classic infantile form of Pompe disease.

Patient 6

Patient 6 carried a homozygous c.1552-3C>G mutation. This mutation is located in intron 10 close to exon 11 (FIG. 4D). Flanking exon PCR analysis showed aberrant splicing of exon 10 with three major products (12-14; FIG. 4E). Sequence analysis indicated that in product 14, exon 10 was completely skipped while a novel splice acceptor site near exon 11 at c.1552-30 was utilized (FIGS. 4D and 11C). This mRNA leaves the reading frame intact (Table 2). Product 13 was identified as wild type spliced mRNA. Product 12 consisted of mRNA in which the complete intron 10 was retained. The reading frame is disrupted in this splicing product. While products 13 and 14 have been detected previously [27], product 12 is novel. Interestingly, splicing prediction programs were ambivalent on predicting the extent of utilization of the canonical or the cryptic splice acceptor sites of exon 11 (FIG. 14F). Moreover, the outcome was unexpected in any case: weakening of the splice acceptor site of exon 11 would not be expected to result in the skipping of exon 10. Instead, two products could be envisioned: one in which the splice donor site of exon 10 splices to the cryptic acceptor at c.1552-30, resulting in extension of exon 11 with a part of intron 10 and further normal splicing. The other expected product would be a perfect skipping of exon 11. The completely different outcome illustrates that experimental validation is required to analyze the molecular consequences of potential splicing mutations.

Quantification of splicing defects was performed with the exon-internal qPCR assay. This showed expression of all exons at ~20% of healthy control levels (FIG. 4G). No extra reduction of exon 10 expression was observed, suggesting that the majority of mRNA included exon 10, favoring products 12 and 13 above 14. The presence of leaky wild type splicing (product 13) is consistent with residual GAA enzyme activity and the milder phenotype with adult onset of Pompe disease in this patient (table 1). In conclusion, c.1552-3C>G results in several splicing defects around exon 10 and intron 10, and it allows leaky wild type splicing compatible with adult disease onset.

Patient 7

Figure 14E:
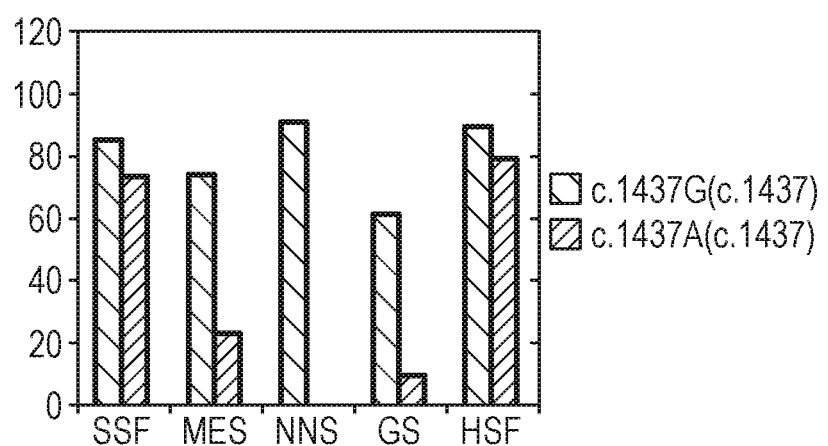
FIG. 14. Splicing predictions using five programs (SpliceSiteFinder-like (SSF), MaxEntScan (MES), NNSplice (NNS), GeneSplicer (GS) and Human Splicing Finder (HSF)) applied to wild type and mutant sequences. A) The predicted effect on splice site strength of the c.-32-13T>G and c.1636+5G>T variants. B) The predicted effect on splice site strength of the c.1548G>A variant. C) The predicted effect on splice site strength of the c.-32-3C>G and c.1551+1G>A variants. D) The predicted effect on splice site strength of the c.1075G>A variant. E) The predicted effect on splice site strength of the c.1437G>A variant. F) The predicted effect on splice site strength of the c.1552-3C>G variant. G) The predicted effect on splice site strength of the c.1256A>T and c.1551+1T>G variants.

Patient 7 was homozygous for c.1437G>A, a silent mutation located at the splice donor site of exon 9 (FIG. 4F). Flanking exon PCR analysis showed two products instead of one for exon 9 amplification, and low yields for exon 8 and exon 10 amplification (FIG. 4E). Sequence analysis indicated that product 15 represented wild type spliced exon 9, while in product 16, exon 9 was perfectly skipped, resulting in a shorter transcript in which the reading frame was unchanged (FIG. 4F and FIG. 11D). As expected from its location, the c.1437G>A mutation was predicted in silico to weaken to splice donor site of exon 9 (FIG. 14E). However, the experimental result was surprising as failure of the splice donor site of exon 9 would be expected to result in inclusion of intron 9 rather than skipping of exon 9. Products of exon 8 and exon 10 amplification had correct sizes but lower yield because exon 9 had reduced availability to serve as template for annealing of the reverse PCR primer (for exon 8) or the forward PCR primer (for exon 10).

Quantification using exon-internal qPCR showed near-normal (70-80% of control) expression levels for all exons except for exon 9, which showed expression of only 5% of healthy control. The juvenile/adult disease onset of this patient is consistent with the leaky nature of the splice site mutation (Table 1). In summary, the c.1437G>A mutation results in precise skipping of exon 9 leaving the reading frame intact, and allows a low level of leaky wild type GAA splicing.

Characterization of a Complex Case: Patient 8

Genotype

Patient 8 contained the missense mutation c.1256A>T on allele 1. It is located in the middle of exon 8, results in p.Asp419Val, and has been classified as mildly pathogenic (FIG. 5B) [26]. The 2nd allele contained a c.1551+1G>T mutation, which is located in intron 10 close to the splice donor site of exon 10[26]. It resembles the c.1551+1G>A mutation described above for patient 4.

Analysis of Splicing Products

Figure 5A:
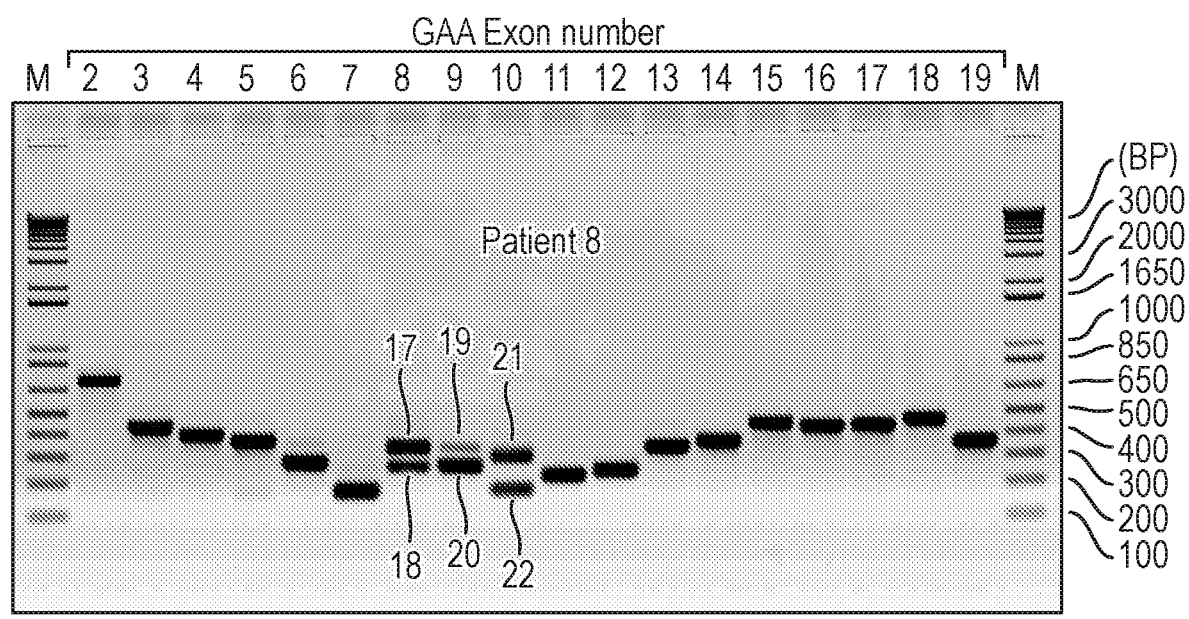
FIG. 5. Analysis of complex splicing changes in Pompe patient 8. A) Flanking exon PCR analysis. B) Cartoon of the splicing variants from allele 1, detected from analysis of exon 8. C) Cartoon of the splicing variants from allele 1, detected from analysis of exon 9. D) Cartoon of the splicing variants from allele 2, detected from analysis of exon 10. E) Exon-internal qPCR analysis. Error bars indicate SD (n=3).
Figure 5B:
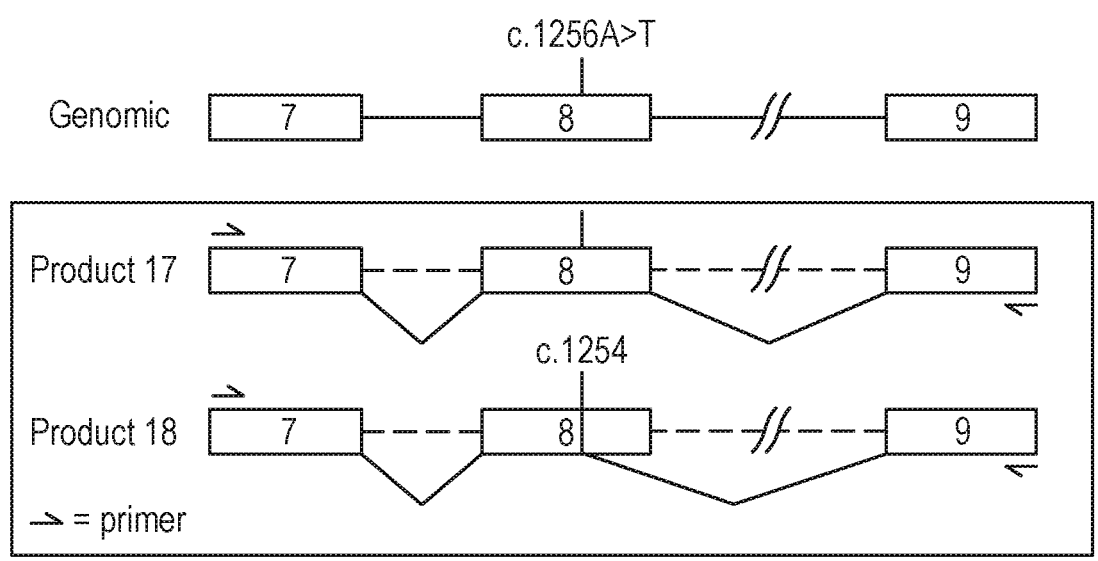
Figure 5C:
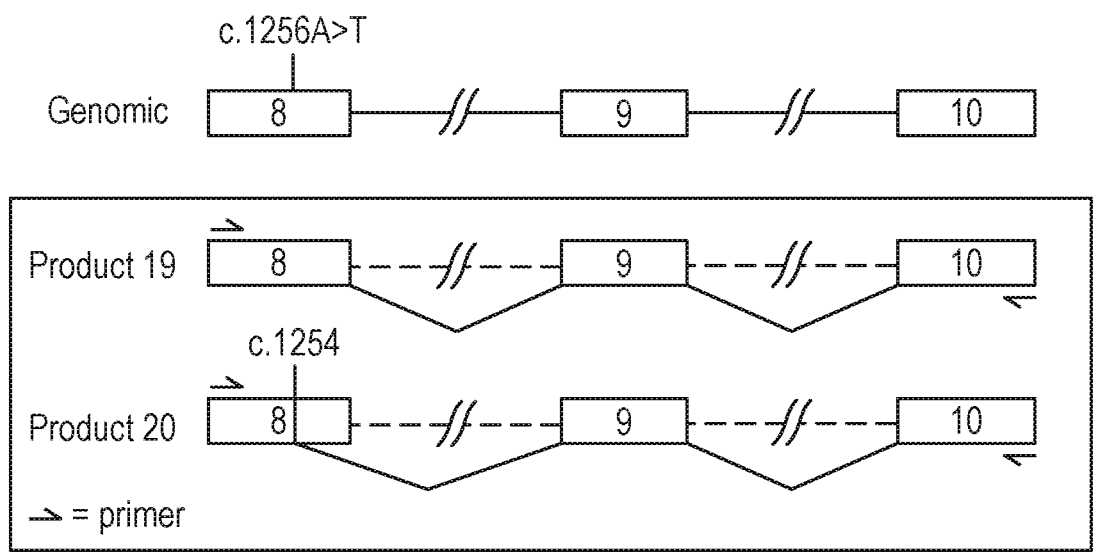
Figure 5D:
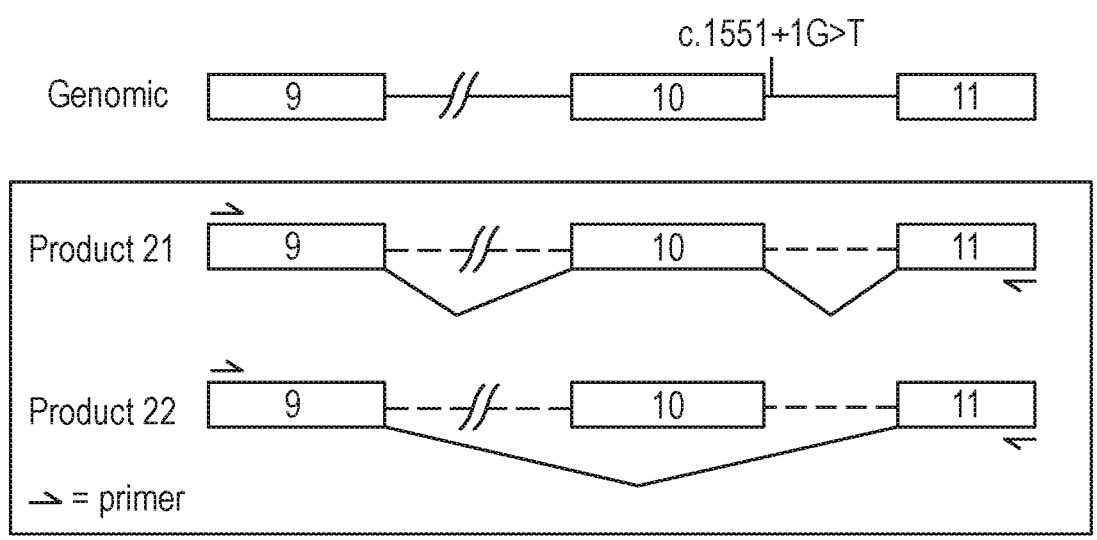
Figure 5E:
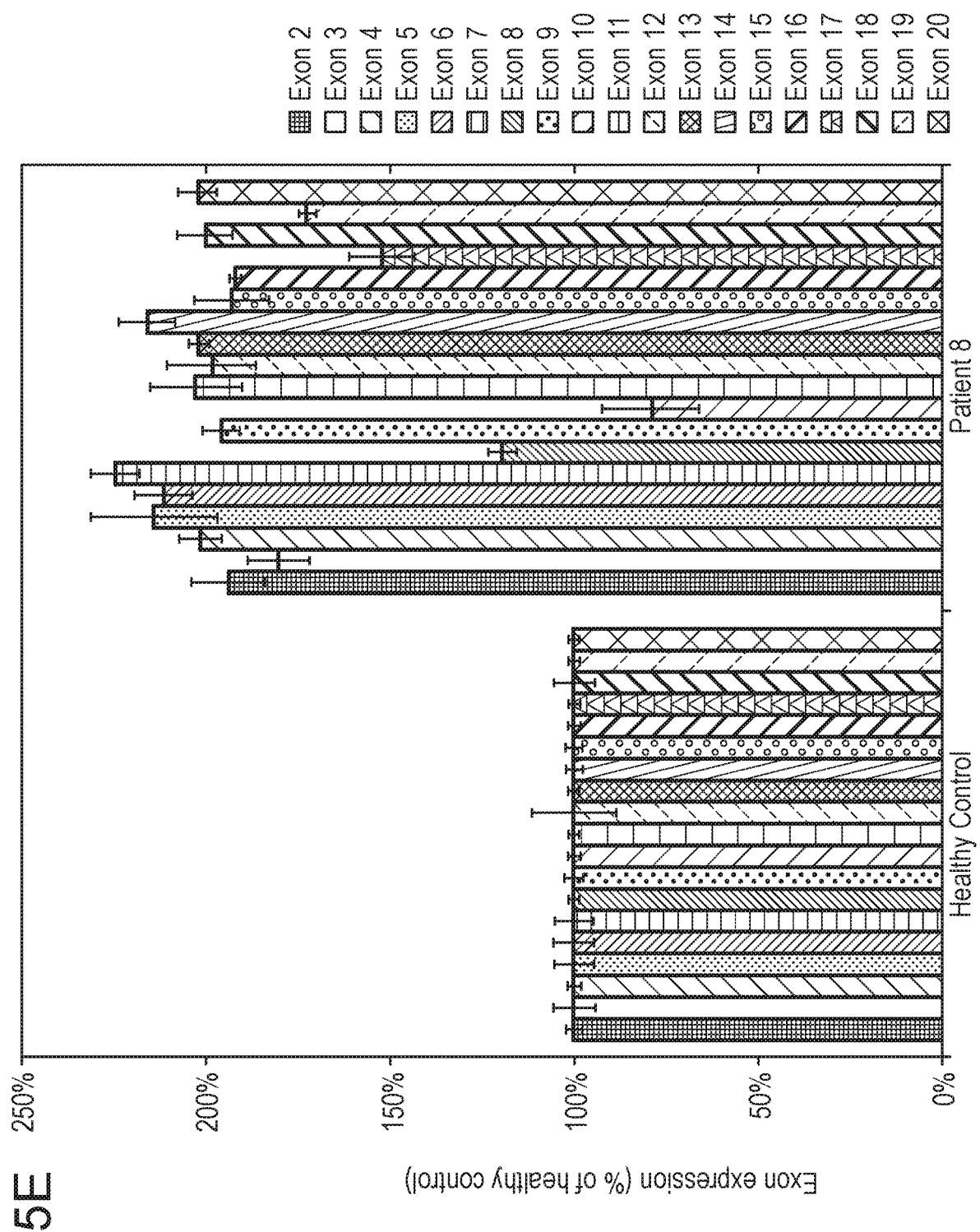
Figure 12:
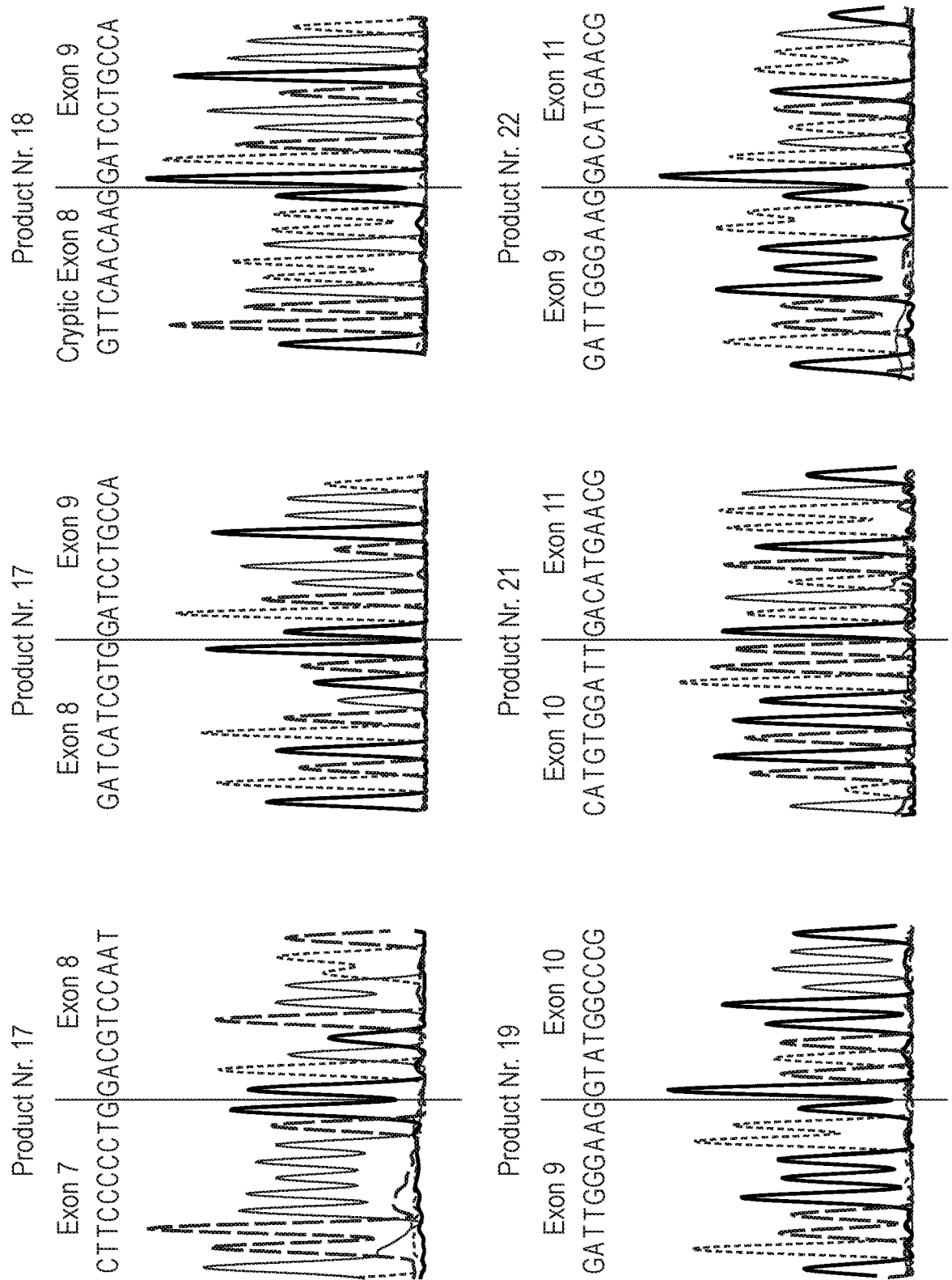
FIG. 12. Sequence analysis of patient 8. Product Nr. 17 Exon 7-Exon 8: SEQ ID NO: 643; Product Nr. 17 Exon 8-Exon 9: SEQ ID NO: 644; Product Nr. 18 Exon 8-Exon 9: SEQ ID NO: 645; Product Nr. 19 Exon 9-Exon 10: SEQ ID NO: 646; Product Nr. 21 Exon 10-Exon 11: SEQ ID NO: 647; Product Nr. 22 Exon 9-Exon 11: SEQ ID NO: 648.

Flanking exon PCR analysis indicated multiple PCR products from amplification of exons 8, 9, and 10 (FIG. 5A). All these products were analyzed by sequencing (FIG. 12). This indicated the presence of wild type exon 8 splicing (product 17) and utilization of a novel splice donor site in exon 8 at c.1254, which is located 2 nt upstream of the c.1256A>T mutation (product 18; FIG. 5B-C). This donor spliced to the canonical splicing acceptor site of exon 9 and the resulting reading frame was unchanged (Table 2). Splicing prediction programs indeed showed that c.1254 turned into a splice donor site due to the c.1256A>T mutation (FIG. 14G). The canonical splice donor site of exon 8 remained unchanged, and it was unclear which of the two sites would be preferred from in silico predictions. Product 21 represented wild type splicing of exon 10, while product 22 was the result of perfect exon 10 skipping in which the reading frame remained intact (FIG. 5D and FIG. 12). Loss of the exon 10 splice donor site by the c.1551+1G>T mutation was consistent with splicing predictions (FIG. 14G), but the outcome was not anticipated, as intron 10 inclusion rather than exon 10 skipping seemed the most logical consequence.

Evidence for Low Levels of Leaky Wild Type Splicing

Along with the exon-internal qPCR analysis described below, the flanking exon PCR assay provides information on the severity of the mutations via the relative intensities of the products. These can be explained based on the identification of the splicing products (FIGS. 5B-D) and on the locations of the primers used for amplification (FIG. 13).

Exon 7

Detection of exon 7 is performed with a forward primer that anneals to the 3' end of exon 6 and a reverse primer to the 5'end of exon 8 (FIG. 13). The 5'end of exon 8 is retained in all cases while the 3'part is spliced out in the c.1256A>T allele. Flanking exon PCR detection of exon 7 should therefore not be affected in this patient and this was indeed the case (FIG. 5A).

Exon 8

Flanking exon PCR primers used for detection of exon 8 are anneal to exon 7 and 9 (FIG. 13). Both exons are not affected in this patient predicting that all splicing alterations of exon 8 itself should be detected in a semi-quantitative manner. Indeed, a strong wild type product (number 17) was detected, dominated by allele 2, and a slightly weaker smaller product 18 was detected due to the novel cryptic splice donor site at c.1254 in allele 1. Maximal 50% of product 17 is expected to be derived from allele 2 and its stronger abundance compared to product 18 therefore suggests that allele 1 has leaky wild type splicing.

Exon 9

PCR primers for detection of exon 9 by flanking exon PCR anneal to the 5' part of exon 8, which is the part that is not skipped in allele 1, and to exon 10, which is completely skipped in allele 2 (FIG. 12). This complicates detection of exon 9 from these two alleles: a product from allele 1 would be shorter than normal due to the partial skipping of exon 8. A product from allele 2 is not possible due to the precise skipping of exon 10, while this exon is required for primer annealing. The predominant product obtained was the shorter product number 20 which was derived from allele 1. However, a small amount of wild type product number 19 was also observed. This indicates that at least one of the two alleles allows leaky wild type splicing.

Exon 10

Flanking exon PCR analysis of exon 10 is performed with primers annealing in exon 9 and exon 11, both of which are unaffected. The result therefore reflects the splicing alterations of exon 10 in a semi-quantitative way. Product 21 representing wild type splicing was the most abundant, while product 22 in which exon 10 was perfectly skipped was slightly less abundant. Because exon 10 splicing of allele 1 is unaffected and can account for 50% of wild type product, this result suggests that allele 2 also has leaky wild type splicing similar to allele 1.

Quantification Using Exon-Internal qPCR Analysis

Quantification of mRNA expression of each exon revealed that all exons except exons 8 and 10 showed ~2 fold higher abundance compared to the healthy control. Exons 8 and 10 were expressed at 2-fold lower levels with respect to the other exons but still at 80-120% of the levels of the healthy control. This indicates abnormally high mRNA expression in this patient. Allele 1 (1256A>T) suffers from partial skipping of exon 8 resulting in failure in detection of a qPCR product. The residual detection of exon 8 is therefore derived from allele 2 (c.1551+1G>T), expected to contribute 50%, and the remaining expression is likely derived from leaky wild type splicing from allele 1. The same rationale applies to detection of exon 10. In this case, expression was close to 50% relative to other exons, suggesting that the c.1551+1G>T mutation allowed much lower levels of wild type splicing. It should be noted that it is unclear why this patient shows 2-fold higher GAA expression relative to the healthy control, and whether this increase applies to both alleles to similar extents. This patient has a childhood/juvenile disease onset but is clearly less affected compared to classic infantile Pompe patients, consistent with low levels of residual wild type expression of GAA (table 1).

In summary, patient 8 contained two splicing mutations. c.1256A>T is a missense mutation in exon 8 that causes p.Asp419Val and in addition generates a novel splice donor site at c.1254, resulting in partial skipping of exon 8 and in leaky wild type splicing. c.1551+1G>T is located in intron 10 and causes perfect skipping of exon 10 and in leaky wild type splicing. The childhood/juvenile onset of Pompe disease suggests that both mutations are moderately to severely pathogenic. This is consistent with the GAA enzyme activity levels, which are lower compared to adult onset patients.

Verification of Known Splicing Events and Quantification of Splicing Products.

This patient was tested to validate whether a well-described splicing variant could be accurately detected in primary fibroblasts using the approach described here. c.-32-13T>G is located in intron 1 close to the splice acceptor site of exon 2, and causes aberrant splicing of exon 2, but also allows leaky wild type splicing. The second allele of this patient carried the c.1636+5G>T variant. This variant is similar to the c.1636+5G>C variant, which is known to be expressed at very low levels due to NMD, caused by intron 11 inclusion and a premature termination codon. For this reason, the allele harboring the IVS1 variant is preferentially amplified in the splicing approach described below.

Figure 25B:
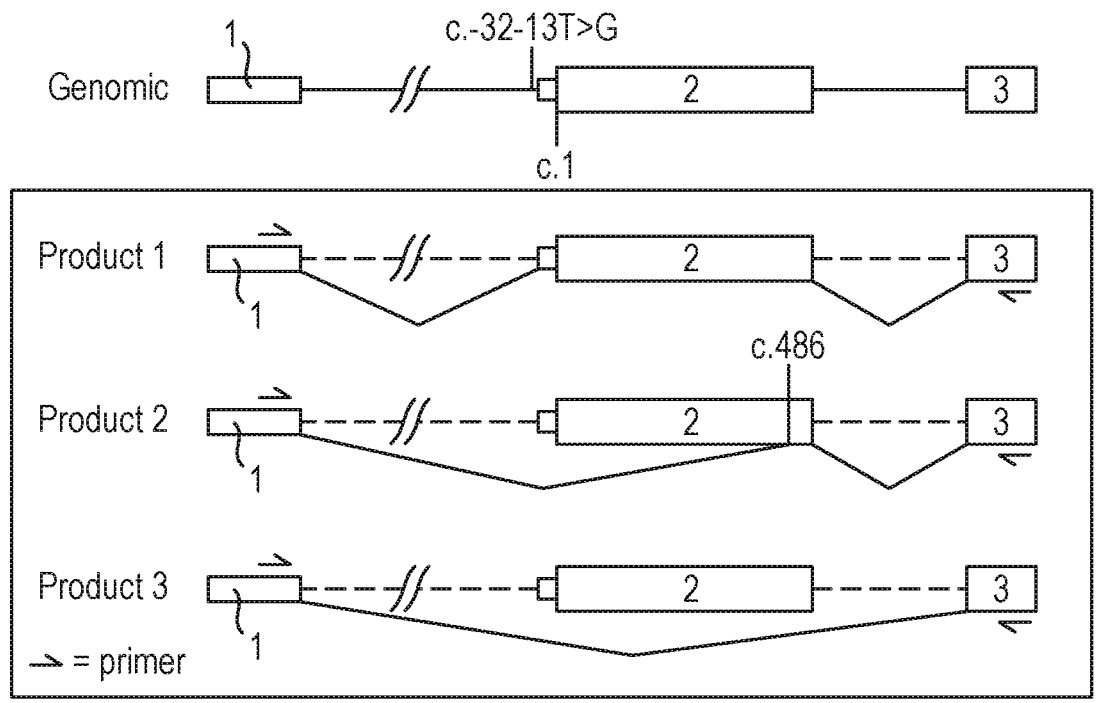
FIG. 25. Examples of mutations identified in the IVS1 minigene screen. HEK293 cells were transfected with minigene constructs and splicing was analysed after 24 hrs. A. RT-PCR analysis of the wild type minigene (WT), the minigene containing the IVS1 mutation (IVS1), and clones 115 and 97, which were identified in the unbiased minigene-based screen. Product 1: wild type mRNA, product 2: partially skipped exon 2 mRNA, product 3: fully skipped mRNA. B. Cartoon of the splice products. C. RT-qPCR analysis. Values were normalized for transfection efficiency by RT-qPCR analysis of neomycin (expressed from the same plasmid backbone from a separate promoter) and for cell numbers using beta-actin RT-qPCR analysis.

Flanking exon PCR analysis of exon 2 to 19 yielded three major products from exon 2 amplification (FIG. 25A). Numbers indicate splicing products that were sequenced, which indicated that product 1 represented full-length exon 2 with canonical splice junctions (FIG. 25B). Product 2 contained partially skipped exon 2 due to the utilization of a cryptic splice acceptor site at c.486, while product 3 represented fully skipped exon 2 (FIG. 25B). These products correspond to the major splicing variants reported for the IVS1 variant, namely normal (N) (product 1), splice variant (SV) 3 (product 2) and SV2 (product 3). The known minor IVS1 splicing variants are expressed at levels too low to allow detection by flanking exon PCR and sequencing. No aberrant flanking exon PCR products around exon 11 were observed, consistent with nonsense-mediated-dacay (NMD) of the products of the c.1636+5G>T variant.

Figure 25C:
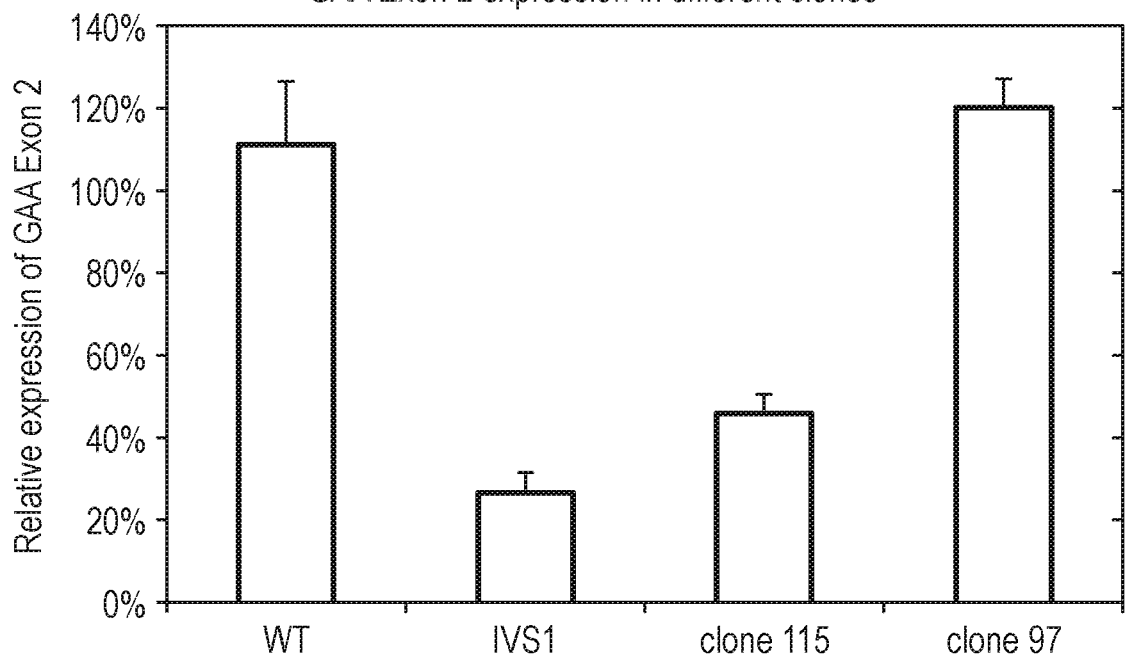

Exon-internal qPCR analysis for all coding exons showed 10-20% expression of exon 2 and all other exons (FIG. 25C). This can be explained as follows. The IVS1 variant allows leaky wild type splicing of exon 2 (product 1 in FIG. 25A) yielding a normal mRNA containing all exons. The two other major products 2 and 3 both result in the deletion of the canonical translation start site, which is located in exon 2. This leads to mRNA degradation, resulting in minor contribution in the quantitative exon-internal qPCR assay, and predominant detection of the leaky wild type GAA mRNA from the IVS1 allele.

Whereas the exon-internal qPCR enables quantification of individual exons, it cannot be used to separately quantify the aberrantly spliced products. This requires the development of an isoform-specific qPCR method. To demonstrate that this is feasible, we have developed a qPCR strategy to quantify the splicing products of exon 2 of patient 1. The results are shown in FIG. 24D and the PCR strategy in FIG. 24E and Table S2. This shows that expression in patient 1 of the N, SV3, and SV2 is 18%, 1%, and 3% of the healthy control, respectively. SV2 and SV3 were not detected in the healthy control. The relatively low levels of SV2 and SV3 in patient 1 are most likely caused by NMD.

Primers were designed that specifically amplify splicing variants caused by the IVS1 variant (FIGS. 26D and E; Table S2). For detection of the normal variant (N), the forward primer annealed to exon 1, and the reverse primer to the beginning of exon 2, which is the part that is retained in this variant but is removed by splicing in the other two main variants. For detection of SV3, the forward primer partially annealed to exon 1 and partially to exon 2 after the cryptic splice site, while the reverse primer partially annealed to exon 3 and partially to exon 2. For detection of SV2, the forward primer partially annealed to exon 1 and partially to exon 3, and the reverse primer to exon 3.

Quantitation was performed after normalization for β-actin using the delta-delta-Ct method. The different qPCR amplifications had similar efficiencies: 99% (β-actin), 92% (N), 99% (SV2), and 103% (SV3).

| | Forward | SEQ ID NO | Reverse | Product size (nt) | SEQ ID NO |
|---|---|---|---|---|---|
| GAA Exon 2 | AGCTCCT CTGAAAT GGGCTAC AC | 547 | GGTTCTC AGTCTCC ATCATCA CG | 109 | 569 |
| GAA Exon 3 | ATCCAGC TAACAGG CGCTAC | 548 | GCTCCTC GGAGAAC TCCAC | 96 | 570 |
| GAA Exon 4 | CTGTTCT TTGCGGA CCAGTT | 549 | CTGAGCA TCAGGGG ACTGAG | 95 | 571 |
| GAA Exon 5 | CGAACCT CTACGGG TCTCAC | 550 | TGCTGTT TAGCAGG AACACC | 81 | 572 |
| GAA Exon 6 | CTTAGCT GGAGGTC GACAGG | 551 | CACAACG TCCAGGT ACTGCT | 93 | 573 |
| GAA Exon 7 | CGTTCAT GCCGCCA TACT | 552 | GGTCATG TTCTCCA CCACCT | 95 | 574 |
| GAA Exon 8 | GACGTCC AGTGGAA CGACCT | 553 | GAAGTCC CGGAAGC CATC | 78 | 575 |
| GAA Exon 9 | ATCCTGC CATCAGC AGCTC | 554 | GGTCTCG TTGGTGA TGAAAA | 89 | 576 |
| GAA Exon 10 | CACTGCC TTCCCCG ACTT | 555 | ACCTGGT CATGGAA CTCAGC | 78 | 577 |
| GAA Exon 11 | ACATGAA CGAGCCT TCCAAC | 556 | ACGTAGG GTGGGTT CTCCAG | 79 | 578 |
| GAA Exon 12 | CCTCCAG CCACCAG TTTCTCT | 557 | TGTGGGA GGCGATG GCTT | 78 | 579 |
| GAA Exon 13 | GACACGC CCATTTG TGATCT | 558 | CCAGGAG CTCCACA CGTC | 88 | 580 |
| GAA Exon 14 | CTCAGAG GAGCTGT GTGTGC | 559 | CAGACTG AGCAGGC TGTTGT | 82 | 581 |
| GAA Exon 15 | CAGCAGG CCATGAG GAAG | 560 | GGCCTGG TGGAACA GTGTG | 75 | 582 |
| GAA Exon 16 | CCCAAGG ACTCTAG CACCTG | | CAAGGGG AAGTAGC CAGTCA | 114 | 583 |
| GAA Exon 17 | GTGCCAG TAGAGGC CCTTG | | GAGGTGG ACGTTGA TGGTGT | 123 | 584 |
| GAA Exon 18 | GCCTCAC AACCACA GAGTCC | | TCTCTCC ATCGTCC CAGAAC | 102 | 585 |
| GAA Exon 19 | TGCAGAA GGTGACT GTCCTG | | GGGCTGT AGGTGAA GTTGGA | 88 | 586 |
| GAA Exon 20 | GGGCGGA GTGTGTT AGTCTC | | CTCCAGG TGACACA TGCAAC | 110 | 587 |
| GAA N | AAACTGA GGCACGG AGCG | | GAGTGCA GCGGTTG CCAA | 129 | 588 |
| GAA SV2 | GGCACGG AGCGGGA CA | | CTGTTAG CTGGATC TTTGATC GTG | 92 | 589 |
| GAA SV3 | AGGCACG GAGCGGG ATCA | | TCGGAGA ACTCCAC GCTGTA | 111 | 590 |

Mucopolycaccharidosis type VI (Maroteaux-Lamy syndrome) is a autosomal recessive monogenic disorder caused by defects in the gene coding for N-acetylgalactosamine 4-sulfatase (arylsulfatase B; ARSB). To demonstrate the generic nature of the splicing assay, the assay was adapted for MPSVI. To this end, flanking exon primers were designed for all coding exons of the ARSB gene (exons 2-7; the first and the last exons cannot be flanked). The following primer sequences and the expected product sizes (column "WT product size") were used:

| Exon | primer | SEQ ID NO: | WT product | 1142 + 2T > C |
|---|---|---|---|---|
| 2 | Forward GGGTGCTCCTG GACAACTAC | 591 | 378 | 378 |
|   | Reverse CCTGTTGCAAC TTCTTCGCC | 592 | | |
| 3 | Forward ATGGCACCTGG GAATGTACC | 593 | 444 | 444 |
|   | Reverse GTGTTGTTCCA GAGCCCACT | 594 | | |
| 4 | Forward ACGCTCTGAAT GTCACACGA | 595 | 514 | 514 |
|   | Reverse GTTGGCAGCCA GTCAGAGAT | 596 | | |
| 5 | Forward AAAAAGCAGTG GGCTCTGGA | 597 | 361 | 117 |
|   | Reverse CGGTGAAGAGT CCACGAAGT | 598 | | |
| 6 | Forward CAGAAGGGCGT GAAGAACCG | 599 | 314 | 314 |
|   | Reverse CCCGTGAGGAG TTTCCAATTTC | 600 | | |
| 7 | Forward ACTTCGTGGAC TCTTCACCG | 601 | 348 | 348 |
|   | Reverse AGTACACGGGG ACTGAGTGT | 602 | | |

Figure 34:
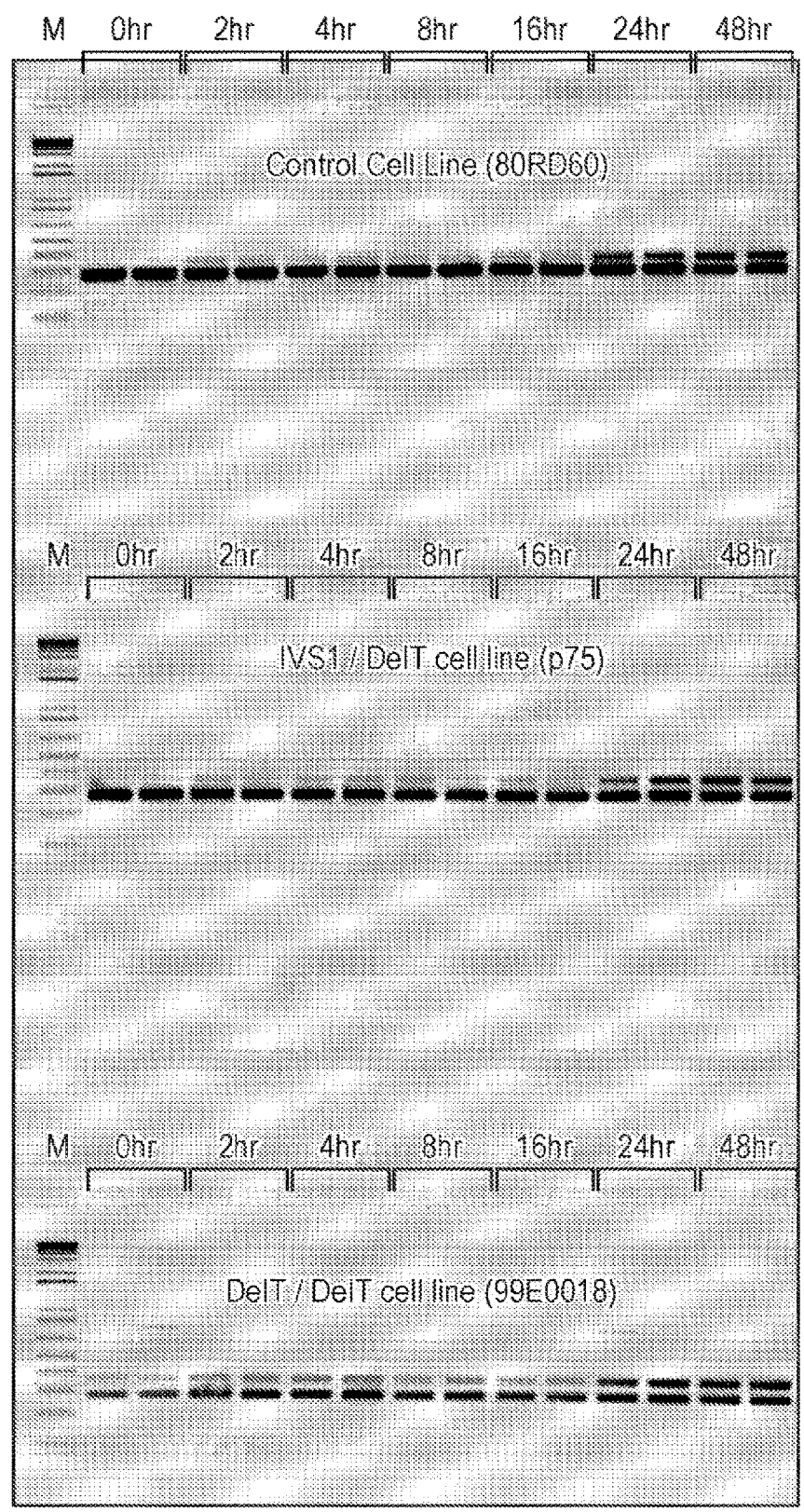
FIG. 34: Result of inhibition of the nonsense mediated decay (NMD) pathway on inclusion of intron 6 of the GAA mRNA.

Primary fibroblasts from a healthy control were grown, total RNA was harvested, cDNA was synthesized, and exons 2-7 were amplified by PCR, see FIG. 34. Products were separated on an agarose gel and visualized using ethidium bromide. FIG. 34 shows that all exons gave a predominant single band at the expected size (size markers are indicated on the left and numbers refer to sizes in bp). Next, fibroblasts were grown from a patient homozygous for the ARSB variant c.1142+2T>C. This patient has been described previously in Brands et al. (Orphanet J Rare Dis. 2013 Apr. 4; 8:51). While a splicing defect was suspected, it has not been demonstrated. In addition, it was not known how severe the potential splicing defect may be. Application of the splicing assay to analyze the nature of this variant revealed a severe splicing defect with two major outcomes, as shown in FIG. 35, left part: 1) The product for amplification of exon 5 was lower compared to the healthy control: now a single product of 117 bp instead of 361 bp was obtained, which is consistent with a skipping of exon 5 and a deletion of 244 nucleotides in the mRNA, see above, all products had a lower abundance compared to the healthy control. This is consistent with the idea that the deletion of 244 nucleotides results in a reading frame shift, resulting in activation of the nonsense mediated decay pathway and degradation of the mRNA. Interestingly, no leaky wild type splicing could be detected. This is consistent with the severe and fast disease progression in this patient as described in Brands et al. (Orphanet J Rare Dis. 2013 Apr. 4; 8:51). Taken together, the expression and splicing assay was successfully applied to MPSVI, in which is resulted in the identification of the splicing defect caused by the c.1142+2T>C ARSB variant. The absence of leaky wild type splicing was consistent with the severe phenotype of the patient involved.

Example 2

1 Generation of the SF-U7 snRNA Antisense Vector

The U7snRNA gene with promoter was obtained from female mouse genomic DNA by using Fw-GCGCctgcag-TAACAACATAGGAGCTGTG (SEQ ID NO: 603) and Rv-GCGCgtcgacCAGATACGCGTTTCCTAGGA (SEQ ID NO: 604) primers with PstI and SalI overhang (indicated in bold regular letter type) in a PCR amplification. The whole PCR reaction was loaded on a 1% gel and the PCR fragment (425 bp) was cloned into a Topo-II-vector according to the manufacture's manual (Invitrogen). SMopt and StuI sites were generated by using site directed mutagenesis according to an inner and outer primer design with Fw-(GCTCTTT-TAGAATTTTTGGAGCAGGTTTTCTGACTTCG) (SEQ ID NO: 605) and Rv-U7snRNA-SmOPT (CGAAGTCA-GAAAACCTGCTCCAAAAATTCTAAAAGAGC) (SEQ ID NO: 606) or Fw-(CCTGGCTCGCTACAGAGGC CTTTCCGCAAGTGTTACAGC) (SEQ ID NO: 607) and Rv-U7snRNA-StuI (GCTGTAACACTTGCGGAAAGGC CTCTGTAGCGAGCCAGG) (SEQ ID NO: 608) as inner primers and with Fw-M13 (GTAAAACGACGGCCAG) (SEQ ID NO: 609) and Rv-M13 (CAGGAAACAGCTAT-GAC) (SEQ ID NO: 610) as outer primers [Heckman, K. L. and L. R. Pease, Gene splicing and mutagenesis by PCR-driven overlap extension. Nat Protoc, 2007. 2(4): p. 924-32]. The modified U7 snRNA sequence was cloned back into pRRL.PPT.SF.pre vector [Warlich E et al., Lentiviral vector design and imaging approaches to visualize the early stages of cellular reprogramming Mol Ther. 2011 April; 19(4):782-9.] by using PstI and SalI sites and replaced the original SFFV promoter. This is the procedure for generating the SF_U7snRNA vector.

2 Optimization of the SF-U7 snRNA Antisense Vector for High Throughput Screening The originally used StuI site is not unique in the lentiviral vector of Warlich et al and was replaced by a NsiI restriction site by site directed mutagenesis by using Fw-cctggctcgc-tacagatgcaTaggaggacggaggacg (SEQ ID NO: 611) and Rv-cgtcctccgtcctcctAtgcatctgtagcgagccagg (SEQ ID NO: 612) primers. Capital letters indicate mutated residues.

3 Insertion of Antisense Sequences

New antisense sequences were inserted with an overhang PCR by using overhang forward primers containing the desired antisense sequences (gcgcATGCAT-antisense sequence-ttggagcagg) (SEQ ID NO:613). Bold capital letters indicate the NsiI restriction site. The reverse primer Rv_ms_U7snRNA_SalI is (GCGCgtcgacCAGA-TACGCGTTTCCTAGGA) (SEQ ID NO: 614) and was the same for every construct, the small letters indicate the SalI restriction site. Overhang PCR was performed on the modified vector (SF_U7snRNA_NSI) using PfuUltra HF (Agilent Technologies) The PCR program consisted of a 30 second initial denaturation step at 95° C., 35 cycles at 95° C. for 10 seconds, 60° C. for 30 seconds and 72° C. for 10 seconds. Final extension step was at 72° C. for 10 minutes. The PCR reaction containing the desired antisense sequence and U7 snRNA loaded on a 2% agarose gel with 0.2% ethidiumbromide staining Bands were then visualized under a transilluminator (UVP, LLC) excised and extracted using the QIAquick Gel Extraction Kit (Qiagen GmbH, Hilden, Germany).

After gel extraction, 16 μl of purified product was digested using SalI and NsiI (Roche) for 1 hour at 37° C. and purified using the QIAquick PCR Purification Kit (Qiagen GmbH, Hilden, Germany).

Meanwhile the original vector was digested with SalI and NsiI for 1 hour at 37° C., resulting in a vector without antisense sequence. The digested vector was loaded on a 1% agarose gel with ethidiumbromide staining Bands were visualized under a transilluminator and the band corresponding with the digested vector (6358 bp) was excised and purified using the QIAquick Gel Extraction Kit (Qiagen GmbH, Hilden, Germany).

Purified digested vector and digested PCR products were ligated with T4 DNA ligase with ATP (New England BioLabs) for 1 hour at room temperature.

The ligation products were transformed in *E. coli* (TOP10) and inoculated on LB agar plates containing 100 μg/ml ampicillin (Sigma). After overnight incubation, three colonies were picked per ligation product for miniprep cultures. Picked colonies were grown overnight in 2 ml LB containing 100 μg/ml ampicillin at 37° C. Purification of the plasmids was carried out using the QIAprep Spin Miniprep Kit (Qiagen GmbH, Hilden, Germany). After extraction, DNA concentration was measured with the Nanovue Spectrophotometer.

Sequences of newly generated constructs were validated with Sanger Sequencing using BigDye Terminator v3.1 (Applied Biosystems) for the sequence reaction and were then purified with Sephadex G-50 (Sigma) according to manufacturer's protocol.

TABLE 1 sequences identified for targeting to include exon 2 of GAA

| Sequence in cDNA to which AON anneals* | sequence of AON (5' → 3'): | SEQ ID NO: |
|---|---|---|
| c-32-156_-210 | GCTCTGCACTCCCCTGCTGGAGCT TTTCTCGCCCTTCCTTCTGGCCCT CTCCCCA | 1 |
| c-32-156_-200 | GCTCTGCACTCCCCTGCTGGAGCT TTTCTCGCCCTTCCTTCTGGC | 37 |
| c-32-160_-190 | TGCACTCCCCTGCTGGAGCTTTTC TCGCCCT | 38 |
| c-32-160_195 | TGCACTCCCCTGCTGGAGCTTTTC TCGCCCTTCCTT | 39 |
| c-32-165_-195 | TCCCCTGCTGGAGCTTTTCTCGCC CTTCCTT | 40 |

TABLE 2 sequences identified for targeting to exclude intron 6 of GAA

| Sequence in cDNA to which AON anneals* | sequence of region (5' → 3'): | Seq ID |
|---|---|---|
| c.956-25_1194 + 25 | AACCCCAGAGCTGCTTCC CTTCCAGATGTGGTCCTG CAGCCGAGCCCTGCCCTT AGCTGGAGGTCGACAGGT GGGATCCTGGATGTCTAC ATCTTCCTGGGCCCAGAG CCCAAGAGCGTGGTGCAG CAGTACCTGGACGTTGTG GGTAGGGCCTGCTCCCTG GCCGCGGCCCCCGCCCCA AGGCTCCCTCCTCCCTCC CTCATGAAGTCGGCGTTG GCCTGCAGGATACCCGTT CATGCCGCCATACTGGGG CCTGGGCTTCCACCTGTG CCGCTGGGGCTACTCCTC CACCGCTATCACCCGCCA GGTGGTGGAGAACATGAC CAGGGCCCACTTCCCCCT GGTGAGTTGGGGTGGTGG CAGGGGAG | 541 |
| c.956-25_1004 | AACCCCAGAGCTGCTTCC CTTCCAGATGTGGTCCTG CAGCCGAGCCCTGCCCTT AGCTGGAGGTCGACAGGT GG | 542 |
| c.1005_1075 + 3 | GATCCTGGATGTCTACAT CTTCCTGGGCCCAGAGCC CAAGAGCGTGGTGCAGCA GTACCTGGACGTTGTGGG TA | 543 |
| c.1075 + 4_1076-2 | GGGCCTGCTCCCTGGCCG CGGCCCCCGCCCCAAGGC TCCCTCCTCCCTCCCTCA TGAAGTCGGCGTTGGCCT GC | 544 |
| c.1076-2_1147 | AGGATACCCGTTCATGCC GCCATACTGGGGCCTGGG CTTCCACCTGTGCCGCTG GGGCTACTCCTCCACCGC TA | 545 |
| c.1148_1194 + 25 | TCACCCGCCAGGTGGTGG AGAACATGACCAGGGCCC ACTTCCCCCTGGTGAGTT GGGGTGGTGGCAGGGGAG | 546 |

TABLE 3 sequences identified by U7 screen

| Sequence in cDNA to which AON anneals* | sequence of AON (5' → 3'): | Seq ID |
|---|---|---|
| c.-32-180_-156 | TGGGGAGAGGGCCAGAAGGAAGGGC | 2 |
| c.-32-181_-157 | GGGGAGAGGGCCAGAAGGAAGGGCG | 3 |
| c.-32-182_-158 | GGGAGAGGGCCAGAAGGAAGGGCGA | 4 |
| c.-32-183_-159 | GGAGAGGGCCAGAAGGAAGGGCGAG | 5 |
| c.-32-184_-160 | GAGAGGGCCAGAAGGAAGGGCGAGA | 6 |

TABLE 3-continued sequences identified by U7 screen

| | | |
|---|---|---|
| c.-32-185_-161 | AGAGGGCCAGAAGGAAGGGCGAGAA | 7 |
| c.-32-186_-162 | GAGGGCCAGAAGGAAGGGCGAGAAA | 8 |
| c.-32-187_-163 | AGGGCCAGAAGGAAGGGCGAGAAAA | 9 |
| c.-32-188_-164 | GGGCCAGAAGGAAGGGCGAGAAAAG | 10 |
| c.-32-189_-165 | GGCCAGAAGGAAGGGCGAGAAAAGC | 11 |
| c.-32-190_-166 | GCCAGAAGGAAGGGCGAGAAAAGCT | 12 |
| c.-32-191_-167 | CCAGAAGGAAGGGCGAGAAAAGCTC | 13 |
| c.-32-192_-168 | CAGAAGGAAGGGCGAGAAAAGCTCC | 14 |
| c.-32-193_-169 | AGAAGGAAGGGCGAGAAAAGCTCCA | 15 |
| c.-32-194_-170 | GAAGGAAGGGCGAGAAAAGCTCCAG | 16 |
| c.-32-195_-171 | AAGGAAGGGCGAGAAAAGCTCCAGC | 17 |
| c.-32-196_-172 | AGGAAGGGCGAGAAAAGCTCCAGCA | 18 |
| c.-32-197_-173 | GGAAGGGCGAGAAAAGCTCCAGCAG | 19 |
| c.-32-198_-174 | GAAGGGCGAGAAAAGCTCCAGCAGG | 20 |
| c.-32-199_-175 | AAGGGCGAGAAAAGCTCCAGCAGGG | 21 |
| c.-32-200_-176 | AGGGCGAGAAAAGCTCCAGCAGGGG | 22 |
| c.-32-201_-177 | GGGCGAGAAAAGCTCCAGCAGGGGA | 23 |
| c.-32-202_-178 | GGCGAGAAAAGCTCCAGCAGGGGAG | 24 |
| c.-32-203_-179 | GCGAGAAAAGCTCCAGCAGGGGAGT | 25 |
| c.-32-204_-180 | CGAGAAAAGCTCCAGCAGGGGAGTG | 26 |
| c.-32-205_-181 | GAGAAAAGCTCCAGCAGGGGAGTGC | 27 |
| c.-32-206_-182 | AGAAAAGCTCCAGCAGGGGAGTGCA | 28 |
| c.-32-207_-183 | GAAAAGCTCCAGCAGGGGAGTGCAG | 29 |
| c.-32-208_-184 | AAAAGCTCCAGCAGGGGAGTGCAGA | 30 |
| c.-32-209_-185 | AAAGCTCCAGCAGGGGAGTGCAGAG | 31 |
| c.-32-210_-186 | AAGCTCCAGCAGGGGAGTGCAGAGC | 32 |
| c.-32-187_-167 | CCAGAAGGAAGGGCGAGAAAA | 33 |

| Sequence in GAA cDNA to which AON anneals | AON sequence 5' → 3' | Seq ID |
|---|---|---|
| c.-32-319_-300 | CCAAACAGCTGTCGCCTGGG | 41 |
| c.-32-299_-280 | AGGTAGACACTTGAAACAGG | 42 |
| c.-32-279_-260 | CCCAGGAAGACCAGCAAGGC | 43 |
| c.-32-259_-240 | TCAAACACGCTTAGAATGTC | 44 |
| c.-32-239_-220 | GTCTGCTAAAATGTTACAAA | 45 |
| c.-32-219_-200 | GAGTGCAGAGCACTTGCACA | 46 |
| c.-32-199_-180 | CGAGAAAAGCTCCAGCAGGG | 47 |
| c.-32-179_-160 | GAGAGGGCCAGAAGGAAGGG | 48 |
| c.-32-159_-140 | GCCCTGCTGTCTAGACTGGG | 49 |
| c.-32-139_-120 | AGGTGGCCAGGGTGGGTGTT | 50 |

TABLE 3-continued sequences identified by U7 screen

| | | |
|---|---|---|
| c.-32-119_-100 | GCACCCAGGCAGGTGGGGTA | 51 |
| c.-32-99_-80 | CAACCGCGGCTGGCACTGCA | 52 |
| c.-32-79_-60 | TCAAAGCAGCTCTGAGACAT | 53 |
| c.-32-59_-40 | GGGCGGCACTCACGGGGCTC | 54 |
| c.-32-39_-20 | GCTCAGCAGGGAGGCGGGAG | 55 |
| c.-32-19_-0 | CCTGCGGGAGAAGAAAGCGG | 56 |
| c.-30_-12 | GCCTGGACAGCTCCTACAGG | 57 |
| c.-10_+9 | CACTCCCATGGTTGGAGATG | 58 |
| c.10_+29 | TGGGAGCAGGGCGGGTGCCT | 59 |
| c.30_+49 | CGCAGACGGCCAGGAGCCGG | 60 |
| c.50_+69 | GGTTGCCAAGGACACGAGGG | 61 |
| c.70_+89 | ATGTGCCCCAGGAGTGCAGC | 62 |
| c.90_+109 | GCAGGAAATCATGGAGTAGG | 63 |
| c.110_+129 | ACTCAGCTCTCGGGGAACCA | 64 |
| c.130_+149 | TCCAGGACTGGGGAGGAGCC | 65 |
| c.150_+169 | GGTGAGCTGGGTGAGTCTCC | 66 |
| c.170_+189 | TGGTCTGCTGGCTCCCTGCT | 67 |
| c.190_+209 | GCCTGGGCATCCCGGGGCCC | 68 |
| c.210_+229 | CTCTGGGACGGCCGGGGTGT | 69 |
| c.230_+249 | GTCGCACTGTGTGGGCACTG | 70 |
| c.250_+269 | AAGCGGCTGTTGGGGGGGAC | 71 |
| c.270_+289 | CCTTGTCAGGGGCGCAATCG | 72 |
| c.290_+309 | GCACTGTTCCTGGGTGATGG | 73 |
| c.310_+329 | TAGCAACAGCCGCGGGCCTC | 74 |
| c.330_+349 | GCCCCTGCTTTGCAGGGATG | 75 |
| c.350_+369 | CCCCATCTGGGCTCCCTGCA | 76 |
| c.370_+389 | GGGAAGAAGCACCAGGGCTG | 77 |
| c.390_+409 | TGTAGCTGGGGTAGCTGGGT | 78 |
| c.410_+429 | GGAGCTCAGGTTCTCCAGCT | 79 |
| c.430_+449 | GCCGTGTAGCCCATTTCAGA | 80 |
| c.450_+469 | GGGTGGTACGGGTCAGGGTG | 81 |
| c.470_+489 | GTCCTTGGGGAAGAAGGTGG | 82 |
| c.490_+509 | TCCAGCCGCAGGGTCAGGAT | 83 |
| c.510_+529 | TCTCAGTCTCCATCATCACG | 84 |
| c.530_+546 | GTGAAGTGGAGGCGGT | 85 |
| c.-32-225_-206 | AGAGCACTTGCACAGTCTGC | 86 |
| c.-32-223_-204 | GCAGAGCACTTGCACAGTCT | 87 |
| c.-32-221_-202 | GTGCAGAGCACTTGCACAGT | 88 |
| c.-32-217_-198 | GGGAGTGCAGAGCACTTGCA | 89 |

TABLE 3-continued

| sequences identified by U7 screen | | |
|---|---|---|
| c.-32-215_-196 | AGGGGAGTGCAGAGCACTTG | 90 |
| c.-32-213_-194 | GCAGGGGAGTGCAGAGCACT | 91 |
| c.-32-185_-166 | GCCAGAAGGAAGGGCGAGAA | 92 |
| c.-32-183_-164 | GGGCCAGAAGGAAGGGCGAG | 93 |
| c.-32-181_-162 | GAGGGCCAGAAGGAAGGGCG | 94 |
| c.-32-177_-158 | GGGAGAGGGCCAGAAGGAAG | 95 |
| c.-32-175_-156 | TGGGGAGAGGGCCAGAAGGA | 96 |
| c.-32-173_-154 | ACTGGGGAGAGGGCCAGAAG | 97 |

The antisense sequence above is depicted as DNA as it is cloned into a vector, however in the cell it is transcribed as a RNA molecule. The skilled person knows then that T is U.

Figure 23:
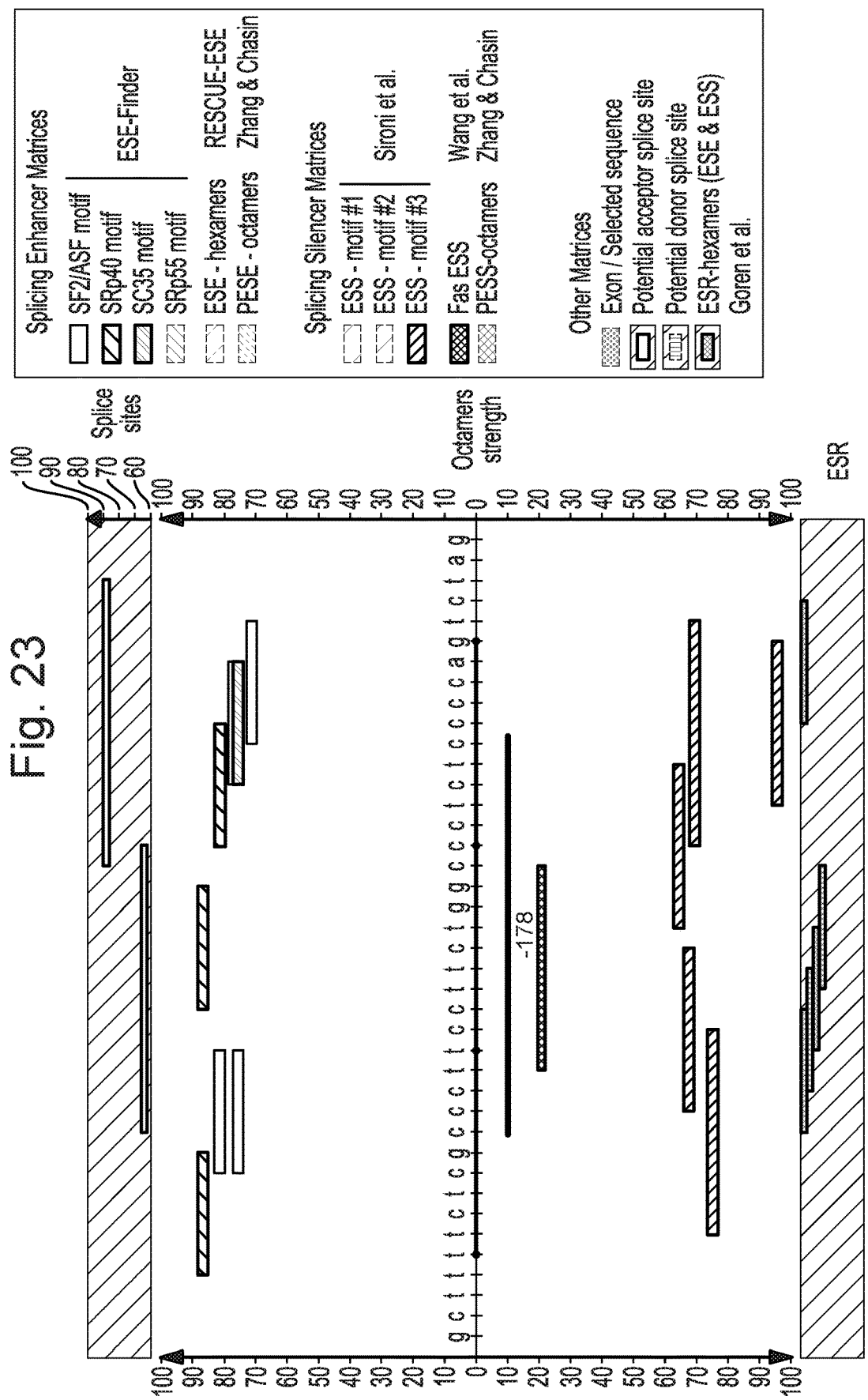
FIG. 23. Example of a splice prediction with the human splice finder demonstrated an ambivalent prediction for the identified −178 sequence as both enhancer and silencer motifs were predicted.

FIG. 23 shows examples of positions of antisense sequences targeting GAA for the unbiased intron 1 and exon 2 screen.

Enzyme Activity Assay

Enzyme activity was measured using the 4-methylumbelliferone assay. Samples were harvested after twelve days of transduction. The lysis buffer consisted of 50 mM Tris (pH 7.5), 100 mM NaCl, 50 mM NaF, 1% Tx-100 and one tablet protease inhibitor with EDTA (Roche). Lysis buffer was incubated on transduced fibroblasts for 5 minutes on ice before harvesting. Samples were either directly used or snap-freezed using liquid nitrogen and stored at −80° C. Otherwise, samples were kept on ice for further use in 4-methylumbelliferone assay.

GAA activity was measured using the substrate 4-methylumbelliferyl-α-D-glucopyranoside, which is fluorogenic in nature. Protein concentrations of the samples was determined by the Lowry protein method using the BCA Protein Assay Kit (Pierce, Thermo Scientific). Bovine serum albumin (BSA) standards consisted of 0, 0.1, 0.2, 0.4, 0.5, 0.6, 1.0, 2.0 mg/ml. Absorbance was measured at 562 nm for the BCA Protein Assay, and for the 4-methylumbelliferone assay excitation was at 365 nm and emission at 448 nm, using the Varioskan (Thermo Scientific) microplate reader. GAA enzyme activity was expressed as nanomoles of substrate hydrolyzed per hour per milligram of total protein.

Lentiviral Vector Production

For lentiviral vector production, 293T cells 90% confluent growing on 10 cm culture dishes were seeded ⅛ on 10 cm culture dishes. After 16-24 hours, a total of 3 μg U7 snRNA construct, 2 μg Pax2 and 1 μg VSV were cotransfected using Fugene 6 Transfection Agent (Promega). Viral supernatants (9 ml) were harvested 72 hours post-transfection, filtered over 0.45 μm filters (MillexHV, Millipore) and concentrated by ultra-centrifugation in a Beckman Ultracentrifuge (Beckman Coulter) at 20.000 rpm, 4° C. for 2 hours. Viral pellets were resuspended in 100 μl Dulbecco's modified Eagle's medium Low Glucose (Gibco, Paisley, UK), aliquoted in CryoTubes (Thermo Scientific) and stored at −80° C. Lentiviral titers were determined after concentration by ultra-centrifugation with the HIV p24 Antigen ELISA Kit (Retrotek, ZeptroMetrix Corporation). The assay was measured with a Varioskan microplate reader (Thermo Scientific)

Transduction of Cells

Culture media was replaced with new culture media containing 6 ng/ml protamine sulphate (sigma) 24 hours after seeding. The cells were transduced with equal titers of lentiviruses (see above).

Figure 19:
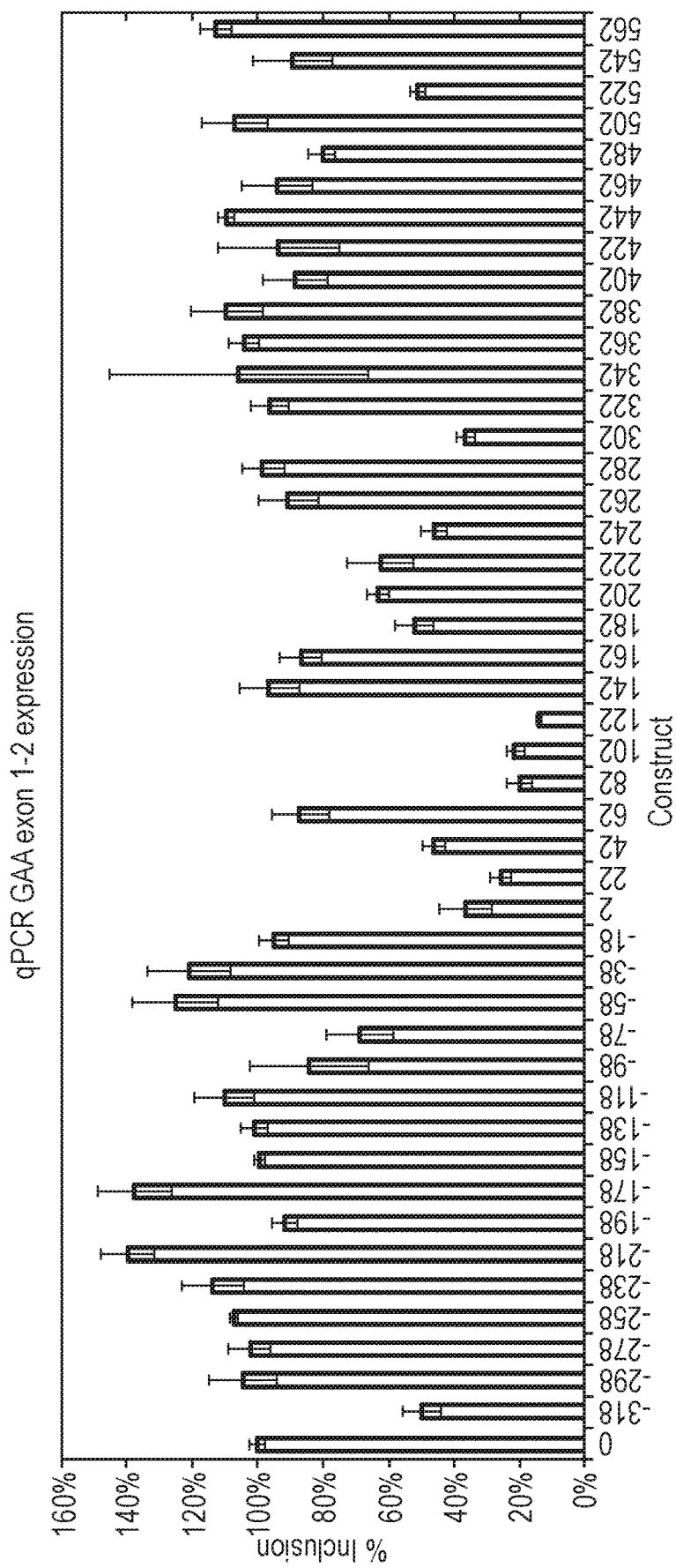
FIG. 19. RNA expression analysis using RT-qPCR of a screen performed for sequences in intron 1 and exon 2 of the GAA pre-mRNA with antisense sequences using the U7 small nuclear RNA system. Numbers indicate antisense sequence positions according to table 1.

Primary fibroblasts from patient were transduced, see above with lentivirus containing the U7snRNA AON construct and splicing was allowed to occur. The screen on fibroblasts was performed by infection of individual wells containing primary fibroblasts with lentiviruses expressing a single type of U7 snRNA AONs. RNA was analysed 5 days after infection. Splicing products were analysed with RT-qPCR. GAA enzyme activity was analysed 12 days after infection (see above: enzyme activity assay). FIG. 19 shows changes in exon 2 inclusion by different AONs. RNA expression analysis using RT-qPCR of a screen on intron 1 and exon 2 of GAA with antisense sequences with the use of the U7 small nuclear RNA system. Numbers indicate antisense sequence positions according to table 1. The control is the patient fibroblast without added AON vector.

Figure 20:
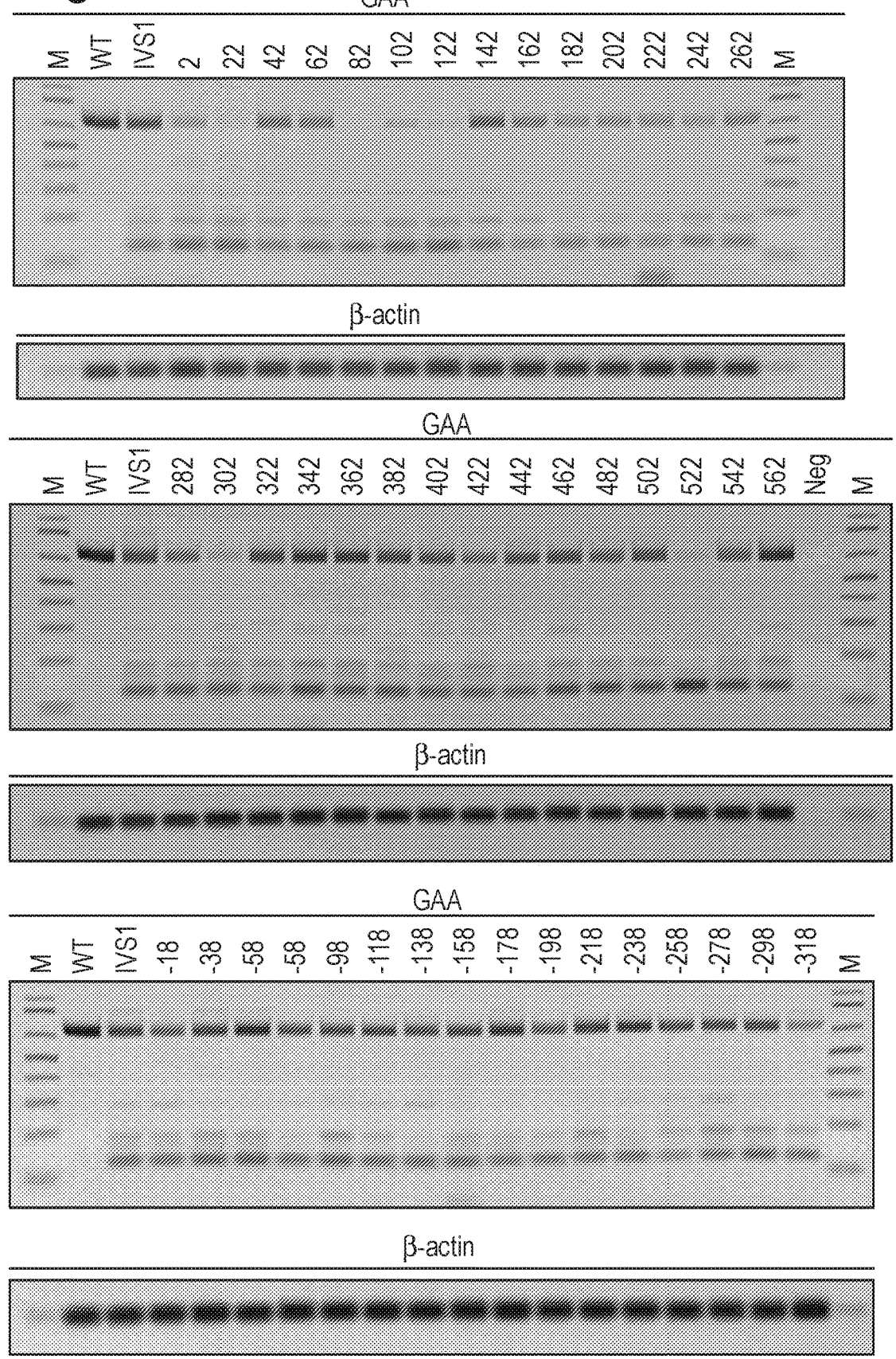
FIG. 20 RNA expression analysis using RT-PCR of a screen performed for sequences in intron 1 and exon 2 of the GAA pre-mRNA with antisense sequences using the U7 small nuclear RNA system. Numbers indicate antisense sequence positions according to table 1. In the GAA RT-PCR, three major products are observed. The upper product represents exon 2 inclusion, the lower doublet represents partial skipping of exon 2 (upper band of the doublet) and complete skipping of exon 2 (lower band of the doublet). Beta-actin RT-PCR was used as loading control.

FIG. 20 shows RNA analysis with RT-PCR of a screen on intron 1 and exon 2 of GAA with antisense sequences used in the U7 small nuclear RNA system. Numbers indicate antisense sequence positions according to table 1. In the GAA RT-PCR, three major products are observed. The upper product represents exon 2 inclusion, the lower doublet represents partial skipping of exon 2 (upper band of the doublet) and complete skipping of exon 2 (lower band of the doublet). Beta-actin RT-PCR was used as loading control.

Figure 21:
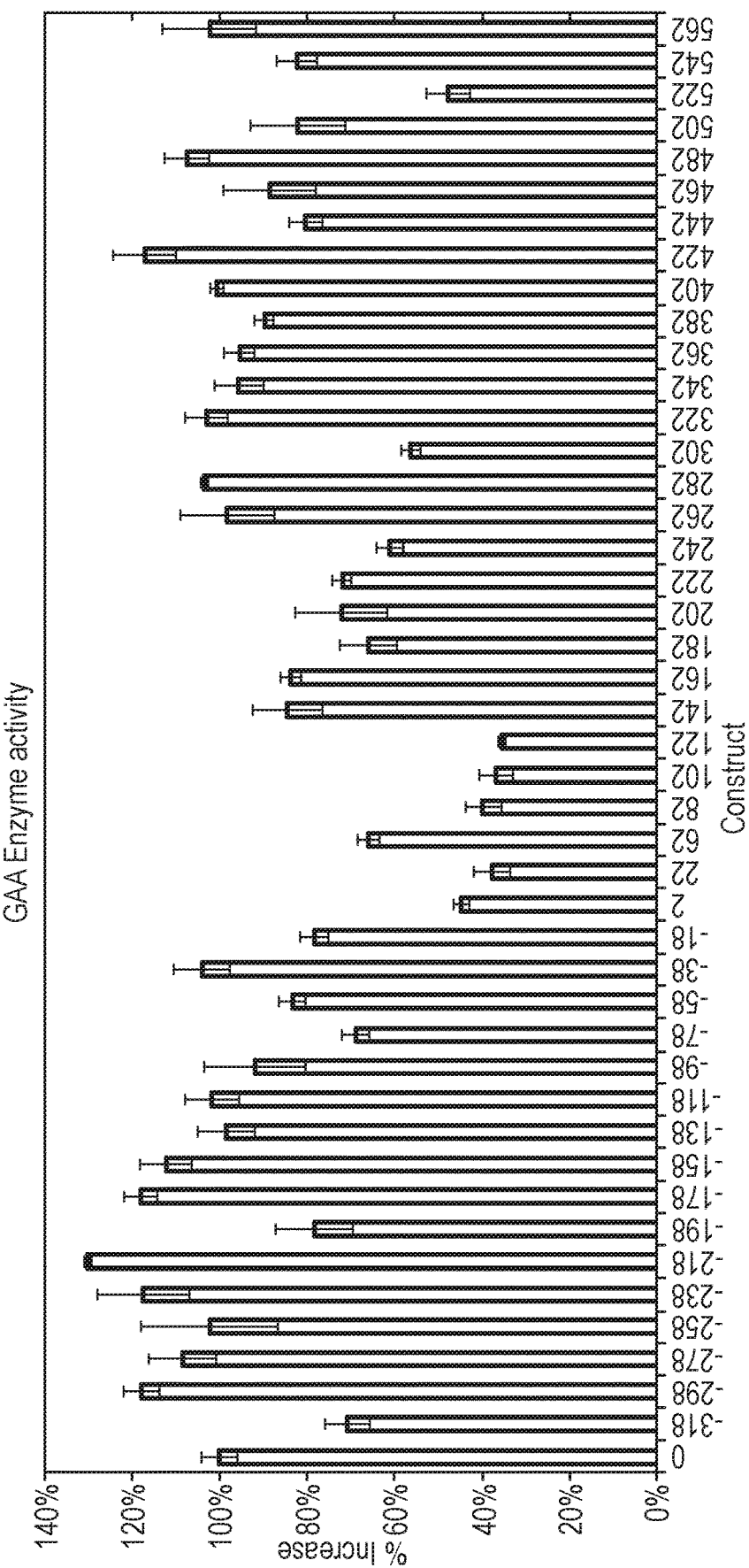
FIG. 21. Enzyme activity of GAA of a screen performed for sequences in intron 1 and exon 2 of the GAA pre-mRNA with antisense sequences using the U7 small nuclear RNA system. Numbers indicate antisense sequence positions according to table 1.
Figure 22:
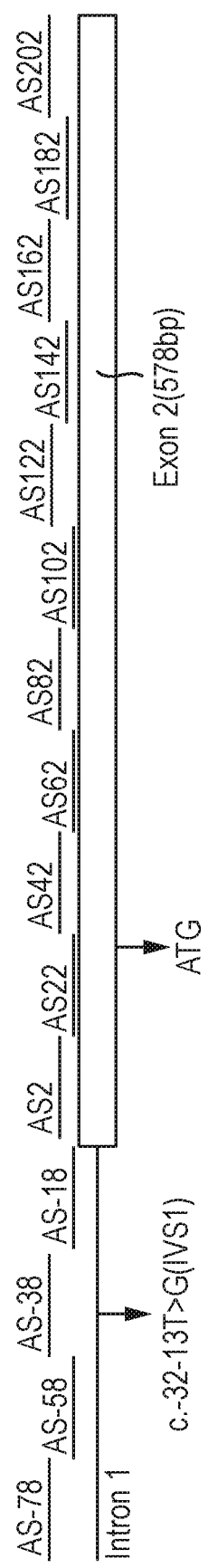
FIG. 22. Examples of positions of antisense sequences targeting GAA for the unbiased intron 1 and exon 2 screen.

FIG. 21 shows GAA enzyme activity of the screen on intron 1 and exon 2 of GAA with antisense sequences in the U7 small nuclear RNA system. Numbers indicate antisense sequence positions according to table 1. The control is the patient fibroblast without added AON vector.

It is clear that some clones significantly increase the inclusion of exon 2 and thereby provide potential candidates for a therapy for pompe patients having the IVS1 mutation. FIG. 23 shows an example illustrating that the identified sequence could not be predicted as the identified sequence was identified both as enhancer and as silencer motif.

Example 3

By far the most common mutation causing Pompe disease is the c.-32-13T>G (IVS1) mutation. This mutation in the GAA gene is located in an intron 13 basebairs upstream of exon 2, the exon that contains the start codon for translation of the GAA mRNA. The IVS1 mutation causes misssplicing of exon 2 in approximately 90% of GAA transcripts because it disrupts the polypyrimidine tract which reduces the strength of the exon 2 splice acceptor site.

To counteract this reduced strength of the splice site, we want to identify sequences that bind splicing factors that have a negative effect on splicing of GAA exon 2. By integration of random mutations in and around exon 2 we could be able to find these sequences.

For quick screening of a large number of mutations we generated a minigene containing GAA exon 1, intron 1, exon 2, intron 2, exon 3 and a part of intron 3 (FIG. 25B). By integration of 2 unique restriction sites, we are able to quickly exchange part of the minigene surrounding exon 2 with mutant sequences (FIG. 25C). A PCR is carried out at suboptimal conditions to integrate random mutations in the PCR products (FIG. 25A). These PCR products, which also contain the restriction sites located around exon 2, can then be ligated directly into the destination vector. After transformation of the ligated products, clones can be picked and the plasmid can be isolated from the clone, containing a random mutation. Separate transfection of these clones into HEK293 cells generate RNA-transcripts from the GAA minigene that result in differential splicing compared to the control. An example is shown in figure part 5, were a flanking exon RT-PCR and an exon internal qPCR is carried out against cDNA generated from 3 clones (indicated in FIG. 25, part 5). Sequencing of the plasmids that yield a higher inclusion of exon 2 results in identification on an important sequence that influences splicing in a negative manner. These sequences can sequentially be used to test as a potential target for antisense therapy or to screen for compounds that bind to this area.

FIG. 25C provides the results of two of the clones. Clone 115 and clone 97 demonstrate a 118% and a 297% increase of exon 2 inclusion, respectively, in comparison to the IVS1 mutation. Clone 115 contains the mutations: c.17C>T, c.469C>T, and c.546+23C>A. It results in increased wild type splicing (band 1) and decreased perfect skipping (band 3). Clone 97 contains the mutations: c.-32-102C>T, c.-32-56C>T, c.11G>A, c.112G>A, and c.137C>T. This clone also misses c.-32-553 to c.-32-122, however, this does not affect exon 2 exclusion (as determined by us by comparing splicing from minigene constructs that do or do not contain this region). Wild type splicing (band 3) is strongly increased, while both partial (band 2) and perfect (band 3) skipping are decreased.

Figure 26:
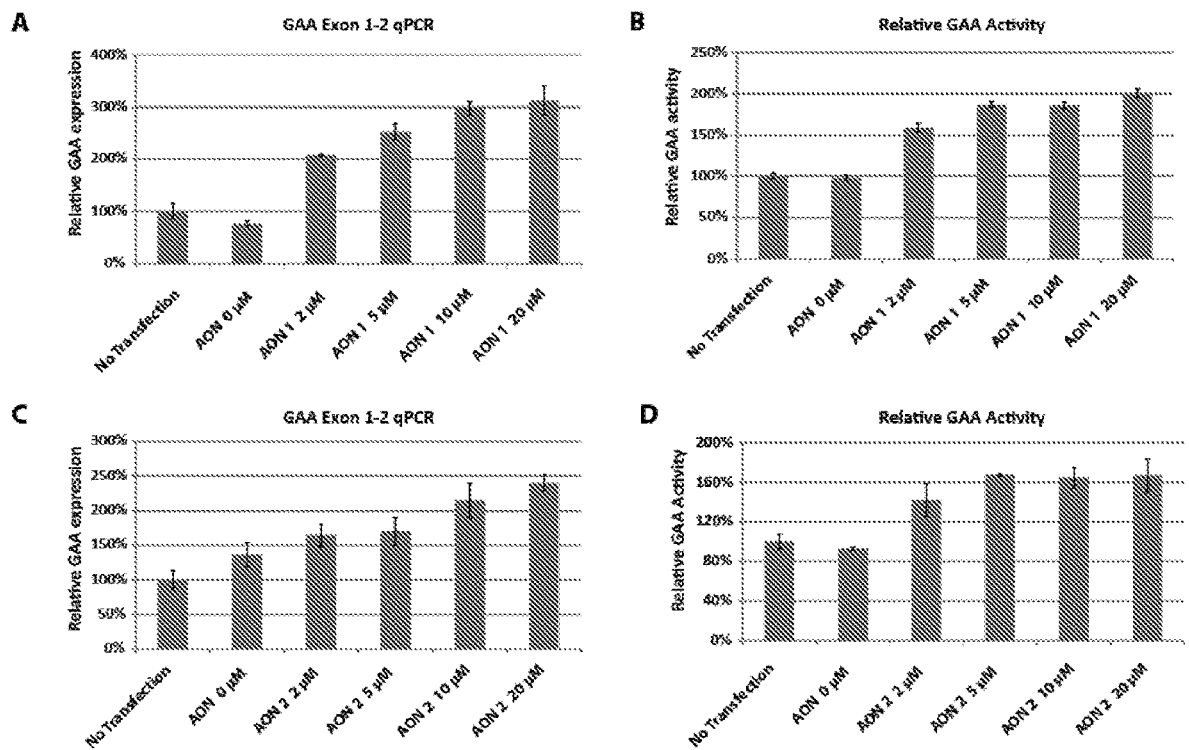
FIG. 26: Correction of aberrant splicing of GAA exon 2 using antisense oligonucleotides in patient 1.

The FIG. 26 shows a dose-response curve for SEQ ID NO: 12 (AON 1) (upper panels) and SEQ ID NO: 33 (AON 2) (lower panels). Patient-derived fibroblasts with the genotype c.-32-13T>G (IVS1) on one allele and c.525delT on the other allele were either untreated ('no transfection') or incubated with antisense oligomeric compound at 0-20 µM. Please note that the c.525delT undergoes nonsense-mediated decay, which explains why the effects at the RNA level are derived primarily from the IVS1 allele. Cells were harvested for RNA analysis after 3 days (A, C), and for protein analysis after 5 days (B, D). Both SEQ ID NO: 12 AON 1 and SEQ ID NO: 33 (AON 2) bind to a sequence present in intron 1 of the GAA pre-mRNA, which was identified using the U7 snRNA assay. This results in promotion of exon 2 inclusion, yielding higher expression of wild type GAA mRNA. This is measured at the mRNA level (using primers that specifically detect wild type GAA) and at the protein level (using an assay for GAA enzymatic activity).

RNA analysis: total RNA was isolated, cDNA was synthesized, and RT-qPCR analysis was performed to detect GAA exon 2 inclusion (using a forward primer specific for exon 1 and a reverse primer specific for exon 2).

Protein analysis: GAA enzyme activity was measured using the 4-MU assay. Activities were normalized for total protein as measured using the BCA assay.

Antisense oligomeric compound treatment: Antisense oligomeric compound used herein are morpholino's obtained from gene tools. Antisense oligomeric compound were transfected into the cells using endoporter (gene tools) according to the manufacturer's instructions.

Figure 27:
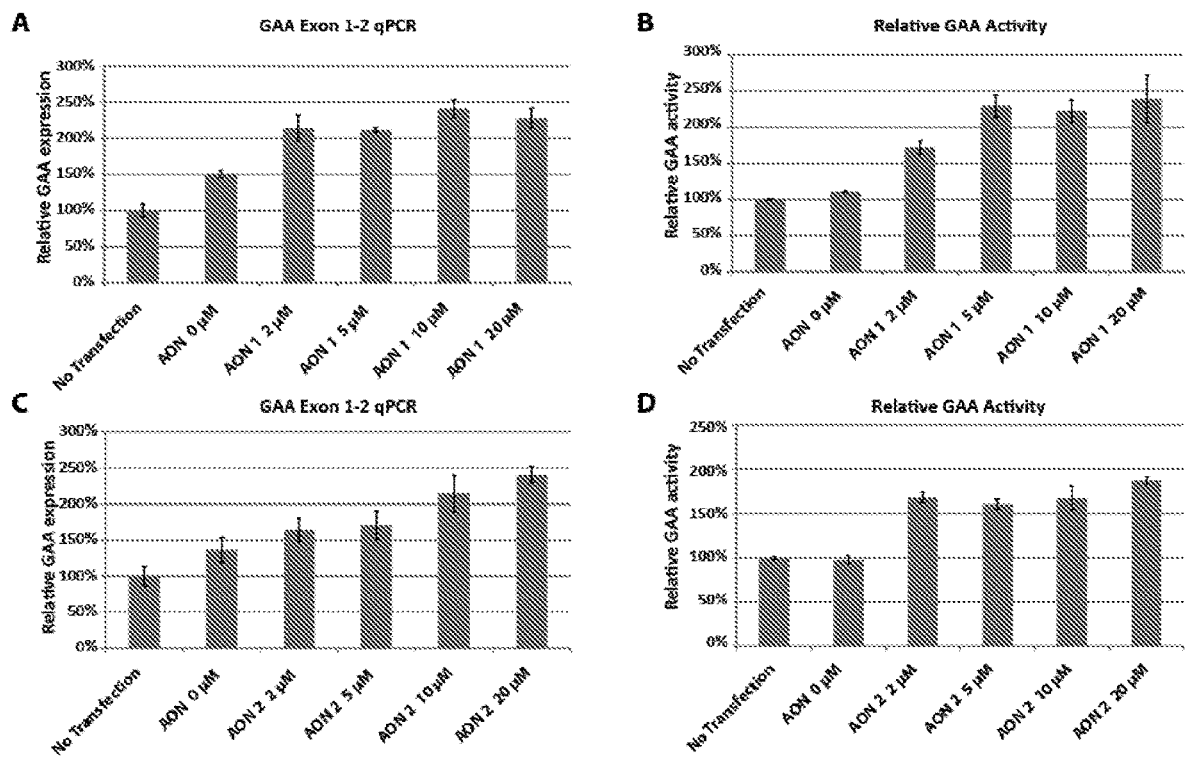
FIG. 27. Correction of aberrant splicing of GAA exon 2 using antisense oligonucleotides in patient 2.
Figure 29:
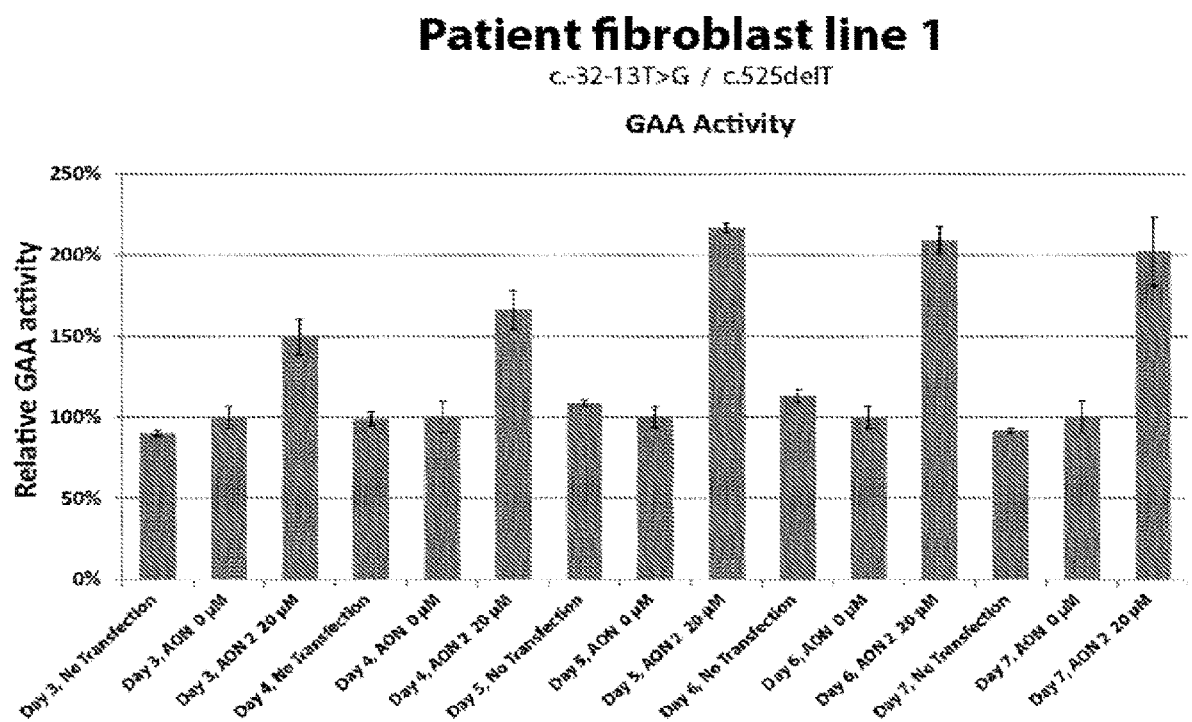
FIG. 29: Time course of the effect of the SEQ ID NO: 33 AON 2 on patient fibroblast line 1.
Figure 30:
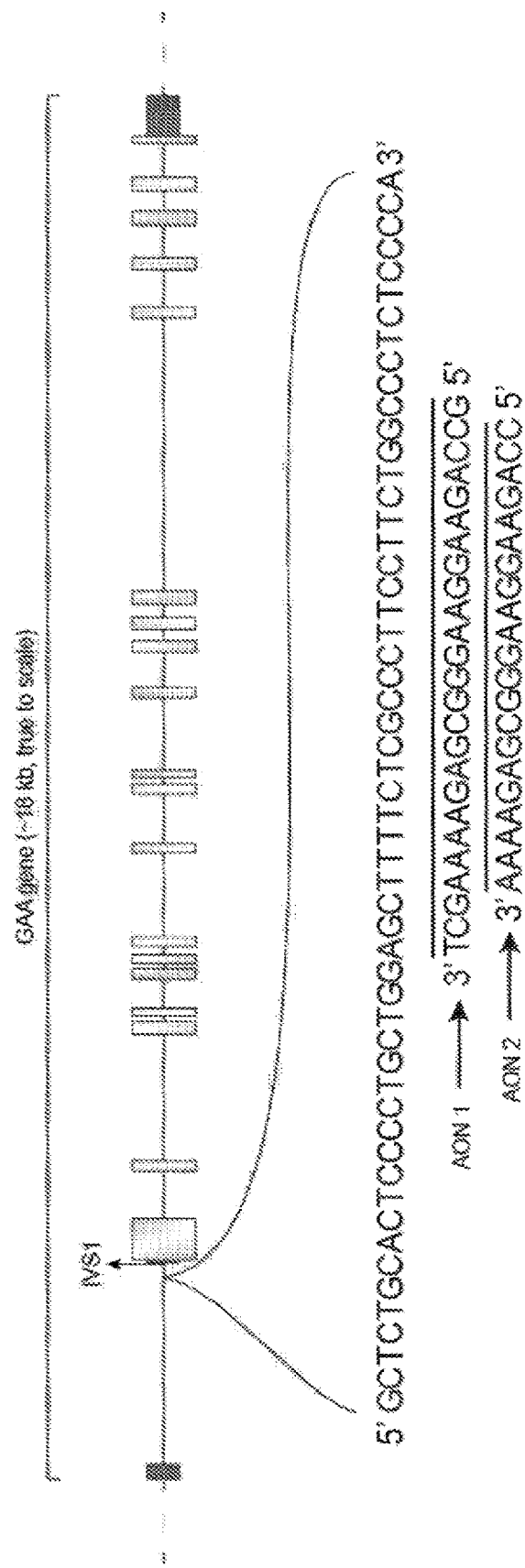
FIG. 30: Genomic target sequence for GAA exon inclusion, 5'GCTCTGCACTCCCCTGCTG-GAGCTTTTCTCGCCCTTCCTTCTGGCCCTCTC-CCCA3': SEQ ID NO:1; AON 1: SEQ ID NO: 12; AON 2: SEQ ID NO: 33.
Figure 31:
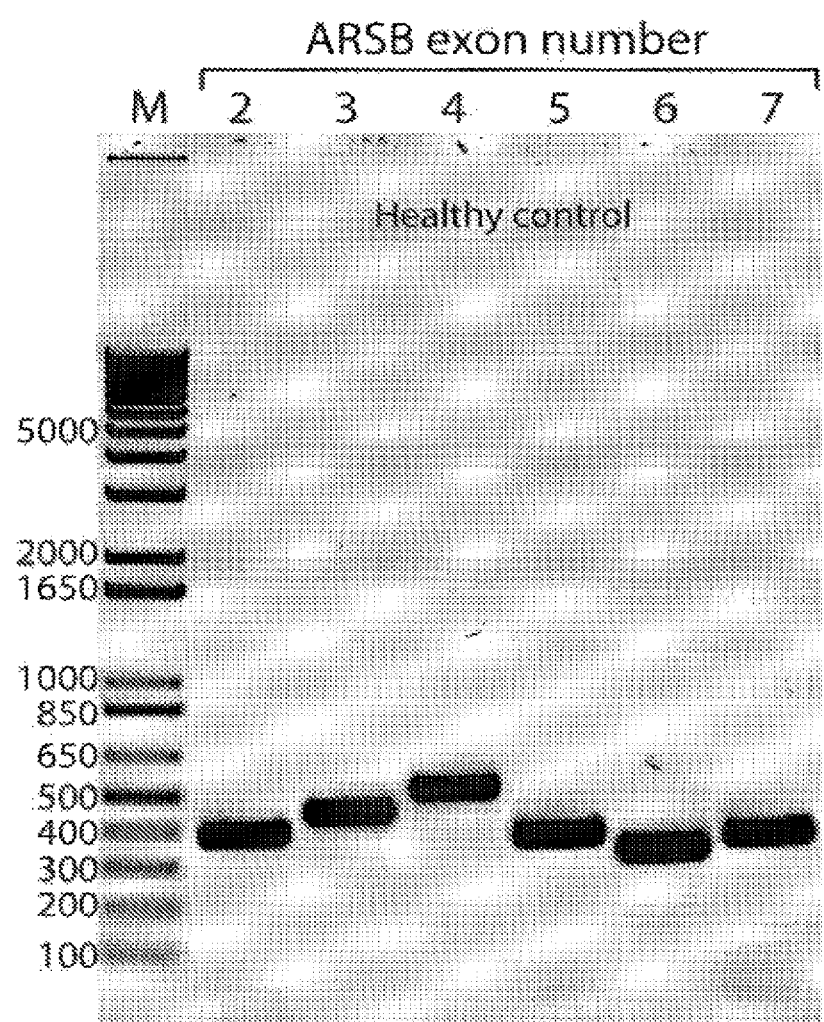
FIG. 31: Splicing assay of healthy person for N-acetylgalactosamine 4-sulfatase (arylsulfatase B; ARSB).

This following experiment is similar to that of patient fibroblast line 1 (FIG. 26) and served to demonstrate that the antisense oligomeric compounds also work in an independent cell line 2 from another patient. In this case, the genotype was IVS1 on one allele and a missense variant (c.923A>C) on the other allele. Please note that the c.923A>C allele does not undergo nonsense-mediated decay, and mRNA levels represent a mix of both alleles, making the effects on the IVS1 allele less pronounced compared to patient 1. The FIG. 27 shows a dose-response curve for SEQ ID NO: 12 (AON 1) (upper panels) and SEQ ID NO: 33 (AON 2) (lower panels).

FIG. 28 shows the specificity of antisense oligomeric compounds SEQ ID NO: 12 (AON 1) and SEQ ID NO: 33 (AON 2) for promoting exon 2 inclusion.

SEQ ID NO: 35 (control AON 2) and SEQ ID NO: 36 (control AON 3) target another region in intron 1 of GAA but is ineffective in promoting exon 2 inclusion. An unrelated AON targeting the CypA mRNA (control AON 1; SEQ ID NO: 34) does not affect GAA exon 2 inclusion. SEQ ID NO: 12 (AON 1) and SEQ ID NO: 33 (AON 2) efficiently promote inclusion of GAA exon 2 as shown by RT-qPCR analysis (A) and concomitant GAA enzyme activity assay (B). This shows that only when the in the U7 snRNA assay identified intronic splice silencing (ISS) sequence is targeted, as with SEQ ID NO: 12 (AON 1) and SEQ ID NO: 33 (AON 2), GAA exon 2 inclusion is promoted.

| Sequence number | Target Gene | Sequence in cDNA to which AON anneals | sequence of AON (5' → 3'): | Seq ID |
|---|---|---|---|---|
| Control AON 1 | CypA | c.354_362 + 11* | TGTACCCTTACCAC TCAGTC | 34 |
| Control AON 2 | GAA | c.-32-224_-200** | GAGTGCAGAGCACT TGCACAGTCTG | 35 |
| Control AON 3 | GAA | c.-32-219_-200** | GAGTGCAGAGCACT TGCACAGTCTG | 36 |

*CypA cDNA sequence is Refseq entry NM_021130.4
**GAA cDNA sequence is Refseq entry NM_000152.3

Figure 32:
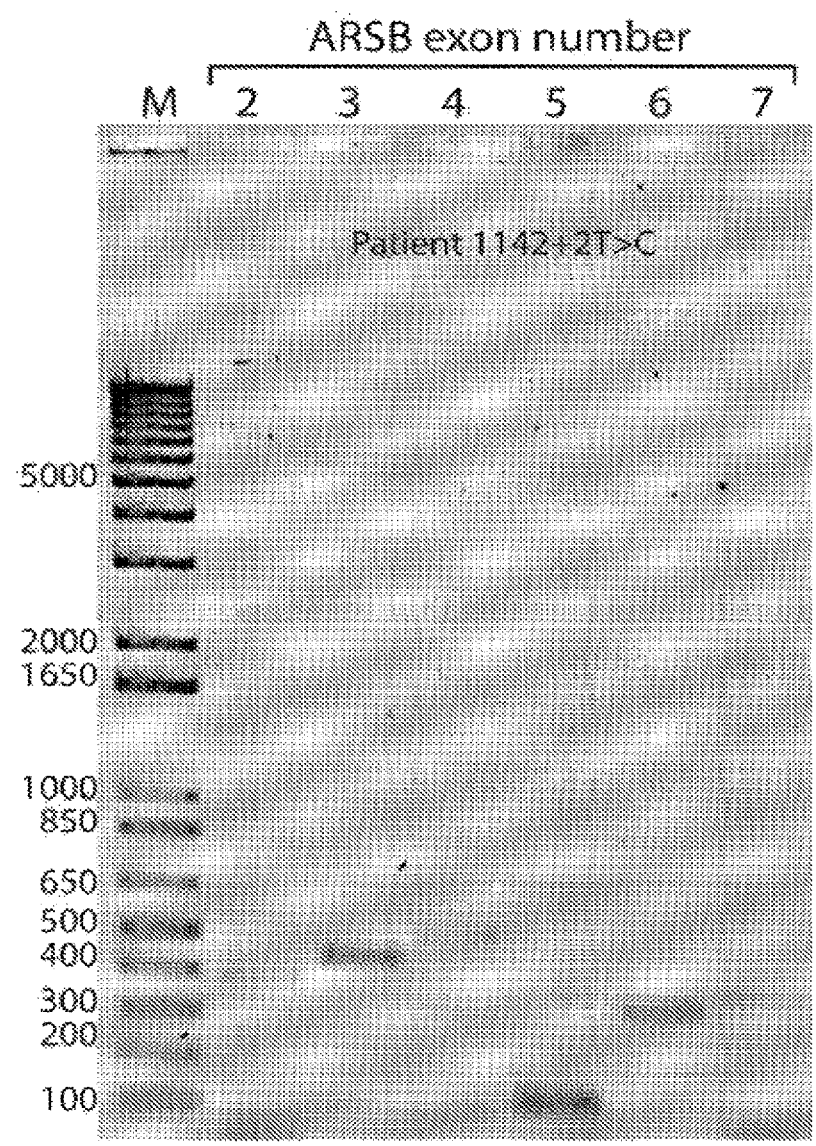
FIG. 32: Splicing assay of patient with Mucopolycaccharidosis type VI (Maroteaux-Lamy syndrome) for N-acetylgalactosamine 4-sulfatase (arylsulfatase B; ARSB).
Figure 33:
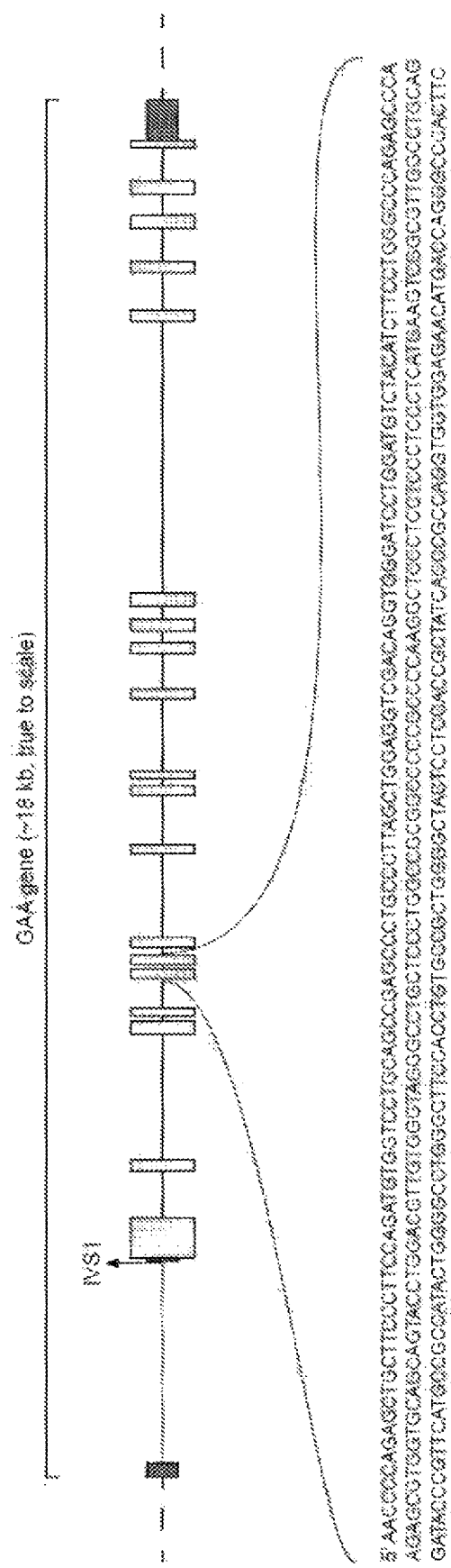
FIG. 33: Result of inhibition of the nonsense mediated decay (NMD) pathway on inclusion of intron 6 of the GAA mRNA. Sequence: SEQ ID NO: 541.

FIG. 32 shows the time course of the effect of the SEQ ID NO: 33 (AON 2) on patient fibroblast line 1. Cells were assayed for GAA activity at 3-7 days after the addition of antisense oligomeric compound. Antisense oligomeric compound was continuously present in the medium throughout the experiment.

The figure shows that the effect on GAA activity starts after 3 days and reaches a maximum at 5 days after AON addition.

Apart from the minigene for Exon 1-Exon 3, we also generated a minigene containing the genomic region from GAA exon 5 to GAA exon 8. With this minigene we can test other mutations that influence splicing much like the IVS1 mutation. FIG. 36 shows the result of inhibition of the nonsense mediated decay (NMD) pathway on inclusion of intron 6 of the GAA mRNA. Cyclohexamide treatment of primary fibroblasts from a healthy control (upper gel), a Pompe patient with the genotype c.-32-13T>G, c.525delT (middle gel), and a Pompe patient with the genotype c.525delT, c.525delT (lower gel) was performed. Without inhibition of the NMD pathway (lanes labelled with 0 hr), a strong band was detected using RT-PCR representing canonical splicing of exon 6 and exon 7. A faint band just above the canonical band was observed. This band was determined by DNA sequence analysis to represent inclusion of intron 6. Because such product changes the reading frame resulting in activation of the NMD pathway, we speculated that intron 6 inclusion may in fact be a frequent event that escapes proper detection. This idea was confirmed by inhibition of the NMD pathway: this resulted in the detection of a strong band representing intron 6 inclusion. This indicated that many GAA pre-mRNA species escape canonical splicing in both healthy controls and in Pompe patients. The minigene containing GAA exon 5-8 mentioned above and the U7 snRNA screen will be used to identify sequences that can prevent inclusion of intron 6 in the final mRNA by blocking a repressor of exon 6/7 splicing. This would represent a generic therapy for all splicing mutations with leaky wild type splicing causing Pompe disease, because correct splicing of exons 6/7 will be enhanced thereby also enhancing the levels of leaky wild type splicing.

| variants that affect aberrant splicing of exon 2 caused by IVS1 in GAA exon 1-3 minigene system | AON sequence designed to block the region surrounding the identified splice element (5' → 3') | Seq ID |
|---|---|---|
| c.-32-102C > T | CACCCAGGCAGGTGGGGTAAGGTGG | 98 |
| | AGCACCCAGGCAGGTGGGGTAAGGT | 99 |
| | GCAGCACCCAGGCAGGTGGGGTAAG | 100 |
| | CTGCAGCACCCAGGCAGGTGGGGTA | 101 |
| | CACTGCAGCACCCAGGCAGGTGGGG | 102 |
| | GGCACTGCAGCACCCAGGCAGGTGG | 103 |
| | CTGGCACTGCAGCACCCAGGCAGGT | 104 |
| | GGCTGGCACTGCAGCACCCAGGCAG | 105 |
| | GCGGCTGGCACTGCAGCACCCAGGC | 106 |
| | CCGCGGCTGGCACTGCAGCACCCAG | 107 |
| | TCAACCGCGGCTGGCACTGCAGCAC | 108 |
| | ACCCAGGCAGGTGGGGTAAGGTGGC | 109 |
| | GCACCCAGGCAGGTGGGGTAAGGTG | 110 |
| | CAGCACCCAGGCAGGTGGGGTAAGG | 111 |
| | TGCAGCACCCAGGCAGGTGGGGTAA | 112 |
| | ACTGCAGCACCCAGGCAGGTGGGGT | 113 |
| | GCACTGCAGCACCCAGGCAGGTGGG | 114 |
| | TGGCACTGCAGCACCCAGGCAGGTG | 115 |
| | GCTGGCACTGCAGCACCCAGGCAGG | 116 |
| | CGGCTGGCACTGCAGCACCCAGGCA | 117 |
| | CGCGGCTGGCACTGCAGCACCCAGG | 118 |
| | ACCGCGGCTGGCACTGCAGCACCCA | 119 |
| | CAACCGCGGCTGGCACTGCAGCACC | 120 |
| | ATCAACCGCGGCTGGCACTGCAGCA | 121 |
| c.-32-56C > T, | GGCTCTCAAAGCAGCTCTGAGACAT | 122 |
| c.-32-46G > A, | GGGGCTCTCAAAGCAGCTCTGAGAC | 123 |
| c.-32-28C > A, | ACGGGGCTCTCAAAGCAGCTCTGAG | 124 |
| c.-32-28C > T, | TCACGGGGCTCTCAAAGCAGCTCTG | 125 |
| c.-32-21G > A | ACTCACGGGGCTCTCAAAGCAGCTC | 126 |
| | GCACTCACGGGGCTCTCAAAGCAGC | 127 |
| | CGGCACTCACGGGGCTCTCAAAGCA | 128 |
| | GGCGGCACTCACGGGGCTCTCAAAG | 129 |
| | GGGGCGGCACTCACGGGGCTCTCAA | 130 |
| | GAGGGGCGGCACTCACGGGGCTCTC | 131 |
| | GGGAGGGGCGGCACTCACGGGGCTC | 132 |
| | GCGGGAGGGGCGGCACTCACGGGGC | 133 |
| | AGGCGGGAGGGGCGGCACTCACGGG | 134 |
| | GGAGGCGGGAGGGGCGGCACTCACG | 135 |
| | AGGGAGGCGGGAGGGGCGGCACTCA | 136 |
| | GCAGGGAGGCGGGAGGGGCGGCACT | 137 |
| | CAGCAGGGAGGCGGGAGGGGCGGCA | 138 |
| | CTCAGCAGGGAGGCGGGAGGGGCGG | 139 |
| | GGCTCAGCAGGGAGGCGGGAGGGGC | 140 |
| | CGGGCTCAGCAGGGAGGCGGGAGGG | 141 |
| | AGCGGGCTCAGCAGGGAGGCGGGAG | 142 |
| | AAAGCGGGCTCAGCAGGGAGGCGGG | 143 |
| | AGAAAGCGGGCTCAGCAGGGAGGCG | 144 |
| | GAAGAAAGCGGGCTCAGCAGGGAGG | 145 |
| | GAGAAGAAAGCGGGCTCAGCAGGGA | 146 |
| | GGGAGAAGAAAGCGGGCTCAGCAGG | 147 |
| | GCGGGAGAAGAAAGCGGGCTCAGCA | 148 |
| | CTGCGGGAGAAGAAAGCGGGCTCAG | 149 |
| | GCCTGCGGGAGAAGAAAGCGGGCTC | 150 |
| | AGGCCTGCGGGAGAAGAAAGCGGGC | 151 |
| | ACTCCCATGGTTGGAGATGGCCTGG | 152 |
| | TCACTCCCATGGTTGGAGATGGCCT | 153 |
| | CCTCACTCCCATGGTTGGAGATGGC | 154 |
| | TGCCTCACTCCCATGGTTGGAGATG | 155 |
| | GGTGCCTCACTCCCATGGTTGGAGA | 156 |
| | CGGTGCCTCACTCCCATGGTTGGA | 157 |
| | GGCGGGTGCCTCACTCCCATGGTTG | 158 |
| | AGGGCGGGTGCCTCACTCCCATGGT | 159 |
| | GCAGGGCGGGTGCCTCACTCCCATG | 160 |
| | GAGCAGGGCGGGTGCCTCACTCCCA | 161 |
| | GGGAGCAGGGCGGGTGCCTCACTCC | 162 |
| | GTGGGAGCAGGGCGGGTGCCTCACT | 163 |
| | CGGTGGGAGCAGGGCGGGTGCCTCA | 164 |
| | GCCGGTGGGAGCAGGGCGGGTGCCT | 165 |

| variants that affect aberrant splicing of exon 2 caused by IVS1 in GAA exon 1-3 minigene system | AON sequence designed to block the region surrounding the identified splice element (5' → 3') | Seq ID |
|---|---|---|
| | GAGCCGGTGGGAGCAGGGCGGGTGC | 166 |
| | AGGAGCCGGTGGGAGCAGGGCGGGT | 167 |
| | CCAGGAGCCGGTGGGAGCAGGGCGG | 168 |
| | GGCCAGGAGCCGGTGGGAGCAGGGC | 169 |
| | ACGGCCAGGAGCCGGTGGGAGCAGG | 170 |
| | AGACGGCCAGGAGCCGGTGGGAGCA | 171 |
| | GCAGACGGCCAGGAGCCGGTGGGAG | 172 |
| | GCGCAGACGGCCAGGAGCCGGTGGG | 173 |
| | GGGCGCAGACGGCCAGGAGCCGGTG | 174 |
| | GAGGGCGCAGACGGCCAGGAGCCGG | 175 |
| | ACGAGGGCGCAGACGGCCAGGAGCC | 176 |
| | ACACGAGGGCGCAGACGGCCAGGAG | 177 |
| | GGACACGAGGGCGCAGACGGCCAGG | 178 |
| | AAGGACACGAGGGCGCAGACGGCCA | 179 |
| | CCAAGGACACGAGGGCGCAGACGGC | 180 |
| | TGCCAAGGACACGAGGGCGCAGACG | 181 |
| | GCTCTCAAAGCAGCTCTGAGACATC | 182 |
| | GGGCTCTCAAAGCAGCTCTGAGACA | 183 |
| | CTCACGGGGCTCTCAAAGCAGCTCT | 184 |
| | CACTCACGGGGCTCTCAAAGCAGCT | 185 |
| | GGCACTCACGGGGCTCTCAAAGCAG | 186 |
| | GCGGCACTCACGGGGCTCTCAAAGC | 187 |
| | GGGCGGCACTCACGGGGCTCTCAAA | 188 |
| | AGGGGCGGCACTCACGGGGCTCTCA | 189 |
| | GGAGGGGCGGCACTCACGGGGCTCT | 190 |
| | CGGGAGGGGCGGCACTCACGGGGCT | 191 |
| | GGCGGGAGGGGCGGCACTCACGGGG | 192 |
| | GAGGCGGGAGGGGCGGCACTCACGG | 193 |
| | GGGAGGCGGGAGGGGCGGCACTCAC | 194 |
| | CAGGGAGGCGGGAGGGGCGGCACTC | 195 |
| | AGCAGGGAGGCGGGAGGGGCGGCAC | 196 |
| | TCAGCAGGGAGGCGGGAGGGGCGGC | 197 |
| | GCTCAGCAGGGAGGCGGGAGGGGCG | 198 |
| | GGCTCAGCAGGGAGGCGGGAGGGGC | 199 |
| | GCGGGCTCAGCAGGGAGGCGGGAGG | 200 |
| | AAGCGGGCTCAGCAGGGAGGCGGGA | 201 |
| | GAAAGCGGGCTCAGCAGGGAGGCGG | 202 |
| | AAGAAAGCGGGCTCAGCAGGGAGGC | 203 |
| | AGAAGAAAGCGGGCTCAGCAGGGAG | 204 |
| | GGAGAAGAAAGCGGGCTCAGCAGGG | 205 |
| | CGGGAGAAGAAAGCGGGCTCAGCAG | 206 |
| | TGCGGGAGAAGAAAGCGGGCTCAGC | 207 |
| | CCTGCGGGAGAAGAAAGCGGGCTCA | 208 |
| | GGCCTGCGGGAGAAGAAAGCGGGCT | 209 |
| | CAGGCCTGCGGGAGAAGAAAGCGGG | 210 |
| | CGGGGCTCTCAAAGCAGCTCTGAGA | 211 |
| | CACGGGGCTCTCAAAGCAGCTCTGA | 212 |
| c.7G > A, | CTCCCATGGTTGGAGATGGCCTGGA | 213 |
| c.11G > A, | CACTCCCATGGTTGGAGATGGCCTG | 214 |
| c.15_17AAA, | CTCACTCCCATGGTTGGAGATGGCC | 215 |
| c.17C > T, | GCCTCACTCCCATGGTTGGAGATGG | 216 |
| c.19_21AAA, | GTGCCTCACTCCCATGGTTGGAGAT | 217 |
| c.26_28AAA, | GGGTGCCTCACTCCCATGGTTGGAG | 218 |
| c.33_35AAA, | GCGGGTGCCTCACTCCCATGGTTGG | 219 |
| c.39G > A, | GGGCGGGTGCCTCACTCCCATGGTT | 220 |
| c.42C > T | CAGGGCGGGTGCCTCACTCCCATGG | 221 |
| | AGCAGGGCGGGTGCCTCACTCCCAT | 222 |
| | GGAGCAGGGCGGGTGCCTCACTCCC | 223 |
| | TGGGAGCAGGGCGGGTGCCTCACTC | 224 |
| | GGTGGGAGCAGGGCGGGTGCCTCAC | 225 |
| | CCGGTGGGAGCAGGGCGGGTGCCTC | 226 |
| | AGCCGGTGGGAGCAGGGCGGGTGCC | 227 |
| | GGAGCCGGTGGGAGCAGGGCGGGTG | 228 |
| | CAGGAGCCGGTGGGAGCAGGGCGGG | 229 |
| | GCCAGGAGCCGGTGGGAGCAGGGCG | 230 |
| | CGGCCAGGAGCCGGTGGGAGCAGGG | 231 |
| | GACGGCCAGGAGCCGGTGGGAGCAG | 232 |
| | CAGACGGCCAGGAGCCGGTGGGAGC | 233 |
| | CGCAGACGGCCAGGAGCCGGTGGGA | 234 |
| | GGCGCAGACGGCCAGGAGCCGGTGG | 235 |

| variants that affect aberrant splicing of exon 2 caused by IVS1 in GAA exon 1-3 minigene system | AON sequence designed to block the region surrounding the identified splice element (5' → 3') | Seq ID |
|---|---|---|
| | AGGGCGCAGACGGCCAGGAGCCGGT | 236 |
| | CGAGGGCGCAGACGGCCAGGAGCCG | 237 |
| | CACGAGGGCGCAGACGGCCAGGAGC | 238 |
| | GACACGAGGGCGCAGACGGCCAGGA | 239 |
| | AGGACACGAGGGCGCAGACGGCCAG | 240 |
| | CAAGGACACGAGGGCGCAGACGGCC | 241 |
| | GCCAAGGACACGAGGGCGCAGACGG | 242 |
| | TTGCCAAGGACACGAGGGCGCAGAC | 243 |
| c.90C > T, c.112G > A, c.137C > T, c.164C > T | GGATGTGCCCCAGGAGTGCAGCGGT | 244 |
| | TAGGATGTGCCCCAGGAGTGCAGCG | 245 |
| | AGTAGGATGTGCCCCAGGAGTGCAG | 246 |
| | GGAGTAGGATGTGCCCCAGGAGTGC | 247 |
| | ATGGAGTAGGATGTGCCCCAGGAGT | 248 |
| | TCATGGAGTAGGATGTGCCCCAGGA | 249 |
| | AATCATGGAGTAGGATGTGCCCCAG | 250 |
| | GAAATCATGGAGTAGGATGTGCCCC | 251 |
| | AGGAAATCATGGAGTAGGATGTGCC | 252 |
| | GCAGGAAATCATGGAGTAGGATGTG | 253 |
| | CAGCAGGAAATCATGGAGTAGGATG | 254 |
| | ACCAGCAGGAAATCATGGAGTAGGA | 255 |
| | GAACCAGCAGGAAATCATGGAGTAG | 256 |
| | GGGAACCAGCAGGAAATCATGGAGT | 257 |
| | CGGGGAACCAGCAGGAAATCATGGA | 258 |
| | CTCGGGGAACCAGCAGGAAATCATG | 259 |
| | CTCTCGGGGAACCAGCAGGAAATCA | 260 |
| | AGCTCTCGGGGAACCAGCAGGAAAT | 261 |
| | TCAGCTCTCGGGGAACCAGCAGGAA | 262 |
| | ACTCAGCTCTCGGGGAACCAGCAGG | 263 |
| | CCACTCAGCTCTCGGGGAACCAGCA | 264 |
| | AGCCACTCAGCTCTCGGGGAACCAG | 265 |
| | GGAGCCACTCAGCTCTCGGGGAACC | 266 |
| | GAGGAGCCACTCAGCTCTCGGGGAA | 267 |
| | GGGAGGAGCCACTCAGCTCTCGGGG | 268 |
| | TGGGGAGGAGCCACTCAGCTCTCGG | 269 |
| | ACTGGGGAGGAGCCACTCAGCTCTC | 270 |
| | GGACTGGGGAGGAGCCACTCAGCTC | 271 |
| | CAGGACTGGGGAGGAGCCACTCAGC | 272 |
| | TCCAGGACTGGGGAGGAGCCACTCA | 273 |
| | CCTCCAGGACTGGGGAGGAGCCACT | 274 |
| | CTCCTCCAGGACTGGGGAGGAGCCA | 275 |
| | GTCTCCTCCAGGACTGGGGAGGAGC | 276 |
| | GAGTCTCCTCCAGGACTGGGGAGGA | 277 |
| | GTGAGTCTCCTCCAGGACTGGGGAG | 278 |
| | GGGTGAGTCTCCTCCAGGACTGGGG | 279 |
| | CTGGGTGAGTCTCCTCCAGGACTGG | 280 |
| | AGCTGGGTGAGTCTCCTCCAGGACT | 281 |
| | TGAGCTGGGTGAGTCTCCTCCAGGA | 282 |
| | GGTGAGCTGGGTGAGTCTCCTCCAG | 283 |
| | CTGGTGAGCTGGGTGAGTCTCCTCC | 284 |
| | TGCTGGTGAGCTGGGTGAGTCTCCT | 285 |
| | CCTGCTGGTGAGCTGGGTGAGTCTC | 286 |
| | TCCCTGCTGGTGAGCTGGGTGAGTC | 287 |
| | GCTCCCTGCTGGTGAGCTGGGTGAG | 288 |
| | TGGCTCCCTGCTGGTGAGCTGGGTG | 289 |
| | GCTGGCTCCCTGCTGGTGAGCTGGG | 290 |
| | CTGCTGGCTCCCTGCTGGTGAGCTG | 291 |
| | GTCTGCTGGCTCCCTGCTGGTGAGC | 292 |
| | GATGTGCCCCAGGAGTGCAGCGGTT | 293 |
| | AGGATGTGCCCCAGGAGTGCAGCGG | 294 |
| | GTAGGATGTGCCCCAGGAGTGCAGC | 295 |
| | GAGTAGGATGTGCCCCAGGAGTGCA | 296 |
| | TGGAGTAGGATGTGCCCCAGGAGTG | 297 |
| | CATGGAGTAGGATGTGCCCCAGGAG | 298 |
| | ATCATGGAGTAGGATGTGCCCCAGG | 299 |
| | AAATCATGGAGTAGGATGTGCCCCA | 300 |
| | GGAAATCATGGAGTAGGATGTGCCC | 301 |
| | CAGGAAATCATGGAGTAGGATGTGC | 302 |
| | AGCAGGAAATCATGGAGTAGGATGT | 303 |
| | CCAGCAGGAAATCATGGAGTAGGAT | 304 |
| | AACCAGCAGGAAATCATGGAGTAGG | 305 |
| | GGAACCAGCAGGAAATCATGGAGTA | 306 |
| | GGGGAACCAGCAGGAAATCATGGAG | 307 |
| | TCGGGGAACCAGCAGGAAATCATGG | 308 |
| | TCTCGGGGAACCAGCAGGAAATCAT | 309 |
| | GCTCTCGGGGAACCAGCAGGAAATC | 310 |
| | CAGCTCTCGGGGAACCAGCAGGAAA | 311 |
| | CTCAGCTCTCGGGGAACCAGCAGGA | 312 |
| | CACTCAGCTCTCGGGGAACCAGCAG | 313 |
| | GCCACTCAGCTCTCGGGGAACCAGC | 314 |
| | GAGCCACTCAGCTCTCGGGGAACCA | 315 |
| | AGGAGCCACTCAGCTCTCGGGGAAC | 316 |
| | GGAGGAGCCACTCAGCTCTCGGGGA | 317 |
| | GGGGAGGAGCCACTCAGCTCTCGGG | 318 |
| | CTGGGGAGGAGCCACTCAGCTCTCG | 319 |
| | GACTGGGGAGGAGCCACTCAGCTCT | 320 |
| | AGGACTGGGGAGGAGCCACTCAGCT | 321 |
| | CCAGGACTGGGGAGGAGCCACTCAG | 322 |
| | CTCCAGGACTGGGGAGGAGCCACTC | 323 |
| | TCCTCCAGGACTGGGGAGGAGCCAC | 324 |
| | TCTCCTCCAGGACTGGGGAGGAGCC | 325 |
| | AGTCTCCTCCAGGACTGGGGAGGAG | 326 |
| | TGAGTCTCCTCCAGGACTGGGGAGG | 327 |
| | GGTGAGTCTCCTCCAGGACTGGGGA | 328 |
| | TGGGTGAGTCTCCTCCAGGACTGGG | 329 |
| | GCTGGGTGAGTCTCCTCCAGGACTG | 330 |
| | GAGCTGGGTGAGTCTCCTCCAGGAC | 331 |
| | GTGAGCTGGGTGAGTCTCCTCCAGG | 332 |
| | TGGTGAGCTGGGTGAGTCTCCTCCA | 333 |
| | GCTGGTGAGCTGGGTGAGTCTCCTC | 334 |
| | CTGCTGGTGAGCTGGGTGAGTCTCC | 335 |
| | CCCTGCTGGTGAGCTGGGTGAGTCT | 336 |
| | CTCCCTGCTGGTGAGCTGGGTGAGT | 337 |
| | GGCTCCCTGCTGGTGAGCTGGGTGA | 338 |
| | CTGGCTCCCTGCTGGTGAGCTGGGT | 339 |
| | TGCTGGCTCCCTGCTGGTGAGCTGG | 340 |
| | TCTGCTGGCTCCCTGCTGGTGAGCT | 341 |
| | GGTCTGCTGGCTCCCTGCTGGTGAG | 342 |
| c.348G > A, c.373C > T | AGCCCCTGCTTTGCAGGGATGTAGC | 343 |
| | GCAGCCCCTGCTTTGCAGGGATGTA | 344 |
| | CTGCAGCCCCTGCTTTGCAGGGATG | 345 |
| | CCCTGCAGCCCCTGCTTTGCAGGGA | 346 |
| | CTCCCTGCAGCCCCTGCTTTGCAGG | 347 |
| | GGCTCCCTGCAGCCCCTGCTTTGCA | 348 |
| | TGGGCTCCCTGCAGCCCCTGCTTTG | 349 |
| | TCTGGGCTCCCTGCAGCCCCTGCTT | 350 |
| | CATCTGGGCTCCCTGCAGCCCCTGC | 351 |
| | CCCATCTGGGCTCCCTGCAGCCCCT | 352 |
| | GCCCATCTGGGCTCCCTGCAGCCC | 353 |
| | CTGCCCATCTGGGCTCCCTGCAGC | 354 |
| | GCTGCCCATCTGGGCTCCCTGCA | 355 |
| | AGGGCTGCCCATCTGGGCTCCCTG | 356 |
| | CCAGGGCTGCCCATCTGGGCTCCC | 357 |
| | CACCAGGGCTGCCCATCTGGGCTC | 358 |
| | AGCACCAGGGCTGCCCATCTGGGC | 359 |
| | GAAGCACCAGGGCTGCCCCATCTGG | 360 |
| | AAGAAGCACCAGGGCTGCCCCATCT | 361 |
| | GGAAGAAGCACCAGGGCTGCCCCAT | 362 |
| | TGGGAAGAAGCACCAGGGCTGCCCC | 363 |
| | GGTGGGAAGAAGCACCAGGGCTGCC | 364 |
| | TGGGTGGGAAGAAGCACCAGGGCTG | 365 |
| | GCTGGGTGGGAAGAAGCACCAGGGC | 366 |
| | GCCCCTGCTTTGCAGGGATGTAGCA | 367 |
| | CAGCCCCTGCTTTGCAGGGATGTAG | 368 |
| | TGCAGCCCCTGCTTTGCAGGGATGT | 369 |
| | CCTGCAGCCCCTGCTTTGCAGGGAT | 370 |
| | TCCCTGCAGCCCCTGCTTTGCAGGG | 371 |
| | GCTCCCTGCAGCCCCTGCTTTGCAG | 372 |
| | GGGCTCCCTGCAGCCCCTGCTTTGC | 373 |
| | CTGGGCTCCCTGCAGCCCCTGCTTT | 374 |
| | ATCTGGGCTCCCTGCAGCCCCTGCT | 375 |

| variants that affect aberrant splicing of exon 2 caused by IVS1 in GAA exon 1-3 minigene system | AON sequence designed to block the region surrounding the identified splice element (5' → 3') | Seq ID |
|---|---|---|
| | CCATCTGGGCTCCCTGCAGCCCCTG | 376 |
| | CCCCATCTGGGCTCCCTGCAGCCCC | 377 |
| | TGCCCCATCTGGGCTCCCTGCAGCC | 378 |
| | GCTGCCCCATCTGGGCTCCCTGCAG | 379 |
| | GGGCTGCCCCATCTGGGCTCCCTGC | 380 |
| | CAGGGCTGCCCCATCTGGGCTCCCT | 381 |
| | ACCAGGGCTGCCCCATCTGGGCTCC | 382 |
| | GCACCAGGGCTGCCCCATCTGGGCT | 383 |
| | AAGCACCAGGGCTGCCCCATCTGGG | 384 |
| | AGAAGCACCAGGGCTGCCCCATCTG | 385 |
| | GAAGAAGCACCAGGGCTGCCCCATC | 386 |
| | GGGAAGAAGCACCAGGGCTGCCCCA | 387 |
| | GTGGGAAGAAGCACCAGGGCTGCCC | 388 |
| | GGGTGGGAAGAAGCACCAGGGCTGC | 389 |
| | CTGGGTGGGAAGAAGCACCAGGGCT | 390 |
| | AGCTGGGTGGGAAGAAGCACCAGGG | 391 |
| c.413T > A | CAGCTTGTAGCTGGGGTAGCTGGGT | 392 |
| | TCCAGCTTGTAGCTGGGGTAGCTGG | 393 |
| | TCTCCAGCTTGTAGCTGGGGTAGCT | 394 |
| | GTTCTCCAGCTTGTAGCTGGGGTAG | 395 |
| | AGGTTCTCCAGCTTGTAGCTGGGGT | 396 |
| | TCAGGTTCTCCAGCTTGTAGCTGGG | 397 |
| | GCTCAGGTTCTCCAGCTTGTAGCTG | 398 |
| | GAGCTCAGGTTCTCCAGCTTGTAGC | 399 |
| | AGGAGCTCAGGTTCTCCAGCTTGTA | 400 |
| | AGAGGAGCTCAGGTTCTCCAGCTTG | 401 |
| | TCAGAGGAGCTCAGGTTCTCCAGCT | 402 |
| | TTTCAGAGGAGCTCAGGTTCTCCAG | 403 |
| | AGCTTGTAGCTGGGGTAGCTGGGTG | 404 |
| | CCAGCTTGTAGCTGGGGTAGCTGGG | 405 |
| | CTCCAGCTTGTAGCTGGGGTAGCTG | 406 |
| | TTCTCCAGCTTGTAGCTGGGGTAGC | 407 |
| | GGTTCTCCAGCTTGTAGCTGGGGTA | 408 |
| | CAGGTTCTCCAGCTTGTAGCTGGGG | 409 |
| | CTCAGGTTCTCCAGCTTGTAGCTGG | 410 |
| | AGCTCAGGTTCTCCAGCTTGTAGCT | 411 |
| | GGAGCTCAGGTTCTCCAGCTTGTAG | 412 |
| | GAGGAGCTCAGGTTCTCCAGCTTGT | 413 |
| | CAGAGGAGCTCAGGTTCTCCAGCTT | 414 |
| | TTCAGAGGAGCTCAGGTTCTCCAGC | 415 |
| | ATTTCAGAGGAGCTCAGGTTCTCCA | 416 |
| c.469C > T, | GGGGTGGTACGGGTCAGGGTGGCCG | 417 |
| c.476T > C, | TGGGGGTGGTACGGGTCAGGGTGGC | 418 |
| c.476T > G, | GGTGGGGGTGGTACGGGTCAGGGTG | 419 |
| c.478T > G, | AAGGTGGGGGTGGTACGGGTCAGGG | 420 |
| c.482C > T | AGAAGGTGGGGGTGGTACGGGTCAG | 421 |
| | GAAGAAGGTGGGGGTGGTACGGGTC | 422 |
| | GGGAAGAAGGTGGGGGTGGTACGGG | 423 |
| | TGGGGAAGAAGGTGGGGGTGGTACG | 424 |
| | CTTGGGGAAGAAGGTGGGGGTGGTA | 425 |
| | TCCTTGGGGAAGAAGGTGGGGGTGG | 426 |
| | TGTCCTTGGGGAAGAAGGTGGGGGT | 427 |
| | GATGTCCTTGGGGAAGAAGGTGGGG | 428 |
| | AGGATGTCCTTGGGGAAGAAGGTGG | 429 |
| | TCAGGATGTCCTTGGGGAAGAAGGT | 430 |
| | GGTCAGGATGTCCTTGGGGAAGAAG | 431 |
| | AGGGTCAGGATGTCCTTGGGGAAGA | 432 |
| | GCAGGGTCAGGATGTCCTTGGGGAA | 433 |
| | CCGCAGGGTCAGGATGTCCTTGGGG | 434 |
| | AGCCGCAGGGTCAGGATGTCCTTGG | 435 |
| | GGGTGGTACGGGTCAGGGTGGCCGT | 436 |
| | GGGGGTGGTACGGGTCAGGGTGGCC | 437 |
| | GTGGGGGTGGTACGGGTCAGGGTGG | 438 |
| | AGGTGGGGGTGGTACGGGTCAGGGT | 439 |
| | GAAGGTGGGGGTGGTACGGGTCAGG | 440 |
| | AAGAAGGTGGGGGTGGTACGGGTCA | 441 |
| | GGAAGAAGGTGGGGGTGGTACGGGT | 442 |
| | GGGGAAGAAGGTGGGGGTGGTACGG | 443 |
| | TTGGGGAAGAAGGTGGGGGTGGTAC | 444 |
| | CCTTGGGGAAGAAGGTGGGGGTGGT | 445 |
| | GTCCTTGGGGAAGAAGGTGGGGGTG | 446 |
| | ATGTCCTTGGGGAAGAAGGTGGGGG | 447 |
| | GGATGTCCTTGGGGAAGAAGGTGGG | 448 |
| | CAGGATGTCCTTGGGGAAGAAGGTG | 449 |
| | GTCAGGATGTCCTTGGGGAAGAAGG | 450 |
| | GGGTCAGGATGTCCTTGGGGAAGAA | 451 |
| | CAGGGTCAGGATGTCCTTGGGGAAG | 452 |
| | CGCAGGGTCAGGATGTCCTTGGGGA | 453 |
| | GCCGCAGGGTCAGGATGTCCTTGGG | 454 |
| | CAGCCGCAGGGTCAGGATGTCCTTG | 455 |
| c.510C > T, | CGTCCAGCCGCAGGGTCAGGATGTC | 456 |
| c.515T > A, | CACGTCCAGCCGCAGGGTCAGGATG | 457 |
| c.520G > A | ATCACGTCCAGCCGCAGGGTCAGGA | 458 |
| | TCATCACGTCCAGCCGCAGGGTCAG | 459 |
| | CATCATCACGTCCAGCCGCAGGGTC | 460 |
| | TCCATCATCACGTCCAGCCGCAGGG | 461 |
| | TCTCCATCATCACGTCCAGCCGCAG | 462 |
| | AGTCTCCATCATCACGTCCAGCCGC | 463 |
| | TCAGTCTCCATCATCACGTCCAGCC | 464 |
| | TCTCAGTCTCCATCATCACGTCCAG | 465 |
| | GTTCTCAGTCTCCATCATCACGTCC | 466 |
| | CGGTTCTCAGTCTCCATCATCACGT | 467 |
| | GGCGGTTCTCAGTCTCCATCATCAC | 468 |
| | GAGGCGGTTCTCAGTCTCCATCATC | 469 |
| | TGGAGGCGGTTCTCAGTCTCCATCA | 470 |
| | AGTGGAGGCGGTTCTCAGTCTCCAT | 471 |
| | GAAGTGGAGGCGGTTCTCAGTCTCC | 472 |
| | GTCCAGCCGCAGGGTCAGGATGTCC | 473 |
| | ACGTCCAGCCGCAGGGTCAGGATGT | 474 |
| | TCACGTCCAGCCGCAGGGTCAGGAT | 475 |
| | CATCACGTCCAGCCGCAGGGTCAGG | 476 |
| | ATCATCACGTCCAGCCGCAGGGTCA | 477 |
| | CCATCATCACGTCCAGCCGCAGGGT | 478 |
| | CTCCATCATCACGTCCAGCCGCAGG | 479 |
| | GTCTCCATCATCACGTCCAGCCGCA | 480 |
| | CAGTCTCCATCATCACGTCCAGCCG | 481 |
| | CTCAGTCTCCATCATCACGTCCAGC | 482 |
| | TTCTCAGTCTCCATCATCACGTCCA | 483 |
| | GGTTCTCAGTCTCCATCATCACGTC | 484 |
| | GCGGTTCTCAGTCTCCATCATCACG | 485 |
| | AGGCGGTTCTCAGTCTCCATCATCA | 486 |
| | GGAGGCGGTTCTCAGTCTCCATCAT | 487 |
| | GTGGAGGCGGTTCTCAGTCTCCATC | 488 |
| | AAGTGGAGGCGGTTCTCAGTCTCCA | 489 |
| | TGAAGTGGAGGCGGTTCTCAGTCTC | 490 |
| c.546 + 11C > T, | TGCCCTGCCCACCGTGAAGTGGAGG | 491 |
| c.546 + 14G > A, | CCTGCCCTGCCCACCGTGAAGTGGA | 492 |
| c.546 + 19G > A, | CCCCTGCCCTGCCCACCGTGAAGTG | 493 |
| c.546 + 23C > A | CGCCCCTGCCCTGCCCACCGTGAAG | 494 |
| | CCCGCCCCTGCCCTGCCCACCGTGA | 495 |
| | GCCCTGCCCACCGTGAAGTGGAGGC | 496 |
| | CTGCCCTGCCCACCGTGAAGTGGAG | 497 |
| | CCCTGCCCTGCCCACCGTGAAGTGG | 498 |
| | GCCCTGCCCTGCCCACCGTGAAGT | 499 |
| | CCGCCCCTGCCCTGCCCACCGTGAA | 500 |
| | CCCCGCCCCTGCCCTGCCCACCGTG | 501 |
| | GCCCCGCCCCTGCCCTGCCCACCG | 502 |
| | CCGCCCCGCCCCTGCCCTGCCCAC | 503 |
| | CGCCGCCCCGCCCCTGCCCTGCCC | 504 |
| | GCCGCCGCCCCGCCCCTGCCCTGC | 505 |
| | TGGCCGCCGCCCCGCCCCTGCCCT | 506 |
| | CCTGGCCGCCGCCCCGCCCCTGCC | 507 |
| | GCCCTGGCCGCCGCCCCGCCCCTG | 508 |
| | CTGCCCTGGCCGCCGCCCCGCCCC | 509 |
| | CTCTGCCCTGGCCGCCGCCCCGCC | 510 |
| | CCCTCTGCCCTGGCCGCCGCCCCG | 511 |
| | CACCCTCTGCCCTGGCCGCCGCCCC | 512 |
| | CGCACCCTCTGCCCTGGCCGCCGCC | 513 |

-continued

| variants that affect aberrant splicing of exon 2 caused by IVS1 in GAA exon 1-3 minigene system | AON sequence designed to block the region surrounding the identified splice element (5' → 3') | Seq ID |
|---|---|---|
| | CGCGCACCCTCTGCCCTGGCCGCCG | 514 |
| | CCCCGCCCCTGCCCTGCCCACCGT | 515 |
| | CGCCCCCGCCCCTGCCCTGCCCACC | 516 |
| | GCCGCCCCCGCCCCTGCCCTGCCCA | 517 |
| | CCGCCGCCCCCGCCCCTGCCCTGCC | 518 |
| | GGCCGCCGCCCCCGCCCCTGCCCTG | 519 |
| | CTGGCCGCCGCCCCCGCCCCTGCCC | 520 |
| | CCCTGGCCGCCGCCCCCGCCCCTGC | 521 |
| | TGCCCTGGCCGCCGCCCCCGCCCCT | 522 |
| | TCTGCCCTGGCCGCCGCCCCCGCCC | 523 |
| | CCTCTGCCCTGGCCGCCGCCCCCGC | 524 |
| | ACCCTCTGCCCTGGCCGCCGCCCCC | 525 |
| | GCACCCTCTGCCCTGGCCGCCGCCC | 526 |
| | GCGCACCCTCTGCCCTGGCCGCCGC | 527 |
| c.547-6 | AGAGATGGGGGTTTATTGATGTTCC | 528 |
| | GAAGAGATGGGGGTTTATTGATGTT | 529 |
| | TAGAAGAGATGGGGGTTTATTGATG | 530 |
| | TCTAGAAGAGATGGGGGTTTATTGA | 531 |
| | GATCTAGAAGAGATGGGGGTTTATT | 532 |
| | TTGATCTAGAAGAGATGGGGGTTTA | 533 |
| | CTTTGATCTAGAAGAGATGGGGGTT | 534 |
| | ATCTTTGATCTAGAAGAGATGGGGG | 535 |
| | GGATCTTTGATCTAGAAGAGATGGG | 536 |
| | CTGGATCTTTGATCTAGAAGAGATG | 537 |
| | AGCTGGATCTTTGATCTAGAAGAGA | 538 |
| | TTAGCTGGATCTTTGATCTAGAAGA | 539 |
| | TGTTAGCTGGATCTTTGATCTAGAA | 540 |

REFERENCES

1. Boycott, K. M., et al., Rare-disease genetics in the era of next-generation sequencing: discovery to translation. Nat Rev Genet, 2013. 14(10): p. 681-91.
2. Havens, M. A., D. M. Duelli, and M. L. Hastings, Targeting RNA splicing for disease therapy. Wiley Interdiscip Rev RNA, 2013. 4(3): p. 247-66.
3. Desmet, F. O., et al., Human Splicing Finder: an online bioinformatics tool to predict splicing signals. Nucleic Acids Res, 2009. 37(9): p. e67.
4. Yeo, G. and C. B. Burge, Maximum entropy modeling of short sequence motifs with applications to RNA splicing signals. J Comput Biol, 2004. 11(2-3): p. 377-94.
5. Reese, M. G., et al., Improved splice site detection in Genie. J Comput Biol, 1997. 4(3): p. 311-23.
6. Pertea, M., X. Lin, and S. L. Salzberg, GeneSplicer: a new computational method for splice site prediction. Nucleic Acids Res, 2001. 29(5): p. 1185-90.
7. Palacios, I. M., Nonsense-mediated mRNA decay: from mechanistic insights to impacts on human health. Brief Funct Genomics, 2013. 12(1): p. 25-36.
8. van der Ploeg, A. T. and A. J. Reuser, Pompe's disease. Lancet, 2008. 372(9646): p. 1342-53.
9. Umapathysivam, K., J. J. Hopwood, and P. J. Meikle, Correlation of acid alpha-glucosidase and glycogen content in skin fibroblasts with age of onset in Pompe disease. Clin Chim Acta, 2005. 361(1-2): p. 191-8.
10. Van den Hout, H., et al., Recombinant human alpha-glucosidase from rabbit milk in Pompe patients. Lancet, 2000. 356(9227): p. 397-8.
11. Kishnani, P., et al., Enzyme replacement therapy with recombinant human acid alpha glucosidase (rhGAA) in infantile Pompe disease (IPD): Results from a Phase 2 study. Pediatric Research, 2003. 53(4): p. 259a-259a.
12. Kishnani, P. S., et al., Recombinant human acid alpha-glucosidase—Major clinical benefits in infantile-onset Pompe disease. Neurology, 2007. 68(2): p. 99-109.
13. Gungor, D., et al., Impact of enzyme replacement therapy on survival in adults with Pompe disease: results from a prospective international observational study. Orphanet Journal of Rare Diseases, 2013. 8.
14. den Dunnen, J. T. and S. E. Antonarakis, Mutation nomenclature extensions and suggestions to describe complex mutations: A discussion. Human Mutation, 2000. 15(1): p. 7-12.
15. Butterworth, J. and D. M. Droadhead, Diagnosis of Pompe's disease in cultured skin fibroblasts and primary amniotic fluid cells using 4-methylumbelliferyl-alpha-D-glucopyranoside as substrate. Clin Chim Acta, 1977. 78(2): p. 335-42.
16. Pickrell, J. K., et al., Noisy splicing drives mRNA isoform diversity in human cells. PLoS Genet, 2010. 6(12): p. e1001236.
17. Huie, M. L., et al., Aberrant splicing in adult onset glycogen storage disease type II (GSDII): molecular identification of an IVS1 (−13T→G) mutation in a majority of patients and a novel IVS10 (+1GT→CT) mutation. Hum Mol Genet, 1994. 3(12): p. 2231-6.
18. Boerkoel, C. F., et al., Leaky splicing mutation in the acid maltase gene is associated with delayed onset of glycogenosis type II. Am J Hum Genet, 1995. 56(4): p. 887-97.
19. Pittis, M. G., et al., Molecular and functional characterization of eight novel GAA mutations in Italian infants with Pompe disease. Hum Mutat, 2008. 29(6): p. E27-36.
20. Dardis, A., et al., Functional characterization of the common c.-32-13T>G mutation of GAA gene: identification of potential therapeutic agents. Nucleic Acids Res, 2014. 42(2): p. 1291-302.
21. Hermans, M. M., et al., The effect of a single base pair deletion (delta T525) and a C1634T missense mutation (pro545leu) on the expression of lysosomal alpha-glucosidase in patients with glycogen storage disease type II. Hum Mol Genet, 1994. 3(12): p. 2213-8.
22. Hermans, M. M., et al., Twenty-two novel mutations in the lysosomal alpha-glucosidase gene (GAA) underscore the genotype-phenotype correlation in glycogen storage disease type II. Hum Mutat, 2004. 23(1): p. 47-56.
23. Orlikowski, D., et al., Recombinant human acid alpha-glucosidase (rhGAA) in adult patients with severe respiratory failure due to Pompe disease. Neuromuscul Disord, 2011. 21(7): p. 477-82.
24. Stroppiano, M., et al., Aberrant splicing at catalytic site as cause of infantile onset glycogen storage disease type II (GSDII): molecular identification of a novel IVS9 (+2GT→GC) in combination with rare IVS10 (+1GT→CT). Am J Med Genet, 2001. 101(1): p. 55-8.
25. Muller-Felber, W., et al., Late onset Pompe disease: clinical and neurophysiological spectrum of 38 patients including long-term follow-up in 18 patients. Neuromuscul Disord, 2007. 17(9-10): p. 698-706.
26. Kroos, M., et al., Update of the pompe disease mutation database with 60 novel GAA sequence variants and additional studies on the functional effect of 34 previously reported variants. Hum Mutat, 2012. 33(8): p. 1161-5.
27. Kroos, M., et al., Seven cases of Pompe disease from Greece. J Inherit Metab Dis, 2006. 29(4): p. 556-63.

28. Barbosa-Morais, N. L., et al., The evolutionary landscape of alternative splicing in vertebrate species. Science, 2012. 338(6114): p. 1587-93.
29. Wang, G. S. and T. A. Cooper, Splicing in disease: disruption of the splicing code and the decoding machinery. Nat Rev Genet, 2007. 8(10): p. 749-61.
30. Kwan, T., et al., Genome-wide analysis of transcript isoform variation in humans. Nat Genet, 2008. 40(2): p. 225-31.
31. Castle, J. C., et al., Expression of 24,426 human alternative splicing events and predicted cis regulation in 48 tissues and cell lines. Nat Genet, 2008. 40(12): p. 1416-25.
32. Wang, E. T., et al., Alternative isoform regulation in human tissue transcriptomes. Nature, 2008. 456(7221): p. 470-6.
33. Lappalainen, T., et al., Transcriptome and genome sequencing uncovers functional variation in humans. Nature, 2013. 501(7468): p. 506-11.
34. Lalonde, E., et al., RNA sequencing reveals the role of splicing polymorphisms in regulating human gene expression. Genome Res, 2011. 21(4): p. 545-54.
35. Wokke, J. H., et al., Genotype-phenotype correlation in adult-onset acid maltase deficiency. Ann Neurol, 1995. 38(3): p. 450-4.
36. Kishnani, P. S., et al., Cross-reactive immunologic material status affects treatment outcomes in Pompe disease infants. Mol Genet Metab, 2010. 99(1): p. 26-33.
37. Lim, K. H., et al., Using positional distribution to identify splicing elements and predict pre-mRNA processing defects in human genes. Proc Natl Acad Sci USA, 2011. 108(27): p. 11093-8.
38. Fan, L., et al., Sudemycins, novel small molecule analogues of FR901464, induce alternative gene splicing. ACS Chem Biol, 2011. 6(6): p. 582-9.
39. Webb, T. R., A. S. Joyner, and P. M. Potter, The development and application of small molecule modulators of SF3b as therapeutic agents for cancer. Drug Discov Today, 2013. 18(1-2): p. 43-9.
40. Warlich, E., et al., *Lentiviral vector design and imaging approaches to visualize the early stages of cellular reprogramming.* Mol Ther, 2011. 19(4): p. 782-9.

The invention claimed is:

1. A method for characterizing a spliced isoform of an mRNA, said mRNA comprising n exons, comprising
providing a biological sample comprising said mRNA isoform,
performing flanking exon PCR on each internal exon corresponding to the mRNA to obtain one or more flanking exon amplification products,
wherein exon 2 to exon n-1 are internal exons,
whereby each flanking exon PCR is performed with a primer specific to cDNA located 3' in and/or to an internal exon and a primer that is specific to cDNA located 5' in and/or to said internal exon, and
whereby the entire region of the mRNA between the primers that flank an exon is included in the exon amplification product,
detecting the presence and length of the said flanking exon amplification products, and
determining the quantity of each protein encoding exon of said mRNA, wherein said alternatively or aberrantly spliced mRNA isoform is characterized based on the presence and/or size of said flanking exon amplification products and from the quantity of each protein encoding exon.

2. The method according to claim 1 comprising a method for quantifying an alternatively or aberrantly spliced isoform of an mRNA.

3. The method of claim 1, further comprising determining at least part of the sequence of at least one flanking exon amplification product.

4. The method of claim 3, comprising determining at least part of the sequence of at least one flanking exon amplification product that is alternatively spliced.

5. The method of claim 3, comprising determining the sequence of more than one flanking exon amplification product.

6. The method of claim 3, comprising determining the sequence of all internal exons.

7. The method of claim 3, comprising determining the sequence of all exons.

8. The method of claim 3, comprising determining the sequence of the mRNA.

9. The method of claim 1, wherein the biological sample comprises tissue from an individual.

10. The method of claim 1, comprising determining the quantity of each exon of said mRNA.

11. The method of claim 1, wherein the quantity of each exon is determined using quantitative PCR (qPCR).

12. The method of claim 11 wherein the qPCR is RTqPCR.

13. The method of claim 9, wherein the cells are primary fibroblast cells.

14. The method of claim 9, wherein the biological sample comprises primary or transformed or otherwise modified cells from the individual.

15. The method of claim 9, wherein the individual is diagnosed or suspected to have a disease.

16. The method of claim 15, wherein the disease is a disease which involves alternative splicing.

17. The method of claim 15, wherein the disease is Pompe disease.

18. The method of claim 1, wherein the flanking exon PCR comprises performing RT-PCR amplification with primers that flank the internal exons.

19. The method of claim 1, additionally comprising the step of detecting a mutation.

20. The method of claim 19, further comprising a step of linking the mutation to the alternatively or aberrantly spliced mRNA isoform.

21. The method according to claim 1, wherein
a primer specific to cDNA located 3' in and/or to an internal exon binds to a region 3' to the exon or to a 3' region within the exon, or a combination thereof, and
a primer specific to cDNA located 5' in and/or to an internal exon binds to a region 5' to the exon or to a 5' region within the exon, or a combination thereof.

* * * * *